(12) United States Patent
Liu et al.

(10) Patent No.: US 10,081,821 B2
(45) Date of Patent: Sep. 25, 2018

(54) **METHODS FOR EFFICIENT PRODUCTION OF POLYUNSATURATED FATTY ACIDS (PUFA) IN *RHODOSPORIDIUM* AND *RHODOTORULA* SPECIES**

(71) Applicant: Temasek Life Sciences Laboratory Limited, Singapore (SG)

(72) Inventors: Yanbin Liu, Singapore (SG); Chong Mei Koh, Singapore (SG); Lianghui Ji, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 15/326,077

(22) PCT Filed: Aug. 21, 2015

(86) PCT No.: PCT/SG2015/050273
§ 371 (c)(1),
(2) Date: Jan. 13, 2017

(87) PCT Pub. No.: WO2016/039685
PCT Pub. Date: Mar. 17, 2016

(65) Prior Publication Data
US 2017/0198315 A1 Jul. 13, 2017

Related U.S. Application Data

(60) Provisional application No. 62/047,300, filed on Sep. 8, 2014.

(51) Int. Cl.
| | |
|---|---|
| *C12N 1/14* | (2006.01) |
| *C12N 1/15* | (2006.01) |
| *C12N 9/02* | (2006.01) |
| *C12P 7/64* | (2006.01) |
| *C12N 15/52* | (2006.01) |
| *C12N 15/81* | (2006.01) |
| *C12N 9/04* | (2006.01) |
| *C12N 9/10* | (2006.01) |
| *C12N 9/88* | (2006.01) |
| *C12N 9/90* | (2006.01) |
| *C12N 9/00* | (2006.01) |

(52) U.S. Cl.
CPC .......... *C12P 7/6427* (2013.01); *C12N 9/0006* (2013.01); *C12N 9/0008* (2013.01); *C12N 9/0071* (2013.01); *C12N 9/1025* (2013.01); *C12N 9/1029* (2013.01); *C12N 9/88* (2013.01); *C12N 9/90* (2013.01); *C12N 9/93* (2013.01); *C12N 15/52* (2013.01); *C12N 15/81* (2013.01); *C12P 7/6463* (2013.01); *C12Y 101/0104* (2013.01); *C12Y 102/01003* (2013.01); *C12Y 102/01012* (2013.01); *C12Y 114/19* (2013.01); *C12Y 114/19001* (2013.01); *C12Y 114/19003* (2013.01); *C12Y 114/19006* (2013.01); *C12Y 203/0102* (2013.01); *C12Y 203/03008* (2013.01); *C12Y 401/01001* (2013.01); *C12Y 402/01011* (2013.01); *C12Y 502/01008* (2013.01); *C12Y 602/01003* (2013.01); *C12Y 604/01002* (2013.01)

(58) Field of Classification Search
CPC ..................................................... C12P 7/6427
See application file for complete search history.

(56) References Cited

FOREIGN PATENT DOCUMENTS

| | | |
|---|---|---|
| WO | 2011/068708 A2 | 6/2011 |
| WO | 2011/161317 A2 | 12/2011 |
| WO | 2013/071172 A1 | 5/2013 |
| WO | 2014/100461 A2 | 6/2014 |

OTHER PUBLICATIONS

Zhu, Zhiwei et al. "A multi-omic map of the lipid-producing yeast Rhodosporidium toruloides." Nature Communications, Oct. 2012, pp. 1-11, vol. 3.
Zhou, Yongjin J. et al. "Fatty acid-derived biofuels and chemicals production in *Saccharomyces cerevisiae*." Frontiers in Bioengineering and Biotechnology, Sep. 2014, pp. 1-6, vol. 2, Art 32.
Minard, Karyl I. et al. "Sources of NADPH in Yeast Vary with Carbon Source." The Journal of Biological Chemistry, Dec. 2005, pp. 39890-39896, vol. 280, No. 48.
Bommareddy, Rajesh Reddy et al. "Metabolic network analysis and experimental study of lipid production in Rhodosporidium toruloides grown on single and mixed substrates." Microbial Cell Factories, Mar. 2015, pp. 1-13, vol. 14.
Tang, Xiaoling. "Engineering the fatty acid metabolic pathway in *Saccharomyces cerevisiae* for advanced biofuel production." Metabolic Engineering Communications, Jun. 2015, pp. 58-66, vol. 2
Sheng, Jiayuan et al. "Metabolic engineering of yeast to produce fatty acid-derived biofuels: bottlenecks and solutions." Frontiers in Microbiology. Jun. 2015. pp. 1-11, vol. 6, Art 554.
Beopoulos, Athanasio et al. "An overview of lipid metabolism in yeasts and its impact on biotechnological processes." Applied Microbiology & Biotechnology. 2011, pp. 1193-1206, vol. 90.
Beopoulos, Athanasio et al. "Ch. 45: Yarrowia lipolytica as a Cell Factory for Olechemical Biotechnology." Handbook of Hydrocarbon and Lipid Microbiology. 2010, pp. 3003-3010.

(Continued)

*Primary Examiner* — Rebecca E Prouty
(74) *Attorney, Agent, or Firm* — Rothwell, Figg, Ernst & Manbeck, P.C.

(57) ABSTRACT

The present invention relates to the field of fungal biotechnology, more particularly to genetic engineering methods for the production of polyunsaturated fatty acids (PUFA) in fungal hosts selected from *Rhodosporidium* and *Rhodotorula* genera. The present invention further relates to a modified fungal host cell having reduced native aldehyde dehydrogenase (ALD 1) enzyme activity, and methods for producing omega-3 and omega-6 fatty acids and triacylglycerides, by growing said fungal host cell under suitable conditions.

17 Claims, 20 Drawing Sheets

Specification includes a Sequence Listing.

(56) References Cited

OTHER PUBLICATIONS

Iwama, Ryo et al. "Identification and characterization of fatty aldehyde dehydrogenase genes involved in n-alkane metabolism of Yarrowia lipolytica." YEAST 2013. Aug. and Sep. 2013, p. S229, Abstact (2 pages).

Written Opinion dated Oct. 6, 2015 in PCT/SG2015/050273 (5 pages).

FIG. 3
A
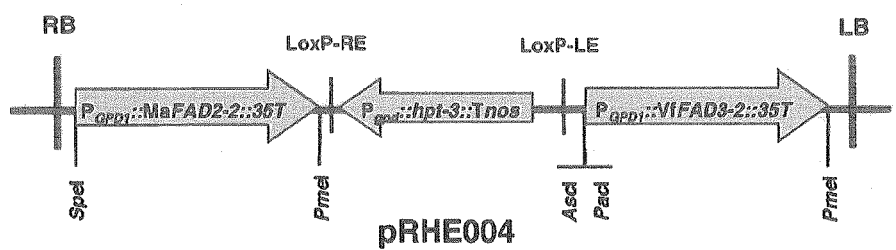
B
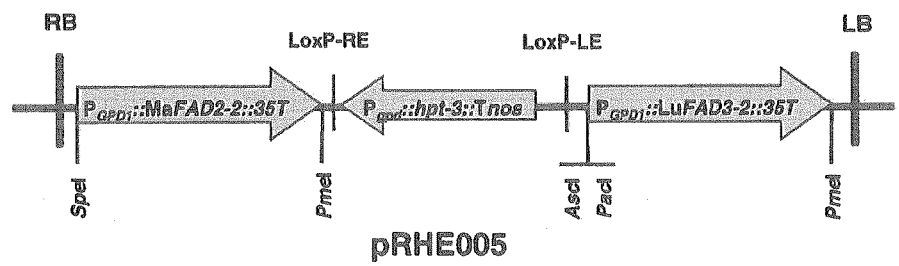
C
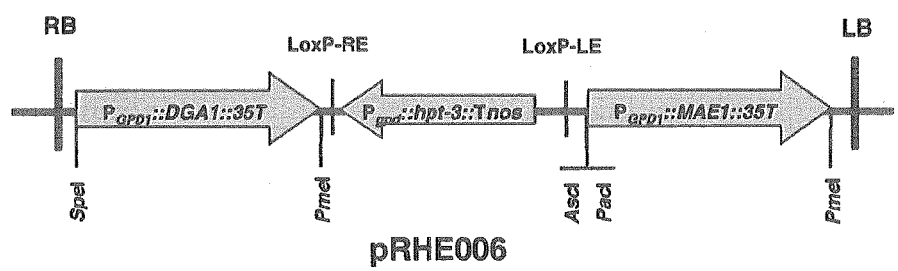

```
Ab   ::  ---------------------------------------------------------------
Pc   ::  ---------------------------------------------------------------
Mg   ::  ---------------------------------------------------------------
Sr   ::  ---------------------------------------------------------------
Um   ::  MREWLGGNLRFAAIFIRIQSRPDHSLRFTVLDPLPVHYRLSPPSSTLARLHQPRLALTSFAHLALLPSSI
Ml   ::  ---------------------------------------------------------------
Pg   ::  ---------------------------------------------------------------
Pt   ::  ---------------------------------------------------------------
Ps   ::  ---------------------------------------------------------------
Mv   ::  ---------------------------------------------------------------
Rg2  ::  ---------------------------------------------------------------
Rt3  ::  ---------------------------------------------------------------
Rt1  ::  ---------------------------------------------------------------
```

FIG. 6

```
         80              *            100              *            120            :
    :: ---------------------------------------------------------------MVDLKYTPV :   9
    :: ---------------------------------------------------------------MTRLEYTNI :   9
    :: ---------------------------------------------------------------MKTTPA    :   6
    :: ----------------------------------------MAAAATAAAEAGLQYTPI              :  18
    :: SPSPTTLRLVVCLVTNSHHSVSSSLKRQSPIMAAAAATAATEAGLQYTPI                        : 120
    :: ----------------------------------MSLSSKAQDQLNSQFTTSI                    :  18
    :: ---------------------------------------MSSTSPLEFTPT                      :  12
    :: ---------------------------------------MSSTSPLEFTPT                      :  12
    :: ------------------------------------------MASLEYTPT                      :   9
    :: --------------------------------------------SSDYTPV                      :   7
    :: ---------------------------------------------MODTPI                      :   6
    :: ------------------------------------------MAAMODTPI                      :   9
    :: ---------------------------------------------MODTPI                      :   6
                                                      Tp
```

```
                  *         620         *         640         *         660         *
Ab  :  FPPY IDKST KASQRILKSLPPR--PTGPPRTNNAMANGSATKWWGKYFFLAFVLATIGGLTKPVKILGRKF
Pc  :  YPPY TPEKL ARLRTALKVRMPP-RPGGARPAQKSA-----------------------------------
Mg  :  YPPY SKSKI DFFRFVLPKLVMFGRPPQPTRSSKS-----IDHPPSKVRTTAPRHGGHPLSLV---------
Sr  :  VPPY INANI NKMRMLAEYSVSFKRPSNPHKSTTSSSSGQGAVAKRLAVVLLISLVLGARNRGLIGWI----
Um  :  VPPY IEANL KLRALAAYSVSFKRPSNPHKSIASSSVSLCLSHSRPSPFLSMSQSLFPMVHYNMLPTQ----
Ml  :  YPPY IPFL KLFSAIMGPARIKGKSNP-----G--LVPKSAEVGKRS----WLPTLTPLSFSTLLLAGYY
Pg  :  YPPY ISFK FMQAVLGPSKLKGKSNPNPPALTDPLDFKRLLDPSSTG-----WLAKIPVKLSLMALLFAF
Pt  :  YPPY ISFK FMQAVLGPSKLKGKSNPQPPALTDPLDFKRLLDPSSAG-----CLAKVPVKFSLLVLLFAF
Ps  :  YPPY INNL KLQSALGPSKLKGKSNPIVPTLTDPLNFKKLFLNPNHSSSSLLPKGFPPVKLSLLALLLSF
Mv  :  YPPY IPKL KLMRESKWSLKSLFGVLAVVAAIVRYRQSKL-----------------------------
Rg2 :  VPPY IQKKI KMLLFATKAVIKKPSKFGSISRLLKKLTGQA------------------------------
Rt3 :  VPPY IQKKI KMLLFATKAVIKKPSKFGSISRLLKKLTGQA------------------------------
Rt1 :  VPPY IQKKI KMLLFATKAVIKKPSKFGSISRLLKKLTGQA------------------------------
       5PPY         k    k
```

FIG. 6
CONTINUED

```
             680         *         700         *
    VPKILG---------------------------------------  :  527
    -------------------------------------------  :  487
    -------------------------------------------  :  514
    -------------------------------------------  :  538
    -------------------------------------------  :  640
    ALSR--R--------YGSDYLKIWMTRFIGAIKQSNR-------  :  578
    YCSR--RQDS-----LGQKGLFNSFKKVQDQVKQFISS------  :  576
    YFSR--RQDS-----LGQKGLFNSIKKLQDQVKQFISS------  :  576
    YYSRNRRESSVFSPLVSSQKAFSDLIQKIQEYLKKNLST-----  :  591
    -------------------------------------------  :  505
    -------------------------------------------  :  501
    -------------------------------------------  :  504
    -------------------------------------------  :  501
```

FIG. 15
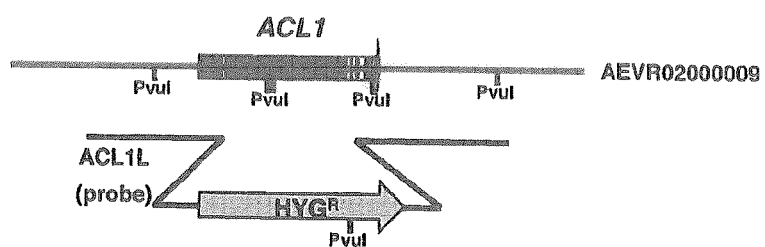
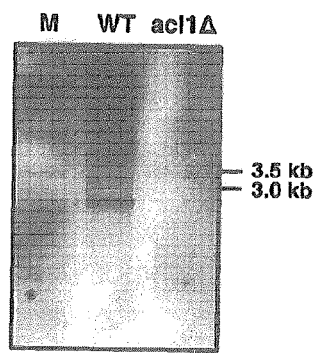
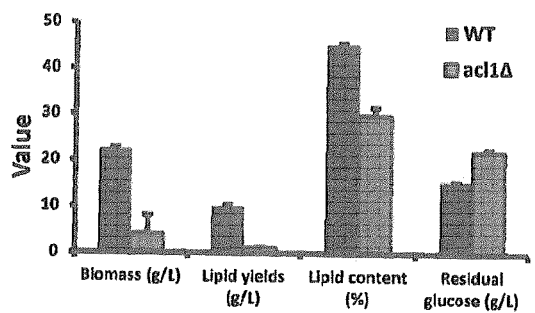
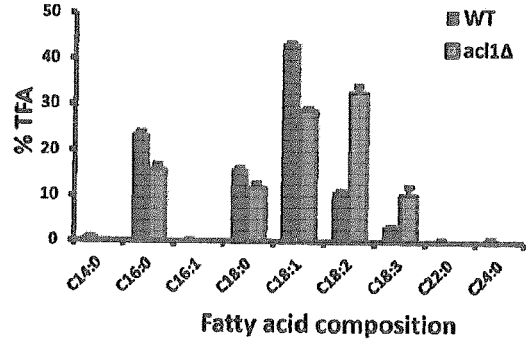

METHODS FOR EFFICIENT PRODUCTION OF POLYUNSATURATED FATTY ACIDS (PUFA) IN *RHODOSPORIDIUM* AND *RHODOTORULA* SPECIES

CROSS-REFERENCE TO RELATED APPLICATIONS

The present application is a national stage filing under 35 U.S.C. § 371 of PCT/SG2015/050273, filed on 21 Aug. 2015, which in turn claims the benefit of priority to and the benefit of U.S. provisional patent application Ser. No. 62/047,300 filed 8 Sep. 2014. Each application is incorporated herein by reference in its entirety.

SEQUENCE SUBMISSION

The present application is being filed along with a Sequence Listing in electronic format. The Sequence Listing is entitled 2577237PCTSequenceListing.txt, created on 2 Jul. 2015 and is 321 kb is size. The information in the electronic format of the Sequence Listing is incorporated herein by reference in their entirety.

BACKGROUND OF THE INVENTION

The present invention relates to the field of fungal biotechnology, more particularly to genetic engineering methods for the production of omega-3 polyunsaturated fatty acids (PUFAs) in fungal hosts selected from *Rhodospordium* and *Rhodotorula* genera.

The publications and other materials used herein to illuminate the background of the invention or provide additional details respecting the practice, are incorporated by reference, and for convenience are respectively grouped in the Bibliography.

Omega-3 fatty acids (also called ω-3 fatty acids or n-3 fatty acids) refer to alpha-linolenic acid (ALA) [(9Z,12Z,15Z)-9,12,15-Octadecatrienoic acid], EPA (eicosapentaenoic acid, or [(5Z,8Z,11Z,14Z,17Z)-5,8,11,14,17-Eicosapentaenoic acid]) and DHA [docosahexaenoic acid, or (4Z,7Z,10Z,13Z,16Z,19Z)-docosa-4,7,10,13,16,19-hexaenoic acid]. Common sources of animal omega-3 EPA and DHA fatty acids include fish oils, egg oil, squid oils and krill oil while some plant oils, such as oil from seabuckthorn seed and berry, algal cells, flax seed, Chia seed and hemp seed, contain high levels of ALA.

Linoleic acid [(9Z,12Z)-9,12-Octadecadienoic acid], gamma-linolenic acid (GLA, or all-cis-6,9,12-octadecatrienoic acid) and arachidonic acid [(5Z,8Z,11Z,14Z)-5,8,11,14-Eicosatetraenoic acid]) are omega-6 fatty acids. GLA is an omega-6 fatty acid that is found mostly in plant based oils such as borrage seed oil, evening primrose oil, and black currant seed oil.

Omega-3 fatty acids are vital for normal metabolism. Omega-3s are considered essential fatty acids, i.e., cannot be synthesized by the human body except that mammals have a limited ability, when the diet includes the shorter-chain omega-3 fatty acid ALA, to form the more important long-chain omega-3 fatty acids, EPA and then from EPA, the most crucial, DHA with even greater inefficiency. It is now accepted that omega-3 polyunsaturated fatty acids, especially EPA and DHA play important roles in a number of aspects of human health. However, over-fishing and concerns about pollution of the marine environment indicate a need to develop alternative, sustainable sources of very long chain polyunsaturated fatty acids (VLC-PUFAs) such as EPA and DHA [1]. Omega-6 fatty acids are considered essential fatty acids: They are necessary for human health. Along with omega-3 fatty acids, omega-6 fatty acids play a crucial role in brain function, as well as normal growth and development. Omega-3 fatty acids and omega-6 fatty acids help stimulate skin and hair growth, maintain bone health, regulate metabolism, and maintain the reproductive system [2]. Some preliminary clinical research suggests that GLA may be useful for Diabetic neuropathy, Rheumatoid arthritis, Allergies, Eczema, High blood pressure (Hypertension), Menopausal symptoms, etc. The ratio of dietary intake of omega-6 and omega-3 essential fatty acids is considered important for health in human [3].

A large number of oleaginous microorganisms have been reported to date. The oil they produce, often referred to as Single Cell Oil (SCO), is similar to those of plants and can be used for the production of biodiesel, food and industrial products [4-6]. SCO is now widely accepted in the market place and there is a growing awareness of the health benefits of PUFAs, such as γ-linolenic acid (GLA), arachidonic acid (ARA), DHA and EPA. ARA and DHA have also been used for fortification of infant formulae in many parts of the world. Fish oils are rich sources of DHA and EPA and a limited number of plant oilseeds are good sources of other PUFAs. Marine protists and dinoflagellates, such as species of *Thraustochytrium, Schizochytrium* and *Crypthecodinium* are the rich sources of DHA, whereas microalgae like *Phaeodactylum* and *Monodus* are good sources of EPA. Species of lower fungi *Mortierella* accumulate a high percentage of ARA in the lipid fraction [7].

While yeast *Yarrowia lipolytica* perhaps has enjoyed long history of research and development as a bioengineering host for SCO [8-12], *Rhodosporidium toruloides* (also known as *Rhodotorula glutenis*) has attracted increasing attention due to its ability to perform higher cell density fermentation at a fast growth rate, efficiently producing cell mass with an oil content of >67% (w/w dry cell mass) [13-16].

The *Pucciniomycotina* is a subphylum of fungi in the phylum of *Basidiomycota* [17]. It holds many species that have important industrial applications. For example, a number of species in the *Rhodosporidium* and *Sporidiobolus* genera, such as *Rhodosporidium toruloides* (also known as *Rhodotorula gracilis, Rhodosporidium glutinis, Rhodotorula glutinis, Torula koishikawensis* and *Torula rubescens*) and *Sporobolomyces salmonicolor*, are oil-rich single-cell yeasts capable of high density fermentation [6, 18]. These species hold great potential as a host for the production of long chain hydrocarbons, such as triacylglycerol (TAG, or fat), fatty acid esters (biodiesel), fatty alcohols, alcohols, lactones, terpenoids and vitamins [14, 19-21].

*Rhodosporidium* and *Rhodotorula* genomes are highly GC-rich, which has been found to profoundly influence genetic transformation and protein expression [22-24]. Metabolic engineering is an effective technique for improving production of metabolites in plants and microbes. In terms of bioengineering for omega-3 fatty acids, expressing various desaturases and elongases, both in plants and oleaginous yeast, are critical for the production of PUFAs [25]. GLA is synthesized from linoleic acid (LA; C18:2Δ9,12 cis) by Δ6-desaturase. The seed oil of safflower (*Carthamus tinctorius*) contains high LA and has been modified by transformation with Δ6-desaturases from *Mortierella alpina* and *Saprolegnia diclina* to achieve more than 50% (v/v) of GLA respectively [26].

ALA and GLA are both precursors for the production of longer chains omega-3 fatty acids, such as arachidonic acid (AA), EPA and docosahexaenoic acid (DHA) [7, 27]. Therefore, the ability to produce high levels of ALA and GLA at high volumetric productivity is crucial for the bioengineering of longer chain PUFAs in *Rhodosporidium toruloides*. Thus, there is a need to develop fungal species of the *Rhodospordium* and *Rhodotorula* genera that produce high levels of ALA and GLA that are then available in the fungal species for the production of longer chain PUFAs.

SUMMARY OF THE INVENTION

The present invention relates to the field of fungal biotechnology, more particularly to genetic engineering methods for the production of omega-3 polyunsaturated fatty acids (PUFA) in fungal hosts selected from *Rhodospordium* and *Rhodotorula* genera.

In a first aspect, the present invention provides a fungal host having an α-linolenic acid (ALA) present in an amount of at least 9% of total fatty acids in cells of the fungal host. In one embodiment, the fungal host is a species of the *Rhodospordium* genera. In another embodiment, the fungal host is a species of the *Rhodotorula* genera. In some embodiments, the fungal host has reduced activity of a native aldehyde dehydrogenase (ALD) that uses fatty acid aldehyde as a substrate. The native ALD is encoded by a native ALD gene. In one the native ALD gene encodes an aldehyde dehydrogenase (ALD) having the amino acid sequence set forth in SEQ ID NO:3. In another embodiment, the native ALD gene encodes an ALD having 75%, 80%, 85%, 90%, 95%, 98% or 99% of the amino acid sequence set forth in SEQ ID NO:3. In one embodiment, the native ALD gene has the genomic nucleotide sequence set forth in SEQ ID NO:1. In another embodiment, the native ALD gene has the cDNA nucleotide sequence set forth in SEQ ID NO:2. In a further embodiment, the native ALD gene has the nucleotide sequence having 75%, 80%, 85%, 90%, 95%, 98% or 99% of the nucleotide sequence set forth in SEQ ID NO: 1 or SEQ ID NO:2.

In some embodiments, the reduced activity of the native ALD is caused by reduced expression of the native ALD gene. The reduced expression can be caused by any genetic or epigenetic mechanism. In one embodiment, the reduced expression is caused by an RNAi mechanism, such as siRNA, shRNA, miRNA and the like. In another embodiment, the reduced expression is caused by an artificial transcription repressor. In a further embodiment, the reduced expression is caused by an antisense mechanism. In one embodiment, the reduced expression is caused by sense suppression. In a further embodiment, the reduced activity is caused by a mutation of the native gene. In one embodiment, the mutation may be a substitutions, deletion, insertions, addition, or inversion and the like which results in reduced activity. In another embodiment, the mutation may be caused by homologous recombination. In a further embodiment, the mutation may be caused by T-DNA or transposon insertion.

In a second aspect, the present invention provides a fungal host having an α-linolenic acid (ALA) present in an amount of at least 49% of total fatty acids in cells of the fungal host. In one embodiment, the fungal host is a species of the *Rhodospordium* genera. In another embodiment, the fungal host is a species of the *Rhodotorula* genera. In some embodiments, the fungal host has reduced activity of a native aldehyde dehydrogenase (ALD) as described herein. In other embodiments, the genome of the fungal host has been modified to stably include two or more genes that encode proteins that are involved in fatty acid biosynthesis. Examples of such proteins are an acyl-CoA delta-12 desaturase, a stearoyl-CoA-delta-9-desaturase, an omega-3 desaturase, a fatty acid elongase, an acetyl-CoA carboxylase (ACC), an ATP:citrate lyase (ACL), a diacylglycerol acyltransferase (DGA) or a malic enzyme (MAE). In some embodiments, the coding sequences of such genes have been modified to contain at least 55% G and C content, preferably 60%-70% G and C content. In other embodiments, at least 70% of the codons have a C or G at the third position.

In one embodiment, an ATP:citrate lyase (ACL) has the amino acid sequence set forth in SEQ ID NO:88. In another embodiment, this ATP:citrate lyase (ACL1) is encoded by a genomic DNA nucleic acid having a nucleotide sequence set forth in SEQ ID NO:86. In another embodiment, this ATP:citrate lyase (ACL1) is encoded by a cDNA nucleic acid having a nucleotide sequence set forth in SEQ ID NO:87. In another embodiment, the ATP:citrate lyase (ACL1) gene has a nucleotide sequence having 75%, 80%, 85%, 90%, 95%, 98% or 99% of the nucleotide sequence described herein.

In one embodiment, a diacylglycerol acyltransferase (DGA1) has the amino acid sequence set forth in SEQ ID NO:82. In another embodiment, this diacylglycerol acyltransferase (DGA1) is encoded by a genomic DNA having a nucleotide sequence set forth in SEQ ID NO:80. In a further embodiment, this diacylglycerol acyltransferase (DGA1) is encoded by a nucleic acid having a nucleotide sequence set forth in SEQ ID NO:81. In another embodiment, the diacylglycerol acyltransferase (DGA1) gene has the nucleotide sequence having 75%, 80%, 85%, 90%, 95%, 98% or 99% of the nucleotide sequence described herein.

In one embodiment, a malic enzyme (MAE1) has the amino acid sequence set forth in SEQ ID NO:85. In another embodiment, this malic enzyme (MAE1) is encoded by a genomic DNA nucleic acid having a nucleotide sequence set forth in SEQ ID NO:83. In a further embodiment, this malic enzyme (MAE1) is encoded by a nucleic acid having a nucleotide sequence set forth in SEQ ID NO:84. In another embodiment, a malic enzyme (MAE1) gene has a nucleotide sequence having 75%, 80%, 85%, 90%, 95%, 98% or 99% of the nucleotide sequence described herein.

In a another aspect, the present invention provides a fungal host having a gamma-linolenic acid (GLA) present in an amount of at least 30% of total fatty acids in cells of the fungal host. In one embodiment, the fungal host is a species of the *Rhodospordium* genera. In another embodiment, the fungal host is a species of the *Rhodotorula* genera. In some embodiments, the fungal host has reduced activity of a native aldehyde dehydrogenase (ALD) as described herein. In other embodiments, the genome of the fungal host has been modified to stably express two or more additional genes encoding proteins that are involved in fatty acid biosynthesis. Examples of such proteins are an acyl-CoA delta-12 desaturase, a stearoyl-CoA-delta-9-desaturase, acyl-CoA delta-6 desaturase, a fatty acid elongase, an acetyl-CoA carboxylase (ACC), an ATP:citrate lyase (ACL), a diacylglycerol acyltransferase (DGA) or a malic enzyme (MAE). In some embodiments, the coding sequences of such genes have been modified to contain at least 55% G and C content, preferably 60%-70% G and C content. In other embodiments, at least 70% of the codons have a C or G at the third position.

In one embodiment, an acetyl-CoA carboxylase (ACC1) has the amino acid sequence set forth in SEQ ID NO:91. In another embodiment, this acetyl-CoA carboxylase (ACC1) is encoded by a genomic DNA nucleic acid having a nucleotide sequence set forth in SEQ ID NO:89. In a further embodiment, this acetyl-CoA carboxylase (ACC1) is encoded by a cDNA nucleic acid having a nucleotide sequence set forth in SEQ ID NO:90. In another embodiment, the an acetyl-CoA carboxylase (ACC1) gene has the nucleotide sequence having 75%, 80%, 85%, 90%, 95%, 98% or 99% of the nucleotide sequence described herein.

In one embodiment, an acyl-CoA delta-12 desaturase has an amino acid sequence set forth in SEQ ID NOs:5 and 94. In another embodiment, this acyl-CoA delta-12 desaturase is encoded by a nucleic acid having a nucleotide sequence set forth in SEQ ID NOs:4, 92 and NO:93. In another embodiment, the acyl-CoA delta-12 desaturase genes have a nucleotide sequence having 75%, 80%, 85%, 90%, 95%, 98% or 99% of the nucleotide sequences described herein.

In one embodiment, a stearoyl-CoA-delta-9-desaturase has an amino acid sequence set forth in SEQ ID NO:8. In one embodiment, this stearoyl-CoA-delta-9-desaturase is encoded by a genomic nucleic acid having a nucleotide sequence set forth in SEQ ID NO:6. In another embodiment, this stearoyl-CoA-delta-9-desaturase is encoded by a nucleic acid having a nucleotide sequence set forth in SEQ ID NO:7. In another embodiment, the stearoyl-CoA-delta-9-desaturase gene has a nucleotide sequence having 75%, 80%, 85%, 90%, 95%, 98% or 99% of the nucleotide sequence described herein.

In one embodiment, an omega-3 desaturase has an amino acid sequence set forth in SEQ ID NO: 10. In one embodiment, this omega-3 desaturase is encoded by a nucleic acid having a nucleotide sequence set forth in SEQ ID NO:9. In an additional embodiment, an omega-3 desaturase has an amino acid sequence set forth in SEQ ID NO:12. In one embodiment, this latter omega-3 desaturase is encoded by a nucleic acid having a nucleotide sequence set forth in SEQ ID NO: 11. In another embodiment, omega-3 desaturase gene has a nucleotide sequence having 75%, 80%, 85%, 90%, 95%, 98% or 99% of the nucleotide sequence described herein.

In one embodiment, an acyl-CoA delta-6 desaturase has an amino acid sequence set forth in SEQ ID NOs:96 and 98 wherein the sequences encoded by DNA containing at least G and C, preferably 60%-70% G and C. In other embodiments, at least 70% of the codons have a C or G at the third position. In one embodiment, the acyl-CoA delta-6 desaturases is encoded by a nucleic acid set forth in SEQ ID NOs:95 and 97.

In one embodiment, a fatty acid elongase has the amino acid sequence set forth in SEQ ID NOs:101 and 104. In another embodiment, this fatty acid elongase is encoded by a nucleic acid having a nucleotide sequence set forth in SEQ ID NOs:99, 100, 102 and 103. In another embodiment, the fatty acid elongase gene has a nucleotide sequence having 75%, 80%, 85%, 90%, 95%, 98% or 99% of the nucleotide sequence described herein.

In some embodiments, the genes described herein that have been stably incorporated in the fungal genome are operatively linked to a promoter which permits efficient expression in species of the *Rhodospordium* genera and the *Rhodotorula* genera. The promoters for each incorporated gene may be the same or different. In some embodiments, the promoters are promoters found in species of the *Rhodospordium* genera and the *Rhodotorula* genera. Examples of suitable promoters include, but are not limited to, promoters of the following genes encoding the following proteins: glyceraldehyde 3-phosphate dehydrogenase (GPD), acyl-CoA carrier protein (ACP), fatty acid desaturase, translation elongation factor (TEF), pyruvate decarboxylase (PDC), enolase (2-phosphoglycerate dehydratase) (ENO), peptidylprolyl isomerase (PPI), acetyl-CoA carboxylase (ACC) or transaldolase. In other embodiments, the genes described herein also include a mRNA transcriptional terminator that may be one found in any eukaryotic species and their DNA viruses.

In a another aspect, the present invention provides a method for producing omega-3 and omega-6 polyunsaturated fatty acids (PUFAs), comprising growing a fungal host cell described herein under conditions suitable to produce PUFAs. Any medium with at least 5% carbon source, such glucose, mannose, glycerol, sucrose can be used. Example of the medium is Medium MinLG containing 30-100 g glucose, 1.5 g yeast extract, 0.5 g $(NH_4)_2SO_4$, 2.05 g $K_2HPO_4$, 1.45 g $KH_2PO_4$, 0.6 g $MgSO_4$, 0.3 g NaCl, 10 mg $CaCl_2$, 1 mg $FeSO_4$, 0.5 mg $ZnSO_4$, 0.5 mg $CuSO_4$, 0.5 mg $H_3BO_4$, 0.5 mg $MnSO_4$, 0.5 mg $NaMoO_4$ (per liter). The medium pH is adjusted to 6-7. Cell culturing is performed at 25° C.-32° C.

BRIEF DESCRIPTION OF THE FIGURES

FIG. 1A: pEC3GPD-GUS. FIG. 1B: pEC3Pxxx-HPT3. FIG. 1C: pRH2034. FIG. 1D: pRH-DGA1 and pRHMAE1. FIG. 1E: pRH201. LB: left border of T-DNA; RB: right border of T-DNA; Pgpd: 595 bp promoter of Umgpd1; $P_{GPD1}$: 795 bp promoter of RtGPD1; Pxxx: various promoters; hpt-3: codon-optimized hygromycin resistance gene based on the codon usage bias in *R. toruloides*; GUS: *E. coli* β-glucuronidase gene; $T_{35S}$: terminator of cauliflower mosaic virus 35S gene; Tnos: terminator of *A. tumefaciens* nopaline synthase gene. Unique restriction enzymes cutting sites in the plasmid are shown.

FIG. 2A: pRHE001. FIG. 2B: pRHE002.

FIG. 2C: pRHE003. LB: left border of T-DNA; RB: right border of T-DNA; Pgpd: 595 bp promoter of Umgpd1; $P_{GPD1}$: 795 bp promoter of RtGPD1; hpt-3: codon-optimized hygromycin resistance gene based on the codon usage bias in *R. toruloides*; $T_{35S}$: terminator of cauliflower mosaic virus 35S gene; Tnos: terminator of *A. tumefaciens* nopaline synthase gene. Unique restriction enzymes cutting sites in the plasmid are shown.

FIGS. 3A-3C show the T-DNA organization in constructs used in this invention. All binary vectors have the same pPZP200 backbone [28]. FIG. 3A: pRHE004. FIG. 3B: pRHE005. FIG. 3C: pRHE006. LB: left border of T-DNA; RB: right border of T-DNA; Pgpd: 595 bp promoter of Umgpd1; $P_{GPD1}$: 795 bp promoter of RtGPD1; hpt-3: codon-optimized hygromycin resistance gene based on the codon usage bias in *R. toruloides*; $T_{35S}$: terminator of cauliflower mosaic virus 35S gene; Tnos: terminator of *A. tumefaciens* nopaline synthase gene Unique restriction enzymes cutting sites in the plasmid are shown.

FIG. 4A: Comparison of average ALA (C18:3n=9) levels in WT and T-DNA mutants (RCMs) selected against cerulenin. FIG. 4B: Relative ALA levels in individual RCM mutant. FIG. 4C: Comparison of lipid accumulation in WT and mutants selected against tetrazeolium violet. FIG. 4D: Comparison of lipid accumulation in WT and mutants selected against fluorescent dye Nile red.

FIG. 5A: Schematic diagram of ALD1 and its deletion strategy. Homologous sequences used for deletion of ALD1 were 730 bp and 829 bp in length, between −185 to +535 and +1948 to +2776 from the translational start codon. FIG. 5B: Southern blot analysis of Δald1. Digoxigenin labeled DNA sequence (labelled ALD1R in FIG. 5A) was used as the probe against genomic DNA digested with HincII. FIG. 5C: Relative lipid yields in WT and Δald1 at day 3 and 4. FIG. 5D: Relative α-linolenic acid (ALA) yields in WT and Δald1. ** represents very significant difference by statistic t-test (P<0.01). FIG. 5E: Dry cell biomass (Biomass) and ALA contents (percentage of total fatty acids, % TFA) of WT and Δald1. FIG. 5F: Colors of cell cultured in potato detrose agar (PDA) and YPD broth.

FIG. 6 shows an alignment of fatty aldehyde dehydrogenases from various Basidiomycotous species. Ab: *Agaricus bisporus* (EKM75339.1; SEQ ID NO:105); Pc: *Phanerochaete carnosa* (EKM57674.1; SEQ ID NO:106); Mg: *Malassezia globosa* (XP_001730031.1; SEQ ID NO:107); Sr: *Sporisorium reilianum* (CBQ71609.1; SEQ ID NO:108); Um: *Ustilago maydis* (XP_762570.1; SEQ ID NO:109); Ml: *Melampsora larici-populina* (EGG04055.1; SEQ ID NO:110); Pg: *Puccinia graminis* f. sp. *tritici* (XP_003338710.1; SEQ ID NO:111); Pt: *Puccinia triticina* (XP_003338710.1; SEQ ID NO:112); Ps: *Puccinia striiformis* (genome locus CQM_00777.1; SEQ ID NO:113); Mv: *Microbotryum violaceum* (genome locus MVLG_02667.1; SEQ ID NO:114); Rg2: *R. glutinis* ATCC 204091 (SEQ ID NO:115); Rt3: *R. toruloides* NP1 (EMS18750.1; SEQ ID NO:116); Rt1: *R. toruloides* ATCC 10657 (SEQ ID NO:117). [Note: the sequence listing includes only a partial sequence for SEQ ID NOs: 112, 113, 115 and 117. See Figure for complete sequences.]

FIG. 7A: Quantitative RT-PCR analysis of DGA1 and MAE1 in *R. toruloides* ATCC 10657. Gene expressions in the engineering mutants (DGA1 and MAE1) were normalized against that in WT strain. FIG. 7B: Relative lipid yields in wild type and two engineering strains (WT, DGA1 and MAE1). Lipid quantities were normalized against that in WT. FIG. 7C: Fatty acid profiles in above strains. The intracellular lipids were extracted from above strains after 3-day bioprocess. FIG. 7D: Composition of unsaturated fatty acids in above strains. % TFA represents percentage of total fatty acids. FIG. 7E: Schematic diagram of DGA1 deletion. FIG. 7F: Southern blot analysis of Δdga1. Genomic DNAs of wild type and candidate mutant were digested with HincII and probed against DIG-labeling DGA1L DNA fragment as marked in FIG. 7E.

FIG. 9A: ALA content in wild type and different desaturase engineering strains. FIG. 9B: ALA content in ald1 null strain (ald1e) and ald1e strain containing both the RtGPD1::MaFAd2-2 and RtGPD1::LuFAD3-2 gene cassettes.

FIG. 11A: Southern blot analysis of WT and FAD2 knockout strain (fad2Δ). Total DNA was digested with PstI and the blot was hybridized using digoxiginin-labeled right homology PCR fragment of FAD2 (FAD2R, FIG. 11C). FIG. 11B: Fatty acid content profile of WT and fad2Δ performed in triplicates. FIG. 11D: Fatty acid content profile of WT and fad2Δ cultured in YNB medium supplemented with and without LA (C18:2).

(FIG. 12B) and (FIG. 12D) Fatty acid content profiles of elo1Δ and elo2Δ.

FIG. 13A: FAD1 (delta-9-oleate desaturase, ELO1) over-expression construct. FIG. 13B: FAD2 (delta-12 desaturase) over-expression construct. FIG. 13C: omega-3 desaturase (delta-15 desaturase) over-expression construct. FIG. 13D: FAD1 and FAD2 double gene over-expression vector. FIG. 13E: FAD1, FAD2 and omega-3 desaturase triple gene over-expression vector. LB: left border of T-DNA; RB: right border of T-DNA; RgGPD1: 685 bp GPD1 promoter derived from *Rhodotorula grammis* WP1; RtGPD1: 795 bp GPD1 promoter derived from *R. toruloides* ATCC 10657; hpt-3: codon-optimized hygromycin resistance gene based on codon usage bias in *R. toruloides*; TSV40: Simian vacuolating virus 40 large T antigen gene terminator; T$_{35S}$: terminator of cauliflower mosaic virus 35S gene; Tnos: terminator of *A. tumefaciens* nopaline synthase gene; RtENO1: 445 bp version ENO1 gene promoter from *R. toruloides* ATCC 10657; RtACC1: 805 bp version of ACC1 gene promoter from *R. toruloides* ATCC 10657; MaFAD2-2 is SEQ ID NO:4, and VfFAD3-2 is SEQ ID NO: 11.

FIG. 13A; MA: FIG. 13B; AF3: FIG. 13C; OM2: FIG. 13D; OMA2: FIG. 13E.

FIGS. 15A-15D show the characterization of putative ATP-citrate lyase gene in *R. toruloides* ATCC 10657 (RtACL1). FIG. 15A: Schematic diagram of ACL1 gene and its deletion strategy. FIG. 15B: Southern blot analysis of knockout strain acl1Δ. Total DNA was digested with PvuI and hybridized against digoxiginin-labeled ACL1L. M: Digoxigenin-labeled DNA Molecular Weight Marker VII (Roche Diagnosis, USA). FIG. 15C: Effects of ACL1 disruption on biomass, lipid yields, lipid content and residual glucose. FIG. 15D: Fatty acid content profile of Wt and acl1Δ strains.

DETAILED DESCRIPTION OF THE INVENTION

Figure 1:
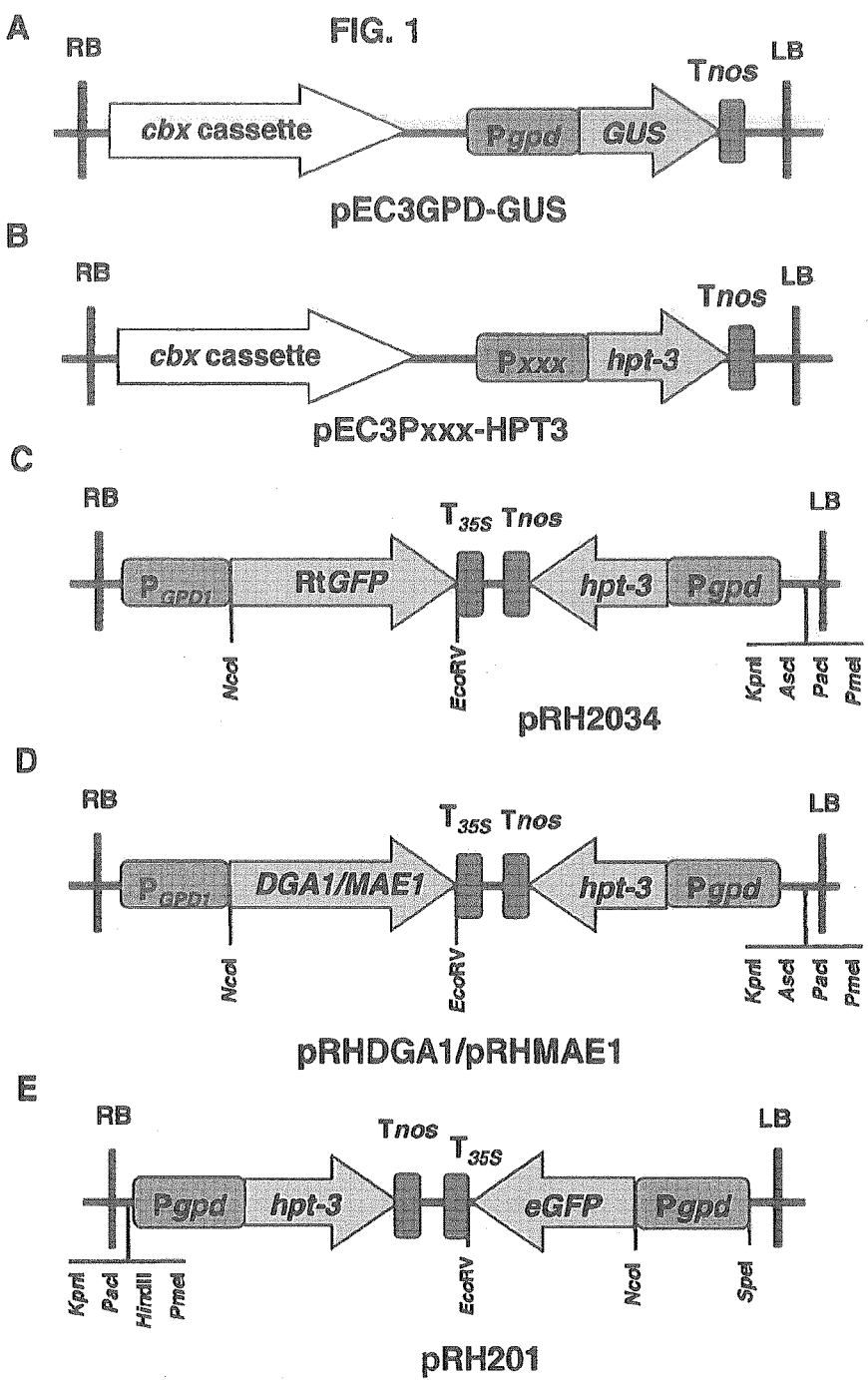
FIGS. 1A-1E show the T-DNA organization in constructs used in this invention. All binary vectors have the same pPZP200 backbone [28].

The present invention relates to the field of fungal biotechnology, more particularly to genetic engineering methods for the production of polyunsaturated fatty acids (PUFA) in fungal hosts selected from *Rhodospordium* and *Rhodotorula* genera.

Unless defined otherwise, all technical and scientific terms used herein have the same meaning as is commonly understood by one of skill in the art to which the invention belongs.

As used herein, "ALD1" is an aldehyde dehydrogenase that uses fatty acid aldehydes as a substrate.

As used herein, "allele" refers to any of one or more alternative forms of a gene locus, all of which alleles relate to a trait or characteristic. In a diploid cell or organism, the two alleles of a given gene occupy corresponding loci on a pair of homologous chromosomes.

A "dsRNA" or "RNAi molecule," as used herein in the context of RNAi, refers to a compound, which is capable of down-regulating or reducing the expression of a gene or the activity of the product of such gene to an extent sufficient to achieve a desired biological or physiological effect. The term "dsRNA" or "RNAi molecule," as used herein, refers to one or more of a dsRNA, siRNA, shRNA, ihpRNA, synthetic shRNA, miRNA.

The term "down regulated," as it refers to genes inhibited by the subject RNAi method, refers to a diminishment in the level of expression of a gene(s) in the presence of one or more RNAi construct(s) when compared to the level in the absence of such RNAi construct(s). The term "down regulated" is used herein to indicate that the target gene expression is lowered by 1-100%. For example, the expression may be reduced by about 5%, 10%, 15%, 20%, 25%, 30%, 35%, 40%, 45%, 50%, 55%, 60%, 65%, 70%, 75%, 80%, 85%, 90%, 95%, or 99%.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence.

As used herein, "gene" refers to a nucleic acid sequence that encompasses a 5' promoter region associated with the expression of the gene product, any intron and exon regions and 3' or 5' untranslated regions associated with the expression of the gene product.

The term "gene silencing" refers to the suppression of gene expression, e.g., transgene, heterologous gene and/or endogenous gene expression. Gene silencing may be mediated through processes that affect transcription and/or through processes that affect post-transcriptional mechanisms. Gene silencing may be allele-specific wherein specific silencing of one allele of a gene occurs.

As used herein, "genotype" refers to the genetic constitution of a cell or organism.

The term "heterologous" or "exogenous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous or exogenous protein indicates that the protein comprises two or more subsequences that are not found in the same relationship to each other in nature (e.g., a fusion protein).

The term "homolog" as used herein refers to a gene related to a second gene by descent from a common ancestral DNA sequence. The term, homolog, may apply to the relationship between genes separated by the event of speciation (ortholog) or to the relationship between genes separated by the event of genetic duplication (paralog). The term homolog is used generically to refer to all species.

As used herein, "phenotype" refers to the detectable characteristics of a cell or organism, which characteristics are the manifestation of gene expression.

The terms "polynucleotide," "nucleic acid" and "nucleic acid molecule" are used interchangeably herein to refer to a polymer of nucleotides which may be a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

"Operable linkage" or "operably linked" or "operatively linked" as used herein is understood as meaning, for example, the sequential arrangement of a promoter and the nucleic acid to be expressed and, if appropriate, further regulatory elements such as, for example, a terminator, in such a way that each of the regulatory elements can fulfill its function in the recombinant expression of the nucleic acid to make dsRNA. This does not necessarily require direct linkage in the chemical sense. Genetic control sequences such as, for example, enhancer sequences, can also exert their function on the target sequence from positions which are somewhat distant, or indeed from other DNA molecules (cis or trans localization). Preferred arrangements are those in which the nucleic acid sequence to be expressed recombinantly is positioned downstream of the sequence which acts as promoter, so that the two sequences are covalently bonded with one another. Regulatory or control sequences may be positioned on the 5' side of the nucleotide sequence or on the 3' side of the nucleotide sequence as is well known in the art.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

As used herein, the term "sequence identity," "sequence similarity" or "homology" is used to describe sequence relationships between two or more nucleotide sequences. The percentage of "sequence identity" between two sequences is determined by comparing two optimally aligned sequences over a comparison window such as the full length of a referenced SEQ ID NO:, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

As used herein, a "comparison window" or "window of comparison" refers to a conceptual segment of at least 6 contiguous positions, usually about 50 to about 100, more usually about 100 to about 150, in which a sequence is compared to a reference sequence of the same number of contiguous positions after the two sequences are optimally aligned. The comparison window may comprise additions or deletions (i.e. gaps) of about 20% or less as compared to the reference sequence (which does not comprise additions or deletions) for optimal alignment of the two sequences Those skilled in the art should refer to the detailed methods used for sequence alignment, such as in the Wisconsin Genetics Software Package Release 7.0 (Genetics Computer Group, 575 Science Drive Madison, Wis., USA).

In a first aspect, the present invention provides a fungal host having an α-linolenic acid (ALA) present in an amount of at least 9% of total fatty acids in cells of the fungal host. In one embodiment, the fungal host is a species of the *Rhodosporidium* genera. In another embodiment, the fungal host is a species of the *Rhodotorula* genera. In some embodiments, the fungal host has reduced activity of a native aldehyde dehydrogenase (ALD) that uses fatty acid aldehyde as a substrate. The native ALD is encoded by a native ALD gene. In one native ALD gene encodes an aldehyde dehydrogenase (ALD) having the amino acid sequence set forth in SEQ ID NO:3. In another embodiment, the native ALD gene encodes an ALD having 75%, 80%, 85%, 90%, 95%, 98% or 99% of the amino acid sequence set forth in SEQ ID NO:3. In one embodiment, the native ALD gene has the genomic nucleotide sequence set forth in SEQ ID NO:1. In another embodiment, the native ALD gene has the cDNA nucleotide sequence set forth in SEQ ID NO:2. In a further embodiment, the native ALD gene has the nucleotide sequence having 75%, 80%, 85%, 90%, 95%, 98% or 99% of the nucleotide sequence set forth in SEQ ID NO:1 or SEQ ID NO:2.

In some embodiments, the reduced activity of the native ALD is caused by reduced expression of the native ALD gene. The reduced expression can be caused by any genetic or epigenetic mechanism. In one embodiment, the reduced expression is caused by an RNAi mechanism, such as siRNA, shRNA, miRNA and the like. In another embodiment, the reduced expression is caused by an artificial transcription repressor. In a further embodiment, the reduced expression is caused by an antisense mechanism. In one embodiment, the reduced expression is caused by sense suppression. In a further embodiment, the reduced activity is caused by a mutation of the native gene. In one embodiment, the mutation may be a substitutions, deletion, insertions, addition, or inversion and the like which results in reduced activity. In another embodiment, the mutation may be caused by homologous recombination. In a further embodiment, the mutation may be caused by T-DNA or transposon insertion.

In a second aspect, the present invention provides a fungal host having an α-linolenic acid (ALA) present in an amount of at least 49% of total fatty acids in cells of the fungal host. In one embodiment, the fungal host is a species of the *Rhodosporidium* genera. In another embodiment, the fungal host is a species of the *Rhodotorula* genera. In some embodiments, the fungal host has reduced activity of a native aldehyde dehydrogenase (ALD) as described herein. In other embodiments, the genome of the fungal host has been modified to stably include two or more genes that encode proteins that are involved in fatty acid biosynthesis. Examples of such proteins are an acyl-CoA delta-12 desaturase, a stearoyl-CoA-delta-9-desaturase, an omega-3 desaturase, a fatty acid elongase, an acetyl-CoA carboxylase (ACC), an ATP:citrate lyase (ACL), a diacylglycerol acyltransferase (DGA) or a malic enzyme (MAE). In some embodiments, the coding sequences of such genes have been modified to contain at least 55% G and C content, preferably 60%-70% G and C content. In other embodiments, at least 70% of the codons have a C or G at the third position.

In one embodiment, an ATP:citrate lyase (ACL) has the amino acid sequence set forth in SEQ ID NO:88. In another embodiment, this ATP:citrate lyase (ACL1) is encoded by a genomic DNA nucleic acid having a nucleotide sequence set forth in SEQ ID NO:86. In another embodiment, this ATP:citrate lyase (ACL1) is encoded by a cDNA nucleic acid having a nucleotide sequence set forth in SEQ ID NO:87. In another embodiment, the ATP:citrate lyase (ACL1) gene has a nucleotide sequence having 75%, 80%, 85%, 90%, 95%, 98% or 99% of the nucleotide sequence described herein.

In one embodiment, a diacylglycerol acyltransferase (DGA1) has the amino acid sequence set forth in SEQ ID NO:82. In another embodiment, this diacylglycerol acyltransferase (DGA1) is encoded by a genomic DNA having a nucleotide sequence set forth in SEQ ID NO:80. In a further embodiment, this diacylglycerol acyltransferase (DGA1) is encoded by a nucleic acid having a nucleotide sequence set forth in SEQ ID NO:81. In another embodiment, the diacylglycerol acyltransferase (DGA1) gene has the nucleotide sequence having 75%, 80%, 85%, 90%, 95%, 98% or 99% of the nucleotide sequence described herein.

In one embodiment, a malic enzyme (MAE1) has the amino acid sequence set forth in SEQ ID NO:85. In another embodiment, this malic enzyme (MAE1) is encoded by a genomic DNA nucleic acid having a nucleotide sequence set forth in SEQ ID NO:83. In a further embodiment, this malic enzyme (MAE1) is encoded by a nucleic acid having a nucleotide sequence set forth in SEQ ID NO:84. In another embodiment, a malic enzyme (MAE1) gene has a nucleotide sequence having 75%, 80%, 85%, 90%, 95%, 98% or 99% of the nucleotide sequence described herein.

In a another aspect, the present invention provides a fungal host having a gamma-linolenic acid (GLA) present in an amount of at least 30% of total fatty acids in cells of the fungal host. In one embodiment, the fungal host is a species of the *Rhodosporidium* genera. In another embodiment, the fungal host is a species of the *Rhodotorula* genera. In some embodiments, the fungal host has reduced activity of a native aldehyde dehydrogenase (ALD) as described herein. In other embodiments, the genome of the fungal host has been modified to stably express two or more additional genes encoding proteins that are involved in fatty acid biosynthesis. Examples of such proteins are an acyl-CoA delta-12 desaturase, a stearoyl-CoA-delta-9-desaturase, acyl-CoA delta-6 desaturase, a fatty acid elongase, an acetyl-CoA carboxylase (ACC), an ATP:citrate lyase (ACL), a diacylglycerol acyltransferase (DGA) or a malic enzyme (MAE). In some embodiments, the coding sequences of such genes contain at least 55% G and C content, preferably 60%-70% G and C content. In other embodiments, at least 70% of the codons have a C or G at the third position.

In one embodiment, an acetyl-CoA carboxylase (ACC) has the amino acid sequence set forth in SEQ ID NO:91. In another embodiment, this acetyl-CoA carboxylase (ACC1) is encoded by a genomic DNA nucleic acid having a nucleotide sequence set forth in SEQ ID NO:89. In a further embodiment, this acetyl-CoA carboxylase (ACC1) is encoded by a cDNA nucleic acid having a nucleotide sequence set forth in SEQ ID N:90. In another embodiment, the an acetyl-CoA carboxylase (ACC1) gene has the nucleotide sequence having 75%, 80%, 85%, 90%, 95%, 98% or 99% of the nucleotide sequence described herein.

In one embodiment, an acyl-CoA delta-12 desaturase has an amino acid sequence set forth in SEQ ID NOs:5 and 94. In another embodiment, this acyl-CoA delta-12 desaturase is encoded by a nucleic acid having a nucleotide sequence set forth in SEQ ID NOs:4, 92 and NO:93. In another embodiment, the acyl-CoA delta-12 desaturase genes have a nucleotide sequence having 75%, 80%, 85%, 90%, 95%, 98% or 99% of the nucleotide sequences described herein.

In one embodiment, a stearoyl-CoA-delta-9-desaturase has an amino acid sequence set forth in SEQ ID NO:8. In one embodiment, this stearoyl-CoA-delta-9-desaturase is encoded by a genomic nucleic acid having a nucleotide sequence set forth in SEQ ID NO:6. In another embodiment, this stearoyl-CoA-delta-9-desaturase is encoded by a nucleic acid having a nucleotide sequence set forth in SEQ ID NO:7. In another embodiment, the stearoyl-CoA-delta-9-desaturase gene has a nucleotide sequence having 75%, 80%, 85%, 90%, 95%, 98% or 99% of the nucleotide sequence described herein.

In one embodiment, an omega-3 desaturase has an amino acid sequence set forth in SEQ ID NO:10. In one embodiment, this omega-3 desaturase is encoded by a nucleic acid having a nucleotide sequence set forth in SEQ ID NO:9. In an additional embodiment, an omega-3 desaturase has an amino acid sequence set forth in SEQ ID NO:12. In one embodiment, this latter omega-3 desaturase is encoded by a nucleic acid having a nucleotide sequence set forth in SEQ ID NO: 11. In another embodiment, omega-3 desaturase gene has a nucleotide sequence having 75%, 80%, 85%, 90%, 95%, 98% or 99% of the nucleotide sequence described herein.

In one embodiment, an acyl-CoA delta-6 desaturase has an amino acid sequence set forth in SEQ ID NOs:96 and 98 wherein the sequences encoded by DNA containing at least G and C, preferably 60%-70% G and C. In other embodiments, at least 70% of the codons have a C or G at the third position. In one embodiment, the acyl-CoA delta-6 desaturases is encoded by a nucleic acid set forth in SEQ ID NOs:95 and 97.

In one embodiment, a fatty acid elongase has the amino acid sequence set forth in SEQ ID NOs:101 and 104. In another embodiment, this fatty acid elongase is encoded by a nucleic acid having a nucleotide sequence set forth in SEQ ID NOs:99, 100, 102 and 103. In another embodiment, the fatty acid elongase gene has a nucleotide sequence having 75%, 80%, 85%, 90%, 95%, 98% or 99% of the nucleotide sequence described herein.

In some embodiments, the genes described herein that have been stably incorporated in the fungal genome are operatively linked to a promoter which permit efficient expression in species of the *Rhodospordium* genera and the *Rhodotorula* genera. The promoters for each incorporated gene may be the same or different. In some embodiments, the promoters are promoters found in species of the *Rhodospordium* genera and the *Rhodotorula* genera. Examples of suitable promoters include, but are not limited to, promoters of the following genes encoding the following proteins: glyceraldehyde 3-phosphate dehydrogenase (GPD), acyl-CoA carrier protein (ACP), fatty acid desaturase, translation elongation factor (TEF), pyruvate decarboxylase (PDC), enolase (2-phosphoglycerate dehydratase) (ENO), peptidylprolyl isomerase (PPI), acetyl-CoA carboxylase (ACC) or transaldolase. In other embodiments, the genes described herein also include a mRNA transcriptional terminator that may be one found in any eukaryotic species and their DNA viruses.

In a another aspect, the present invention provides a method for producing omega-3 and omega-6 polyunsaturated fatty acids (PUFAs) which comprising growing a fungal host cell described herein under conditions suitable to produce PUFAs. Any medium with at least 5% carbon source, such glucose, mannose, glycerol, sucrose can be used. Example of the medium is Medium MinLG containing 30-100 g glucose, 1.5 g yeast extract, 0.5 g $(NH_4)_2SO_4$, 2.05 g $K_2HPO_4$, 1.45 g $KH_2PO_4$, 0.6 g $MgSO_4$, 0.3 g NaCl, 10 mg $CaCl_2$, 1 mg $FeSO_4$, 0.5 mg $ZnSO_4$, 0.5 mg $CuSO_4$, 0.5 mg $H_3BO_4$, 0.5 mg $MnSO_4$, 0.5 mg $NaMoO_4$ (per liter). The medium pH is adjusted to 6-7. Cell culturing is performed at 25° C.-32° C.

In some embodiments, the genes described herein that have been stably incorporated in the fungal genome are operatively linked to a promoter which permit efficient expression in species of the *Rhodospordium* genera and the *Rhodotorula* genera. The promoters for each incorporated gene may be the same or different. In some embodiments, the promoters are promoters found in species of the *Rhodospordium* genera and the *Rhodotorula* genera. In other embodiments, the promoters are promotes found in other fungal species. Examples of suitable promoters include, but are not limited to, promoters of the following genes encoding the following proteins: glyceraldehyde 3-phosphate dehydrogenase (GPD), acyl-CoA carrier protein (ACP), fatty acid desaturase, translation elongation factor (TEF), pyruvate decarboxylase (PDC), enolase (2-phosphoglycerate dehydratase) (ENO), peptidylprolyl isomerase (PPI), acetyl-CoA carboxylase (ACC) or transaldolase. In other embodiments, the genes described herein also include a mRNA transcriptional terminator that may be one found in any eukaryotic species and their DNA viruses.

In some embodiments, a suitable promoter is one described in International Patent Application Publication No. WO 2012/169969, incorporated by reference herein in its entirety. This published application describes several polynucleotide sequences derived from the upstream region of glyceraldehyde phosphate dehydrogenase gene (GPD1), translation initiation factor gene (TEF1), and stearoyl-CoA-delta 9-desaturase gene (FAD1) that function as promoters in fungi. The promoters described in this published application are set forth in SEQ ID NOs:55-62. In other embodiments, additional promoters are described in International Patent Application No. PCT/SG2014/000114 filed 10 Mar. 2014, incorporated by reference herein in its entirety. In one embodiment, the promoter sequences comprises the sequence set forth in any one of SEQ ID NOs:63-79. In another embodiment, the polynucleotide promoter sequences comprises the promoter sequence of any one of SEQ ID NOs:63-79, i.e., the sequence without the cloning sites.

In addition, operable fragments of the promoter sequences described herein can be isolated using convention promoter screening assays and can be screened for efficient selection of transformed fungal cells using the techniques described herein. In one embodiment, an operable fragment, also termed a promoter portion herein, is about 400 base pairs up to about 1100 base pairs in length starting from the −1 position from the ATG codon. As used herein "up to" refers to the length of the promoter portion of the promoters set forth in the disclosed SEQ ID NOs. Thus, "up to" refers to the maximal length of the promoter sequence if less than 1100 nucleotides of the promoters of the disclosed SEQ ID NOs.

In one embodiment, a promoter sequence is provided which has at least 60% identity with any one of these promoter sequences. In another embodiment, a promoter sequence is provided which has at least 70% identity with any one of these promoter sequences. In an additional embodiment, a promoter sequence is provided which has at least 80% identity with any one of these promoter sequences. In a further embodiment, a promoter sequence is provided which has at least 90% identity with any one of these promoter sequences. In another embodiment, a promoter sequence is provided which has at least 95% identity with any one of these promoter sequences. In another embodiment, a promoter sequence is provided which has at least 98% identity with any one of these promoter sequences.

The genes to be stably incorporated into the fungal genome are typically in the form of a DNA or polynucleotide construct comprising the promoter sequences described herein, an operably linked polypeptide encoding sequence described herein and an operably linked RNA transcriptional terminator sequence. In one embodiment, any transcriptional terminator operable in species of the fungi can be used. Terminators are typically located downstream (3') of the gene, after the stop codon (TGA, TAG or TAA). Terminators play an important role in the processing and stability of RNA as well as in translation. Most, but not all terminators, contain a polyadenylation sequence or cleavage site. Examples of specific polyadenylation sequences are AAUAAA or AAUAAU. These sequences are known as the near upstream elements (NUEs) (Nagaya et al., 2010). NUEs usually reside approximately 30 bp away from a GU-rich region (Mogen et al., 1990; Mogen et al., 1992; Rothnie et al. 1994), known as far upstream elements (FUEs). The FUEs enhance processing at the polyadenylation sequence or cleavage site, which is usually a CA or UA in a U-rich region (Bassett, 2007). Within the terminator, elements exist that increase the stability of the transcribed RNA (Ohme-Takagi et al., 1993; Newman et al., 1993; Gutiérrez et al., 1999) and may also control gene expression (Ingelbrecht, 1989; An et al., 1989).

A DNA or nucleic acid construct that comprises a fungi operable promoter, protein encoding DNA sequence and a fungi operable terminator may also be referred to herein as an expression cassette. The expression cassette may include other transcriptional regulatory regions as are well known in the art. In other embodiments, the DNA or nucleic acid construct or expression cassette further comprises a selectable marker. Selectable markers are well known to the skilled artisan as are expression cassettes incorporating such selectable markers and promoters to drive their expression, such as described in International Patent Application Publication No. WO 2012/169969. Any suitable promoter operably linked to any suitable selectable marker can be used in the present invention.

In one embodiment, the coding sequence for the selectable marker is one that is either naturally existent or artificially created and contains at least about 60% GC. In a second embodiment, the coding sequence for the selectable marker is one that is either naturally existent or artificially created and contains about 70% GC. In a third embodiment, the coding sequence for the selectable marker is one that is either naturally existent or artificially created and contains about 75% GC. In one embodiment, at least about 70% of the codon triplets of such coding sequences end with C or G. In another embodiment, more than about 80% of the codon triplets of such coding sequences end with C or G. In one embodiment, the coding sequence for a selectable marker is at least 60% GC, preferably about 70% GC and most preferably about 75% GC in which at least 70% of the codon triplets end with C or G, preferably more than 80% of the codon triplets end with C or G. In one embodiment, such coding sequences are composed of UCG codons in at least about 40% of the total serine (Ser) residues.

In some embodiments, the selectable marker is part of a recombination marker free system. In one embodiment, the recombination marker free system is a Cre-lox recombination marker free system, such as described by Zuo et al. [29]. Such a system is useful for producing selection marker free transgenic plants, including transgenic Jatropha plants. In some embodiments, the recombination marker free system is positioned between the plant operable promoter and the one or more nucleic acid fragments. In this embodiment, the removal of the marker gene by the recombination event places the plant operable promoter in operable linkage with the one or more nucleic acid fragments as described herein.

In preparing the nucleic acid construct or an expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

Nucleic acids of the present invention may also be synthesized, either completely or in part, especially where it is desirable to provide plant-preferred sequences, by methods known in the art. Thus, all or a portion of the nucleic acids of the present invention may be synthesized using codons preferred by a selected host. Species-preferred codons may be determined, for example, from the codons used most frequently in the proteins expressed in a particular host species. Other modifications of the nucleotide sequences may result in mutants having slightly altered activity.

It may be useful to generate a number of individual transformed fungi with any recombinant construct in order to recover fungi free from any positional effects. It may also be preferable to select fungi that contain more than one copy of the introduced polynucleotide construct such that high levels of expression of the recombinant molecule are obtained.

It may be desirable to produce fungal lines that are homozygous for a particular gene if possible in the particular species. In some species this is accomplished by the use monosporous cultures. By using these techniques, it is possible to produce a haploid line that carries the inserted gene and then to double the chromosome number either spontaneously or by the use of colchicine. This gives rise to a fungus that is homozygous for the inserted gene, which can be easily assayed for if the inserted gene carries with it a suitable selection marker gene for detection of fungi carrying that gene. Alternatively, fungi may be self-fertilized, leading to the production of a mixture of spores that consists of, in the simplest case, three types, homozygous (25%), heterozygous (50%) and null (25%) for the inserted gene. Although it is relatively easy to score null fungi from those that contain the gene, it is possible in practice to score the homozygous from heterozygous fungi by Southern blot analysis in which careful attention is paid to the loading of exactly equivalent amounts of DNA from the mixed population, and scoring heterozygotes by the intensity of the signal from a probe specific for the inserted gene. It is advisable to verify the results of the Southern blot analysis by allowing each independent transformant to self-fertilize, since additional evidence for homozygosity can be obtained by the simple fact that if the fungi was homozygous for the inserted gene, all of the subsequent fungal lines from the selfed individual will contain the gene, while if the fungus was heterozygous for the gene, the generation grown from the selfed seed will contain null fungal lines. Therefore, with simple selfing one can select homozygous fungal lines that can also be confirmed by Southern blot analysis.

Creation of homozygous parental lines makes possible the production of hybrid fungus and spores that will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Green and Sambrook, 2012, *Molecular Cloning*, 4th Ed. (Cold Spring Harbor Laboratory Press, Cold Spring Harbor, N.Y.); Ausubel et al., 1992, *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Strains, Chemicals, Media and Culture Conditions

*R. toruloides* strains ATCC 10657 and ATCC 10788; *R. glutinis* strain ATCC 90781 and *R. glutinis* ATCC 204091 were purchased from ATCC (USA). *R. graminis* strain WP1 and *Sporobolomyces roseus* FGSC 10293 (IAM13481) were obtained from Fungal Genetics Stock Center (University of Missouri, USA). *A. tumefaciens* strain AGL1 [30] was used for *Agrobacterium tumefaceins*-mediated transformation (ATMT). Hygromycin B was purchased from Roche Diagnostics (USA). Nylon N and N+ membranes (Φ 82 mm, 0.45 μm) were obtained from GE Healthcare (Uppsala, Sweden). Cerulenin (Sigma-Aldrich, USA) was made as 5 mg/ml stock in DMSO. Other chemicals were purchased from Sigma-Aldrich unless indicated otherwise.

*Rhodosporidium* strains were maintained at 28° C. in YPD broth (1% yeast extract, 2% peptone, 2% glucose) or on solid potato-dextrose agar (PDA). *A. tumefaciens* was grown at 28° C. in either liquid or solid 2YT medium (1.6% tryptone, 1% yeast extract, 0.5% NaCl). *R. toruloides* was cultured in lipid accumulation medium at 30° C. with constant shaking (200 rpm) as described previously [21] with some modifications. Medium MinLG contains (per liter) 30 g glucose, 1.5 g yeast extract, 0.5 g $(NH_4)_2SO_4$, 2.05 g $K_2HPO_4$, 1.45 g $KH_2PO_4$, 0.6 g $MgSO_4$, 0.3 g NaCl, 10 mg $CaCl_2$, 1 mg $FeSO_4$, 0.5 mg $ZnSO_4$, 0.5 mg $CuSO_4$, 0.5 mg $H_3BO_4$, 0.5 mg $MnSO_4$, 0.5 mg $NaMoO_4$ (pH6). For analysis of gene expression, a nitrogen-limitation variant, MinLG-N that is modified from MinLG with the concentration of yeast extract and ammonium sulfate reduced to 0.3 and 0.1 g/l respectively, was used. Lipid accumulation process was conducted at 30° C. with constant shaking (200 rpm).

Example 2

DNA Constructs

Oligonucleotides used are listed in Table 1. All restriction and modification enzymes were purchased from New England Biolabs (NEB, Massachusetts, USA). Binary vector pEX2 is pPZP200 derivatives used for dominant selection using hygromycin B [22].

TABLE 1

Sequences of Oligonucleotides

| Name | Sequence (5'-3') (SEQ ID NO:) | Restriction Site | Purpose |
|---|---|---|---|
| Tnos-Sf | TTT*CCGCGG*TCGAATTTCCCCGATCGTTCA (13) | SmaI | Tnos terminator |
| Tnos-Pmr | GAGTCGCTCACCTACTGCATC (14) | PmeI | |
| 35T-Pmr | TTTGTTTAAACATGCTAATTCGGGGGATCTG (15) | PmeI | |
| Rt025 | CACGTCGACTGAAACGCAG (16) | | |
| Rt026 | GACGAGGTCATCCGCGAG (17) | | |
| Rt027 | GTGCGGGTCGTGATGGAC (18) | | |
| Rt028 | CTGGAAGGCGTACGAGGAC (19) | | |
| Rt033 | GTCAAGCCGCCCAGGCTGTC (20) | | |
| Rt034 | GGATCCGCCAAGTCGCGCAG (21) | | |
| HptRU | GAGTCGCTCACCTACTGCATC (22) | | Colony PCR of hpt-3 |
| HptRSL | GAGAACTCGCCGATGTCGAG (23) | | |
| HptRSL2 | AGCGACTGGTAGAGCTGGTC (24) | | |
| Natf | CTCTTGACGACACGGCTTAC (25) | | Colony PCR of nourseothricin acetyltransferase gene |
| Natr | CAGGCCGCAGAGGGTGAAC (26) | | |
| Rsp1 | GATGAGTTTGGACAAACCACAACTAG (27) | | HiTAIL PCR |
| Rsp2 | GGTTCAGGGGGAGATGTGGGAG (28) | | |
| Rsp3 | GTACCGGCGCGCCCACCTG (29) | | |
| HRSP1 | GAATCCTGTTGCCGGTCTTGCGATG (30) | | |
| HRSP2 | TTATGATTAGAGTCCCGCAATTATACA (31) | | |
| HRSP3 | CTAGCTTAGCTTGAGCTTGGATC (32) | | |
| HRRSP1 | GTGCTGACGCGGGCATAGCCCAG (33) | | |
| HRRSP2 | ATGCGACTAAAACACGCGACAAGA (34) | | |
| HRRSP3 | AGCAGCGGAGGGGTTGGATC (35) | | |
| LAD1-1 | ACGATGGACTCCAGAGCGGCCGC(GCA)N(GCA)NNNGGAA (36) | | |
| LAD1-4 | ACGATGGACTCCAGAGCGGCCGC(GCT)(GAT)N(GCT)NNNCGGT (37) | | |
| AC1 | ACGATGGACTCCAGAG (38) | | |
| GAS | CATACACCGGGCAAAGCAG (39) | | |
| Rt055N | TTT*CCATGG*GCCAGCAGGCGACGC (40) | NcoI | Engineering of DGA1 |
| Rt056Ev | TTT*GATATC*AGGCGATAATATTGAGCTCC (41) | EcoRV | |
| Rt057N | TTT*CCATGG*GCGGGAGTGAAGGGTTGCC (42) | NcoI | Engineering of MAE1 |
| Rt058Ev | TTT*GAGATC*CTACTGCGCCTGCTGCTC (43) | EcoRV | |
| PgpdR-Sf | TTT*ACTAGT*CTCTTCAGACGGCTTGITCTC (44) | SpeI | |
| ALD1Lf | CACCCGTCCTCTCCGCTTC (45) | | Gene targeted deletion-ALD1 |
| ALD1Rr | CCTCGCTCTTTCGCTGGTTC (46) | | |
| Rt113 | CCGCCAATAACCTCACCTCAG (47) | | Gene targeted deletion-DGA1 |
| Rt114 | GGCGATGGGAGCGTAGAATAC (48) | | |
| Rt148 | CAGGTTTCATCGCAACTACATTGA (49) | | DIG-probes-ALD1 |
| Rt149 | AACAGAGCGAGTTGAAGAGTAGCC (50) | | |
| Rt113 | CCGCCAATAACCTCACCTCAG (51) | | DIG-probes-DGA I |
| Dga1-1 | GAAGAAGACGCCGAGTAGGATG (52) | | |

Various promoters, such as *U. maydis* gpd1 (Pgpd, 595 bp in length) [31, 32], *Aspergillus nidulans* gpdA (PgpdA, 884 bp) [33], *Ashbya gossypii* translational elongation factor 1α gene (Ptef, 348 bp) [34] and RtGPD1 (1429 bp) [22], have been described previously. The promoter DNA fragments were obtained by PCR using plasmid DNA as template and primer pair Pgpd-Sf/Pgpd-Nr, PgpdA-Sf/PgpdA-Nr, Ptef-Sf/Ptef-Nr and Rt011S/Rt012N for Pgpd, PgpdA, Ptef and PRtGPD1 respectively. The resultant PCR fragments were digested with SpeI and NcoI and individually used for 3-fragment ligation with the 1030 bp BspHI/SmaI digested synthetic hpt-3 fragment [22] and 8855 bp SpeI/SacI (blunt-ended) digested vector pEC3GPD-GUS (FIG. 1), to create pEC3GPD-HPT3, pEC3GPDA-HPT3, pEC3TEF-HPT3 and pEC3GPDR-HPT3, respectively (FIG. 1).

To create knockout mutants of ALD1 and DGA1, complete or partial coding sequences (3 kb and 2.8 kb for ALD1 and DGA1, respectively) were amplified using total DNA of R. toruloides ATCC 10657 as the template and oligo pairs ALD1Lf/ALD1Rr and Rt113/Rt114 as primers respectively. Blunt-ended PCR products were ligated to the PmeI/SacI double-digested pEX2 vector after with T4 DNA polymerase treatment in the presence of dNTP to create the intermediate plasmids pEX2ALD1 and pEX2DGA1, to which the blunt-ended hygromycin resistance cassette $P_{GPD1}$::hpt-3::Tnos amplified from plasmid pRH2031 was inserted into XhoI/BspHI and SmaI/SpeI site respectively to create gene targeting plasmid pKOALD1 and pKODGA1.

Diacyl glycerol acyl-transferase gene DGA1 (GenBank accession number AB453835) and the mitochondrial malic enzyme gene MAE1 (locus tag RTG_03106 in Rhodotorula glutinis ATCC 204091 genomic scaffold GL989657) were amplified using the cDNA template of R. toruloides ATCC 10657 and R. glutinis ATCC 204091, respectively. Primer pair Rt055N/Rt056Ev and Rt057N/Rt058Ev was used for the amplification of DGA1 and MAE1, respectively. Both PCR products were digested with NcoI and EcoRV, ligated with NcoI/EcoRV-double digested pRH2034, which contains a protein expression cassette containing the 795 bp RtGPD1 promoter and cauliflower mosaic virus 35S gene terminator and a Cre-recombinase excisable Umgpd::HPT-3:nos hygromycin selection cassette [22] to create pRH-DGA1 and pRHMAE1 (FIG. 1).

Figure 2:
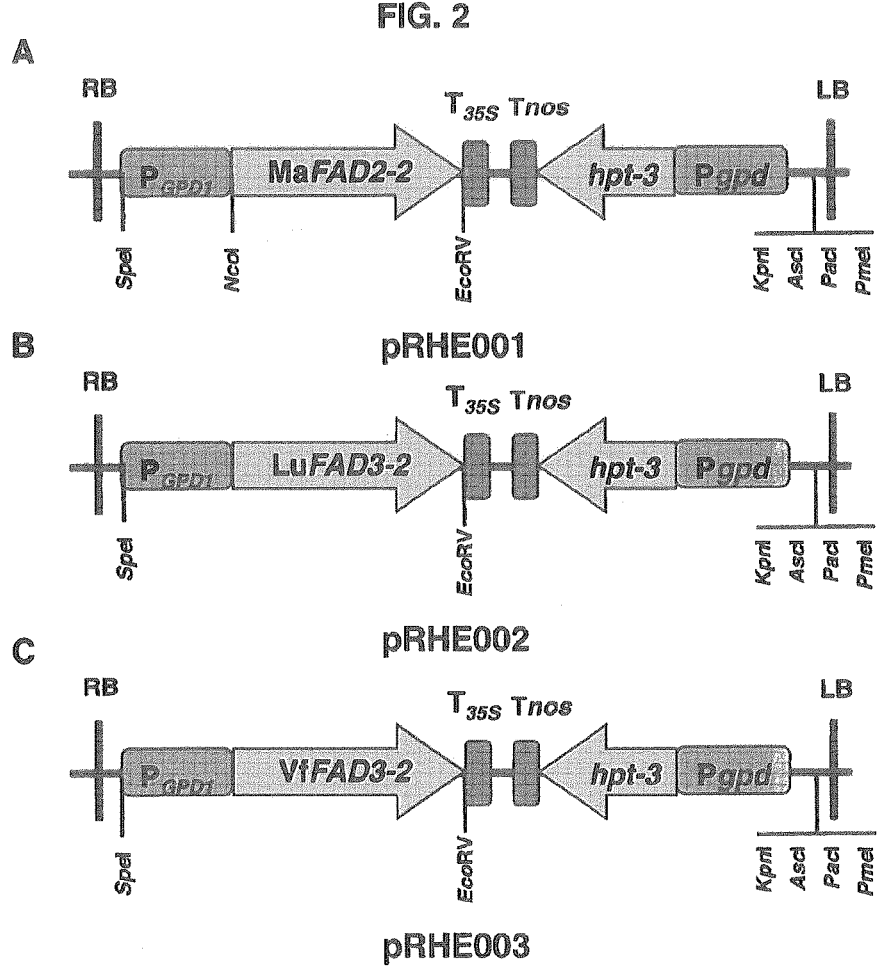
FIGS. 2A-2C show the T-DNA organization in constructs used in this invention. All binary vectors have the same pPZP200 backbone [28].

For engineering studies in α-linolenic acid, codon-optimized genes encoding Mortierella alpine Δ12 desaturase MaFAD2 (SEQ ID NO:5), Linum usitatissimum omega-3 desaturase LuFAD3 (GenBank accession number ABA02173.1; SEQ ID NO:10) and Vernicia fordii (also known as Aleurites fordii) omega-3 desaturase VfFAD3 (SEQ ID NO:12) were synthesized according to the codon preference of R. toruloides, creating synthetic genes, MaFAD2-2 (SEQ ID NO:4), LuFAD3-2 (SEQ ID NO:9) and VfFAD3-2 (SEQ ID NO:11), which was inserted to pRH2034 under the regulation of RtGPD1 promoter to create pRHE001, pRHE002 and pRHE003, respectively (FIG. 2). To make FAD2-FAD3 double genes overexpression cassette, the VfFAD3-2 and LuFAD3-2 cassettes were amplified from plasmid pRHE002 and pRHE003 using oligos Rt012Sf/35T-Pmr, digested with SpeI (blunt-ended) and PmeI and ligated with PmeI-cut pRHE001 to create plasmid pRHE004 and pRHE005, respectively (FIG. 3). Similarly, the MAE1 cassette was amplified from pRH-MAE1, digested (SpeI-PmeI), blunt-ended and subsequently ligated with PmeI-cut pRHDGA1 to create the plasmid pRHE006 (FIG. 3).

Example 3

Agrobacterium tumefaciens-Mediated Transformation

The binary vectors were electroporated into A. tumefaciens AGL1 (2.5 kV, 25 µF, 400Ω) and subsequently selected with 2YT agar medium supplemented with strep-tomycin (100 µg/ml). Fungi transformation via ATMT was performed as described previously unless indicated otherwise [22].

Example 4

Southern Blot Analysis

Genomic DNA of R. toruloides was extracted as described previously [22]. Genomic DNA was digested with PstI and separated by electrophoresis on 0.8% agarose gels and DIG-labeled probe of the partial hpt-3 gene fragment (from nt 375 to 1036) was amplified using oligos HptRU and HptRSL2. For gene deletion analysis, genomic DNAs were digested with HincII, PstI and HincII for the putative knock-out mutants Δald1, and Δdga1, respectively. DIG-labeled probes of approximately 0.6 kb upstream flanking sequence of ALD1 and DGA1 were amplified using oligos Rt148/Rt149 and Rt113/Dga1-1 respectively. Southern hybridization was carried out according to the manufacturer's instructions (DIG-High prime DNA labeling and detection starter Kit II, Roche Diagnostics).

Example 5

Quantitative Reverse Transcription PCR (q-RT-PCR)

Total RNA of R. toruloides was extracted as described previously [22]. To remove the trace of contaminating DNA, the RNA samples were treated with DNase I (Roche Diagnostics, USA) followed by precipitation with ethanol. cDNA was synthesized using the Improm-II Reverse Transcription system (Promega, USA) and real-time PCR was conducted in iCycler™ real-time PCR machine (Bio-Rad, USA) using the Platinum SYBR-Green qPCR SuperMix (Invitrogen, USA). Real-time conditions were as followed: an initial 95° C. denaturation step for 2 min followed by 35 cycles of denaturation at 95° C. for 15 s, annealing at 58° C. for 15 s and extension step at 72° C. for 15 s. The data was acquired using the iCycler™ software (Bio-Rad). The expression level of RtGPD1 mRNA was used as the reference for normalization of target gene expression.

Example 6

Identification of T-DNA Tagging Positions

T-DNA tag positions in the genome was identified using High Efficient Thermal Asymmetric InterLaced PCR (hi-TAIL-PCR) [35, 36]. Specific primers (HRSP1, HRSP2 and HRSP3) and arbitrary primer LAD1-4 were used for T-DNA left border (LB) flanking sequences whereas specific primers (HRRSP1, HRRSP2 and HRRSP3) and arbitrary primer LAD1-4 were used for the right border (RB) flanking sequences. PCR reactions were carried out with i-Taq DNA polymerase (i-DNA, Singapore) in a PTC-200™ Programmable Thermal Controller (Bio-Rad, USA). PCR products were purified using gel extraction kit (Qiagen) and sequenced directly using BigDye terminator kit (Applied Biosystems, USA) with oligo HRRSP3 (for RB) or HRSP3 (LB). In some cases, PCR products were cloned in pGTM-T easy vector (Promega, USA) and sequenced using oligos M13FP and M13RP as primers.

23

Example 7

Screening of Lipid Accumulation Mutants

R. toruloides ATCC 90781 genome was mutagenized by random insertion of T-DNA of pRH201 (FIG. 1E). Transformants were selected on YPD agar medium supplemented with 300 µg/ml cefotaxime, 150 µg/ml hygromycin and either 50 µg/ml cerulenin, 10 µg/ml tetrazolium violet or 0.5 µg/ml nile red (Sigma, USA). After incubated at 28° C. for 5 days, transformants showing larger sizes (for selection against cerulenin), darker purple-color pigmentation (for selection against tetrazolium violet) or higher fluorescence intensity (for screening in Nile red) were transferred to liquid YPD medium (300 µg/ml cefotaxime, 150 µg/ml hygromycin) for propagation. After streaking on PDA plates supplemented with above antibiotics, single colonies were used for secondary screening using 50 ml cultures to verify the phenotypes expected.

Example 8

Comparison of Lipid Accumulation Levels by Nile Red Staining

Nile red staining for fast estimation of lipid content was performed as described previously [37] with some modifications. Briefly, 10 µL cell culture and 2 µl Nile red stock (50 mM in acetone) were mixed with 200 µl PBS buffer (pH7.4) in a well of a FluoroNunc plate (Thermo Fisher Scientific, Langenselbold, Germany). Each sample was accompanied with a Nile red-free well as the background control. Another fraction of the cell culture (10 µl) was loaded to 90 µl PBS buffer (pH7.4) in a 96-well flat-bottom transparent plate (Nunc, Roskilde, Denmark) to measure cell optical density. The data was acquired and analyzed using the Infinite M200 µlate reader (Tecan, Salzburg, Austria) using the iControl™ version 3.0 software (Tecan, Salzburg, Austria). Cell optical density was read at 600 nm after deducing background control while fluorescence intensity was measured with excitation and emission wavelength at 488 nm and 508 nm, respectively. The relative lipid content is calculated by normalization against absorptance at 600 nm after subtracting the background control. In all tests, both biological and statistical triplicates were included.

Example 9

Fatty Acid Profiling by GCMS

Total lipid was extracted as described previously [38] with some modifications. Cell cultures (1 ml) were pelleted and resuspended with 500 µl of lipid extraction solvent (chloroform:methanol=2:1). After adding 100 µg glass beads (1 mm in diameter, Sigma-Aldrich, Missouri, USA), vigorous vortexing was applied to the mixture for 10 min and the solvent phase was removed with a pipette. Preparation of fatty acid methyl esters (FAMEs) and gas-liquid chromatography (GC) analyses were performed as described previously [39] with some modifications. Lipids were rotary evaporated to near dryness (Concentrator, Eppendorf. USA), dissolved in 1 ml methanol with of 5% (vol/vol) $H_2SO_4$, and incubated in a sealed glass vial at 90° C. for 2 hr. Fatty acid methyl esters were extracted with 300 µl of n-hexane after addition of 1 ml of PBS in water. 1 µl of the hexane extraction was injected to on a DB-WAX fused silica capillary column (30-m length, 0.25-µm diameter, and 0.25-mm film thickness) (Agilent J&W Scientific, Folsom, Calif., USA) in a gas chromatography mass spectrometry (GCMS QP2010, Shimadzu, Japan). The running conditions were typically 42.3 ml/min nitrogen flow, 180° C. for starting temperature (3 min), a 15-min ramp to 240° C., and holding at 240° C. for 7 min. The fatty acid methyl esters peaks were identified by searching against Shimadzu NIST08 compound library and quantified as percentages of total fatty acids (% TFA).

Example 10

Identification of ALD1 by Direct Screening of R. toruloides T-DNA Insertion Libraries T-DNA is known to integrate into the nuclear genomes predominately as single copies and this feature has been exploited extensively as a mutagenesis tool in plants and fungi [32, 40-43]. To investigate whether novel genes regulating oil yield or quality can be identified by direct screening of T-DNA mutant libraries, we designed three independent screening strategies aimed to identify changes in fatty acid profiles or contents in the T-DNA mutants using the aid of drugs or florescent dye.

Figure 4:
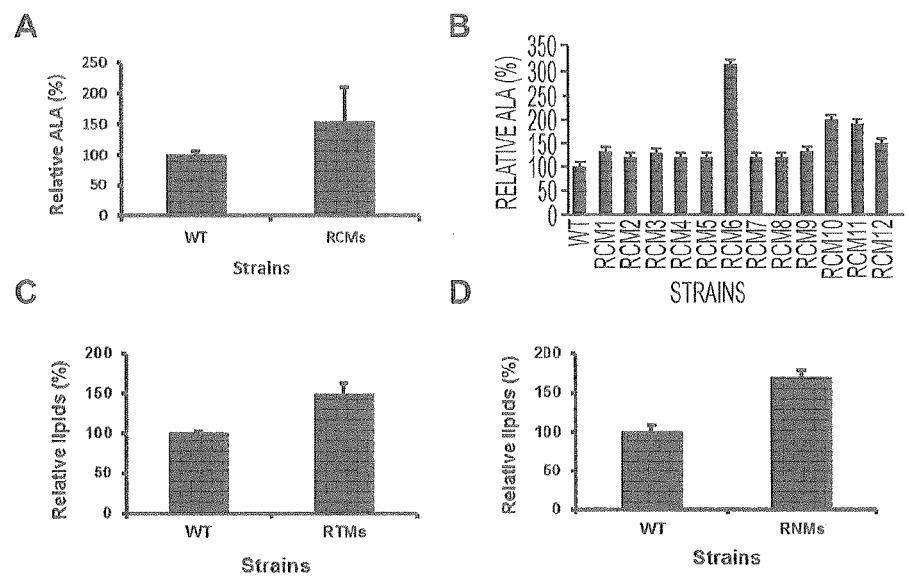
FIGS. 4A-4D show mutant strains identified by forward genetics.

Cerulenin, (2S)(3R)2,3-epoxy-4-oxo-7,10-dodecadienoylamide, is a drug isolated from the culture broth of Cephalosporium caerulens [44, 45] and has been successfully used to improve the accumulation of intracellular polyunsaturated fatty acids [46] or lipid content in oleaginous microorganisms [47, 48]. Being used as a fungicide due to its ability to block fatty acid biosynthesis [49], mutants that survive this treatment are expected to have higher level of lipid or polyunsaturated fatty acids. We screened ~10,000 transformants against 50 µg/ml cerulenin in YPD agar medium and found 12 mutants that appeared to be more resistant to cerulenin. We named these putative Rhodosporidium Cerulenin Mutants as RCM1 to RCM12, respectively. Although lipid contents were found to little different from Wt in small scale liquid cultures, RCMs exhibited significantly higher levels of α-linolenic acid (ALA) (FIG. 4). Notably, RCM6 produced more than 3-fold higher level of ALA than WT (FIG. 4B).

Secondly, nile red (NR) has been extensively used as a fluorescent tracker for lipid [50]. Through screening of ~10,000 T-DNA mutants, we identified four candidates that appeared to showed stronger red florescence, which were named as RNM1-4 (for Rhodosporidium Nile red Mutant). Quantitation of lipid yields revealed significant improvement in RNM mutants as compared to WT (FIG. 4D). However, little differences in fatty acid compositions could be observed (data not shown).

Similarly, tetrazolium violet, which is used as either a dye indicator for lipid accumulation [51], or a redox indicator for microbial growth [52] was used as an indicator to screen ~3,000 transformants, leading to the identification of 6 deeper pigmented mutants (FIG. 4C). However, repeated analysis of fatty acid profiles failed to verify the change of fatty acid accumulation (data not shown).

T-DNA tagging positions in the above mutants were identified through Hi-TAIL PCR technique, and results showed that 11 out of 12 RCMs, 2 out of 4 RNMs and 6 out of 6 RTMs were successfully obtained and sequenced (Table 2). The affected genes were dominantly involved in maintenance of cell wall integration, lipid metabolism, signal transduction, protein folding and trafficking, metabolisms of secondary metabolites, amino acids, vitamins, cofactors etc. (Table 2).

TABLE 2

T-DNA Tagging Positons of *R. turoloides* Cerulenin Mutants (RCMs), *R. turoloides* Tetrazolium Violet Mutants (RTMs), *R. turoloides* Nile Red Mutants (RNMs) and *R. toruloides* Albino Mutants (RAMs)

| Sequence number[a] RB sequences | Genic site[b, c] | Best hit[d] | Annotation[e] | Organism[f] | Identity[g] |
|---|---|---|---|---|---|
| RCM1 | Upstream-0.5 kb | XP_001549261 | mesothelin-like | *Botryotinia fuckeliana* | 26% |
| RCM2 | Upstream-1.0 kb | GENE ID: 5545759 Kpol_534p16 | mannosyltransferase | *Vanderwaltozyma polyspora* | 77% |
| RCM3 | Upstream-0.5 kb | XP_001789963 | regulator of nonsense transcripts; NADP-dependent isocitrate dehydrogenase | *Bos taurus* | 40% |
| RCM4 | Genic sequence | XP_001607008 | pipsqueak | *Nasonia vitripennis* | 29% |
| RCM5 | Upstream-0.5 kb | XP_003174510 | C6 zinc finger domain-containing protein | *Arthroderma gypseum* | 32% |
| RCM6 | Genic sequence | XP_001629556 | Fatty aldehyde dehydrogenase | *Nematostella vectensis* | 51% |
| RCM7 | Genic sequence | XP_571856 | Hexose transport-related protein | *Cryptococcus neoformans* | 53% |
| RCM8 | Genic sequence | XP_001731990 | Transcription initiation factor TFIID subunit 2 | *Malassezia globosa* | 40% |
| RCM9 | Genic sequence | NP_001125572 | stAR-related lipid transfer protein 3 | *Pongo abelii* | 29% |
| RCM10 | Upstream-1.0 kb | XP_001645395 | GPI mannosyltransferase 3 | *Vanderwaltozyma polyspora* | 77% |
| RCM11 | Upstream-0.5 kb | XP_662119 | Cell wall protein that functions in the transfer of chitin to beta (1-6) glucan | *Aspergillus nidulans* | 36% |
| RCM12 | NA[h] | — | — | — | — |
| RTM1 | Genic sequence | EGU12290 | Proteophosphoglycan ppg4 | *Rhodotorula glutinis* ATCC 204091 | 93% |
| RTM2 | Upstream 0.5 kb | EGU13095.1 | salicylate hydroxylase | *Rhodotorula glutinis* ATCC 204091 | 73% |
| RTM3 | Genic | XP_501740.1 | YALI0C11858p | *Yarrowia lipolytica* | 71% |
| RTM4 | Upstream 0.5 kb | ZP_08453184.1 | putative zinc-binding oxidoreductase | *Streptomyces* sp. | 47% |
| RTM5 | Genic | ZP_07628725.1 | putative lipoprotein | *Prevotella amnii* | 45% |
| RTM6 | Genic | YP_001220603.1 | resolvase site-specific recombinase | *Aeromonas bestiarum* | 94% |
| RNM1 | Downstream 0.3 kb | AAC98967.2 | omega-3 fatty acid desaturase | *Vernicia fordii* | 41% |
| RNM2 | NA | | | | |
| RNM3 | Upstream 0.5 kb | ZP_03104366 | amino acid permease | *Bacillus cereus* W | 87% |
| RNM4 | NA | | | | |
| RAM1 | Genic sequence | XP_003032296 | Riboflavin transporter MCH5 | *Schizophyllum commune* | 52% |
| RAM2 | Upstream-0.5 kb | YP_001220603 | resolvase | *Aeromonas bestiarum* | 95% |
| RAM3 | Genic sequence | XP_571856 | hexose transport-related protein | *Cryptococcus neoformans* | 36% |
| RAM4 | Genic sequence | XP_758766 | TATA-binding protein (TBP) associated factor Taf2 (MTCC 457 contig458_1: 18376-18377+) | *Ustilago maydis* | 35% |
| RAM5 | Genic sequence | KF601426.1 | phytoene synthase | *Rhodosporidium diobovatum* | 98% |
| RAM6 | Downstream-0.2 kb | EGU11996 | Serine/threonine kinase | *Rhodotorula glutinis* ATCC204091 | 56% |

TABLE 2-continued

T-DNA Tagging Positons of R. turoloides Cerulenin Mutants (RCMs), R. turoloides Tetrazolium Violet Mutants (RTMs), R. turoloides Nile Red Mutants (RNMs) and R. toruloides Albino Mutants (RAMs)

| Sequence number[a] RB sequences | Genic site[b, c] | Best hit[d] | Annotation[e] | Organism[f] | Identity[g] |
|---|---|---|---|---|---|
| RAM7 | Genic sequence | XP_001629556 | Fatty aldehyde dehydrogenase | Nematostella vectensis | 51% |

[a]LB-Flanking sequences
[b]T-DNA tagged genes were determined according to the BLASTx results
[c]Upstream 1.0 kb, Upstream 0.5 kb and downstream 0.3 kb denotes T-DNA insertions within upstream 501~1000 bp, 500 bp and downstream 300 bp of the corresponding tagged gene, respectively
[d]Best hit denotes the BLASTx result with the highest E-score
[e]Annotations were determined according to the BLASTx results
[f]Microorganism denotes the host of Best hit
[g]Identity values were from BLASTx results
[h]Not available due to the bad sequencing result Example 11

Characterization of the T-DNA Tagging Mutant RCM6

To further investigate the mutants screened through the above forward genetics, and as a proof of principle, reverse genetics was approached for studies of potential regulatory effect on lipid accumulation and carotenoid biosynthesis in the mutants RCM6 and RAM5, respectively.

Figure 5:
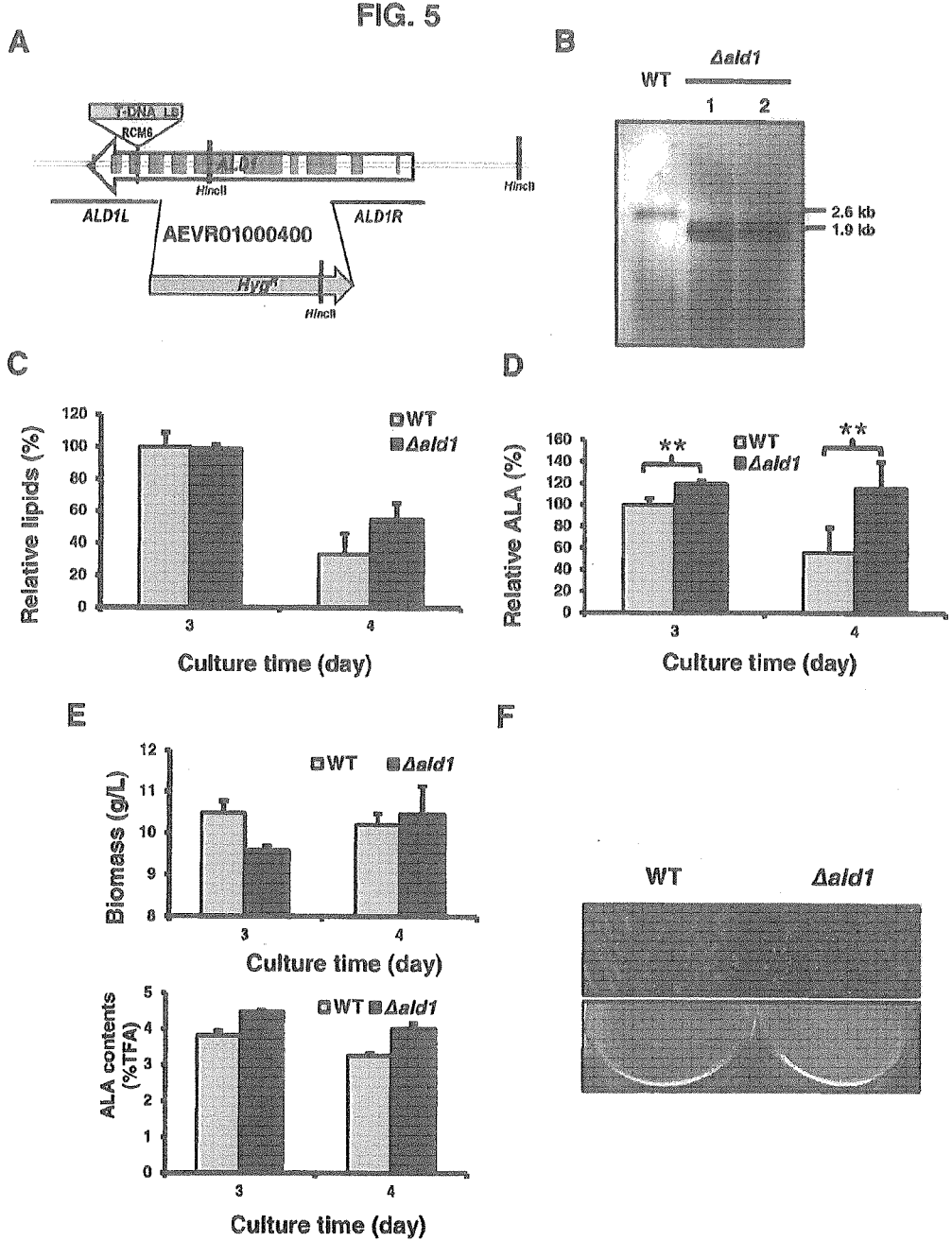
FIGS. 5A-5F show reverse genetic studies of ALD1 in *R. toruloides*.
Figure 6:
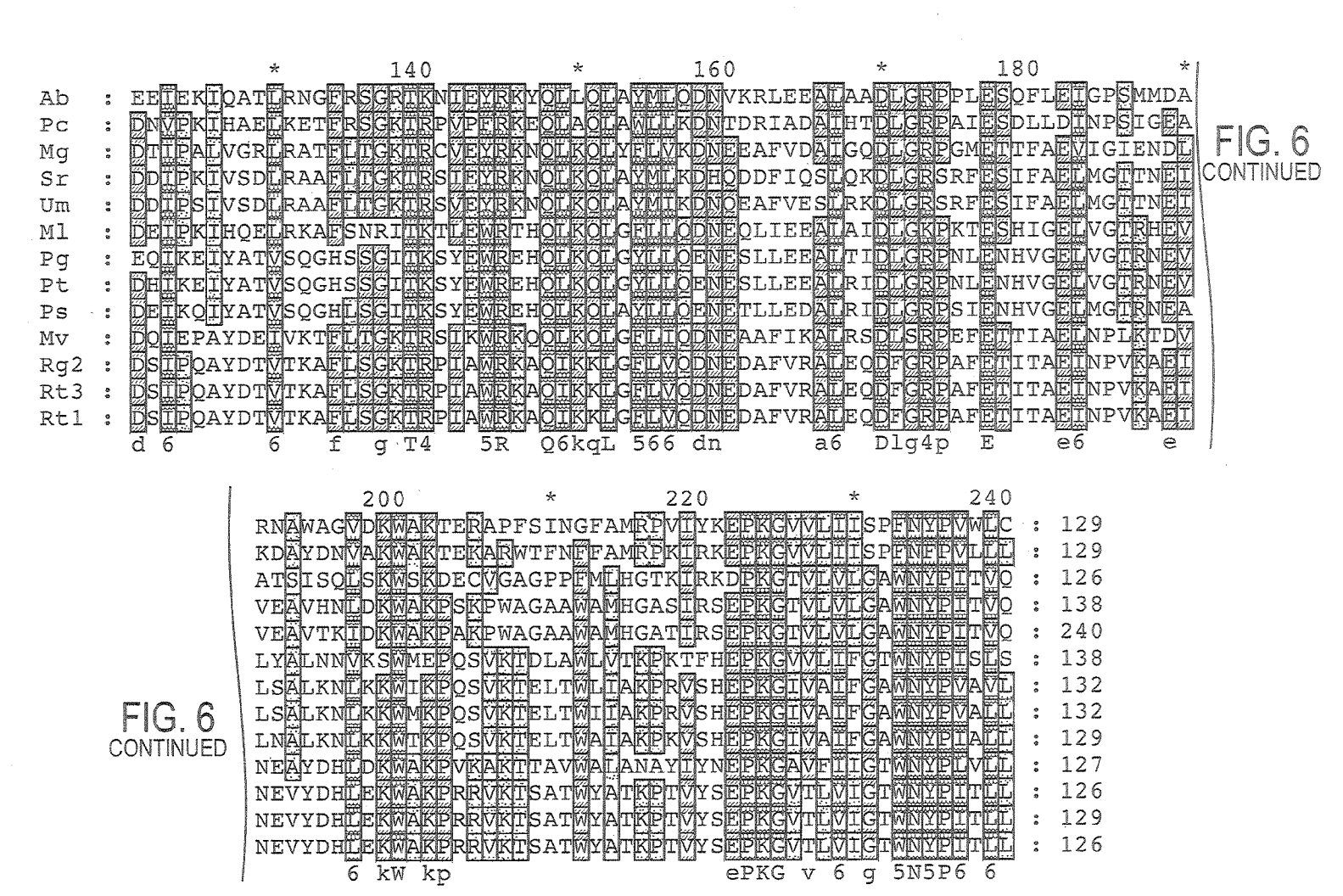
Figure 6:
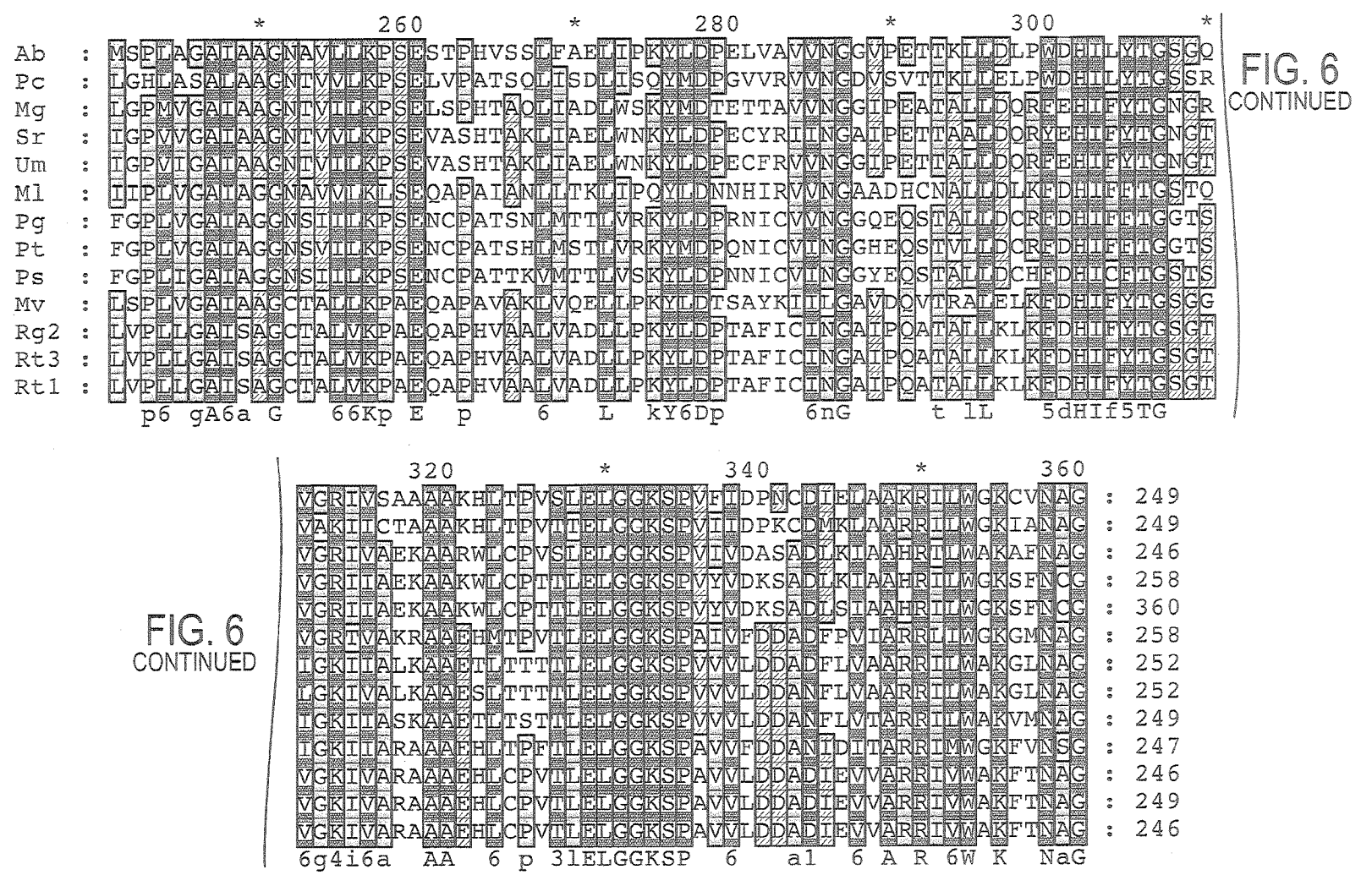
Figure 6:
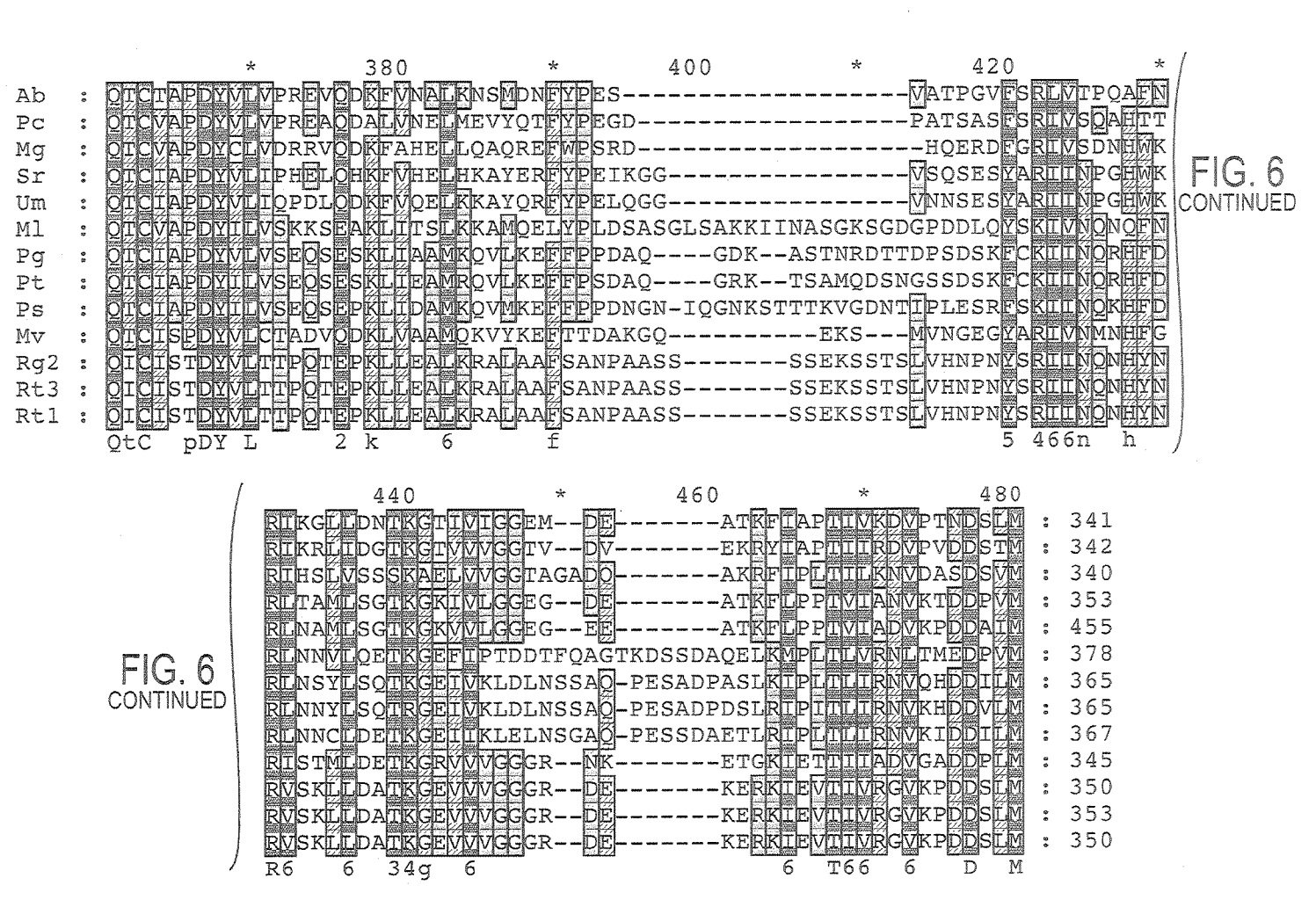
Figure 6:
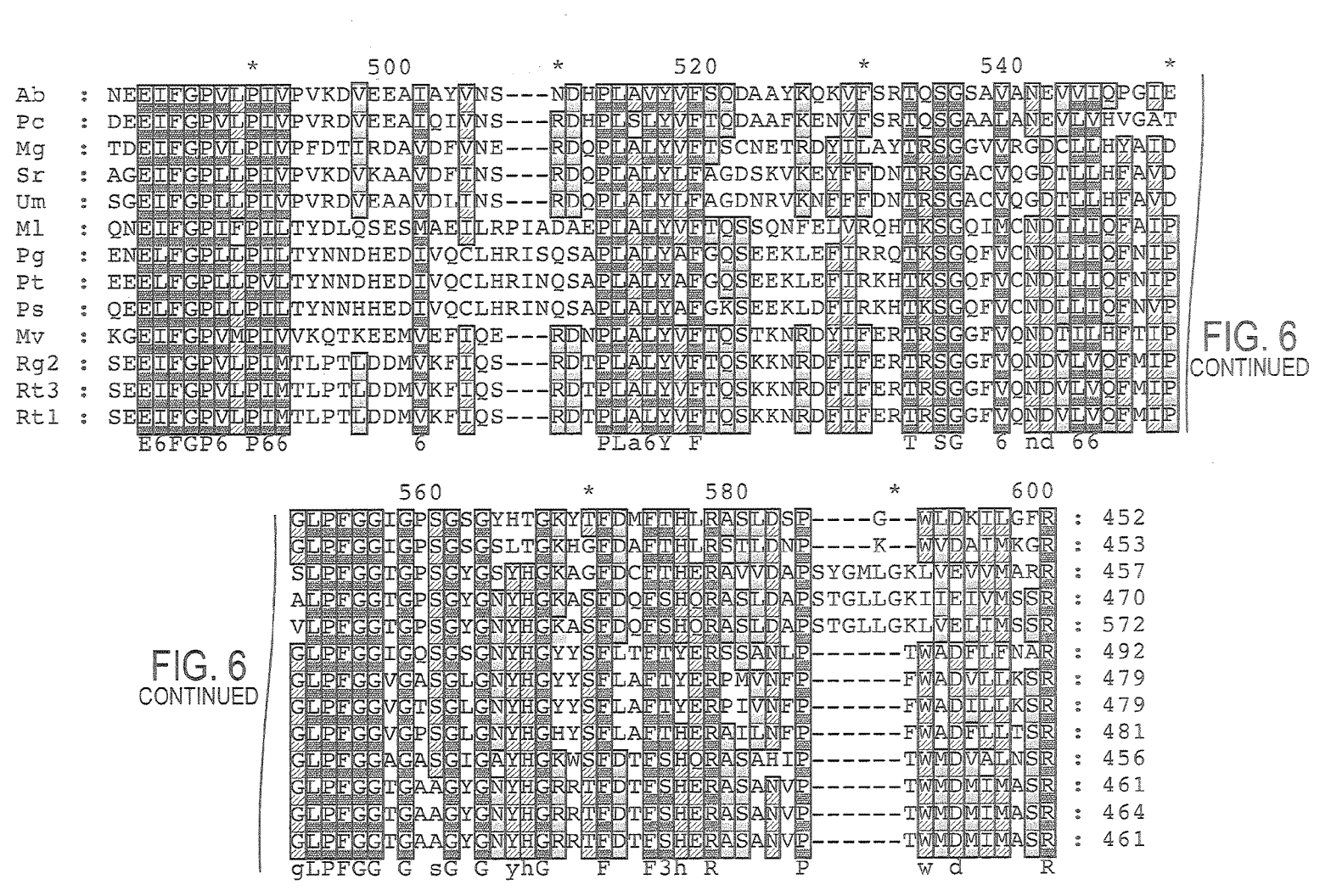

Homologous analysis revealed that T-DNA in RCM6 was integrated within 72542-72543 nt of $400^{th}$ contig (GenBank Accession No. AEVR01000400). BLASTx of sequences adjacent to the T-DNA tagging position exhibited a putative aldehyde dehydrogenase domain-containing protein was disrupted by T-DNA integration in RCM6 (FIG. 6A). The target protein was located between a putative thiazole biosynthetic enzyme (EGU11956) and a candidate dipeptidyl aminopeptidase (EGU11957), showing highly homologous to aldehyde hydrogenases from other fungal species such as Streptomyces sviceus (EDY60340.1, E-value=2E-68) and Mycobacterium sp. (YP_936108, E-value=3E-66), etc. Hence, the putative aldehyde hydrogenase (named as ALD1) encoding gene disrupted by T-DNA would result in the phenotype of RCM6. Further analyses of RT-PCR and rapid amplification cDNA ends (RACE) revealed that ALD1 gene spans 2461 bp in contig#400, containing 11 exons separated by 10 introns (FIG. 5A). It's 5' UTR is 18 nt in length, followed a short stretch of CT-rich motif (CT box, data not shown). The mRNA splicing strictly abides by the canonical GU-AG rule, which produces a 1506-nt mRNA in length, encoding a 501-aa protein with the strictly conserved NAD-binding fingerprint motif Gly-X-Gly-X-X-Gly (SEQ ID NO:53) (GSGTVG, aa 193-198; SEQ ID NO:54), adenosine ribose (NAD)-binding amino acid ($E_{148}$) and catalytic center Cys ($C_{249}$) (FIG. 6). In RCM6, T-DNA was integrated into the position between 2097th and $2098^{th}$ nucleotide from the start codon of ALD1, disrupting $9^{th}$ exon resulting in the deletion of the C-terminal 58 aa that form part of the RYPP motif (FIG. 6).

To further demonstrate the function in lipid accumulation, ALD1 was deleted through homologous recombination with the aid of ATMT. Nucleotide sequence in ALD1 ranging from +536 to +1947 was replaced by the hygromycin resistant cassette ($P_{GPD}$::hpt-3::Tnos, FIG. 5A) and the correct ald1 null mutants were verified by Southern blot analysis (FIG. 5B). When cultured in either liquid broth or on agar medium, Δald1 showed a orange-pigmented color in contrast to the pink-pigmented color in Wt (FIG. 5E). Δald1 grew a little slower than WT in lipid-accumulating medium, but it yielded similar biomass when carbon source in the media was exhausted at the $4^{th}$ day (FIG. 5E). Before the glucose exhausted ($3^{rd}$ day), Δald1 mutants showed little differences with WT in lipid yields. When glucose exhausted, lipid levels were decreased in both strains, however, lipids content was significantly higher in Δald1 mutant (FIGS. 5C and 5D). Strikingly, nearly half of the ALA was degraded in WT whereas little degradation was found in the Δald1 mutant (FIG. 5F). These results are consistent with those of the T-DNA tagged mutant, RCM6 (FIG. 4B).

Example 12

Improving Total TAG Accumulation Levels in R. toruloides by Rationale Design

Figure 7:
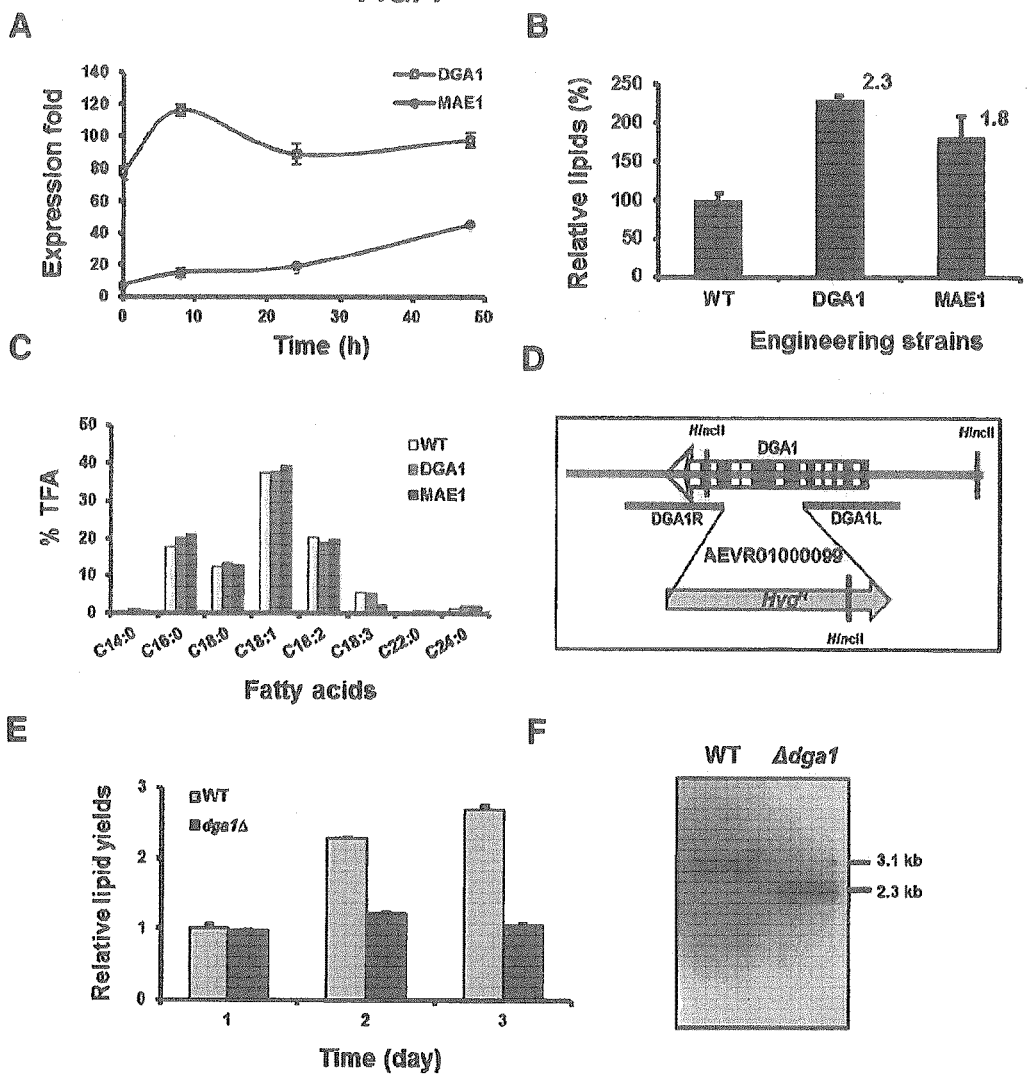
FIGS. 7A-7F show the effects of DGA1 and MAE1 in improving lipid accumulation.

Triacylglycerol (TAG) is the major neutral lipids occurring in most eukaryotic cells and the biosynthetic pathways are highly conserved [53]. Metabolic engineering by rationale designs has been quite successful in improving lipid content and productivity [54-56]. In R. toruloides, the sequence information for diacylglycerol acetyltransferase (Dga1) and malic enzyme (MAE1) are available (see for example SEQ ID NO:81 and SEQ ID NO:84, respectively). Overexpression cassettes for both genes were constructed to be driven by the 795-bp RtGPD1 promoter, $P_{GPD1}$::DGA1 and $P_{GPD1}$::MAE1, FIG. 1D, which were integrated into the chromosome of R. toruloides ATCC 10657 by Agrobacterium tumefaciens-mediated transformation. Quantitative RT-PCR analysis revealed that the mRNA transcript levels of both genes were dramatically enhanced throughout the 3-day bioprocess (FIG. 7A), resulted in 2.3 and 1.8-fold improvement of the peak lipid yield over Wt strain with DGA1 and MAE1 over-expression strain respectively (FIG. 7B). Fatty acid profile was not significantly changed in both strains (FIGS. 7C and 7F). As expected, a null mutant dga1 constructed (FIG. 7D) had a dramatically decreased lipid accumulation (FIG. 5E).

Example 13

Figure 8:
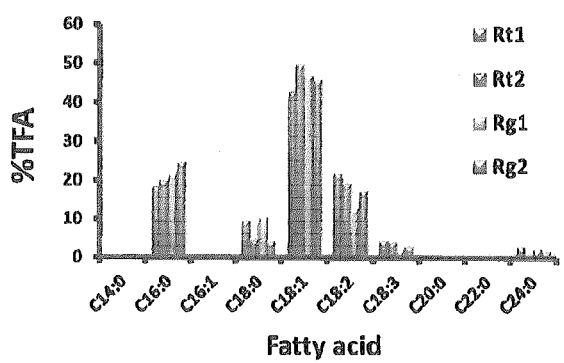
FIG. 8 shows the fatty acid profiles in different *R. toruloides* (*R. glutinis*) strains. Rt1: *R. toruloides* ATCC 10657; Rt2: *R. toruloides* ATCC 10788; Rg1: *R. glutinis* ATCC 90781; Rg2: *R. glutinis* ATCC 204091. *R. toruloides* (*R. glutinis*) was cultured in lipid accumulation medium (MinLG) as described previously [21] with some modifications. Medium MinLG contains 30 g glucose, 1.5 g yeast extract, 0.5 g (NH$_4$)$_2$SO$_4$, 2.05 g K$_2$HPO$_4$, 1.45 g KH$_2$PO$_4$, 0.6 g MgSO$_4$, 0.3 g NaCl, 10 mg CaCl$_2$, 1 mg FeSO$_4$, 0.5 mg ZnSO$_4$, 0.5 mg CuSO$_4$, 0.5 mg H$_3$BO$_4$, 0.5 mg MnSO$_4$, 0.5 mg NaMoO$_4$ (per liter). The medium pH was adjusted to 6.1. Cell culturing was conducted at 28° C. for 4 days with constant shaking (250 rpm).

Improving Polyunsaturated Fatty Acid (PUFA) Production in R. toruloides by Rationale Design In R. toruloides strains, oleic acid (C18:1) is the premoninant fatty acid component (~50%) while palmitoleic acid (C16:1) and linoleic acid (C18:2) consists of ~20% of total FA. α-linolenic acid (C18:3n=9, ALA), a polyunsaturated omega-3 fatty acids, is a minor component present at 3~4% of total fatty acids (% TFA) (FIG. 8). To produce ALA from oleic acid, a delta-12 desaturase (Fad2) and a omega-3 desaturase (Fad3) is required [57, 58]. Full-length genes of flax (*L. usitatissimum*) FAD3, tung (*V. fordii*) FAD3 and *M. alpine* FAD2 were designed and commercially synthesized according to the codon usage preference of *R. toruloides* [22], in which all rare codons were replaced with those that are frequently used in *R. toruloides*. The GC content of the genes ranged was 65.3% in LuFAD3-2 (SEQ ID NO:9), 64.8% in MaFAD2-2 (SEQ ID NO:4) and 63.3% in VfFAD3-2 (SEQ ID NO: 1).

Figure 9:
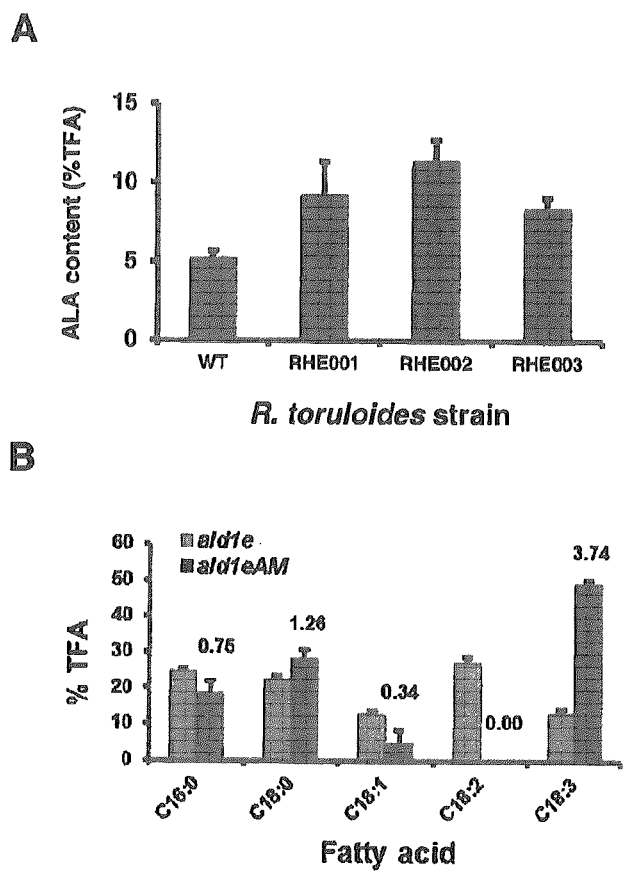
FIGS. 9A and 9B show engineering processes for high ALA strains.

The high level expression of the three synthetic genes was achieved by operatively linking to the RtGPD1 promoter and cauliflower mosaic virus 35S terminator, followed by profiling fatty acid compositions of selected ATMT strains. Elite strains over-expressing the LuFAD3-2 (RHE001), VfFAD3-2 (RHE002) or MaFAD2-3 (RHE003) showed an improvement of ALA content of 1.8, 2.2 and 1.6 folds respectively (FIG. 9A). Subsequently, the RtGPD1::Af-FAD3-2:35S and RtGPD1::MaFAD2-2:35S cassettes were stacked into a single T-DNA vector, pRHE004, which was transformed by ATMT to a derivative (RT1CE6, containing a 17β-estradiol inducible Cre gene stably integrated into the genome) of *R. toruloides* ATCC 10657. Selected elite strain (RHE004) was further modified by deleting the ALD1 gene using the pKOALD1 vector. The resultant strain (named ald1eAM) produced 3.74-fold higher ALA than ald1 null mutant (ald1e) (FIG. 9B), with the ALA content reaching ~49% of total fatty acids.

Example 14

Biochemical Analysis of Ald1

Figure 10:
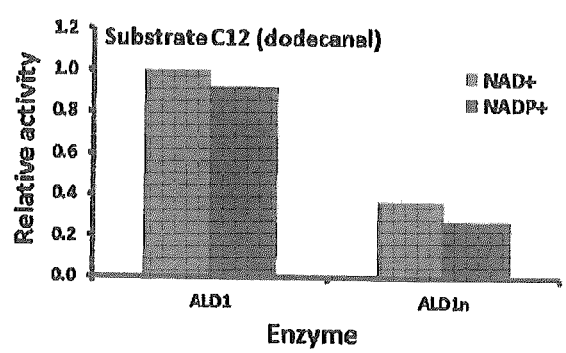
FIG. 10 shows the enzyme assay of ALD1 and C-terminus truncated ALD1 (ALD1n). The reaction was mixed with 20 mM Tris-Ci buffer (pH8.0), 1.5 mM NAD+ or NADP+, 1.0 mM dodecanal and 10 μl purified enzyme. The assay was conducted at 25° C. for 2 min.

To characterize Ald1 and to confirm that the deletion of C-terminal 58 residues resulted from the T-DNA insertion in RCM6 mutant compromised its enzymatic activity, both the full length and the truncated version of Ald1 proteins were expressed in *E coli* BL21(DE3) as a fusion protein with the C-terminal 6× histidine tag. Recombinant Ald1 and Ald1n were purified with HisTrap column (GE healthcare, USA) and assayed using the method reported previously [59] with some modifications. Briefly, the reaction mixture was composed of 40 µl of 100 mM Tris-Cl buffer (pH8.0), 30 µl of 10 mM NAD+ or NADP+ (Sigma-Aldrich, USA), 10 µl of 20 mM dodecanal (dodecyl aldehyde, C12-aldehyde, Sigma-Aldrich, USA), 110 µl water and 10 µl purified enzyme. The reaction was performed at room temperature (25° C.) and initiated by the addition of enzyme. The time course of optical density value at 340 nm was read through the Infinite M200 µlate reader (Tecan, Salzburg, Austria) using the iControl™ version 3.0 software (Tecan, Salzburg, Austria). as described previously [40]. As shown in FIG. 10, both Ald1 and Ald1n showed a clear dehydrogenase activity, with a slightly preference to NAD+. Notably, the mutant protein with the C-terminal 58 aa deletion showed significantly lower enzymatic activity.

Example 15

Characterization of Fatty Acid Biosynthesis Genes in *R. toruloides*

*R. toruloides* homologues of various fatty acid desaturase, elongase and ATP-citrate lyase were identified by BLAST search against the *R. toruloides* ATCC 204091 genome scaffold sequences 204091 (previously named *Rhodotorula glutinis*, GenBank accession no. AEVR02000000, whole genome shotgun sequencing project PRJNA59971, Mississippi State University, USA.) using known *Yarrowia lipolytica* and *Ustilago maydis* enzyme sequences as queries. Genetic manipulation and DNA sequence characterization were done with *R. toruloides* strain ATCC 10657 or its derivative Rt1ck, a KU70-deficient mutant exhibiting extremely high efficiency in homologous recombination [60]. Oligonucleotides used are listed in Table 3.

TABLE 3

| Oligonucleotides Used For: | | |
|---|---|---|
| Deletion of Stearoyl-CoA-delta-9-desaturase gene (RtFAD1) | | |
| DS9L-Sf | GCGAGGGATGGCAGTAAGACG (118)ᵃ | SacI |
| DS9L-Br | AAA*GGATCC*AACTTGCTCGCCCAGTACC (119) | BamHI |
| DS9R-Hf | TTT*AAGCTT*CACGTACAGCCTGTGGTAGCC (120) | HindIII |
| DS9R-Str | TTT*AGGCCT*GGAGGAGTCGAGCGTGAGAGT (121) | StuI |
| Rt227Nf | TTT*cccagg*CTGCCTCGTCGGCACTCGAG (122) | NcoI |
| Rt228Evr | TTT*gatatc*CATTACGCCTTGACCGTCAG (123) | EcoRV |
| For deletion of delta-12 desaturase gene (RtFAD2) | | |
| DS12L-Sf2 | AAA*GAGCTC*GGTGACTGCATGCTCCGTTAC (124) | SacI |
| DS12L-Br2 | AAA*GGATCC*TGATGGAGTAGTTGGGCACGA (125) | BamHI |
| DS12R-Hf | TTT*AAGCTT*CCTCCTCCTTGATCTTTCGCCG (126) | HindIII |
| DS12R-Str | TTT*AGGCCT*GACCTTTGCGTCCTCCCTTCA (127) | StuI |
| OEDS12f | TCAGAACAACACCAGATCACTCACAATGGCCGCTACCCTCCGCC (128) | |
| Rt229Ndf | TTTCATATGGCCGCTACCCTCCGCCA (129) | NdeI |
| Rt230Evr | TTTGATATCTCTAGGGCATCGTCTAGAGTC (130) | EcoRV |
| For deletion of elongase gene 1 (RtELO1) | | |
| ELO1L-Sf | AAA*GAGCTC*TATTGTTCGACTAGACTGCGCCAC (131) | SacI |
| ELO1L-Br | AAA*GGATCC*AAGGAGGATATTGTGCACGAGGA (132) | BamHI |
| ELO1R-Hf | CGACTCCAAATCACCCAGTTCCTC (133) | HindIII |
| ELO1R-Str | TTT*AGGCCT*GACCGACTTTGACGACGAC (134) | StuI |

TABLE 3-continued

Oligonucleotides Used For:

For deletion of ATP-citrate lyase gene (RtACL1)

| | | |
|---|---|---|
| ACL1L-Sf2 | AAA*GAGCTC*GCGGCACTGTACTTCACTACG (135) | SacI |
| ACL1L-Br2 | AAA*GGATCC*ACGAGACCTATCCAAACGC (136) | BamHI |
| ACL1R-Hf2 | TTT*AAGCTT*AAGGTCAAGTCCAAGGCCAAC (137) | HindIII |
| ACL1R-Str2 | TTT*AGGCCT*GGCTGCTGGAGAAACGAAACT )138) | StuI |

For deletion of elongase gene 2 (RtELO2)

| | | |
|---|---|---|
| ELO2L-Stf | AAA*AGGCCT*CATTCCCTCGACTCGACGCAT (139) | StuI |
| ELO2L-Hr | AGAGGAGGAAGTTGTGCAGCA (140) | HindIII |
| ELO2R-Bf | TTT*GGATCC*GTTGCGGCGAGTCCTGTCATC (141) | BamHI |
| ELO2R-Sr | TTT*GAGCTC*CGGAGCGAGTAAGACGAGG (142) | SacI |

For expression of ELO1 cDNA

| | | |
|---|---|---|
| Rt236Nf | TTT*CCATGG*CCTCGTACGCCGCCCATCC (143) | NcoI |
| Rt237Evr | TTT*GATATC*GGAAGGGACCGCGCTAGTT (144) | coRV |

For expression of ELO2 cDNA

| | | |
|---|---|---|
| Rt259Nf | TTT*CCATGG*TCGCACCGTCCCCCG (145) | NcoI |
| Rt260Evr | TTT*GATATC*GAGAAGAAGGTGGGGTGTTTAG (146) | EcoRV |

$^a$SEQ ID NO:

For deletion of delta-9-oleate desaturase gene FAD1 (or OLE1) homologue, left and right homology flanking fragment (~0.9 kb each) were amplified using R. toruloides ATCC 10657 genomic DNA with oligo pairs DS9L-Sf/DS9L-Br and DS9R-Hf/DS9R-Str, respectively. A four-fragment ligation was performed with SacI/PmeI-digested pEX2 binary vector, SacI/BamHI-digested left flanking fragment, BamHI/HindII-digested codon-optimized hygromycin selection cassette from pDXP795hptR ($P_{GPD1}$::hpt-3::$T_{nos}$ [60]) and HindIII/StuI-digested right flanking fragment to generate gene deletion plasmid pKOOLE1. A similar strategy was applied to construct both pKOFAD2 and pKOELO1, for the knockout of putative delta-12 desaturase gene and elongase gene 1, respectively. Oligo pairs DS12L-Sf2/DS12L-Br2 and DS12R-Hf/DS12R-Str were used to amplify the left (0.6 kb) and right (0.9 kb) homology flanking fragment for pKOFAD2, and ELO1L-Sf/ELO1L-Br and ELO1R-Hf/ELO1R-Str used for pKOELO1 (~0.9 kb each). For ELO2, oligo pairs ELO2L-Stf/ELO2L-Hr and ELO2R-Bf/ELO2R-Sr were used (~0.8 kb each) and digested with StuI/HindIII and BamHI/SacI for the left and right homology flanking fragment, respectively. Both fragments were similarly used in the four-fragment ligation to generate pKOELO2.

For deletion of putative ATP-citrate lyase gene (RtACL1), oligo pairs ACL1L-Sf2/ACL1L-Br2 and ACL1R-Hf2/ACL1R-Str2 were used to amplify the left and right homology flanking fragments (0.9 kb each) to generate pKOACL1 using a similar strategy described above.

The cDNA sequences of genes of interest were obtained by RT-PCR, with 5' and 3' RACE performed using BD SMARTer™ RACE cDNA Amplification Kit (Clontech, California, USA) according to the manufacturer's instruction. Oligo pair OLE1U1/OLE1L1, FAD2U1/FAD2L1 was used as the specific primer for 5'/3' RACE of FAD1 (OLE1) and FAD2, respectively.

The predicted ORF of Fad1 (Ole1) and Fad2 encodes protein of 545, 451 aa in length, respectively. Both Fads share a common conserved domain of membrane fatty acid desaturase (protein family no. pfam00487, EMBL-EBI). However, Fad2 lacks of cytochrome β5-like heme/steroid binding domain (pfam00173. BLAST searches revealed that Ole1 and Fad2 exhibited the highest identity to stearoyl-CoA desaturase from Puccinia graminis (XP_003326562.1, 70% identity), Δ12-fatty acid desaturase from Ustilago maydis (XP_757193.1, 57% identity), respectively.

Figure 12:
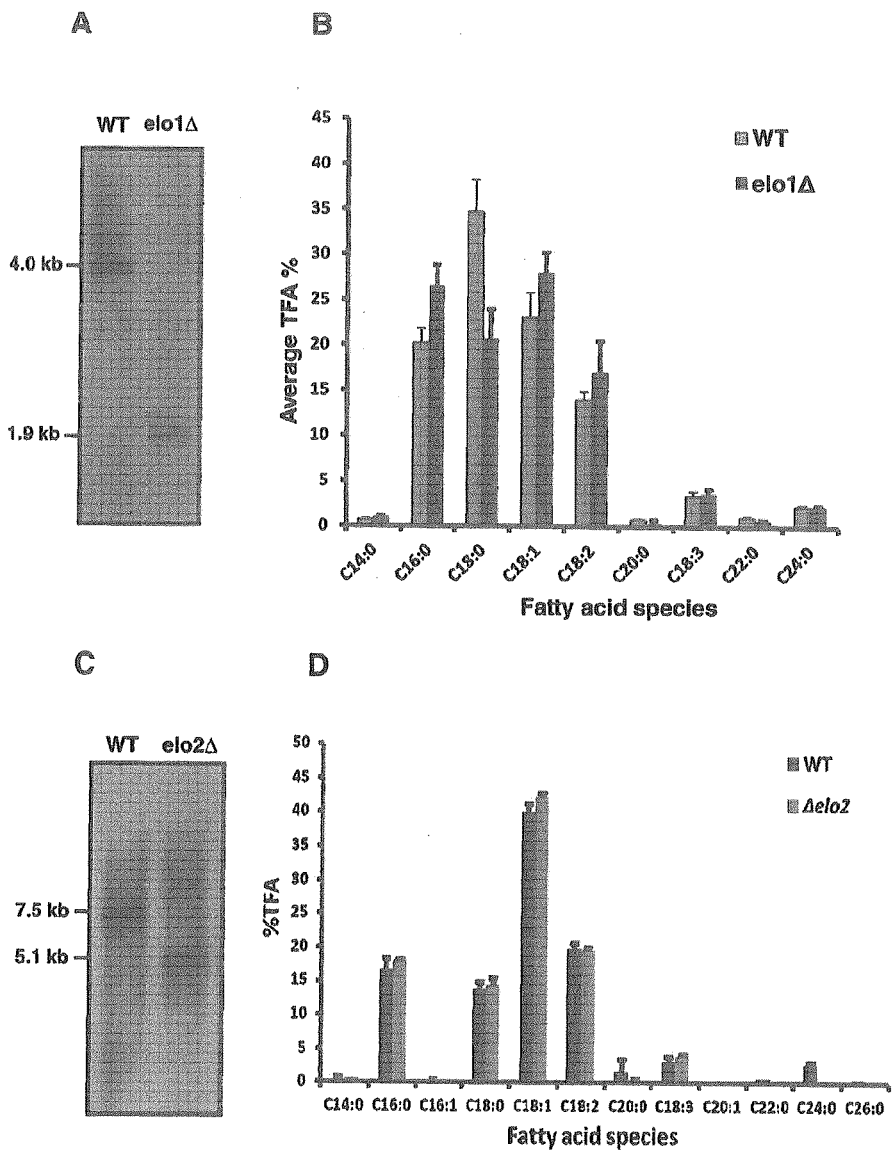
FIGS. 12A-12D show the characterization of ELO1 and ELO2 deletion mutants in *R. toruloides* ATCC 10657. (elo1Δ and elo2Δ) (FIG. 12A) and (FIG. 12C) Southern blot analysis of elo1Δ and elo2Δ. Total DNA was digested with PvuI and hybridized against digoxiginin-labeled ELO1R and ELO2L, respectively.

Two elongase were identified. ELO1 (Seq ID. No. 99 and 100) and ELO2 (Seq ID. No. 102 and 103) encodes protein of 329 (Seq ID 101) and 293 aa (Seq ID 104) in length, respectively. Both putative fatty acid elongases share a common conserved domain of GNS1/SUR4 family that involved in long-chain fatty acid elongation system (pfam01151). Elo1 and Elo2 exhibited the highest identity to the fatty acid elongase from Puccinia graminis (PGTG06945, XP_003325743.2, 43% identity) and Melampsora larici-populina (MELLADRAFT_42723, XP_007407925.1, 65% identity), respectively. Analysis of fatty acid profiles of ELO1 and ELO2 knockouts revealed that ELO1 knockout lead to little change in the profile except a moderate decrease of C18:0 and small increase of C16:0 and C18:1. In contrast, ELO2 knockout lead to complete loss of long chain fatty acid (>C18) synthesis (FIG. 12). These results strongly suggest that that OLE1 is a short chain fatty-CoA elongase whereas ELO2 is able to elongase both long chain and short chain fatty acid-CoA.

For overexpression studies, cDNA of OLE1, FAD2 and ELO2 was amplified using synthesized R. toruloides cDNA template by reverse transcription with primer pairs Rt227Nf/Rt228Evr, Rt229Ndf/Rt230Evr and Rt259Nf/Rt260Evr, respectively. The NcoI/EcoRV-digested PCR products were ligated with NcoI/EcoRV-digested pKC1 vector to create the pKC1OLE1, pKC1FAD2 and pKC1ELO2 resulted in overexpression of the gene because of the strong RtGPD1 promoter used in the vector pKC1.

Example 16

Gene Deletion Analysis

Figure 11:
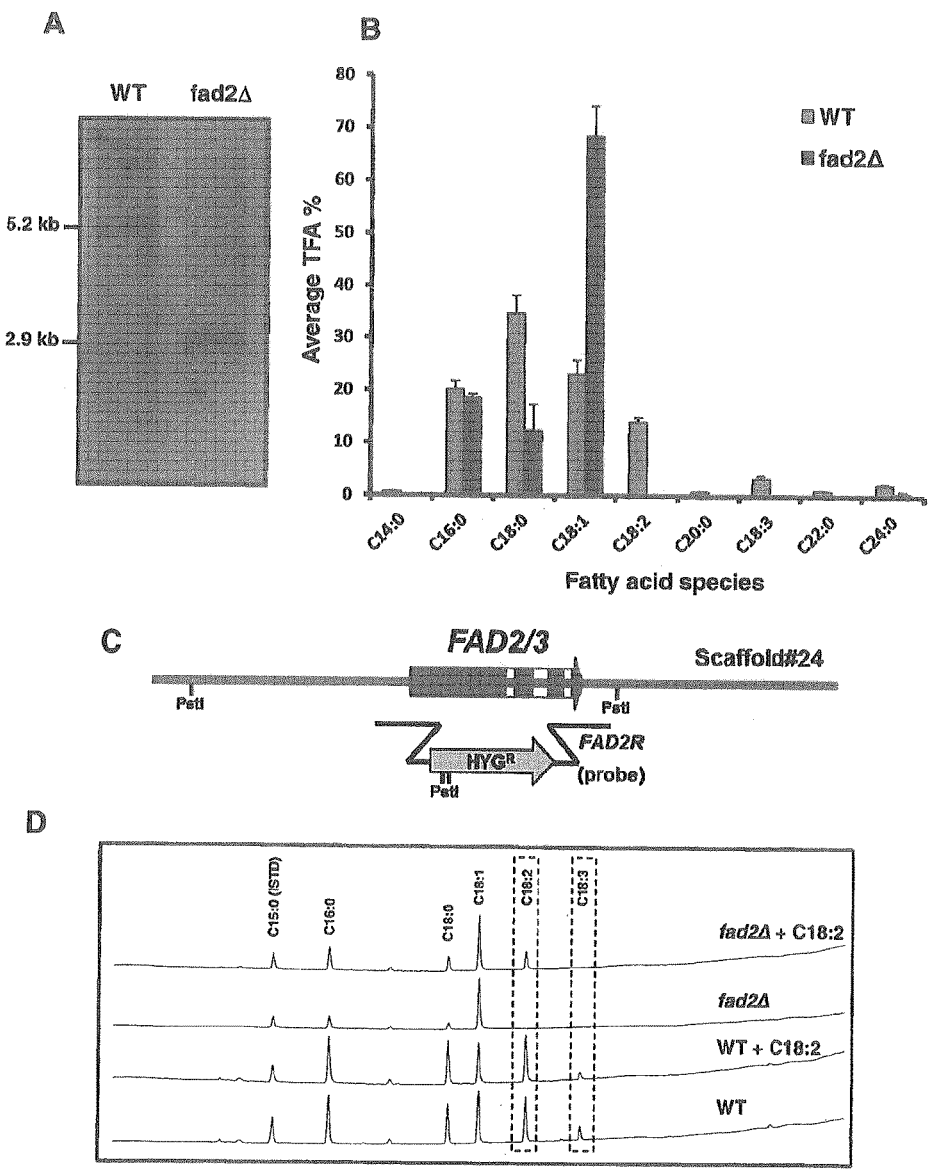
FIGS. 11A-11D show the characterization of delta-12 desaturase gene in *R. toruloides* ATCC 10657 (RtFAD2).

To verify functions of each gene, knockout mutants were created by Agrobacterium-mediated transformation of the respective knockout constructs; screening by colony PCR and Southern blot analysis. FAD1 knockout was unsuccessful in several attempts. Deletion of FAD2 was successful after supplementation of linoleic acid in transformation and propagation media. Linoleic acid (C18:2, LA) and α-linolenic acid (C18:3, ALA) were absent in the FAD2 null mutant while the content of C18:1 was increased to nearly 70% over total fatty acids (FIG. 11B). This confirms that FAD2 gene (SEQ ID NO:92) encodes a Δ12-fatty acid desaturase catalyzing the conversion of oleic acid (C18:1) to form LA. The lack of ALA in the FAD2 knockout mutant suggests that Fad2 is a Δ12 and Δ15 bifunctional fatty acid desaturase. This was supported by the inability of fad2Δ mutant to produce ALA production even when supplemented with LA (C18:2) precursor (FIG. 11D).

Figure 13:
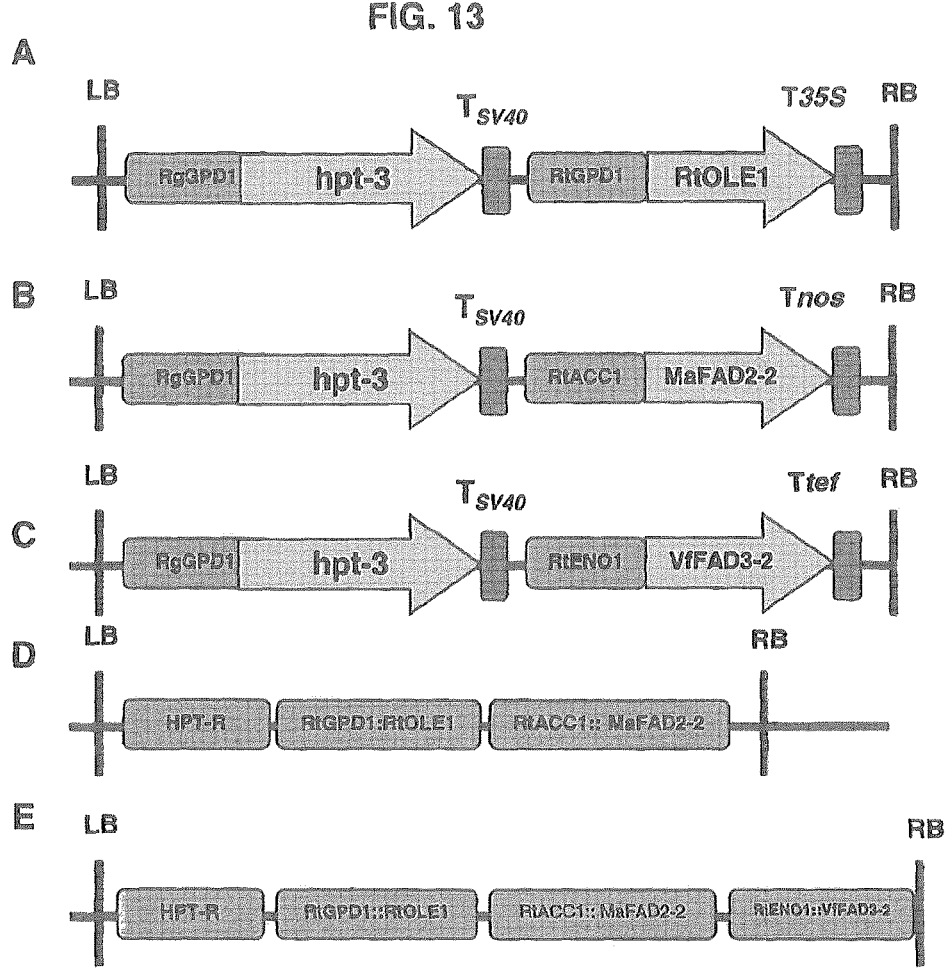
FIGS. 13A-13E show the schematic illustration of vectors used in FIG. 14.
Figure 14:
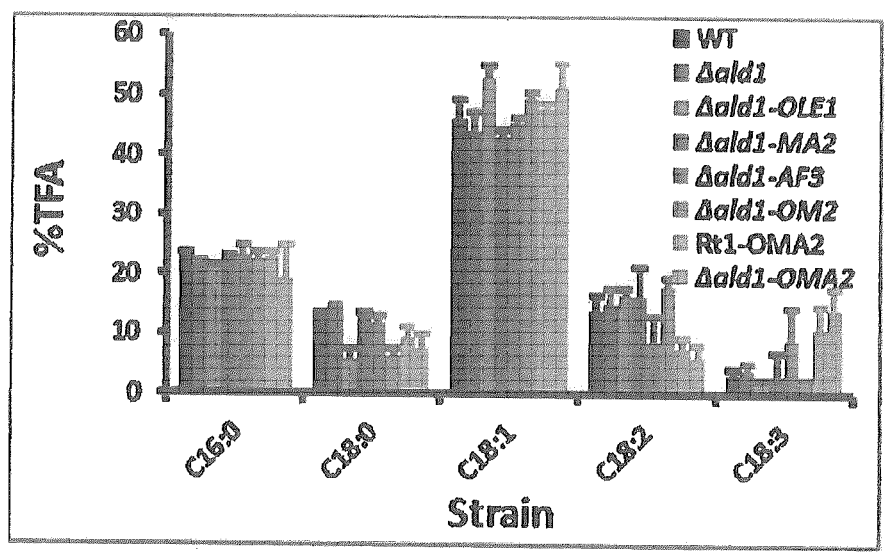
FIG. 14: Fatty acid content profile of engineered strains. Three independent transformants were used for each analysis except for Δald1-OMA2, for which a total 18 independent transformants were analyzed. All transformants were fermented in medium RL2 for 5 days. WT: wild-type *R. toruloides* ATCC 10657 strain; Δald1-: constructs were transformed into ADL1 knockout mutant; Constructs are shown in FIG. 13. OEL1.

The function of FAD1 (OLE1) can be demonstrated by over-expression studies. Transformation of RtGDP1::OLE1 cassette (FIG. 13A) into Wt and ALD1 knockout strain (Δald1e) resulted significant increase in oleic acid content (FIG. 14). Accordingly, stacking RtGDP1::OLE1 to MaFAD2-2 (FIG. 13D), or both to MaFAD2-2 and VfFAD3-2 over-expression cassette (FIG. 13E) resulted into an increase of LA and ALA respectively (FIG. 14). Among 18 of transformants expressing the triple-gene cassette, three showed >20% ALA content with one containing ~24% in ald1e background. The lower ALA content in this series is likely attributed to the weaker ACC1 promoter used for MaFAD2-2 as the LA content was very low (not shown).

Example 17

Characterization ATP-Citrate Lyase (ACL1) Genes in *R. toruloides*

Based on studies in animal, fungal ATP-citrate lyase (ACL) is believed to be an important factor for oil accumulation. A putative ATP-citrate lyase/synthase gene ACL1 (seq ID No. 86 and 87) was identified by BLAST search of *Rhodotorula glutinis* ATCC 204091 partial genome sequences. The putative Acl1 protein sequence is set forth in Seq ID. No. 88. A knockout mutant of the ACL1 gene was created and it showed significantly reduced oil accumulation and biomass growth (FIG. 15). This strongly suggests ACL1 expression facilitates oil accumulation and biomass production in *R. toruloides*.

BIBLIOGRAPHY

An, G., et al., 1989. Functional analysis of the 3' control region of the potato wound-inducible proteinase inhibitor II gene. Plant Cell, 1: 115-122.
1. Venegas-Calerón, M., O. Sayanova, and J. A. Napier, *An alternative to fish oils: metabolic engineering of oil-seed crops to produce omega-3 long chain polyunsaturated fatty acids.* Progress in lipid research, 2010. 49(2): p. 108-119.
2. Horrobin, D., *Nutritional and medical importance of gamma-linolenic acid.* Progress in lipid research, 1992. 31(2): p. 163-194.
3. Simopoulos, A. P., *The importance of the ratio of omega-6/omega-3 essential fatty acids.* Biomedicine & pharmacotherapy, 2002. 56(8): p. 365-379.
4. Gong, Z., et al., *Efficient conversion of biomass into lipids by using the simultaneous saccharification and enhanced lipid production process.* Biotechnology for biofuels, 2013. 6(1): p. 1-12.
5. Ratledge, C., *Regulation of lipid accumulation in oleaginous micro-organisms.* Biochem Soc Trans, 2002. 30(Pt 6): p. 1047-50.
6. Meng, X., et al., *Biodiesel production from oleaginous microorganisms.* Renewable Energy, 2009. 34(1): p. 1-5.
7. Ward, O. P. and A. Singh, *Omega-3/6 fatty acids: alternative sources of production.* Process Biochemistry, 2005. 40(12): p. 3627-3652.
8. Beopoulos, A., et al., *Yarrowia lipolytica as a model for bio-oil production.* Prog Lipid Res, 2009. 48(6): p. 375-87.
9. Katre, G., et al., *Evaluation of single cell oil (SCO) from a tropical marine yeast Yarrowia lipolytica NCIM 3589 as a potential feedstock for biodiesel.* AMB Express, 2012. 2(1): p. 36.
10. Neuveglise, C., et al., *A shuttle mutagenesis system for tagging genes in the yeast Yarrowia lipolytica.* Gene, 1998. 213(1-2): p. 37-46.
11. Sabirova, J. S., et al., *The 'LipoYeasts' project: using the oleaginous yeast Yarrowia lipolytica in combination with specific bacterial genes for the bioconversion of lipids, fats and oils into high-value products.* Microb Biotechnol, 2011. 4(1): p. 47-54.
12. Tai, M. and G. Stephanopoulos, *Engineering the push and pull of lipid biosynthesis in oleaginous yeast Yarrowia lipolytica for biofuel production.* Metab Eng, 2013. 15: p. 1-9.
13. Li, Y., Z. K. Zhao, and F. Bai, *High-density cultivation of oleaginous yeast<i> Rhodosporidium toruloides</i> Y4 in fed-batch culture.* Enzyme and Microbial Technology, 2007. 41(3): p. 312-317.
14. Zhao, X., et al., *Lipid production by Rhodosporidium toruloides Y4 using different substrate feeding strategies.* J Ind Microbiol Biotechnol, 2010.
15. Pan, J. G., M. Y. Kwak, and J. S. Rhee, *High density cell culture of Rhodotorula glutinis using oxygen-enriched air.* Biotechnology letters, 1986. 8(10): p. 715-718.
16. Frengova, G. I. and D. M. Beshkova, *Carotenoids from Rhodotorula and Phaffia: yeasts of biotechnological importance.* Journal of industrial microbiology & biotechnology, 2009. 36(2): p. 163-180.
17. Kirk, M. P., et al., in *Dictionary of the Fungi.* 2008, CABI: Wallingford. p. 716.
18. Hu, C., et al., *Effects of biomass hydrolysis by-products on oleaginous yeast Rhodosporidium toruloides.* Bioresour Technol, 2009. 100(20): p. 4843-7.
19. Zhao, X., et al., *Lipid production from Jerusalem artichoke by Rhodosporidium toruloides Y4.* J Ind Microbiol Biotechnol, 2010. 37(6): p. 581-5.
20. Wu, S., et al., *Microbial lipid production by Rhodosporidium toruloides under sulfate-limited conditions.* Biosour Technol, 2010.
21. Wu, S., et al., *Phosphate-limitation mediated lipid production by Rhodosporidium toruloides.* Bioresour Technol, 2010. 101(15): p. 6124-9.
22. Liu, Y., et al., *Characterization of glyceraldehyde-3-phosphate dehydrogenase gene RtGPD1 and development of genetic transformation method by dominant selection in oleaginous yeast Rhodosporidium toruloides.* Appl Microbiol Biotechnol, 2013. 97(2): p. 719-29.
23. Ji, L., N. Peng, and H.-I. Cheng, *Polynucleotide sequences from Rhodosporidium and Rhodotorula and use thereof,* in U.S. Provisional Application No. 61/782, 832. 2013.
24. Liu, Y., et al., *Genetic manipulation and expression systems for Pucciniomycotina and Ustilaginomycotina subphyla,* in WO patent 2012169969. 2011.

25. Ye, V. M. and S. K. Bhatia, *Metabolic engineering for the production of clinically important molecules: Omega-3 fatty acids, artemisinin, and taxol.* Biotechnology Journal, 2012. 7(1): p. 20-33.
26. Nykiforuk, C., et al., *High level accumulation of gamma linolenic acid (C18:3Δ6.9,12 cis) in transgenic safflower (Carthamus tinctorius) seeds.* Transgenic Research, 2012. 21(2): p. 367-381.
27. Wu, G., et al., *Stepwise engineering to produce high yields of very long-chain polyunsaturated fatty acids in plants.* Nat Biotech, 2005. 23(8): p. 1013-1017.
28. Lee, L. Y. and S. B. Gelvin, *T-DNA binary vectors and systems.* Plant Physiol, 2008. 146(2): p. 325-32.
29. Zuo, J., et al., *Chemical-regulated, site-specific DNA excision in transgenic plants.* Nat Biotechnol, 2001. 19(2): p. 157-61.
30. Lazo, G. R., P. A. Stein, and R. A. Ludwig, *A DNA transformation-competent Arabidopsis genomic library in Agrobacterium.* Biotechnology (N Y), 1991. 9(10): p. 963-7.
31. Smith, T. L. and S. A. Leong, *Isolation and characterization of a Ustilago maydis glyceraldehyde-3-phosphate dehydrogenase-encoding gene.* Gene, 1990. 93(1): p. 111-7.
32. Ji, L., et al., *A simplified and efficient method for transformation and gene tagging of Ustilago maydis using frozen cells.* Fungal Genet Biol, 2010. 47(4): p. 279-87.
33. Punt, P. J., et al., *Functional elements in the promoter region of the Aspergillus nidulans gpdA gene encoding glyceraldehyde-3-phosphate dehydrogenase.* Gene, 1990. 93(1): p. 101-9.
34. Steiner, S. and P. Philippsen, *Sequence and promoter analysis of the highly expressed TEF gene of the filamentous fungus Ashbya gossypii.* Mol Gen Genet, 1994. 242(3): p. 263-71.
35. Liu, Y. G. and R. F. Whittier, *Thermal asymmetric interlaced PCR: automatable amplification and sequencing of insert end fragments from P1 and YAC clones for chromosome walking.* Genomics, 1995. 25(3): p. 674-81.
36. Liu, Y. G. and Y. Chen, *High-efficiency thermal asymmetric interlaced PCR for amplification of unknown flanking sequences.* Biotechniques, 2007. 43(5): p. 649-50, 652, 654 passim.
37. Kimura, K., M. Yamaoka, and Y. Kamisaka, *Rapid estimation of lipids in oleaginous fungi and yeasts using Nile red fluorescence.* J Microbiol Methods, 2004. 56(3): p. 331-8.
38. Elsey, D., et al., *Fluorescent measurement of microalgal neutral lipids.* J Microbiol Methods, 2007. 68(3): p. 639-42.
39. Voelker, T. A. and H. M. Davies, *Alteration of the specificity and regulation of fatty acid synthesis of Escherichia coli by expression of a plant medium-chain acyl-acyl carrier protein thioesterase.* J Bacteriol, 1994. 176(23): p. 7320-7.
40. Liu, Y., et al., *Tartronate semialdehyde reductase defines a novel rate-limiting step in assimilation and bioconversion of glycerol in Ustilago maydis.* PLoS One, 2011. 6(1): p. e16438.
41. An, S., et al., *Generation and analysis of end sequence database for T-DNA tagging lines in rice.* Plant Physiology, 2003. 133(4): p. 2040-2047.
42. Rosso, M. G., et al., *An Arabidopsis thaliana T-DNA mutagenized population (GABI-Kat) for flanking sequence tag-based reverse genetics.* Plant molecular biology, 2003. 53(1-2): p. 247-259.
43. Choi, J., et al., *Genome-wide analysis of T-DNA integration into the chromosomes of Magnaporthe oryzae.* Molecular microbiology, 2007. 66(2): p. 371-382.
44. Omura, S., *The antibiotic cerulenin, a novel tool for biochemistry as an inhibitor of fatty acid synthesis.* Bacteriol Rev, 1976. 40(3): p. 681-97.
45. Vance, D., et al., *Inhibition of fatty acid synthetases by the antibiotic cerulenin.* Biochem Biophys Res Commun, 1972. 48(3): p. 649-56.
46. Zhong, Y., et al., *Application of T-DNA insertional mutagenesis for improving cellulase production in the filamentous fungus Trichoderma reesei.* Bioresour Technol, 2012. 110: p. 572-7.
47. Morita, N., et al., *Enhancement of polyunsaturated fatty acid production by cerulenin treatment in polyunsaturated fatty acid-producing bacteria.* Biotechnol Lett, 2005. 27(6): p. 389-93.
48. Wang, J., et al., *A quick isolation method for mutants with high lipid yield in oleaginous yeast.* World Journal of Microbiology and Biotechnology, 2009. 25(5): p. 921-925.
49. Nguyen, L. N. and J. D. Nosanchuk, *The inhibitory effect of cerulenin to yeasts is fungicidal.* Commun Integr Biol, 2011. 4(6): p. 631-2.
50. Greenspan, P., E. P. Mayer, and S. D. Fowler, *Nile red: a selective fluorescent stain for intracellular lipid droplets.* The Journal of cell biology, 1985. 100(3): p. 965-973.
51. Spiekermann, P., et al., *A sensitive, viable-colony staining method using Nile red for direct screening of bacteria that accumulate polyhydroxyalkanoic acids and other lipid storage compounds.* Arch Microbiol, 1999. 171(2): p. 73-80.
52. Zhao, Y.-F. and Q.-Z. Kong, *Tetrazolium violet inhibits cell growth and induces cell death in C127 mouse breast tumor cells.* Chemico-biological interactions, 2008. 174(1): p. 19-26.
53. Beopoulos, A., J. M. Nicaud, and C. Gaillardin, *An overview of lipid metabolism in yeasts and its impact on biotechnological processes.* Appl Microbiol Biotechnol, 2011. 90(4): p. 1193-206.
54. Li, Z., et al., *Overexpression of malic enzyme (ME) of Mucor circinelloides improved lipid accumulation in engineered Rhodotorula glutinis.* Appl Microbiol Biotechnol, 2012.
55. Zhang, Y., I. P. Adams, and C. Ratledge, *Malic enzyme: the controlling activity for lipid production? Overexpression of malic enzyme in Mucor circinelloides leads to a 2.5-fold increase in lipid accumulation.* Microbiology, 2007. 153(Pt 7): p. 2013-25.
56. Rani, S. H., S. Saha, and R. Rajasekharan, *A soluble diacylglycerol acyltransferase is involved in triacylglycerol biosynthesis in the oleaginous yeast Rhodotorula glutinis.* Microbiology, 2013. 159(Pt 1): p. 155-66.
57. Dyer, J., et al., *Production of linolenic acid in yeast cells expressing an omega-3 desaturase from tung (Aleurites fordii).* Journal of the American Oil Chemists' Society, 2004. 81(7): p. 647-651.
58. Huang, Y. S., et al., *Cloning of delta12-and delta6-desaturases from Mortierella alpina and recombinant production of gamma-linolenic acid in Saccharomyces cerevisiae.* Lipids, 1999. 34(7): p. 649-59.
59. Ueda, M. and A. Tanaka, *Long-chain aldehyde dehydrogenase of Candida yeast.* Methods in enzymology, 1990. 188: p. 176-178.

60. Koh, C. M., et al., *Molecular characterization of KU70 and KU80 homologues and exploitation of a KU70-deficient mutant for improving gene deletion frequency in Rhodosporidium toruloides.* BMC Microbiology, 2014. 14(1): p. 50.
61. Gong, W. F., et al., [*Effect of silencing lycB gene on the carotenoid synthesis in Haematococcus pluvialis*]. Yi Chuan, 2013. 35(2): p. 233-40.
62. Chan, S. T., et al., *Quercetin supplementation suppresses the secretion of pro-inflammatory cytokines in the lungs of Mongolian gerbils and in A549 cells exposed to benzo[a]pyrene alone or in combination with beta-carotene: in vivo and ex vivo studies.* J Nutr Biochem, 2012. 23(2): p. 179-85.
Zuo, J. et al. (2001). Chemical-regulated, site-specific DNA excision in transgenic plants. *Nat Biotechnol* 19:157-161.

What is claimed is:

1. A fungal host cell wherein the total fatty acids are composed of at least 9% alpha-linolenic acid (ALA) or gamma-linolenic acid (GLA), wherein the genome of the fungal host cell has been modified such that the fungal host cell has reduced native aldehyde dehydrogenase (ALD1) enzyme activity compared to a fungal host cell having an unmodified genome, wherein the fungal host is a species of the *Rhodosporidium* genera or the *Rhodotorula* genera, wherein the amino acid sequence of the native ALD1 has the sequence set forth in SEQ ID NO:3 or has at least 90% identity to the sequence set forth in SEQ ID NO:3, and wherein the genome of the host fungal cell has been modified to create a mutation in the gene encoding the native ALD1.

2. The fungal host cell of claim 1, wherein the native ALD1 is encoded by a nucleic acid selected from the group consisting of:
   (a) a nucleic acid having the nucleotide sequence set forth in SEQ ID NO:1;
   (b) a nucleic acid having the nucleotide sequence set forth in SEQ ID NO:2;
   (c) a nucleic acid having at least 90% identity to the nucleic acid of (a); and
   (d) a nucleic acid having at least 90% identity to the nucleic acid of (b).

3. The fungal host cell of claim 1, wherein the mutation is caused by T-DNA insertion, homologous recombination or site-directed mutagenesis.

4. The fungal host cell of claim 1, wherein the genome of the fungal host cell has been further modified to include at least two expression cassettes, wherein each expression cassette comprises a promoter operatively linked to a nucleic acid encoding a protein involved in fatty acid biosynthesis and wherein the proteins are selected from the group consisting of:
   (a) an acyl-CoA delta-12 desaturase;
   (b) a stearoyl-CoA-delta-9-desaturase;
   (c) an omega-3 desaturase;
   (d) a fatty acid elongase;
   (e) an acyl-CoA carboxylase (ACC);
   (f) an ATP:citrate lyase (ACL);
   (g) a diacylglycerol acyltransferase (DGA);
   (h) a malic enzyme (MAE); and
   (i) acyl-CoA delta-6 desaturase.

5. The fungal cell of claim 4, wherein the expression cassette further comprises a transcription terminator operatively linked to the nucleic acid encoding a protein involved in fatty acid biosynthesis.

6. The fungal cell of claim 4, wherein the coding sequences for the nucleic acids contain at least 55% C and G, and wherein at least 70% of the codons have a C or G at the $3^{rd}$ position.

7. The fungal cell of claim 4, wherein the coding sequences for the nucleic acids contain 60%-70% C and G, and wherein at least 70% of the codons have a C or G at the $3^{rd}$ position.

8. The fungal cell of claim 4, wherein the proteins are selected from the group consisting of:
   (a) an acyl-CoA delta-12 desaturase having the amino acid sequence set forth in SEQ ID NO:5 or SEQ ID NO:94 or having at least 90% identity to said amino acid sequence;
   (b) a stearoyl-CoA-delta-9-desaturase having the amino acid sequence set forth in SEQ ID NO:8 or having at least 90% identity to said amino acid sequence;
   (c) an omega-3 desaturase having the amino acid sequence set forth in SEQ ID NO:10 or SEQ ID NO:12 or having at least 90% identity to said amino acid sequence;
   (d) a fatty acid elongase having the amino acid sequence set forth in SEQ ID NO:101 or SEQ ID NO: 104 (Elo2) or having at least 90% identity to said amino acid sequence;
   (e) an acyl-CoA carboxylase (ACC1) having the amino acid sequence set forth in SEQ ID NO:91 or having at least 90% identity to said amino acid sequence;
   (f) an ATP:citrate lyase (ACL1) having the amino acid sequence set forth in SEQ ID NO:88 or having at least 90% identity to said amino acid sequence;
   (g) a diacylglycerol acyltransferase (DGA1) having the amino acid sequence set forth in SEQ ID NO:82 or having at least 90% identity to said amino acid sequence;
   (h) a malic enzyme (MAE1) having the amino acid sequence set forth in SEQ ID NO:85 or having at least 90% identity to said amino acid sequence; and
   (i) acyl-CoA delta-16 desaturase having the amino acid sequence set forth in SEQ ID NO:96 or SEQ ID NO:98, or having at least 90% identity to said amino acid sequences.

9. The fungal cell of claim 8, wherein the proteins are encoded by nucleic acids selected from the group consisting of a nucleic acid having the nucleotide sequence set forth in SEQ ID NO:4, 6, 7, 9, 11, 80, 81, 83, 84 86, 87, 89, 90, 92, 93, 96, 98, 99, 100, 102 and 103 or having at least 90% identity to said nucleotide sequence.

10. The fungal host cell of claim 4, wherein the promoter is a promoter isolated from a gene encoding a protein selected from the group consisting of: glyceraldehyde 3-phosphate dehydrogenase (GPD), acyl-CoA carrier protein (ACP), fatty acid desaturase, translation elongation factor (TEF), pyruvate decarboxylase (PDC), enolase (2-phosphoglycerate dehydratase) (ENO), peptidylprolyl isomerase (PPI), acetyl-CoA carboxylase (ACC) and transaldolase.

11. The fungal host cell of claim 10, wherein the promoter is a promoter sequence selected from the group of promoters set forth in SEQ ID NOs:55-79.

12. The fungal host cell of claim 10, wherein the promoter is isolated from a species of the *Rhodosporidium* genera or the *Rhodotorula* genera.

13. The fungal host cell of claim 1 wherein the ELO1 or ELO2 genes, set forth in SEQ ID No. 99 and 102, or a nucleic acid having at least 90% identity to the sequences thereof, has been artificially manipulated to have increased or reduced level of fatty acid elongase activity.

14. A method for producing omega-3 and omega-6 polyunsaturated fatty acids (PUFAs), comprising growing the fungal host cell of claim 1 under conditions suitable to produce PUFAs.

15. A method for producing triacylglyceride (TAG) comprising growing the fungal host cell of claim 1 under conditions suitable to produce TAG.

16. The fungal host cell of claim 1, wherein the total fatty acids are composed of at least 24% alpha-linolenic acid (ALA) or gamma-linolenic acid (GLA).

17. The fungal host cell of claim 1, wherein the total fatty acids are composed of at least 49% alpha-linolenic acid (ALA) or gamma-linolenic acid (GLA).

* * * * *

SEQUENCE LISTING

```
<160> NUMBER OF SEQ ID NOS: 146

<210> SEQ ID NO 1
<211> LENGTH: 2461
<212> TYPE: DNA
<213> ORGANISM: Rhodosporidium toruloides

<400> SEQUENCE: 1
atgcaggaca ctcccatcga cagcatcccc caggtacatc ccacgctgac ccgcgcttct      60
ctcgctcgct tgcgtgtcgt cctcgctttc ggagcttcga aacaggcggg acgaggggat     120
cgtggtgcag cgcgcgcctg gggaggattc gctggacatc ggggatattg ctggaggata     180
ctcaggactt tctggattgg tcccgccctt cccgcgcccg tcgtcgctct ccagcatcca     240
ttccccactc gacactccgg caaactcgcc gctgactctc cccttcgctc attccgcagg     300
cttacgacac cgtcaccaag gcgttcttgt cgggaaagac taggcccatc gcctggcgca     360
aggcgcagat caaaaagctc gggttccttg tcgtgagttc gcggttcttt cgcgcggtct     420
ttgcgacggc tcgtccagtg caggtcgcgc tggtgcgcgt cgtcaatgta gttgcgatga     480
aacctgaccc agcaactccc cctcccacag caagacaacg aagacgcctt cgtccgcgct     540
cttgagcaag actttggccg cccagccttc gagacaatca ccgccgagat caacccgtc      600 aaggctgaga tcaacgaggt ctacgaccac ctcgagaagt gggccaagcc gaggcgcgtc     660
aagacttcgg cgacgtggta cgctaccaag ccgacggtct actcggagcc taagggtgtc     720
acgctcgtta tcgggacgtg gaactgtgcg tgcacttgtt ttgtacgagg ttgagtgtgt     780
gtactgacgg aagatgtcgc cgcagacccg atcacgctcc tcctcgtccc gcttctcggc     840
gccatctctg ccggctgcac cgcgctcgtc aaggtgcctt gccgttcgaa gtccgtcgta     900
ctgcatgtct cactgacact cgtcgctccc acagcccgct gagcaagccc ctcacgtcgc     960
cgcgctcgtc gccgacctcc tgcccaagta cctcgacccc accgccttca tctgcatcaa    1020
cggcgccatc cctcaagcga ccgctctcct caaactcaag ttcgatcaca tcttctacac    1080
cggttcggga acggtcggca agatcgttgc gcgtgcggcg gcggagcacc tttgcccggt    1140
tacgcttgag ttgggggaa agagtccggc ggttgtgctg gatgatgcgg atattgaggt     1200
tgtggcgagg aggatcgttt gggccaagtt taccaacgct gggcaggtgc gtcgcgagaa    1260
ccgggttgtg tcgttggtct cgccgaagcg ggcgcagatg cttagtcatc cgcttgttgt    1320
tgcgcacaga tctgcatctc gacagactac gtcctcacga cccgcagac cgagcccaag     1380 ctcctcgaag ccctcaagcg cgctctcgcc gccttctccg ccaaccccgc cgcctcctcc    1440
tcctcggaaa agtcgtcaac ctcgctcgtg cacaacccga actactcgcg catcatcaac    1500
cagaaccact acaaccgcgt ttcgaagttg cttgatcgca ctaagggcga ggtggttgtt    1560
ggcggcggga gggacgagaa ggagcgcaag atcgaggtca cgatcgtgag gggcgttaag    1620
ccggatgact cgctcatgtc gggtgcgcac tgcggctctc ccctgaaga acgaatgtgg     1680 ctgacgaatg cgaccgagca gaggagattt tcggcccgt cccccgatc gtgaccctcc      1740
```

```
cgacgctcga cgacatggtc aagttcattc agtcgcgcga cacgcctctc gcgctttacg    1800
tcttcacgca gagcaggaag aaccgcgact ttagtgcgtt ccccgcctct ctctcgctcg    1860
ctgaccttcg actgactcgg tggtggatgc agttttttgag cgcactcgct cgggcggatt    1920
cgttcagaac gatgtgctcg ttcagttcat gatccctggg ttgccgttcg gcggtacggg    1980
cgcggcgggc tacggaaaact accacggcag gcggtgcgtc ccgcttcttc ggcaccgtgc    2040
ttccccgagt ccggctgacc tgctcgcacg cagcacctttc gacacgttct cgcacgagcg    2100
cgcgtcggcc aatgtcccca cctggatgga catgatcatg gcgtcgcggt accctcccta    2160
cacccgttcg tccgggtcgt cccttcctct ctgtgctcgc taacacactc gtcccacacg    2220
tgcagagaag aagctgaaga tgctcctgtt cgcgaccaag gcggtgatca agaagcccag    2280
caagtttggc tcgatctcgc gcttgctcaa ggtgattgcc gcgatggtcg ctctcttggc    2340
tgtcagggcc aggctctgac tgacccgtcg tcgtcccacc cctccccttc tccaccactc    2400
ctcttcctct cgggtcttgg gaatcgtgtg cgctgggcag aagttgacgg gacaggcgtg    2460
a                                                                    2461

<210> SEQ ID NO 2
<211> LENGTH: 1515
<212> TYPE: DNA
<213> ORGANISM: Rhodosporidium toruloides
<220> FEATURE:
<221> NAME/KEY: CDS
<222> LOCATION: (1)..(1515)

<400> SEQUENCE: 2 atg gcc gcc atg cag gac act ccc atc gac agc atc ccc cag gct tac     48
Met Ala Ala Met Gln Asp Thr Pro Ile Asp Ser Ile Pro Gln Ala Tyr
1               5                   10                  15 gac acc gtc acc aag gcg ttc ttg tcg gga aag act agg ccc atc gcc     96
Asp Thr Val Thr Lys Ala Phe Leu Ser Gly Lys Thr Arg Pro Ile Ala
            20                  25                  30 tgg cgc aag gcg cag atc aaa aag ctc ggg ttc ctt gtc caa gac aac    144
Trp Arg Lys Ala Gln Ile Lys Lys Leu Gly Phe Leu Val Gln Asp Asn
        35                  40                  45 gaa gac gcc ttc gtc cgc gct ctt gag caa gac ttt ggc cgc cca gcc    192
Glu Asp Ala Phe Val Arg Ala Leu Glu Gln Asp Phe Gly Arg Pro Ala
    50                  55                  60 ttc gag aca atc acc gcc gag atc aac ccc gtc aag gct gag atc aac    240
Phe Glu Thr Ile Thr Ala Glu Ile Asn Pro Val Lys Ala Glu Ile Asn
65                  70                  75                  80 gag gtc tac gac cac ctc gag aag tgg gcc aag ccg agg cgc gtc aag    288
Glu Val Tyr Asp His Leu Glu Lys Trp Ala Lys Pro Arg Arg Val Lys
                85                  90                  95 act tcg gcg acg tgg tac gct acc aag ccg acg gtc tac tcg gag cct    336
Thr Ser Ala Thr Trp Tyr Ala Thr Lys Pro Thr Val Tyr Ser Glu Pro
            100                 105                 110 aag ggt gtc acg ctc gtt atc ggg acg tgg aac tac ccg atc acg ctc    384
Lys Gly Val Thr Leu Val Ile Gly Thr Trp Asn Tyr Pro Ile Thr Leu
        115                 120                 125 ctc ctc gtc ccg ctt ctc ggc gcc atc tct gcc ggc tgc acc gcg ctc    432
Leu Leu Val Pro Leu Leu Gly Ala Ile Ser Ala Gly Cys Thr Ala Leu
    130                 135                 140 gtc aag ccc gct gag caa gcc cct cac gtc gcc gcg ctc gtc gcc gac    480
Val Lys Pro Ala Glu Gln Ala Pro His Val Ala Ala Leu Val Ala Asp
145                 150                 155                 160 ctc ctg ccc aag tac ctc gac ccc acc gcc ttc atc tgc atc aac ggc    528
Leu Leu Pro Lys Tyr Leu Asp Pro Thr Ala Phe Ile Cys Ile Asn Gly
```

```
                    165                 170                 175
gcc atc cct caa gcg acc gct ctc ctc aaa ctc aag ttc gat cac atc    576
Ala Ile Pro Gln Ala Thr Ala Leu Leu Lys Leu Lys Phe Asp His Ile
            180                 185                 190 ttc tac acc ggt tcg gga acg gtc ggc aag atc gtt gcg cgt gcg gcg    624
Phe Tyr Thr Gly Ser Gly Thr Val Gly Lys Ile Val Ala Arg Ala Ala
                195                 200                 205 gcg gag cac ctt tgc ccg gtt acg ctt gag ttg ggg gga aag agt ccg    672
Ala Glu His Leu Cys Pro Val Thr Leu Glu Leu Gly Gly Lys Ser Pro
        210                 215                 220 gcg gtt gtg ctg gat gat gcg gat att gag gtt gtg gcg agg agg atc    720
Ala Val Val Leu Asp Asp Ala Asp Ile Glu Val Val Ala Arg Arg Ile
225                 230                 235                 240 gtt tgg gcc aag ttt acc aac gct ggg cag atc tgc atc tcg aca gac    768
Val Trp Ala Lys Phe Thr Asn Ala Gly Gln Ile Cys Ile Ser Thr Asp
                245                 250                 255 tac gtc ctc acg acc ccg cag acc gag ccc aag ctc ctc gaa gcc ctc    816
Tyr Val Leu Thr Thr Pro Gln Thr Glu Pro Lys Leu Leu Glu Ala Leu
            260                 265                 270 aag cgc gct ctc gcc gcc ttc tcc gcc aac ccc gcc gcc tcc tcc tcc    864
Lys Arg Ala Leu Ala Ala Phe Ser Ala Asn Pro Ala Ala Ser Ser Ser
        275                 280                 285 tcg gaa aag tcg tca acc tcg ctc gtg cac aac ccg aac tac tcg cgc    912
Ser Glu Lys Ser Ser Thr Ser Leu Val His Asn Pro Asn Tyr Ser Arg
    290                 295                 300 atc atc aac cag aac cac tac aac cgc gtt tcg aag ttg ctt gat gcg    960
Ile Ile Asn Gln Asn His Tyr Asn Arg Val Ser Lys Leu Leu Asp Ala
305                 310                 315                 320 act aag ggc gag gtg gtt gtt ggc ggc ggg agg gac gag aag gag cgc   1008
Thr Lys Gly Glu Val Val Val Gly Gly Gly Arg Asp Glu Lys Glu Arg
                325                 330                 335 aag atc gag gtc acg atc gtg agg ggc gtt aag ccg gat gac tcg ctc   1056
Lys Ile Glu Val Thr Ile Val Arg Gly Val Lys Pro Asp Asp Ser Leu
            340                 345                 350 atg tcg gag gag att ttc ggc ccc gtc ccc ccg atc gtg acc ctc ccg   1104
Met Ser Glu Glu Ile Phe Gly Pro Val Pro Pro Ile Val Thr Leu Pro
        355                 360                 365 acg ctc gac gac atg gtc aag ttc att cag tcg cgc gac acg cct ctc   1152
Thr Leu Asp Asp Met Val Lys Phe Ile Gln Ser Arg Asp Thr Pro Leu
    370                 375                 380 gcg ctt tac gtc ttc acg cag agc agg aag aac cgc gac ttt att ttt   1200
Ala Leu Tyr Val Phe Thr Gln Ser Arg Lys Asn Arg Asp Phe Ile Phe
385                 390                 395                 400 gag cgc act cgc tcg ggc gga ttc gtt cag aac gat gtg ctc gtt cag   1248
Glu Arg Thr Arg Ser Gly Gly Phe Val Gln Asn Asp Val Leu Val Gln
                405                 410                 415 ttc atg atc cct ggt ttg ccg ttc ggc ggt acg ggc gcg gcg ggc tac   1296
Phe Met Ile Pro Gly Leu Pro Phe Gly Gly Thr Gly Ala Ala Gly Tyr
            420                 425                 430 gga aac tac cac ggc agg cgc acc ttc gac acg ttc tcg cac gag cgc   1344
Gly Asn Tyr His Gly Arg Arg Thr Phe Asp Thr Phe Ser His Glu Arg
        435                 440                 445 gcg tcg gcc aat gtc ccc acc tgg atg gac atg atc atg gcg tcg cgg   1392
Ala Ser Ala Asn Val Pro Thr Trp Met Asp Met Ile Met Ala Ser Arg
    450                 455                 460 tac cct ccc tac acc cag aag aag ctg aag atg ctc ctg ttc gcg acc   1440
Tyr Pro Pro Tyr Thr Gln Lys Lys Leu Lys Met Leu Leu Phe Ala Thr
465                 470                 475                 480 aag gcg gtg atc aag aag ccc agc aag ttt ggc tcg atc tcg cgc ttg   1488
```

```
       Lys Ala Val Ile Lys Lys Pro Ser Lys Phe Gly Ser Ile Ser Arg Leu
                       485                 490                 495 ctc aag aag ttg acg gga cag gcg tga                                       1515
Leu Lys Lys Leu Thr Gly Gln Ala
                500

<210> SEQ ID NO 3
<211> LENGTH: 504
<212> TYPE: PRT
<213> ORGANISM: Rhodosporidium toruloides

<400> SEQUENCE: 3

Met Ala Ala Met Gln Asp Thr Pro Ile Asp Ser Ile Pro Gln Ala Tyr
1               5                  10                  15

Asp Thr Val Thr Lys Ala Phe Leu Ser Gly Lys Thr Arg Pro Ile Ala
                20                  25                  30

Trp Arg Lys Ala Gln Ile Lys Lys Leu Gly Phe Leu Val Gln Asp Asn
            35                  40                  45

Glu Asp Ala Phe Val Arg Ala Leu Glu Gln Asp Phe Gly Arg Pro Ala
50                  55                  60

Phe Glu Thr Ile Thr Ala Glu Ile Asn Pro Val Lys Ala Glu Ile Asn
65                  70                  75                  80

Glu Val Tyr Asp His Leu Glu Lys Trp Ala Lys Pro Arg Arg Val Lys
                85                  90                  95

Thr Ser Ala Thr Trp Tyr Ala Thr Lys Pro Thr Val Tyr Ser Glu Pro
            100                 105                 110

Lys Gly Val Thr Leu Val Ile Gly Thr Trp Asn Tyr Pro Ile Thr Leu
        115                 120                 125

Leu Leu Val Pro Leu Leu Gly Ala Ile Ser Ala Gly Cys Thr Ala Leu
130                 135                 140

Val Lys Pro Ala Glu Gln Ala Pro His Val Ala Ala Leu Val Ala Asp
145                 150                 155                 160

Leu Leu Pro Lys Tyr Leu Asp Pro Thr Ala Phe Ile Cys Ile Asn Gly
                165                 170                 175

Ala Ile Pro Gln Ala Thr Ala Leu Leu Lys Leu Lys Phe Asp His Ile
            180                 185                 190

Phe Tyr Thr Gly Ser Gly Thr Val Gly Lys Ile Val Ala Arg Ala Ala
        195                 200                 205

Ala Glu His Leu Cys Pro Val Thr Leu Glu Leu Gly Gly Lys Ser Pro
210                 215                 220

Ala Val Val Leu Asp Asp Ala Asp Ile Glu Val Val Ala Arg Arg Ile
225                 230                 235                 240

Val Trp Ala Lys Phe Thr Asn Ala Gly Gln Ile Cys Ile Ser Thr Asp
                245                 250                 255

Tyr Val Leu Thr Thr Pro Gln Thr Glu Pro Lys Leu Leu Glu Ala Leu
            260                 265                 270

Lys Arg Ala Leu Ala Ala Phe Ser Ala Asn Pro Ala Ala Ser Ser Ser
        275                 280                 285

Ser Glu Lys Ser Ser Thr Ser Leu Val His Asn Pro Asn Tyr Ser Arg
    290                 295                 300

Ile Ile Asn Gln Asn His Tyr Asn Arg Val Ser Lys Leu Leu Asp Ala
305                 310                 315                 320

Thr Lys Gly Glu Val Val Gly Gly Gly Arg Asp Glu Lys Glu Arg
                325                 330                 335

Lys Ile Glu Val Thr Ile Val Arg Gly Val Lys Pro Asp Asp Ser Leu
```

-continued

```
                     340                 345                 350
Met Ser Glu Glu Ile Phe Gly Pro Val Pro Pro Ile Val Thr Leu Pro
            355                 360                 365

Thr Leu Asp Asp Met Val Lys Phe Ile Gln Ser Arg Asp Thr Pro Leu
        370                 375                 380

Ala Leu Tyr Val Phe Thr Gln Ser Arg Lys Asn Arg Asp Phe Ile Phe
385                 390                 395                 400

Glu Arg Thr Arg Ser Gly Gly Phe Val Gln Asn Asp Val Leu Val Gln
                405                 410                 415

Phe Met Ile Pro Gly Leu Pro Phe Gly Gly Thr Gly Ala Ala Gly Tyr
            420                 425                 430

Gly Asn Tyr His Gly Arg Arg Thr Phe Asp Thr Phe Ser His Glu Arg
        435                 440                 445

Ala Ser Ala Asn Val Pro Thr Trp Met Asp Met Ile Met Ala Ser Arg
    450                 455                 460

Tyr Pro Pro Tyr Thr Gln Lys Lys Leu Lys Met Leu Leu Phe Ala Thr
465                 470                 475                 480

Lys Ala Val Ile Lys Lys Pro Ser Lys Phe Gly Ser Ile Ser Arg Leu
                485                 490                 495

Leu Lys Lys Leu Thr Gly Gln Ala
            500
```

```
<210> SEQ ID NO 4
<211> LENGTH: 1206
<212> TYPE: DNA
<213> ORGANISM: Mortierella alpine
<220> FEATURE:
<221> NAME/KEY: CDS
<222> LOCATION: (1)..(1206)

<400> SEQUENCE: 4
```

```
atg gcc ccg ccg aac acc atc gac gcc ggc ctc acc cag cgc cac atc      48
Met Ala Pro Pro Asn Thr Ile Asp Ala Gly Leu Thr Gln Arg His Ile
1               5                   10                  15 tcg acc tcg gcc gcc ccg aac tcg gcc aag ccg acc ttc gag cgc aac      96
Ser Thr Ser Ala Ala Pro Asn Ser Ala Lys Pro Thr Phe Glu Arg Asn
                20                  25                  30 tac cag ctc ccg gag ttc acc atc aag gag atc cgc gag tgc atc ccg     144
Tyr Gln Leu Pro Glu Phe Thr Ile Lys Glu Ile Arg Glu Cys Ile Pro
            35                  40                  45 gcc cac tgc ttc gag cgc tcg ggc ctc cgc ggc ctc tgc cac gtc gcc     192
Ala His Cys Phe Glu Arg Ser Gly Leu Arg Gly Leu Cys His Val Ala
        50                  55                  60 atc gac ctc acc tgg gcc tcg ctc ctc ttc ctc gcc gcc acc cag atc     240
Ile Asp Leu Thr Trp Ala Ser Leu Leu Phe Leu Ala Ala Thr Gln Ile
65                  70                  75                  80 gac aag ttc gag aac ccg ctc atc cgc tac ctc gcc tgg ccg gtc tac     288
Asp Lys Phe Glu Asn Pro Leu Ile Arg Tyr Leu Ala Trp Pro Val Tyr
                85                  90                  95 tgg atc atg cag ggc atc gtc tgc acc ggc atc tgg gtc ctc gcc cac     336
Trp Ile Met Gln Gly Ile Val Cys Thr Gly Ile Trp Val Leu Ala His
            100                 105                 110 gag tgc ggc cac cag tcg ttc tcg acc tcg aag acc ctc aac aac acc     384
Glu Cys Gly His Gln Ser Phe Ser Thr Ser Lys Thr Leu Asn Asn Thr
        115                 120                 125 gtc ggc tgg atc ctc cac tcg atg ctc ctc gtc ccg tac cac tcg tgg     432
Val Gly Trp Ile Leu His Ser Met Leu Leu Val Pro Tyr His Ser Trp
130                 135                 140
```

```
cgc atc tcg cac tcg aag cac cac aag gcc acc ggc cac atg acc aag        480
Arg Ile Ser His Ser Lys His His Lys Ala Thr Gly His Met Thr Lys
145                 150                 155                 160 gac cag gtc ttc gtc ccg aag acc cgc acc cag gtc ggc ctc ccg ccg        528
Asp Gln Val Phe Val Pro Lys Thr Arg Thr Gln Val Gly Leu Pro Pro
                165                 170                 175 aag gag tcg gcc gcc gcc acc gtc cag gag gag gag gac atg tcg gtc        576
Lys Glu Ser Ala Ala Ala Thr Val Gln Glu Glu Glu Asp Met Ser Val
            180                 185                 190 cac ctc gac gag gag gcc ccg atc gtc acc ctc ttc tgg atg gtc atc        624
His Leu Asp Glu Glu Ala Pro Ile Val Thr Leu Phe Trp Met Val Ile
        195                 200                 205 cag ttc ctc ttc ggc tgg ccg gcc tac ctc atc atg aac gcc tcg ggc        672
Gln Phe Leu Phe Gly Trp Pro Ala Tyr Leu Ile Met Asn Ala Ser Gly
    210                 215                 220 cag gac tac ggc cgc tgg acc tcg cac ttc cac acc tac tcg ccg atc        720
Gln Asp Tyr Gly Arg Trp Thr Ser His Phe His Thr Tyr Ser Pro Ile
225                 230                 235                 240 ttc gag ccg cgc aac ttc ttc gac atc atc ctc tcg gac ctc ggc gtc        768
Phe Glu Pro Arg Asn Phe Phe Asp Ile Ile Leu Ser Asp Leu Gly Val
                245                 250                 255 ctc gcc acc ctc ggc gcc ctc atc tac gcc tcg atg cag ctc tcg ctc        816
Leu Ala Thr Leu Gly Ala Leu Ile Tyr Ala Ser Met Gln Leu Ser Leu
            260                 265                 270 ctc acc gtc acc aag tac tac atc atc ccg tac ctc ttc gtc aac ttc        864
Leu Thr Val Thr Lys Tyr Tyr Ile Ile Pro Tyr Leu Phe Val Asn Phe
        275                 280                 285 tgg ctc gtc ctc atc acc ttc ctc cag cac acc gac ccg aag ctc ccg        912
Trp Leu Val Leu Ile Thr Phe Leu Gln His Thr Asp Pro Lys Leu Pro
    290                 295                 300 cac tac cgc gag ggc gcc tgg aac ttc cag cgc ggc gcc ctc tgc acc        960
His Tyr Arg Glu Gly Ala Trp Asn Phe Gln Arg Gly Ala Leu Cys Thr
305                 310                 315                 320 gtc gac cgc tcg ttc ggc aag ttc ctc gac cac atg ttc cac ggc atc       1008
Val Asp Arg Ser Phe Gly Lys Phe Leu Asp His Met Phe His Gly Ile
                325                 330                 335 gtc cac acc cac gtc gcc cac cac ctc ttc tcg cag atg ccg ttc tac       1056
Val His Thr His Val Ala His His Leu Phe Ser Gln Met Pro Phe Tyr
            340                 345                 350 cac gcc gag gag gcc acc tac cac ctc aag aag ctc ctc ggc gag tac       1104
His Ala Glu Glu Ala Thr Tyr His Leu Lys Lys Leu Leu Gly Glu Tyr
        355                 360                 365 tac atc tac gac gcc tcg ccg atc gtc gtc gcc gtc tgg aag tcg ttc       1152
Tyr Ile Tyr Asp Ala Ser Pro Ile Val Val Ala Val Trp Lys Ser Phe
    370                 375                 380 cgc gag tgc cgc ttc gtc gag gac cac ggc gac gtc gtc ttc ttc aag       1200
Arg Glu Cys Arg Phe Val Glu Asp His Gly Asp Val Val Phe Phe Lys
385                 390                 395                 400 aag tag                                                                1206
Lys

<210> SEQ ID NO 5
<211> LENGTH: 401
<212> TYPE: PRT
<213> ORGANISM: Mortierella alpine

<400> SEQUENCE: 5

Met Ala Pro Pro Asn Thr Ile Asp Ala Gly Leu Thr Gln Arg His Ile
1               5                   10                  15

Ser Thr Ser Ala Ala Pro Asn Ser Ala Lys Pro Thr Phe Glu Arg Asn
```

-continued

```
                20                  25                  30
Tyr Gln Leu Pro Glu Phe Thr Ile Lys Glu Ile Arg Glu Cys Ile Pro
             35                  40                  45
Ala His Cys Phe Glu Arg Ser Gly Leu Arg Gly Leu Cys His Val Ala
         50                  55                  60
Ile Asp Leu Thr Trp Ala Ser Leu Leu Phe Leu Ala Ala Thr Gln Ile
 65                  70                  75                  80
Asp Lys Phe Glu Asn Pro Leu Ile Arg Tyr Leu Ala Trp Pro Val Tyr
                 85                  90                  95
Trp Ile Met Gln Gly Ile Val Cys Thr Gly Ile Trp Val Leu Ala His
                100                 105                 110
Glu Cys Gly His Gln Ser Phe Ser Thr Ser Lys Thr Leu Asn Asn Thr
            115                 120                 125
Val Gly Trp Ile Leu His Ser Met Leu Leu Val Pro Tyr His Ser Trp
        130                 135                 140
Arg Ile Ser His Ser Lys His His Lys Ala Thr Gly His Met Thr Lys
145                 150                 155                 160
Asp Gln Val Phe Val Pro Lys Thr Arg Thr Gln Val Gly Leu Pro Pro
                165                 170                 175
Lys Glu Ser Ala Ala Ala Thr Val Gln Glu Glu Asp Met Ser Val
            180                 185                 190
His Leu Asp Glu Glu Ala Pro Ile Val Thr Leu Phe Trp Met Val Ile
        195                 200                 205
Gln Phe Leu Phe Gly Trp Pro Ala Tyr Leu Ile Met Asn Ala Ser Gly
    210                 215                 220
Gln Asp Tyr Gly Arg Trp Thr Ser His Phe His Thr Tyr Ser Pro Ile
225                 230                 235                 240
Phe Glu Pro Arg Asn Phe Phe Asp Ile Ile Leu Ser Asp Leu Gly Val
                245                 250                 255
Leu Ala Thr Leu Gly Ala Leu Ile Tyr Ala Ser Met Gln Leu Ser Leu
            260                 265                 270
Leu Thr Val Thr Lys Tyr Tyr Ile Ile Pro Tyr Leu Phe Val Asn Phe
        275                 280                 285
Trp Leu Val Leu Ile Thr Phe Leu Gln His Thr Asp Pro Lys Leu Pro
    290                 295                 300
His Tyr Arg Glu Gly Ala Trp Asn Phe Gln Arg Gly Ala Leu Cys Thr
305                 310                 315                 320
Val Asp Arg Ser Phe Gly Lys Phe Leu Asp His Met Phe His Gly Ile
                325                 330                 335
Val His Thr His Val Ala His His Leu Phe Ser Gln Met Pro Phe Tyr
            340                 345                 350
His Ala Glu Glu Ala Thr Tyr His Leu Lys Lys Leu Leu Gly Glu Tyr
        355                 360                 365
Tyr Ile Tyr Asp Ala Ser Pro Ile Val Val Ala Val Trp Lys Ser Phe
    370                 375                 380
Arg Glu Cys Arg Phe Val Glu Asp His Gly Asp Val Val Phe Phe Lys
385                 390                 395                 400
Lys
```

<210> SEQ ID NO 6
<211> LENGTH: 2760
<212> TYPE: DNA
<213> ORGANISM: Rhodosporidium toruloides

<400> SEQUENCE: 6

```
caccgcttcc cggagaactt tgctgtactc tgcttctccc ttcacactct cacacccact      60
cacacaccct tccatccaca cacaagctat ccgcacacct ctcacacccg accccagctc     120
gccccatcct cttcgcaccc ggctcatcgc cacacacgca atgactgcct cgtcggcact     180
cgagacctcg ctcccgcact ctgtcgggcc cgagtctgcg actaccaccg caaagccgcc     240
ccgtgcgccg ctcaggatgc gtcaccccga ctacacccag accgacgtcc tcgagtcgtc     300
agactcggac gcagcgtcgg attccgaggg cgagacgacg gctgtcgacg acgggaccta     360
cgaggacgat aactacgtcc gcaaggtcct cagcaaggag aagccgctcc cgcccatcac     420
ctggaagaac atccaccgca acatccagtg gatctcgacc ctcgccctca ccatcgtgcc     480
cctcctctcg atctacggag cgttcacgac gcccctgaag tggcagacgg cggtctggag     540
tgtcgtctac tactacttca ccggtctcgg gtgagtcgcc gcaccctttc ctcgcctctc     600
ctccctcgct ctctacttcc ggcgcctccg ttcttcgttc atgatcgtct gtaagacgtg     660
tttgagcttg gaggggcgtc agatggcccg gcggacgagt cgcatgtcga aaaccgtcg     720
ctgaccttct cttcgccttt tcctcctcct ccattgtccc cgatcgtccc gatccgtctg     780
ttctcgttct acagcatcac cgcaggctac acaggctgt acgtgtcatt tactctgatc     840
tcgaggcgtt gagcgccgaa aaacggactc tgaactgacg aaaactcgct tttctcgcct     900
tcctcgcctg taggtgggcc cacaggtcct acactgcctc cctgcctctc cagtacttcc     960
tggcacttgg cggaagcggc gcagtggagg gttctgtgaa atggtgggcc cgaggacacc    1020
gcgcacacca ccgctacacc gacacggacc tcgacccgta tcagcgcag aagggcttct    1080
ggtgggcaca cctcggctgg atgattgtca agccgcgccg tcgtcccggt gtcgccgatg    1140
tctccgacct caacaacaac ccagtcgtca agtggcagca ccgcttctac ctcccgctca    1200
tcctcggcat gggcttcatc ttccctacca tcgtcgctgg actcggctgg ggcgacttcc    1260
gcggcggatt ttcttcgcc ggcgctgctc gcctcctctt tgtccaccac gtgcgttctc    1320
gccttcctcg tctctcctcc ttcgttcgct gacgttttcg tattgcacag tcgacgttct    1380
gcgtcaactc gctcgcacac tggctcggcg agacgccgtt tgacgacaag cacacgccga    1440
aggaccactg gctcaccgcg ctcgcgacgg tcggcgaggg ctaccacaac ttcgtgagtc    1500
tcccgcccgc tctctgcgtg atctacggcg tcttcgtgta ctgctgccac agtcgcgacg    1560
tcgttcgagt cgtttgccat cgacttcgct ctcctcgacc tcccgctgac cttctccctt    1620
cccctccagc accacgagtt cccctccgac taccgcaacg cgctcagatg gtggcagtat    1680
gatccgacta agtgtttcat ttacgcgatg tcgaaactcg gattggcgtc gcagctcaag    1740
acgttccccg acaacgagat caagaagggt cagtacgcca tgacgctcaa ggctgtcgcg    1800
cgcgaggcgg agaacatcga gtggcccaag tcgtcgaacc acttgcctgt gctcacctgg    1860
gatgagtgta cgttcagctt tcatcgtcgt cgacggcgac ctcgacccttc ctgaacttcc    1920
agcgctgact ttcgtcccccg ctcctctcgc tgcagtcca ggaggcctgc aagactcgcc    1980
agctcctcgt tgtcgccggt ttcatccacg atgtcagcac cttcatcgac cagcaccctg    2040
gcggtgccgc cttgatcaag acccgtctcg gccgcgatgc gacgaccgcc ttctacggtg    2100
gctactacga gtgcgtcttc acattctcct gcatcatctt cgctcaagtc gctgacgctc    2160
tcgctcccgc agccactcga acggcgcagc caacttgctc gcccagtacc gtgtcggcgt    2220
catcgagggc ggctacgagg tcgagcacat gaagaagtac tctgaggtcg tcgagaacct    2280
caagaagcac ggcgccgacg gcgtggccgg caagagcgcc gacctcgcca agggtccgaa    2340
```

-continued

```
gcagatgtcg gtcatcaagg gcgaccctca gctcaagggc gcgccgctcg agacgctcgc    2400
caagccgcct accttcagcg agaccaacct tttgggcggt ctcagcctga cggtcaaggc    2460
gtaatggccc gtcaccgcca tcggttcaag ggagagtcgt cgaccgactc ttccgttcgt    2520
cgcttcaggt tcatccgtct tcgcatgctt agagaccctc ttcctcgttg ttttgtgcat    2580
cagttgcccg cagtcgtccc ttaacgagcc cactactacc ctttccatgc ccagtattct    2640 tgccccgcc ccttcgttc tttgatacgt ccaaccacct cgctctttcg ctgtagctct      2700
acttcgttct ctcccttgcg ggttgcccgc ttactccgca tggaaacttg accagtgtgc    2760
```

<210> SEQ ID NO 7
<211> LENGTH: 1638
<212> TYPE: DNA
<213> ORGANISM: Rhodosporidium toruloides
<220> FEATURE:
<221> NAME/KEY: CDS
<222> LOCATION: (1)..(1638)

<400> SEQUENCE: 7

```
atg act gcc tcg tcg gca ctc gag acc tcg ctc ccg cac tct gtc ggg      48
Met Thr Ala Ser Ser Ala Leu Glu Thr Ser Leu Pro His Ser Val Gly
1               5                   10                  15 ccc gag tct gcg act acc acc gca aag ccg ccc cgt gcg ccg ctc agg      96
Pro Glu Ser Ala Thr Thr Thr Ala Lys Pro Pro Arg Ala Pro Leu Arg
                20                  25                  30 atg cgt cac ccc gac tac acc cag acc gac gtc ctc gag tcg tca gac     144
Met Arg His Pro Asp Tyr Thr Gln Thr Asp Val Leu Glu Ser Ser Asp
            35                  40                  45 tcg gac gca gcg tcg gat tcc gag ggc gag acg acg gct gtc gac gac     192
Ser Asp Ala Ala Ser Asp Ser Glu Gly Glu Thr Thr Ala Val Asp Asp
        50                  55                  60 ggg acc tac gag gac gac aac tac gtc cgc aag gtc ctc agc aag gag     240
Gly Thr Tyr Glu Asp Asp Asn Tyr Val Arg Lys Val Leu Ser Lys Glu
65                  70                  75                  80 aag ccg ctc ccg ccc atc acc tgg aag aac atc cac cgc aac atc cag     288
Lys Pro Leu Pro Pro Ile Thr Trp Lys Asn Ile His Arg Asn Ile Gln
                85                  90                  95 tgg atc tcg acc ctc gcc ctc acc atc gtg ccc ctc ctc tcg atc tac     336
Trp Ile Ser Thr Leu Ala Leu Thr Ile Val Pro Leu Leu Ser Ile Tyr
            100                 105                 110 gga gcg ttc acg acg ccc ctg aag tgg cag acg gcg gtc tgg agt gtc     384
Gly Ala Phe Thr Thr Pro Leu Lys Trp Gln Thr Ala Val Trp Ser Val
        115                 120                 125 gtc tac tac tac ttc acc ggt ctc ggc atc acc gca ggc tac cac agg     432
Val Tyr Tyr Tyr Phe Thr Gly Leu Gly Ile Thr Ala Gly Tyr His Arg
    130                 135                 140 ctg tgg gcc cac agg tcc tac act gcc tcc ctg cct ctc cag tac ttc     480
Leu Trp Ala His Arg Ser Tyr Thr Ala Ser Leu Pro Leu Gln Tyr Phe
145                 150                 155                 160 ctg gca ctt ggc gga agc ggc gca gtc gag ggt tct gtg aaa tgg tgg     528
Leu Ala Leu Gly Gly Ser Gly Ala Val Glu Gly Ser Val Lys Trp Trp
                165                 170                 175 gcc cga gga cac cgc gca cac cac cgc tac acc gac acg gac ctc gac     576
Ala Arg Gly His Arg Ala His His Arg Tyr Thr Asp Thr Asp Leu Asp
            180                 185                 190 ccg tac tca gcg cag aag ggc ttc tgg tgg gca cac ctc ggc tgg atg     624
Pro Tyr Ser Ala Gln Lys Gly Phe Trp Trp Ala His Leu Gly Trp Met
        195                 200                 205 att gtc aag ccg cgc cgt cgt ccc ggt gtc gcc gat gtc tcc gac ctc     672
```

```
            Ile Val Lys Pro Arg Arg Arg Pro Gly Val Ala Asp Val Ser Asp Leu
                210                 215                 220 aac aac aac cca gtc gtc aag tgg cag cac cgc ttc tac ctc ccg ctc         720
Asn Asn Asn Pro Val Val Lys Trp Gln His Arg Phe Tyr Leu Pro Leu
225                 230                 235                 240 atc ctc ggc atg ggc ttc atc ttc cct acc atc gtc gct gga ctc ggc         768
Ile Leu Gly Met Gly Phe Ile Phe Pro Thr Ile Val Ala Gly Leu Gly
                245                 250                 255 tgg ggc gac ttc cgc ggc gga ttt ttc ttc gcc ggc gct gct cgc ctc         816
Trp Gly Asp Phe Arg Gly Gly Phe Phe Phe Ala Gly Ala Ala Arg Leu
        260                 265                 270 ctc ttt gtc cac cac tcg acg ttc tgc gtc aac tcg ctc gca cac tgg         864
Leu Phe Val His His Ser Thr Phe Cys Val Asn Ser Leu Ala His Trp
        275                 280                 285 ctc ggc gag acg ccg ttt gac gac aag cac acg ccg aag gac cac tgg         912
Leu Gly Glu Thr Pro Phe Asp Asp Lys His Thr Pro Lys Asp His Trp
    290                 295                 300 ctc acc gcg ctc gcg acg gtc ggc gag ggc tac cac aac ttc cac cac         960
Leu Thr Ala Leu Ala Thr Val Gly Glu Gly Tyr His Asn Phe His His
305                 310                 315                 320 gag ttc ccc tcc gac tac cgc aac gcg ctc aga tgg tgg cag tat gat        1008
Glu Phe Pro Ser Asp Tyr Arg Asn Ala Leu Arg Trp Trp Gln Tyr Asp
                325                 330                 335 ccg act aag tgt ttc att tac gcg atg tcg aaa ctc gga ttg gcg tcg        1056
Pro Thr Lys Cys Phe Ile Tyr Ala Met Ser Lys Leu Gly Leu Ala Ser
                340                 345                 350 cag ctc aag acg ttc ccc gac aac gag atc aag aag ggt cag tac gcc        1104
Gln Leu Lys Thr Phe Pro Asp Asn Glu Ile Lys Lys Gly Gln Tyr Ala
        355                 360                 365 atg acg ctc aag gct gtc gcg cgc gag gcg gag aac atc gag tgg ccc        1152
Met Thr Leu Lys Ala Val Ala Arg Glu Ala Glu Asn Ile Glu Trp Pro
        370                 375                 380 aag tcg tcg aac cac ttg cct gtg ctc acc tgg gat gag ttc cag gag        1200
Lys Ser Ser Asn His Leu Pro Val Leu Thr Trp Asp Glu Phe Gln Glu
385                 390                 395                 400 gcc tgc aag act cgc cag ctc ctc gtt gtc gcc ggt ttc atc cac gat        1248
Ala Cys Lys Thr Arg Gln Leu Leu Val Val Ala Gly Phe Ile His Asp
                405                 410                 415 gtc agc acc ttc atc gac cag cac cct ggc ggt gcc ggc ttg atc aag        1296
Val Ser Thr Phe Ile Asp Gln His Pro Gly Gly Ala Gly Leu Ile Lys
                420                 425                 430 acc cgt ctc ggc cgc gat gcg acg acc gcc ttc tac ggt ggc tac tac        1344
Thr Arg Leu Gly Arg Asp Ala Thr Thr Ala Phe Tyr Gly Gly Tyr Tyr
        435                 440                 445 gac cac tcg aac ggc gca gcc aac ttg ctc gcc cag tac cgt gtc ggc        1392
Asp His Ser Asn Gly Ala Ala Asn Leu Leu Ala Gln Tyr Arg Val Gly
        450                 455                 460 gtc atc gag ggc ggc tac gag gtc gag cac atg aag aag tac tct gag        1440
Val Ile Glu Gly Gly Tyr Glu Val Glu His Met Lys Lys Tyr Ser Glu
465                 470                 475                 480 gtc gtc gag aac ctc aag aag cac ggc gcc gac ggc gtg gcc ggc aag        1488
Val Val Glu Asn Leu Lys Lys His Gly Ala Asp Gly Val Ala Gly Lys
                485                 490                 495 agc gcc gac ctc gcc aag ggt ccg aag cag atg tcg gtc atc aag ggc        1536
Ser Ala Asp Leu Ala Lys Gly Pro Lys Gln Met Ser Val Ile Lys Gly
                500                 505                 510 gac cct cag ctc aag ggc gcg ccg ctc gag acg ctc gcc aag ccg cct        1584
Asp Pro Gln Leu Lys Gly Ala Pro Leu Glu Thr Leu Ala Lys Pro Pro
        515                 520                 525
```

```
acc ttc agc gag acc aac ctt ttg ggc ggt ctc agc ctg acg gtc aag    1632
Thr Phe Ser Glu Thr Asn Leu Leu Gly Gly Leu Ser Leu Thr Val Lys
530                 535                 540 gcg taa                                                            1638
Ala
545

<210> SEQ ID NO 8
<211> LENGTH: 545
<212> TYPE: PRT
<213> ORGANISM: Rhodosporidium toruloides

<400> SEQUENCE: 8

Met Thr Ala Ser Ser Ala Leu Glu Thr Ser Leu Pro His Ser Val Gly
1               5                   10                  15

Pro Glu Ser Ala Thr Thr Thr Ala Lys Pro Pro Arg Ala Pro Leu Arg
            20                  25                  30

Met Arg His Pro Asp Tyr Thr Gln Thr Asp Val Leu Glu Ser Ser Asp
        35                  40                  45

Ser Asp Ala Ala Ser Asp Ser Glu Gly Glu Thr Thr Ala Val Asp Asp
    50                  55                  60

Gly Thr Tyr Glu Asp Asp Asn Tyr Val Arg Lys Val Leu Ser Lys Glu
65                  70                  75                  80

Lys Pro Leu Pro Pro Ile Thr Trp Lys Asn Ile His Arg Asn Ile Gln
                85                  90                  95

Trp Ile Ser Thr Leu Ala Leu Thr Ile Val Pro Leu Leu Ser Ile Tyr
            100                 105                 110

Gly Ala Phe Thr Thr Pro Leu Lys Trp Gln Thr Ala Val Trp Ser Val
        115                 120                 125

Val Tyr Tyr Tyr Phe Thr Gly Leu Gly Ile Thr Ala Gly Tyr His Arg
    130                 135                 140

Leu Trp Ala His Arg Ser Tyr Thr Ala Ser Leu Pro Leu Gln Tyr Phe
145                 150                 155                 160

Leu Ala Leu Gly Gly Ser Gly Ala Val Glu Gly Ser Val Lys Trp Trp
                165                 170                 175

Ala Arg Gly His Arg Ala His His Arg Tyr Thr Asp Thr Asp Leu Asp
            180                 185                 190

Pro Tyr Ser Ala Gln Lys Gly Phe Trp Trp Ala His Leu Gly Trp Met
        195                 200                 205

Ile Val Lys Pro Arg Arg Pro Gly Val Ala Asp Val Ser Asp Leu
    210                 215                 220

Asn Asn Asn Pro Val Val Lys Trp Gln His Arg Phe Tyr Leu Pro Leu
225                 230                 235                 240

Ile Leu Gly Met Gly Phe Ile Phe Pro Thr Ile Val Ala Gly Leu Gly
                245                 250                 255

Trp Gly Asp Phe Arg Gly Gly Phe Phe Phe Ala Gly Ala Ala Arg Leu
            260                 265                 270

Leu Phe Val His His Ser Thr Phe Cys Val Asn Ser Leu Ala His Trp
        275                 280                 285

Leu Gly Glu Thr Pro Phe Asp Asp Lys His Thr Pro Lys Asp His Trp
    290                 295                 300

Leu Thr Ala Leu Ala Thr Val Gly Glu Gly Tyr His Asn Phe His His
305                 310                 315                 320

Glu Phe Pro Ser Asp Tyr Arg Asn Ala Leu Arg Trp Trp Gln Tyr Asp
                325                 330                 335
```

```
Pro Thr Lys Cys Phe Ile Tyr Ala Met Ser Lys Leu Gly Leu Ala Ser
            340                 345                 350

Gln Leu Lys Thr Phe Pro Asp Asn Glu Ile Lys Lys Gly Gln Tyr Ala
        355                 360                 365

Met Thr Leu Lys Ala Val Ala Arg Glu Ala Glu Asn Ile Glu Trp Pro
    370                 375                 380

Lys Ser Ser Asn His Leu Pro Val Leu Thr Trp Asp Glu Phe Gln Glu
385                 390                 395                 400

Ala Cys Lys Thr Arg Gln Leu Leu Val Val Ala Gly Phe Ile His Asp
                405                 410                 415

Val Ser Thr Phe Ile Asp Gln His Pro Gly Gly Ala Gly Leu Ile Lys
            420                 425                 430

Thr Arg Leu Gly Arg Asp Ala Thr Thr Ala Phe Tyr Gly Gly Tyr Tyr
        435                 440                 445

Asp His Ser Asn Gly Ala Ala Asn Leu Leu Ala Gln Tyr Arg Val Gly
    450                 455                 460

Val Ile Glu Gly Gly Tyr Glu Val Glu His Met Lys Lys Tyr Ser Glu
465                 470                 475                 480

Val Val Glu Asn Leu Lys Lys His Gly Ala Asp Gly Val Ala Gly Lys
                485                 490                 495

Ser Ala Asp Leu Ala Lys Gly Pro Lys Gln Met Ser Val Ile Lys Gly
            500                 505                 510

Asp Pro Gln Leu Lys Gly Ala Pro Leu Glu Thr Leu Ala Lys Pro Pro
        515                 520                 525

Thr Phe Ser Glu Thr Asn Leu Leu Gly Gly Leu Ser Leu Thr Val Lys
    530                 535                 540

Ala
545

<210> SEQ ID NO 9
<211> LENGTH: 1164
<212> TYPE: DNA
<213> ORGANISM: Linum usitatissimum
<220> FEATURE:
<221> NAME/KEY: CDS
<222> LOCATION: (1)..(1164)

<400> SEQUENCE: 9 atg aag cag cag cag tac aag gac acc ccg atc ctc aac ggc gtc aac    48
Met Lys Gln Gln Gln Tyr Lys Asp Thr Pro Ile Leu Asn Gly Val Asn
1               5                   10                  15 ggc ttc cac gcc aag gag gag gag gag gag gac ttc gac ctc tcg         96
Gly Phe His Ala Lys Glu Glu Glu Glu Glu Asp Phe Asp Leu Ser
            20                  25                  30 aac ccg ccg ccg ttc aac atc ggc cag atc cgc gcc gcc atc ccg aag    144
Asn Pro Pro Pro Phe Asn Ile Gly Gln Ile Arg Ala Ala Ile Pro Lys
        35                  40                  45 cac tgc tgg gtc aag aac ccg tgg cgc tcg ctc acc tac gtc ttc cgc    192
His Cys Trp Val Lys Asn Pro Trp Arg Ser Leu Thr Tyr Val Phe Arg
    50                  55                  60 gac gtc gtc gtc gtc ttc gcc ctc gcc gcc gcc gcc ttc tac ttc aac    240
Asp Val Val Val Val Phe Ala Leu Ala Ala Ala Ala Phe Tyr Phe Asn
65                  70                  75                  80 tcg tgg ctc ttc tgg ccg ctc tac tgg ttc gcc cag ggc acc atg ttc    288
Ser Trp Leu Phe Trp Pro Leu Tyr Trp Phe Ala Gln Gly Thr Met Phe
                85                  90                  95 tgg gcc atc ttc gtc ctc ggc cac gac tgc ggc cac ggc tcg ttc tcg    336
Trp Ala Ile Phe Val Leu Gly His Asp Cys Gly His Gly Ser Phe Ser
```

```
                    100                 105                 110
aac aac tcg tcg ctc aac aac gtc gtc ggc cac ctc ctc cac tcg tcg        384
Asn Asn Ser Ser Leu Asn Asn Val Val Gly His Leu Leu His Ser Ser
            115                 120                 125 atc ctc gtc ccg tac cac ggc tgg cgc atc tcg cac cgc acc cac cac        432
Ile Leu Val Pro Tyr His Gly Trp Arg Ile Ser His Arg Thr His His
130                 135                 140 cag aac cac ggc aac gtc gag aag gac gag tcg tgg gtc ccg ctc ccg        480
Gln Asn His Gly Asn Val Glu Lys Asp Glu Ser Trp Val Pro Leu Pro
145                 150                 155                 160 gag aag atc tac aag gag atg gac ctc tcg acc cgc atc ctc cgc tac        528
Glu Lys Ile Tyr Lys Glu Met Asp Leu Ser Thr Arg Ile Leu Arg Tyr
                165                 170                 175 tcg gtc ccg ctc ccg atg ttc gcc ctc ccg ttc tac ctc tgg tgg cgc        576
Ser Val Pro Leu Pro Met Phe Ala Leu Pro Phe Tyr Leu Trp Trp Arg
            180                 185                 190 tcg ccg ggc aag gag ggc tcg cac ttc aac ccg aac tcg gac ttc ttc        624
Ser Pro Gly Lys Glu Gly Ser His Phe Asn Pro Asn Ser Asp Phe Phe
        195                 200                 205 gcc ccg cac gag cgc aag gcc gtc ctc acc tcg aac ttc tgc ttc tcg        672
Ala Pro His Glu Arg Lys Ala Val Leu Thr Ser Asn Phe Cys Phe Ser
    210                 215                 220 atc atg gcc ctc ctc ctc ctc tac tcg tgc ttc gtc ttc ggc ccg gtc        720
Ile Met Ala Leu Leu Leu Leu Tyr Ser Cys Phe Val Phe Gly Pro Val
225                 230                 235                 240 cag gtc ctc aag ttc tac ggc atc ccg tac ctc gtc ttc gtc atg tgg        768
Gln Val Leu Lys Phe Tyr Gly Ile Pro Tyr Leu Val Phe Val Met Trp
                245                 250                 255 ctc gac ttc gtc acc tac atg cac cac cac ggc cac gag gag aag ctc        816
Leu Asp Phe Val Thr Tyr Met His His His Gly His Glu Glu Lys Leu
            260                 265                 270 ccg tgg tac cgc ggc aag gag tgg tcg tac ctc cgc ggc ggc ctc acc        864
Pro Trp Tyr Arg Gly Lys Glu Trp Ser Tyr Leu Arg Gly Gly Leu Thr
        275                 280                 285 acc gtc gac cgc gac tac ggc tgg atc aac aac atc cac cac gac atc        912
Thr Val Asp Arg Asp Tyr Gly Trp Ile Asn Asn Ile His His Asp Ile
    290                 295                 300 ggc acc cac gtc atc cac cac ctc ttc ccg cag atc ccg cac tac cac        960
Gly Thr His Val Ile His His Leu Phe Pro Gln Ile Pro His Tyr His
305                 310                 315                 320 ctc atc gag gcc acc aag gcc gcc aag ccg gtc ctc ggc aag tac tac       1008
Leu Ile Glu Ala Thr Lys Ala Ala Lys Pro Val Leu Gly Lys Tyr Tyr
                325                 330                 335 cgc gag ccg aag aag tcg ggc ccg ttc ccg ttc cac ctc ttc tcg aac       1056
Arg Glu Pro Lys Lys Ser Gly Pro Phe Pro Phe His Leu Phe Ser Asn
            340                 345                 350 ctc gtc cgc tcg atg tcg gag gac cac tac gtc tcg gac atc ggc gac       1104
Leu Val Arg Ser Met Ser Glu Asp His Tyr Val Ser Asp Ile Gly Asp
        355                 360                 365 atc gtc ttc tac cag acc gac ccg gac atc tac aag gtc gac aag tcg       1152
Ile Val Phe Tyr Gln Thr Asp Pro Asp Ile Tyr Lys Val Asp Lys Ser
    370                 375                 380 aag ctc aac tag                                                        1164
Lys Leu Asn
385

<210> SEQ ID NO 10
<211> LENGTH: 387
<212> TYPE: PRT
<213> ORGANISM: Linum usitatissimum
```

<400> SEQUENCE: 10

```
Met Lys Gln Gln Gln Tyr Lys Asp Thr Pro Ile Leu Asn Gly Val Asn
1               5                   10                  15

Gly Phe His Ala Lys Glu Glu Glu Glu Asp Phe Asp Leu Ser
            20                  25                  30

Asn Pro Pro Phe Asn Ile Gly Gln Ile Arg Ala Ala Ile Pro Lys
            35                  40                  45

His Cys Trp Val Lys Asn Pro Trp Arg Ser Leu Thr Tyr Val Phe Arg
        50                  55                  60

Asp Val Val Val Phe Ala Leu Ala Ala Ala Phe Tyr Phe Asn
65                  70                  75                  80

Ser Trp Leu Phe Trp Pro Leu Tyr Trp Phe Ala Gln Gly Thr Met Phe
                85                  90                  95

Trp Ala Ile Phe Val Leu Gly His Asp Cys Gly His Gly Ser Phe Ser
                100                 105                 110

Asn Asn Ser Ser Leu Asn Asn Val Val Gly His Leu Leu His Ser Ser
            115                 120                 125

Ile Leu Val Pro Tyr His Gly Trp Arg Ile Ser His Arg Thr His His
130                 135                 140

Gln Asn His Gly Asn Val Glu Lys Asp Glu Ser Trp Val Pro Leu Pro
145                 150                 155                 160

Glu Lys Ile Tyr Lys Glu Met Asp Leu Ser Thr Arg Ile Leu Arg Tyr
                165                 170                 175

Ser Val Pro Leu Pro Met Phe Ala Leu Pro Phe Tyr Leu Trp Trp Arg
                180                 185                 190

Ser Pro Gly Lys Glu Gly Ser His Phe Asn Pro Asn Ser Asp Phe Phe
            195                 200                 205

Ala Pro His Glu Arg Lys Ala Val Leu Thr Ser Asn Phe Cys Phe Ser
        210                 215                 220

Ile Met Ala Leu Leu Leu Tyr Ser Cys Phe Val Phe Gly Pro Val
225                 230                 235                 240

Gln Val Leu Lys Phe Tyr Gly Ile Pro Tyr Leu Val Phe Val Met Trp
                245                 250                 255

Leu Asp Phe Val Thr Tyr Met His His His Gly His Glu Glu Lys Leu
                260                 265                 270

Pro Trp Tyr Arg Gly Lys Glu Trp Ser Tyr Leu Arg Gly Gly Leu Thr
            275                 280                 285

Thr Val Asp Arg Asp Tyr Gly Trp Ile Asn Asn Ile His His Asp Ile
        290                 295                 300

Gly Thr His Val Ile His His Leu Phe Pro Gln Ile Pro His Tyr His
305                 310                 315                 320

Leu Ile Glu Ala Thr Lys Ala Ala Lys Pro Val Leu Gly Lys Tyr Tyr
                325                 330                 335

Arg Glu Pro Lys Lys Ser Gly Pro Phe Pro Phe His Leu Phe Ser Asn
            340                 345                 350

Leu Val Arg Ser Met Ser Glu Asp His Tyr Val Ser Asp Ile Gly Asp
        355                 360                 365

Ile Val Phe Tyr Gln Thr Asp Pro Asp Ile Tyr Lys Val Asp Lys Ser
                370                 375                 380

Lys Leu Asn
385
```

<210> SEQ ID NO 11
<211> LENGTH: 1164
<212> TYPE: DNA
<213> ORGANISM: Vernicia fordii
<220> FEATURE:
<221> NAME/KEY: CDS
<222> LOCATION: (1)..(1164)

<400> SEQUENCE: 11

| | | | | | | | | | | | | | | | | |
|---|---|---|---|---|---|---|---|---|---|---|---|---|---|---|---|---|
| atg | aag | cag | cag | cag | tac | aag | gac | acc | ccg | atc | ctc | aac | ggc | gtc | aac | 48 |
| Met | Lys | Gln | Gln | Gln | Tyr | Lys | Asp | Thr | Pro | Ile | Leu | Asn | Gly | Val | Asn | |
| 1 | | | | 5 | | | | | 10 | | | | | 15 | | |
| ggc | ttc | cac | gcc | aag | gag | gag | gag | gag | gag | gac | ttc | gac | ctc | tcg | | 96 |
| Gly | Phe | His | Ala | Lys | Glu | Glu | Glu | Glu | Glu | Asp | Phe | Asp | Leu | Ser | | |
| | | | 20 | | | | | 25 | | | | | 30 | | | |
| aac | ccg | ccg | ccg | ttc | aac | atc | ggc | cag | atc | cgc | gcc | gcc | atc | ccg | aag | 144 |
| Asn | Pro | Pro | Pro | Phe | Asn | Ile | Gly | Gln | Ile | Arg | Ala | Ala | Ile | Pro | Lys | |
| | | 35 | | | | | 40 | | | | | 45 | | | | |
| cac | tgc | tgg | gtc | aag | aac | ccg | tgg | cgc | tcg | ctc | acc | tac | gtc | ttc | cgc | 192 |
| His | Cys | Trp | Val | Lys | Asn | Pro | Trp | Arg | Ser | Leu | Thr | Tyr | Val | Phe | Arg | |
| | 50 | | | | | 55 | | | | | 60 | | | | | |
| gac | gtc | gtc | gtc | gtc | ttc | gcc | ctc | gcc | gcc | gcc | gcc | ttc | tac | ttc | aac | 240 |
| Asp | Val | Val | Val | Val | Phe | Ala | Leu | Ala | Ala | Ala | Ala | Phe | Tyr | Phe | Asn | |
| 65 | | | | | 70 | | | | | 75 | | | | | 80 | |
| tcg | tgg | ctc | ttc | tgg | ccg | ctc | tac | tgg | ttc | gcc | cag | ggc | acc | atg | ttc | 288 |
| Ser | Trp | Leu | Phe | Trp | Pro | Leu | Tyr | Trp | Phe | Ala | Gln | Gly | Thr | Met | Phe | |
| | | | | 85 | | | | | 90 | | | | | 95 | | |
| tgg | gcc | atc | ttc | gtc | ctc | ggc | cac | gac | tgc | ggc | cac | ggc | tcg | ttc | tcg | 336 |
| Trp | Ala | Ile | Phe | Val | Leu | Gly | His | Asp | Cys | Gly | His | Gly | Ser | Phe | Ser | |
| | | | 100 | | | | | 105 | | | | | 110 | | | |
| aac | aac | tcg | tcg | ctc | aac | aac | gtc | gtc | ggc | cac | ctc | ctc | cac | tcg | tcg | 384 |
| Asn | Asn | Ser | Ser | Leu | Asn | Asn | Val | Val | Gly | His | Leu | Leu | His | Ser | Ser | |
| | | 115 | | | | | 120 | | | | | 125 | | | | |
| atc | ctc | gtc | ccg | tac | cac | ggc | tgg | cgc | atc | tcg | cac | cgc | acc | cac | cac | 432 |
| Ile | Leu | Val | Pro | Tyr | His | Gly | Trp | Arg | Ile | Ser | His | Arg | Thr | His | His | |
| | 130 | | | | | 135 | | | | | 140 | | | | | |
| cag | aac | cac | ggc | aac | gtc | gag | aag | gac | gag | tcg | tgg | gtc | ccg | ctc | ccg | 480 |
| Gln | Asn | His | Gly | Asn | Val | Glu | Lys | Asp | Glu | Ser | Trp | Val | Pro | Leu | Pro | |
| 145 | | | | | 150 | | | | | 155 | | | | | 160 | |
| gag | aag | atc | tac | aag | gag | atg | gac | ctc | tcg | acc | cgc | atc | ctc | cgc | tac | 528 |
| Glu | Lys | Ile | Tyr | Lys | Glu | Met | Asp | Leu | Ser | Thr | Arg | Ile | Leu | Arg | Tyr | |
| | | | | 165 | | | | | 170 | | | | | 175 | | |
| tcg | gtc | ccg | ctc | ccg | atg | ttc | gcc | ctc | ccg | ttc | tac | ctc | tgg | tgg | cgc | 576 |
| Ser | Val | Pro | Leu | Pro | Met | Phe | Ala | Leu | Pro | Phe | Tyr | Leu | Trp | Trp | Arg | |
| | | | 180 | | | | | 185 | | | | | 190 | | | |
| tcg | ccg | ggc | aag | gag | ggc | tcg | cac | ttc | aac | ccg | aac | tcg | gac | ttc | ttc | 624 |
| Ser | Pro | Gly | Lys | Glu | Gly | Ser | His | Phe | Asn | Pro | Asn | Ser | Asp | Phe | Phe | |
| | | 195 | | | | | 200 | | | | | 205 | | | | |
| gcc | ccg | cac | gag | cgc | aag | gcc | gtc | ctc | acc | tcg | aac | ttc | tgc | ttc | tcg | 672 |
| Ala | Pro | His | Glu | Arg | Lys | Ala | Val | Leu | Thr | Ser | Asn | Phe | Cys | Phe | Ser | |
| | 210 | | | | | 215 | | | | | 220 | | | | | |
| atc | atg | gcc | ctc | ctc | ctc | ctc | tac | tcg | tgc | ttc | gtc | ttc | ggc | ccg | gtc | 720 |
| Ile | Met | Ala | Leu | Leu | Leu | Leu | Tyr | Ser | Cys | Phe | Val | Phe | Gly | Pro | Val | |
| 225 | | | | | 230 | | | | | 235 | | | | | 240 | |
| cag | gtc | ctc | aag | ttc | tac | ggc | atc | ccg | tac | ctc | gtc | ttc | gtc | atg | tgg | 768 |
| Gln | Val | Leu | Lys | Phe | Tyr | Gly | Ile | Pro | Tyr | Leu | Val | Phe | Val | Met | Trp | |
| | | | | 245 | | | | | 250 | | | | | 255 | | |
| ctc | gac | ttc | gtc | acc | tac | atg | cac | cac | cac | ggc | cac | gag | gag | aag | ctc | 816 |
| Leu | Asp | Phe | Val | Thr | Tyr | Met | His | His | His | Gly | His | Glu | Glu | Lys | Leu | |
| | | | 260 | | | | | 265 | | | | | 270 | | | |
| ccg | tgg | tac | cgc | ggc | aag | gag | tgg | tcg | tac | ctc | cgc | ggc | ggc | ctc | acc | 864 |

```
acc gtc gac cgc gac tac ggc tgg atc aac aac atc cac cac gac atc       912
Thr Val Asp Arg Asp Tyr Gly Trp Ile Asn Asn Ile His His Asp Ile
    290                 295                 300 ggc acc cac gtc atc cac cac ctc ttc ccg cag atc ccg cac tac cac       960
Gly Thr His Val Ile His His Leu Phe Pro Gln Ile Pro His Tyr His
305                 310                 315                 320 ctc atc gag gcc acc aag gcc gcc aag ccg gtc ctc ggc aag tac tac      1008
Leu Ile Glu Ala Thr Lys Ala Ala Lys Pro Val Leu Gly Lys Tyr Tyr
                325                 330                 335 cgc gag ccg aag aag tcg ggc ccg ttc ccg ttc cac ctc ttc tcg aac      1056
Arg Glu Pro Lys Lys Ser Gly Pro Phe Pro Phe His Leu Phe Ser Asn
            340                 345                 350 ctc gtc cgc tcg atg tcg gag gac cac tac gtc tcg gac atc ggc gac      1104
Leu Val Arg Ser Met Ser Glu Asp His Tyr Val Ser Asp Ile Gly Asp
        355                 360                 365 atc gtc ttc tac cag acc gac ccg gac atc tac aag gtc gac aag tcg      1152
Ile Val Phe Tyr Gln Thr Asp Pro Asp Ile Tyr Lys Val Asp Lys Ser
370                 375                 380 aag ctc aac tag                                                      1164
Lys Leu Asn
385

<210> SEQ ID NO 12
<211> LENGTH: 387
<212> TYPE: PRT
<213> ORGANISM: Vernicia fordii

<400> SEQUENCE: 12

Met Lys Gln Gln Gln Tyr Lys Asp Thr Pro Ile Leu Asn Gly Val Asn
1               5                   10                  15

Gly Phe His Ala Lys Glu Glu Glu Glu Glu Asp Phe Asp Leu Ser
            20                  25                  30

Asn Pro Pro Pro Phe Asn Ile Gly Gln Ile Arg Ala Ala Ile Pro Lys
        35                  40                  45

His Cys Trp Val Lys Asn Pro Trp Arg Ser Leu Thr Tyr Val Phe Arg
    50                  55                  60

Asp Val Val Val Phe Ala Leu Ala Ala Ala Phe Tyr Phe Asn
65                  70                  75                  80

Ser Trp Leu Phe Trp Pro Leu Tyr Trp Phe Ala Gln Gly Thr Met Phe
                85                  90                  95

Trp Ala Ile Phe Val Leu Gly His Asp Cys Gly His Gly Ser Phe Ser
            100                 105                 110

Asn Asn Ser Ser Leu Asn Asn Val Val Gly His Leu Leu His Ser Ser
        115                 120                 125

Ile Leu Val Pro Tyr His Gly Trp Arg Ile Ser His Arg Thr His His
    130                 135                 140

Gln Asn His Gly Asn Val Glu Lys Asp Glu Ser Trp Val Pro Leu Pro
145                 150                 155                 160

Glu Lys Ile Tyr Lys Glu Met Asp Leu Ser Thr Arg Ile Leu Arg Tyr
                165                 170                 175

Ser Val Pro Leu Pro Met Phe Ala Leu Pro Phe Tyr Leu Trp Trp Arg
            180                 185                 190

Ser Pro Gly Lys Glu Gly Ser His Phe Asn Pro Asn Ser Asp Phe Phe
        195                 200                 205

Ala Pro His Glu Arg Lys Ala Val Leu Thr Ser Asn Phe Cys Phe Ser
```

```
                210                 215                 220
Ile Met Ala Leu Leu Leu Tyr Ser Cys Phe Val Phe Gly Pro Val
225                 230                 235                 240

Gln Val Leu Lys Phe Tyr Gly Ile Pro Tyr Leu Val Phe Val Met Trp
            245                 250                 255

Leu Asp Phe Val Thr Tyr Met His His Gly His Glu Glu Lys Leu
            260                 265                 270

Pro Trp Tyr Arg Gly Lys Glu Trp Ser Tyr Leu Arg Gly Gly Leu Thr
            275                 280                 285

Thr Val Asp Arg Asp Tyr Gly Trp Ile Asn Asn Ile His His Asp Ile
            290                 295                 300

Gly Thr His Val Ile His His Leu Phe Pro Gln Ile Pro His Tyr His
305                 310                 315                 320

Leu Ile Glu Ala Thr Lys Ala Ala Lys Pro Val Leu Gly Lys Tyr Tyr
                325                 330                 335

Arg Glu Pro Lys Lys Ser Gly Pro Phe Pro Phe His Leu Phe Ser Asn
            340                 345                 350

Leu Val Arg Ser Met Ser Glu Asp His Tyr Val Ser Asp Ile Gly Asp
            355                 360                 365

Ile Val Phe Tyr Gln Thr Asp Pro Asp Ile Tyr Lys Val Asp Lys Ser
370                 375                 380

Lys Leu Asn
385

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide

<400> SEQUENCE: 13
tttccgcggt cgaatttccc cgatcgttca                                    30

<210> SEQ ID NO 14
<211> LENGTH: 21
<212> TYPE: DNA
<213> ORGANISM: Artificial Sequence
<220> FEATURE:
<223> OTHER INFORMATION: oligonucleotide

<400> SEQUENCE: 14
gagtcgctca cctactgcat c                                             21

<210> SEQ ID NO 15
<211> LENGTH: 31
<212> TYPE: DNA
<213> ORGANISM: Artificial Sequence
<220> FEATURE:
<223> OTHER INFORMATION: oligonucleotide

<400> SEQUENCE: 15
tttgtttaaa catgctaatt cgggggatct g                                  31

<210> SEQ ID NO 16
<211> LENGTH: 19
<212> TYPE: DNA
<213> ORGANISM: Artificial Sequence
<220> FEATURE:
<223> OTHER INFORMATION: oligonucleotide
```

```
<400> SEQUENCE: 16
cacgtcgact gaaacgcag                                                 19

<210> SEQ ID NO 17
<211> LENGTH: 18
<212> TYPE: DNA
<213> ORGANISM: Artificial Sequence
<220> FEATURE:
<223> OTHER INFORMATION: oligonucleotide

<400> SEQUENCE: 17
gacgaggtca tccgcgag                                                  18

<210> SEQ ID NO 18
<211> LENGTH: 18
<212> TYPE: DNA
<213> ORGANISM: Artificial Sequence
<220> FEATURE:
<223> OTHER INFORMATION: oligonucleotide

<400> SEQUENCE: 18
gtgcgggtcg tgatggac                                                  18

<210> SEQ ID NO 19
<211> LENGTH: 19
<212> TYPE: DNA
<213> ORGANISM: Artificial Sequence
<220> FEATURE:
<223> OTHER INFORMATION: oligonucleotide

<400> SEQUENCE: 19
ctggaaggcg tacgaggac                                                 19

<210> SEQ ID NO 20
<211> LENGTH: 20
<212> TYPE: DNA
<213> ORGANISM: Artificial Sequence
<220> FEATURE:
<223> OTHER INFORMATION: oligonucleotide

<400> SEQUENCE: 20
gtcaagccgc ccaggctgtc                                                20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
ggatccgcca agtcgcgcag                                                20

<210> SEQ ID NO 22
<211> LENGTH: 21
<212> TYPE: DNA
<213> ORGANISM: Artificial Sequence
<220> FEATURE:
<223> OTHER INFORMATION: oligonucleotide

<400> SEQUENCE: 22
gagtcgctca cctactgcat c                                              21

<210> SEQ ID NO 23
<211> LENGTH: 20
```

<212> TYPE: DNA
<213> ORGANISM: Artificial Sequence
<220> FEATURE:
<223> OTHER INFORMATION: oligonucleotide

<400> SEQUENCE: 23
gagaactcgc cgatgtcgag         20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
agcgactggt agagctggtc         20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide

<400> SEQUENCE: 25
ctcttgacga cacggcttac         20

<210> SEQ ID NO 26
<211> LENGTH: 19
<212> TYPE: DNA
<213> ORGANISM: Artificial Sequence
<220> FEATURE:
<223> OTHER INFORMATION: oligonucleotide

<400> SEQUENCE: 26
caggccgcag agggtgaac         19

<210> SEQ ID NO 27
<211> LENGTH: 26
<212> TYPE: DNA
<213> ORGANISM: Artificial Sequence
<220> FEATURE:
<223> OTHER INFORMATION: oligonucleotide

<400> SEQUENCE: 27
gatgagtttg gacaaaccac aactag         26

<210> SEQ ID NO 28
<211> LENGTH: 22
<212> TYPE: DNA
<213> ORGANISM: Artificial Sequence
<220> FEATURE:
<223> OTHER INFORMATION: oligonucleotide

<400> SEQUENCE: 28
ggttcagggg gagatgtggg ag         22

<210> SEQ ID NO 29
<211> LENGTH: 19
<212> TYPE: DNA
<213> ORGANISM: Artificial Sequence
<220> FEATURE:
<223> OTHER INFORMATION: oligonucleotide

<400> SEQUENCE: 29
gtaccggcgc gcccacctg                                              19

<210> SEQ ID NO 30
<211> LENGTH: 25
<212> TYPE: DNA
<213> ORGANISM: Artificial Sequence
<220> FEATURE:
<223> OTHER INFORMATION: oligonucleotide

<400> SEQUENCE: 30
gaatcctgtt gccggtcttg cgatg                                       25

<210> SEQ ID NO 31
<211> LENGTH: 27
<212> TYPE: DNA
<213> ORGANISM: Artificial Sequence
<220> FEATURE:
<223> OTHER INFORMATION: oligonucleotide

<400> SEQUENCE: 31
ttatgattag agtcccgcaa ttataca                                     27

<210> SEQ ID NO 32
<211> LENGTH: 23
<212> TYPE: DNA
<213> ORGANISM: Artificial Sequence
<220> FEATURE:
<223> OTHER INFORMATION: oligonucleotide

<400> SEQUENCE: 32
ctagcttagc ttgagcttgg atc                                         23

<210> SEQ ID NO 33
<211> LENGTH: 23
<212> TYPE: DNA
<213> ORGANISM: Artificial Sequence
<220> FEATURE:
<223> OTHER INFORMATION: oligonucleotide

<400> SEQUENCE: 33
gtgctgacgc gggcatagcc cag                                         23

<210> SEQ ID NO 34
<211> LENGTH: 24
<212> TYPE: DNA
<213> ORGANISM: Artificial Sequence
<220> FEATURE:
<223> OTHER INFORMATION: oligonucleotide

<400> SEQUENCE: 34
atgcgactaa aacacgcgac aaga                                        24

<210> SEQ ID NO 35
<211> LENGTH: 20
<212> TYPE: DNA
<213> ORGANISM: Artificial Sequence
<220> FEATURE:
<223> OTHER INFORMATION: oligonucleotide

<400> SEQUENCE: 35
agcagcggag gggttggatc                                             20

<210> SEQ ID NO 36
<211> LENGTH: 37
<212> TYPE: DNA
<213> ORGANISM: Artificial Sequence

```
<220> FEATURE:
<223> OTHER INFORMATION: oligonucleotide
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (31)..(33)
<223> OTHER INFORMATION: n is a, c, g, or t

<400> SEQUENCE: 36
acgatggact ccagagcggc cgcgcangca nnnggaa                               37

<210> SEQ ID NO 37
<211> LENGTH: 40
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (34)..(36)
<223> OTHER INFORMATION: n is a, c, g, or t

<400> SEQUENCE: 37
acgatggact ccagagcggc cgcgctgatn gctnnncggt                            40

<210> SEQ ID NO 38
<211> LENGTH: 16
<212> TYPE: DNA
<213> ORGANISM: Artificial Sequence
<220> FEATURE:
<223> OTHER INFORMATION: oligonucleotide

<400> SEQUENCE: 38
acgatggact ccagag                                                     16

<210> SEQ ID NO 39
<211> LENGTH: 19
<212> TYPE: DNA
<213> ORGANISM: Artificial Sequence
<220> FEATURE:
<223> OTHER INFORMATION: oligonucleotide

<400> SEQUENCE: 39
catacaccgg gcaaagcag                                                  19

<210> SEQ ID NO 40
<211> LENGTH: 24
<212> TYPE: DNA
<213> ORGANISM: Artificial Sequence
<220> FEATURE:
<223> OTHER INFORMATION: oligonucleotide

<400> SEQUENCE: 40
tttccatggg ccagcaggcg acgc                                            24

<210> SEQ ID NO 41
<211> LENGTH: 29
<212> TYPE: DNA
<213> ORGANISM: Artificial Sequence
<220> FEATURE:
<223> OTHER INFORMATION: oligonucleotide
```

<400> SEQUENCE: 41
tttgatatca ggcgataata ttgagctcc  29

<210> SEQ ID NO 42
<211> LENGTH: 28
<212> TYPE: DNA
<213> ORGANISM: Artificial Sequence
<220> FEATURE:
<223> OTHER INFORMATION: oligonucleotide

<400> SEQUENCE: 42
tttccatggg cgggagtgaa gggttgcc  28

<210> SEQ ID NO 43
<211> LENGTH: 28
<212> TYPE: DNA
<213> ORGANISM: Artificial Sequence
<220> FEATURE:
<223> OTHER INFORMATION: oligonucleotide

<400> SEQUENCE: 43
tttgagatcc tactgcgcct gctgctcc  28

<210> SEQ ID NO 44
<211> LENGTH: 30
<212> TYPE: DNA
<213> ORGANISM: Artificial Sequence
<220> FEATURE:
<223> OTHER INFORMATION: oligonucleotide

<400> SEQUENCE: 44
tttactagtc tcttcagacg gcttgttctc  30

<210> SEQ ID NO 45
<211> LENGTH: 19
<212> TYPE: DNA
<213> ORGANISM: Artificial Sequence
<220> FEATURE:
<223> OTHER INFORMATION: oligonucleotide

<400> SEQUENCE: 45
cacccgtcct ctccgcttc  19

<210> SEQ ID NO 46
<211> LENGTH: 20
<212> TYPE: DNA
<213> ORGANISM: Artificial Sequence
<220> FEATURE:
<223> OTHER INFORMATION: oligonucleotide

<400> SEQUENCE: 46
cctcgctctt tcgctggttc  20

<210> SEQ ID NO 47
<211> LENGTH: 21
<212> TYPE: DNA
<213> ORGANISM: Artificial Sequence
<220> FEATURE:
<223> OTHER INFORMATION: oligonucleotide

<400> SEQUENCE: 47
ccgccaataa cctcacctca g  21

<210> SEQ ID NO 48
<211> LENGTH: 21

```
<212> TYPE: DNA
<213> ORGANISM: Artificial Sequence
<220> FEATURE:
<223> OTHER INFORMATION: oligonucleotide

<400> SEQUENCE: 48
ggcgatggga gcgtagaata c                                              21

<210> SEQ ID NO 49
<211> LENGTH: 24
<212> TYPE: DNA
<213> ORGANISM: Artificial Sequence
<220> FEATURE:
<223> OTHER INFORMATION: oligonucleotide

<400> SEQUENCE: 49
caggtttcat cgcaactaca ttga                                           24

<210> SEQ ID NO 50
<211> LENGTH: 24
<212> TYPE: DNA
<213> ORGANISM: Artificial Sequence
<220> FEATURE:
<223> OTHER INFORMATION: oligonucleotide

<400> SEQUENCE: 50
aacagagcga gttgaagagt agcc                                           24

<210> SEQ ID NO 51
<211> LENGTH: 21
<212> TYPE: DNA
<213> ORGANISM: Artificial Sequence
<220> FEATURE:
<223> OTHER INFORMATION: oligonucleotide

<400> SEQUENCE: 51
ccgccaataa cctcacctca g                                              21

<210> SEQ ID NO 52
<211> LENGTH: 22
<212> TYPE: DNA
<213> ORGANISM: Artificial Sequence
<220> FEATURE:
<223> OTHER INFORMATION: oligonucleotide

<400> SEQUENCE: 52
gaagaagacg ccgagtagga tg                                             22

<210> SEQ ID NO 53
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 53

Gly Xaa Gly Xaa Xaa Gly
1               5
```

```
<210> SEQ ID NO 54
<211> LENGTH: 6
<212> TYPE: PRT
<213> ORGANISM: Artificial Sequence
<220> FEATURE:
<223> OTHER INFORMATION: peptide motif

<400> SEQUENCE: 54

Gly Ser Gly Thr Val Gly
1               5

<210> SEQ ID NO 55
<211> LENGTH: 597
<212> TYPE: DNA
<213> ORGANISM: Ustilago maydis

<400> SEQUENCE: 55
gattagatct tgctgatagg caggtttgct tggagaatgg ggggaaaaga ctgaccgaag      60
aaacagcgag atctagaagt gataagcgga agaatctga cttgctgtga tcagcagcca     120 atttttttt cgttttttt ttttcactcc acatcgtcgt gcgtgcacgg tctgcatgtg      180
taaattgtat tcatcgaaag ccacagttga atacatcagc ccgatgtgga tttcgaaaac     240
caattaatct tggaattcac gcgctcagat cagtccatag agtcgacttc ggctgtttcc     300
aagagcttct tctctgcgag gtggttgccc gtgtttctcg ctgggaaaaa aggatcgatt     360
attattcgct tctacctcgc tcgcacccct ggcctgctga aggaaacagc gccgagactc     420
ggtcacggtt gctgggctcc gtgttgatgc tgggacggcg caaagtgggg cccgcgcact     480
cttcgagcca aggacctcac tcttcaagaa caagcgctgt cgccatcgtc ttcttctttc     540
tgctccacca tcgaatcttt ctttctcgtt tcgaaaccaa aacactcttc caccatg       597

<210> SEQ ID NO 56
<211> LENGTH: 1434
<212> TYPE: DNA
<213> ORGANISM: Rhodosporidium toruloides

<400> SEQUENCE: 56
ctgcagaact acgccctctc acacccaact tccgactcga ccggcggtac gagcacgacc      60
tacttctact gcctgccatc gacatccggg cgggtcgctg cctaccctgt gcgttctgcg     120
ccctccctcg tctcgggagg cagtgtctga cagaagcttt gcgcgcagta ccccgtcaag     180
atgcaactct acgcaacgtt cggcacagaa gtcgccaagc tccgcgcatc gccgcctcaa     240
gctctcgcgc tgcccgacgg tgtcgtctat tacgaggcgg agaagctcga gttgccggct     300
ttgccagcgg cggtcaaggt tgaggtggag acggagaagg cgggagtagc gggggaggac     360
aatgaggcga agggtgagat ggtgctggtg gagactctta cggtggagca ggaggagatt     420
gaattgggct cgggagtcgt gcagattgag gagtcgttgc tcgtcaagct ggaggtcagc     480
ggctgatcct tccgttcgtt gcaaggatcg tctgcatgtt tcgcttctct caatgacaca     540
acctggagag cgctcccgtc agcgagaatc gaggacattc gcagctcgt gagcaagcgg     600 aggtgcgagg ctccctcgaa agctgcgcct cttcagacgg cttgttctct cctgctctgg     660
tgggctggcc tgacatgtaa tgtgctccgc cgcaagtccg tcgtcggtct caattcgacg     720
ttgaaagggc atagcgcaag gaagaacct ctgcggacat gcagaattac tggctcgcct     780
gctccttcgt ctactggaat aagtcctgtc tcgttaaagc cccaacgtcg ttttcgacg     840 tttgtaaggc gcaagaggtg ctatgggcta cgcaggaagc tgagaggaca tagaagtcgg     900
gggaggaacg gcgcagagcg gcagttgcgg aagcatgagg aaagcgagac ggtccagcat     960
```

```
ctgcagcgcc aatccgcaat ctcctggttg agcctgcacc ggaagcgtcg aacagtatg    1020 cgcagagtcg aacgcaagta agaaagacgc accctcacac tcgcttactt cgagccatac    1080
aacggatcaa agctgcgcgt atctcggctt gtaagggccg gaaagcaacc tcggagatgg    1140
acacgtcaca tcaccaactt atcgatctcg gccgtcgacg tcgcagagag ggcgagagaa    1200
gcggtgaagg agggaaacaa cccctcgaga gcatgatccg accgaatctg cagcgcagga    1260
agccgttaca agcccgcctc gagcgcaggt cgggtccagc cggggacga aacgcgcgag    1320 gctgattcgt gagcgaagga agccgcatcg acaagttcgc tccccttttgc cctctttccc    1380 atcacccgtt ctcgccttac ccgctcagaa caacaccaga tcactcacaa tgtc          1434
```

<210> SEQ ID NO 57
<211> LENGTH: 888
<212> TYPE: DNA
<213> ORGANISM: Aspergillus nidulans

<400> SEQUENCE: 57

```
ctgtacagtg accggtgact ctttctggca tgcggagaga cggacggacg cagagagaag    60
ggctgagtaa taagcgccac tgcgccagac agctctggcg gctctgaggt gcagtggatg    120
attattaatc cgggaccggc cgcccctccg ccccgaagtg gaaaggctgg tgtgcccctc    180
gttgaccaag aatctattgc atcatcggag aatatggagc ttcatcgaat caccggcagt    240
aagcgaagga gaatgtgaag ccaggggtgt atagccgtcg gcgaaatagc atgccattaa    300
cctaggtaca gaagtccaat tgcttccgat ctggtaaaag attcacgaga tagtaccttc    360
tccgaagtag gtagagcgag tacccggcgc gtaagctccc taattggccc atccggcatc    420
tgtagggcgt ccaaatatcg tgcctctcct gctttgcccg gtgtatgaaa ccggaaaggc    480
cgctcaggag ctggccagcg gcgcagaccg ggaacacaag ctggcagtcg acccatccgg    540
tgctctgcac tcgacctgct gaggtccctc agtccctggt aggcagcttt gccccgtctg    600
tccgcccggt gtgtcggcgg ggttgacaag gtcgttgcgt cagtccaaca tttgttgcca    660
tattttcctg ctctccccac cagctgctct tttcttttct ctttcttttc ccatcttcag    720
tatattcatc ttcccatcca agaacccttta tttcccctaa gtaagtactt tgctacatcc    780
atactccatc cttcccatcc cttattccttt tgaacctttc agttcgagct ttcccacttc    840
atcgcagctt gactaacagc taccccgctt gagcagacat caccatgg                 888
```

<210> SEQ ID NO 58
<211> LENGTH: 617
<212> TYPE: DNA
<213> ORGANISM: Aspergillus niger

<400> SEQUENCE: 58

```
gtcgacgaga tcgtaggagt gagtacccgg cgtgatggag ggggagcacg ctcattggtc    60
cgtacggcag ctgccgaggg ggagcaggag atccaaatat cgtgagtctc ctgctttgcc    120
cggtgtatga aaccggaaag gactgctggg gaactgggga gcggcgcaag ccgggaatcc    180
cagctgacaa ttgacccatc ctcatgccgt ggcagagctt gaggtagctt ttgccccgtc    240
tgtctccccg gtgtgcgcat tcgactgggc gcggcatctg tgcctcctcc aggagcggag    300
gacccagtag taagtaggcc tgacctggtc gttgcgtcag tccagaggtt ccctccccta    360
ccctttttct acttccccctc cccgccgct caacttttct ttccctttta ctttctctct    420
ctcttcctct tcatccatcc tctcttcatc acttccctct tccctttcatc caattcatct    480
```

```
tccaagtgag tcttcctccc catctgtccc tccatctttc ccatcatcat ctcccctccc      540
agctcctccc ctcctctcgt ctcctcacga agcttgacta accattaccc cgccacatag      600
acacatctaa accatgg                                                     617

<210> SEQ ID NO 59
<211> LENGTH: 388
<212> TYPE: DNA
<213> ORGANISM: Ashibia gossipii

<400> SEQUENCE: 59
cactatacgt gcctcgtccc cgccgggtca cccggccagc gacatggagg cccagaatac       60
cctccttgac agtcttgacg tgcgcagctc aggggcatga tgtgactgtc gcccgtacat      120
ttagcccata catccccatg tataatcatt tgcatccata cattttgatg gccgcacggc      180
gcgaagcaaa aattacggct cctcgctgca gacctgcgag cagggaaacg ctcccctcac      240
agacgcgttg aattgtcccc acgccgcgcc cctgtagaga aatataaaag gttaggattt      300
gccactgagg ttcttctttc atatacttcc ttttaaaatc ttgctaggat acagttctca      360
catcacatcc gaacataaac aaccatgg                                         388

<210> SEQ ID NO 60
<211> LENGTH: 963
<212> TYPE: DNA
<213> ORGANISM: Rhodoturula grammis

<400> SEQUENCE: 60
ggcgcgccta cgtctacgtc aagggcaatg ccgacgtgac caaggccatc ggccaggacc       60
tcgccttctt ctcggtccct gtcgagctcg gcgtgcgtcc cgccgctctc tctctctctt      120
tctctcggcc gcgcctcacg tgatccacga cgtcgtactg acccttgcga atgtgcgcgc      180
ccgcagccca acggcgtcga aaggtgcac ccgctcggcg acctgacggc gttcgagaag      240
gagctcctcg aggcgtgcct cggcgagctg cccgggtcca tctccaaggg cgagtcgttc      300
atccagggct ccaagctctg actcgccggc gcatcgacgg gcgcgagcca caaggcgagg      360
atgtgagagg aggcgtttcc tccacccttgg accccatctg ccgcctccct ttctctctct      420
ttctttccct tcctctctct ctctctctct ctcgttctcc tccttctggg cctctcggac      480
ctcttcctcg ccgtcgactc gtgaaaatgc agtgcgcgtt tctgtacctt gtcctgcgag      540
agagatctgg ttctgcgagg gtgagtcgtt gccttggccg tggcacgcct cgccgcagcg      600
agagagaaga ggccacggtc caggacgacg acgacgagga ggaagcgcaa aaggcgagac      660
accgagtgcc atcgattccc cgctcgaacc tgctcacggc tgtcgaaggc ggtgcgccac      720
ggtgcttgcg ggagcgaaag caagctggcg tcgtcctctt gaactggttc gagtccgtga      780
gggcggcgac gagaactcag gcgaggtgct cgcgtcggaa caagccgggc ttgtggtcga      840
gggagcgaga gcgaggcagc gccgtcgtcg ccgaggcaag agcggcatcg acaagttggc      900
ccgtcgcctc tcgctccctc ttctcctcct cccaccacca cctttctcca gctcgaacca      960
tgg                                                                    963

<210> SEQ ID NO 61
<211> LENGTH: 1009
<212> TYPE: DNA
<213> ORGANISM: Sporobolomyces roseus

<400> SEQUENCE: 61
ggcgcgccga agttataacct cagaggtctc aaaaacgaaa aagtcatgca agaatctcct       60
```

```
ttgacgtgag ggttatttct cttcctctag tagtctacga gaatcgcaaa gatcggaaaa      120
ctgatgcatc tttgtgttca cgggttagcg atttgatctt ttcgattccc aaaatcgtat      180
cgttcctgtc gcagggaact acgctcaaag ccggcactct gatcatcacg ggagtgagtt      240
ttgagctctc cctctatgag agtgcaaggt tcgtcgctga tggtgtaatc cgctcatgcc      300
ttcccctcta ccttctcctt tgtccattct ctctactacg gttgtcacat cttccttctc      360
cgacagaccc cgcacggaat tggagcgtac tcgaatcctc cggaattctt caaggacgga      420
gacgtcttca gggtcgagat ctcgggaggc atcgggagtt tggtcaacaa gatcgaatat      480
gaaaagtaga taatccgtta ctcaggtcaa tggtatggct tcgaagatgc tggaatcagc      540
cggaaagcaa agctggagag aaaaatcgag attgcgaaac gtgcgatgtc atttcgtttc      600
gagctcgcaa ccatctcgta tccctctgag ctacatacaa acgtcactac ggcctcggag      660
tgactccctg cgagcggatt gaaggagatc acggtcgaat cagctagacc ttcgcaacgt      720
tttcgcgctc gcacgttctt atcgatctac tgagattgac tcgaaaaagt cttctctcac      780
ggtcgattga actttgaatg aactctcagg ttgcgcgaga gccaatacga gccgaccaga      840
ggcaattcgg agcttcccgg aacgttccaa ggagagggat tttccgagag attacgattg      900
cgagatagaa aaaggctag ctttcgattt cgagagagat tactttcaag ttcgctgctt       960
ccaactcttg ctccaacccc ctccactcct tctctacaaa acaccatgg                 1009

<210> SEQ ID NO 62
<211> LENGTH: 2148
<212> TYPE: DNA
<213> ORGANISM: Rhodotorula glutinis ATCC 204091

<400> SEQUENCE: 62
ggcgcgccac catctcctcg tcgcttcttc cctctccttc ggcgcccaca ccgcttcgca       60
gggctcacgg actgctcaca tcgtttgtgt gcgtcgctgt gcatgtccac gcaccactcc      120
cagcccccac gagcgcctca aaagacgcgg acgcagacgc ccgccgaacg acggcacgcc      180
cctcttctca ctagcgcgac gaaccagctg cgacgattcg tgcgcttatg ttagccggac      240
ttctggcttg ctttgcgctg ctgcgtccgt cttgtggtgc ggatcggctc gatgggggtt      300
tgctcgtttg ctgggagacg gtcgcctctc cctcctcctc ttcactcctc gttagctttc      360
tacgctcatt ggttctgcga accatctaca tcacgctcgc tcgtcatgct cgtactacga      420
tcaacacccc tgctcgtcgt gctttccctc ctctccgtcc tctcggccgc gtccagcgac      480
ttgcccagcc aacttccccc gcacgccggt gagtctccca cacttccttg cgaccccaac      540
ccagcatctg acatccgcat cacgcagccc tcccgccttc ccactcctcc ctcttcaccg      600
actcctcctc ctcctcccct gattcctcgt ccctcaaagc ccgcagcct cttcccttca      660 aaatcaagcg cccccgctcg ctcgaacaag tgcagcagaa cctcgggaag aggctggcga      720
agcgcggcga ggaggggagt aagacggaga gggtgccgtt tggtcagagg agtgcgacgg      780
cggcgagtgc gggtggacaa ggtggagcgg ggacggggag ggcgacgcag cgcgttacgg      840
gcggaggaag cagaggtgca ggaggaggcg gaggagtgt cgcggctgct cagcctgtcc      900
cttcgactac ccagacggtc gagacaggct ctaagatcgt ctcgactggt cttctgaccg      960
tagcgtcgcc gtcgacggca gatggaggag gcgggacggt cacccaggtc gagacggcct     1020
cctcaggggt attgatcacc agcacggcgg gagcggcgag ttcagcggcg cgtcggacg      1080 tcgctagcgc acaggcagcg gaggcgacgt cgagtacgag catgatcagc ggaggagcgg     1140
```

```
cggctggcgg gagtttaagc aggatgctgg cgggaggagt tgcgggtgca gccctgatcc    1200
tcctcgtgcg gtgagcaggc gaagcgagga gctcatgtag atacagcata gacagtatat    1260
atcgccagga tagcttgcaa cagccgccgg tcggtttatt ccattgtcct cgaccccatg    1320
cgaaggcgag ctctgctcgt cagctggcca agctggccag cagacgagcg ttggggtggc    1380
ggaacgccaa cggcatggag taaagcagcc gtgaggatga cggaggagct cgggcgaggt    1440
gatggggatt ctagcaggaa cagcagagcg gcgaggagga gggaaccgg aagcacagtc     1500 tcgtggccgc ttgttgcaga tcccagtgtc gctagagtgc tcgtcgtcat cagagcgagt    1560
gaacaaagcg atgccctgaa gaacgatgag cgaatgagtc gaagcggcgt ctaccggtga    1620
actcggggtg tggcaaatga gcgagacgag gagtgcccgc cagagttgcc acgtcgaccc    1680
cacgtcggaa tcgacgttga tagagtgaac gaagccattg cagacccag aaggtggcca     1740 tgttgtggaa gcgagggcag gagcgagggg agaaggcgag gaggaggagg ggctggggaa    1800
gcccgtccgg gaatggcgca gctgggtgcc gggatgtgc gcgagtggcg gaggagtcga     1860
gcgtgagagt tctggaacac ggggcgcgca caagggtcga gggccgtgac gagttcgccg    1920
ggcggtggtc gggctgaggg cgagcgcgcg ttggggacga cgacgcccga cgccctcgct    1980
cttcgtcctc accgcttccc ggagaacttt gctgtactct gcttctccct tcacactctc    2040
acacccactc acacacccctt ccatccacac acaagctatc cgcacacctc tcacacccga   2100
ccccagctcg ccccatcctc ttcgcacccg gctcatcgaa aaccatgg                 2148

<210> SEQ ID NO 63
<211> LENGTH: 1027
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1022)..(1027)
<223> OTHER INFORMATION: NcoI cloning site

<400> SEQUENCE: 63
ggtaccgtgc gagaagaagc gaggcacgcg aagcggtaga agcaatgaag cgaggcgaga      60
gcgagagagg cagggcttca gccatgtcca gctgatcggc tgtaacgtcg cgccgggcca    120
gtctgttgaa tttgttgcgt cgcctgagcg taatagaagt gcagtagtct actccgcatg    180
ccgagaacgt cgaagagcgc gaagtaggga gtcgagggaa gcgagggtgg caaacacagc    240
aacgacaagc ggttccgctt cgctcaaaag ctcgttgacg ttgttttgac gttttgaaga    300
cagtacaaca gcagcaagag gcgtgcgaag cgttggtggc gagagcagcg acaaggaggg    360
aggaatgagg gagtggtggc gagggctcgc aaacggcgt acgcctcgaa tggagacgtg      420
cgagtcgttc ttcgacgtcc gagggatgcc gagcgccgag acggagcacg caacgagcga    480
gaggagagca gccgcgcaag gtgattcgag tggcgcaagc ggaggacgac gaggagacgg    540
acgagggagg aggagggatg gcgagcgagc atcggacggc ggggcgcgag agacggcgtg    600
aggagccggg tgtggagagt ttgaggaggc gcggatgcg aagtggctgg gtgtgcggag      660
tgagcggtgg caaagagcgc acttagagtc tagagcgagg cagtagtagt agagctgtat    720
gaatgaatac aaagtgtgaa tacaacagtt tgtaatgcga ttctgagctt ggacgtgtgc    780
gcgcgagagg gcgacttgca agccagcgcc cgctcgctct tcttccttct gcacctcgcg    840 tcaacccctcg catctcacac ctacactcgc attcaaagtg cgtacactct cccacgacac    900
```

```
acggggacgg cgcacaccac cgcgcgtcgc ttgaacggcg tcgccacttc gagccgtcac    960
tgacttcgtc ctcgtcctcc ctcctctact ctcttgtact gtactgtgta ctgggggga   1020 accatgg                                                            1027
```

<210> SEQ ID NO 64
<211> LENGTH: 956
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (951)..(956)
<223> OTHER INFORMATION: NcoI cloning site

<400> SEQUENCE: 64

```
ggtacccatg ctgctgctgc ccctcaaagg tcctctcgtc cacgtccgac gagtctggac     60
agctttcaca gtcccgagag tgcaagagcg aggcgggctc acggttccgc aaaggagcgc    120
gaggtccgac cgccggccgg tctccttgcc cgcctcgcct cacctcctct tgcagcaggt    180
tcacctcttc gaggtcactc gatcgctcgc agcgatgcgc aggtacaagt acgctaggcg    240
agagcgtcga aagcggggtt ctgcgaggga ctggacgctg cagagcgcgg tcgagagagg    300
ctcgagtggc gctttgaccg ctcgacgcaa ggcatgcgct cctccgtttg agctcgcaga    360
tactgccgtg cgaagacgag cataggctgt ggctgcggta gcaaggagcc ggcgagagaa    420
agctgtgctc gagcaggacg agagacggtc cgcgcgcttg agaaggtcga ggtgaggcgt    480
cgcaaccggg ttggatctcg attctcggcg aactacggct tcggcgaggg ccaaagcgac    540
ggcaggccgc gcaagctggc caggcgagag cgcgagagtc gcgagctgaa gcgggcgcgg    600
ggtagagcaa gctggggaag cgagagaggg agagagagag agtgaggggg tggcgaggtg    660
gagacgaggc gagcggttgg cttgcgcgcg cgcgagaggg atcgaggcga gaggcgagcc    720
ccgagagtgg aaggaaggac gaggaaacct gcgtgcggag gcgccgcgcg cgcgtgccac    780
ctggctgagc acgggcccga gcttgaggga gctgggggcg cgcgagcgag acgagggcag    840
ggcgagcccg cgcgtggcgg ccgcctcgca acccaaggct cgccctggcc gccgctcttg    900 ctctcttcc tccaccttcg cgtctcacca ctcgaatctc acttcatcca ccatgg        956
```

<210> SEQ ID NO 65
<211> LENGTH: 1474
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1469)..(1474)
<223> OTHER INFORMATION: NcoI cloning site

<400> SEQUENCE: 65

```
ggtacccaaa gggagaggag cgggcggagg atggtggtgc cggacagggc gagagggaag     60
gtcgagggag agatgggagc gcgaaaggtc gaggcgggga gagggagggt ggggtcggga    120 ccaaggggc agagaggctc acaaggacgg aggagcttac tccgccttga ccttgcgggt    180
ggcggtggtg ccctcgcgga agctgcgcg cgaggaaggt cgtcagggcc gggcccaggg    240
```

```
gaggaacgag gacggcgacg acgacgcacc cgttcttgaa gcggcgcgag acgcccttca    300
ggtgctgcat gcggccagtg ccagtggtgt ggcggcgctt ggccttctgt ccccactcgt    360
ctgcgcggcg agggagaagg cgaggtgagc acgacggcgc gcgagggccg gacgaggctg    420
agagggggac gcacacgagc ggagcttggc cgcggggtag ccgcacgaag cgcacgactt    480
gtgctgcttg tggaacgagc ggcggccgca gcgacggcac agactgtggg accacgaggg    540
tcaaccgggt gctcgcgaga caggagcgcg gcttgtctcg aagcacgggc aaagagagcg    600
ttggacgcac gtgtgactct tggtgtggcg agaccgaac gaggtggtac ccttcgtctg    660
tggggcgcaa ggaggagtgg gtcagcgtcg ggcctcgagg cgcctgggtc gtcgacctcg    720
cccgctcccg atcctcgcgc cgtcctgctc ctcctctctc aaccctgcg acgtgttgcg    780 gcagcagcag cttgctggga catgtgggga gggcggcaag gcgaggggag gtcgaggtgc    840
gaatgtgggt ggtcgcgctt ggcggggcag catgtcgtcg cggcctcgag ccgggcgggc    900
gacctggtgg ccgggtcgag cgagaggcgt gggagggagt ggcgcaaatg gcgtgcgctc    960
agaggcgggt tgtcgaggcg tcgaggcgga cgaggtcgag gaggtcgagg tgggaagctg   1020
ctgctgctgc tcgggcgtcg tcgccgcgtc ccgagtgccc cgtgcgcgcc cctgctgccg   1080
ctccttgggc cgtcctggtc ccacctgccc gtgccgtcct ccacgagagc gcgagtgggg   1140
ctgtgcgccg ggttgcgctc caactttgcg agagagcgag gacgggggca tggctcgctc   1200
gccggcctcg ggtcgttcga ggggtcgggg gcggttgcg ggagggtggt gcgaggtggc   1260
gggcttacca ttgtcgcgtc ggagagggg gtttggcctg cgagaagacg aggagacgag   1320
aggccggggg aggcgaggcg gcgaggcggc gagacggctc ggaccaagcg cgcgccgcca   1380
aagtctgcct cgccgctcgc gctcgcctcc ctcttgctct ccacctcctc ctaggaccac   1440
aaaggcaccc ttgtgtaggc gtaggtcacc atgg                              1474

<210> SEQ ID NO 66
<211> LENGTH: 1327
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1322)..(1327)
<223> OTHER INFORMATION: BspHI cloning site

<400> SEQUENCE: 66
ggtacctgag cgggcgagcc gcgagcgagg agcgttgagg aggaagggag ggagggagga     60
gggagaggga gggaggggac ccccatcttt ctattcattc acaaagacga cggtgcggag    120
gggtccctcg agtgtttggg ctgggcttcg gagtctcgta gcgagcaagt agtgtttctc    180
tccgtttcga cagctcgtat tgtcatttct tgttcattgt cgtttccggc gactgcaggt    240
acgctgattt tcggcggaga cgacaagcac gtgggttgtg agcagcgagt tgagcaagaa    300
aaagcggacg aaggccctcg tcgggggctt caagtcaaga ttctgcggag attctgcgag    360
agactgcaag cgttgaacct gttgagatct cgtcggacga cagcacagtg tccgtctcgc    420
tcaatgcgat aggaagcgag agagaggagg aggatatcgg aggaaggcgt gtttgcgttc    480
gctccaggcg tcgcaagatc cggcgtagag cacaatcgtc gttggttcga cgtttgtagt    540
tcgtcacgag tgagggcgaa gcctggcaag caaagaaggg gacgagcgac tcggcagcta    600
tcgctggagg agggcgactt tgtggcccgt ttccgtcgag ctcgacgcga gtgagcgcag    660
```

```
ggtcggtccg aaccgatgcc atggacgcag tgagcgaggc cggatgtgcg atgctgtttc      720
aagcgagcga aggaagggag aaagcgagcg agaggtcctc ctcctgtctt cctcacgcct      780
tccgaaggcc gacaagaggc gtagacgtcg acgagtcaac ggtttgacgt cgctcaggcc      840
tgtagcgggt cgtcggaagc tgggaaagag aggaaccaac gagtaacaag cgcgagagtc      900
tcctcaaggc ggacaattgc ctcgcttcgg tcccggtcga gctcttccag taccagcgag      960
ggcgaaagtc gtcgatgcgt gcgcatccaa ggccaagcgt cgcagtcgag aagagcgaga     1020
gtgaagcgag tgaagcggga gagtgagagc gggtaatccg cgtacttacg agtgggttgt     1080
attccttctt gtaatggcag attacctcga ttggccacgt cacgttccgg gagtgcccgg     1140
gcgtgggcaa aagggcgagc gcggcgcctc tctctcttgc ttcctcagca gagcagctct     1200
cccctcgagt acgtcgacgg gctcactaca gctagcaaca gcaaggctac cacgccagct     1260
acacgccagc tcacccaact cacaccgctc gttgtcgccg cgcgccgcag gaaaactttg     1320
ttcagtc                                                                1327
```

<210> SEQ ID NO 67
<211> LENGTH: 1509
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1504)..(1509)
<223> OTHER INFORMATION: NcoI cloning site

<400> SEQUENCE: 67

```
ggtaccgctc atcatcgagc gagggcagca gcgacctgcg gactggccga agaacttccc       60
cggccagcgc ttcgaggaca aggacattcg cacgcctcgc tctcagtggc ggtacatcaa      120
gctggcgacc acagacgacc tctcgccgac tgaggagaac acgacgtcct gcgccgtccg      180
gtacggcgag gactcgcagc tcgccatctt ccacgttccc ggcaagggt acttctgcac       240 gcagcagatg tgtcctcgtg cgtcgcgcct gctctctctt tctttatttg ctggctgact      300
cgtgctgact cgcccgaaac ctcagacaag cgcgccttca tcctcgagca tggcatcgtc      360
tcggacgacg ggagtggcca cctctacgtc tcctgcccgc tccacaagcg caacttccgc      420
ctcgacaacg gcgactgcct caacgacgag gagtacaaga tcctcgcgtt tgatgtcaag      480
gaggagaacg gcgacttgct cgttcaggtt cctccgcctg acgagctcga cgctttgatt      540
gggtgcgtct cgcttagccc tctctcaaag acctgagctg acccttctga ttgtccgcag      600
ctcgtcgaag tggatggtgc gcaaagcgac cgccgaagcc ttcggtcgca acgcagcgac      660
agccatcgag tgcgtcccct ccaagcttct gttttccgcg cgcacactag gctgacgaca      720
agtctctgca ggatcgtcgg accgtcaggc gaggttgacg aggacaagaa ggcagcggga      780
acagagtgcg gcgaagcgga taagtcttgc gggacgcaca agctcgagtg gtgattcttg      840
cgggtccgtc acagccaatg tatctatctc tagatgtcct tctcgggtat atcagttgtt      900
cgtgcatcgt agacgtcgtt tagcagctct cgttcagcca cttgcgaagg cccgcttctt      960
cgacgacaag gacggcttcg cttcctttac ctcgtcgtct gagcgttctc aagggaccct     1020
cctacgcccc tcttcgcaca ggagcggccg acgaggcagc cttgctggct tatcgtcgct     1080
tccgcctttc atgctcgagc aagtcctcct gcgagtgtcc cgacgtcggc ccgccttgcc     1140
```

```
caaggtcgcc gactgtccta tcgcgacact gcgaatgcac tgctgtccgc gccggagact    1200
gtgcggcgcg aattgagggc aaagtcgtgc atttgcgaaa cggtatccgc tcgaagggcc    1260
cacgatagac ctccaccggc ctcaaacttg gcgacagggt cgcttccgac ggcggacagc    1320
aagttaggct ttggcgtcgt cgctgcgatc cgctttgcgg gaccccttat cgcgactgcc    1380
ggattcgatt ggcgatatct ctcgctcgct ggcctcgctg gacagctgga cagtctctgc    1440
agcgtcgaag cgacgtcgat aaagtcagcg acgtcctcgc gaaccaagaa gaatcacccg    1500
ccgccatgg                                                           1509
```

<210> SEQ ID NO 68
<211> LENGTH: 1606
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: SpeI cloning site
<220> FEATURE:
<221> NAME/KEY: misc_feature
<222> LOCATION: (1601)..(1606)
<223> OTHER INFORMATION: NcoI cloning site

<400> SEQUENCE: 68

```
actagtcgcc agggaacgca gagaaggcgg gacgagcgag ggtgagtcgc gcaagtcgac     60
gaagaagccg aggtcaacgt cgagggttgt caagttctgg cagacggaca gcagccacac    120
taatcgctgc cgacttctga tgcatcgtcg cgcgggtgtc agctcctagc cgtggaagga    180
ggaagccagg acgttctcac cgggcgacgc attgcttgtg ccagacctcg aggcgagctt    240
gtcgcgtcga aagaccggcg acctcgtccg gctcaaattc cagcccgagt gattgccctg    300
acaacaaagg cgaaaagctg aagccggtac caaaggtcgg tccatcgaaa gtcgcgctcc    360
gaagactggc gtcgacggat ctgaccatcg ctgcccctcc tgcgtctgct ttgaggcacc    420
ttacagcctc ctcgtctcgt tcggagcctc cgcatccgct tggcaggacc acctcgcgac    480
cagtgacctc ccttgcgatg gctcgccaag tcttgcatac tccggcgacg ttgcggaagg    540
cgcaggtggg gcaggagatg cggagcgttg tgaactgtcc gttgacgagg agtgtcggcg    600
aaagaagggc ggtggtgaga gagtaggtga ggatcttgag gaggagttca ggaggaagtg    660
aggaaaggtc tgccggtgac tggtaaggct gaagcatgat ggcgagtgta gccaagtgat    720
ccgagcgacg atcaagagac gaaggacgag acaacgcttc agcgcgcgaa gagagcgagc    780
gaggaccctc ctggtcgaga ggctatccag tcgccaaccg gtacccatcc agtttgcagg    840
gttgaaacac agctgagagg atcagcgagt ggtagcgcaa actcctaagg cgctgaacgt    900
caaggacagc gagcgtgagc gtgtggaagc gacttgcgaa ggccaaactc gtgtcgcgct    960
ggccaaccgc cgtgccgctt tgacgcgctt ctgcgccctc cgcctattca gagagtatgc   1020
ttcgtcacgg cgtgggcgcc aacatcggcg caggagctgg cgggacggga agaaagccgc   1080
aaccgcggtc ctcgaccttc aacgtcccgg gaggcccgtc cacgactccc agacgtctct   1140
gcttgttgtt ctacgtcgtc gcggcgttgt gcagagtcca gcgcgcgccc gtcgtcgact   1200
tctgacaagc gataaattcc gagaccagcg ggagaaggcg gaacgagagg aggaggcgag   1260
ctggcgtcct tgcgaccctcg ttgagcagtt caagcgagca gattgagcag cagtgcgtcg   1320
agtgagccaa ctcacgttct catatcggtc cctgagcgat atcgatgagg cgaaggacga   1380
cgacgagcga actgatctcg cgctctccct cttccccttc actctttcca ctcagaaaca   1440
acacgtgcgt cttctctgaa cgctatcaga caatccagga ccatcgctga ccgcgcgctc   1500
```

<210> SEQ ID NO 69
<211> LENGTH: 1408
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: SpeI cloning site
<220> FEATURE:
<221> NAME/KEY: misc_feature
<222> LOCATION: (1403)..(1408)
<223> OTHER INFORMATION: BamHI cloning site

<400> SEQUENCE: 69

```
actcgtcgcc tgacttcatc gcccaaccaa cccgctcgtc accgactgga tctctccctc    1560
ccctcacacc acctgttgcg ctgcgatact cctctcacag ccatgg                   1606 actagtcggc gaagaggagg ggtgttagga gggagagctg tgcgaggggg agaggtcagt      60
ccgagcacga tacgcgagca ggccaagcgg cttcatgttc actccaagct cgatgcggtc     120
gagaagtacg agctccttga cgagtgaaag ggagagaaga gagactcacc aaccccggcg     180
cgaccttcac gaaccgcaac ttccctcac acgcctcact acacgccctc tcaaacacct      240
cgagcgtcgc gtagtgcgag agcttgaaga ataggtaggc gaggaaggag gaggcgaaga     300
gggcggccat ctagcgaaca agttgggtta gctgggtggg ggaaagggaa gaggggagga     360
agaggggag  ggtaccatga tccagcctat gtcgacttgc agttggaggg gcatcctgtg     420
cgcgtactgg cgtcagcggc ggacgacaag gcaggtagac gagagagggg gccggggaac     480
gcactcgcag ttgcgcacgt ccgagaggaa catgtacgag tagccggccc acatgacgct     540
cagcagcgcc gcaagcgtgt agtggaagat gagcctgccc attggcagtc agcgccgacg     600
cggacaaaact ctgggtgaag agaaaggaga gaacgcacca cttctcctcc ttcagcactc    660
ccctcgccca gaccgccccc aacacaatac agacgagatc gatagttgcc ccagtcacag     720
cgagcgcgag ttggctgtag acgaggtgtt tgagccgtct gtgggcggga gaggtgcgga     780
tgcgctggat ctgcgcgggg gagagttttg ggacgaagtt ggggtcgtcg gccatggtga     840
gcccgtcgta gtagctgtct gagcgagcct agtagtgcgc tggacgagca gagcccagag     900
tcgagacgag cgtgagcagg agacgaggtt cggagtgtcc gcggagggcg acgagacgac     960
gagcgagctt gggagaagcg cgagcatgtc cagcagcgta gtctcgaggc cgccagcagt    1020
agtagagcac agcaatgagg caggaaggag cgcaagggag ggaaagagcg cgacgaaggg    1080
tcgaggtgat gaagtccaag gacaggggga ccaccctcgc ccgcttctcc ctcgctctcc    1140
ccacgaagtg accacttgta aggctggtaa ttcattccat acagtctaca tacacttgca    1200
gccatccgct tccctgcga  tgccagtttc ggtcaccgtg ggactccgat gcgatgatgc    1260
ggccgagttg gcttcctcga cccgctctca cacgctcata ccagcctctc ccagcctgct    1320
accgctctct ggctctgcca aacacccact cgagcacacc cacccaacca gcgaactcgc    1380
ccagcctttg aaccgcaatg gcggatcc                                      1408
```

<210> SEQ ID NO 70
<211> LENGTH: 1480
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: SpeI cloning site
<220> FEATURE:

```
<221> NAME/KEY: misc_feature
<222> LOCATION: (1475)..(1480)
<223> OTHER INFORMATION: NcoI cloning site

<400> SEQUENCE: 70
actagtcgtg cagaaggaac ccgaggaggt cagtgcgcgg tcgagagagg aaaaggagag      60
agagacgcac cgagcgaggc attgcgcgtg ccagcgctca gcctgtacct cgcgactgct     120
gatgaaagcg tcgtcgccgc ccgacatgac cgccgcctcg ctcgactggt cgccgacgac     180
gtcgacgccg gaaggaggtg cgccccagcc gcaggcggcg cgcctcaggc tcacgtcgac     240
gtgccggacg ttcgacgctc gccacgggtc gtgctcgagg gctttgacga cgagctcgtc     300
gcgctcggcg ctgccgcacc cattggcgaa cgtgacgtcc tggccgagca cctcctgcgc     360
gatggcgcgc cacaggcggc agacggacgc gacctggcgg taggcgcacg tgcgacaggt     420
gaccgtgagg tgcgcaaact ggccgtggac gaggagaggc tcagagatga gcgaggtcgt     480
gagggcgtgg cggatgacct tgaggaggag ctcgtgcggc acggcagaga gggtcggcat     540
gatggtgtgc ggcgcggtcg gcagtctcga gagagatgtg tagaggaaga acgatgtcgc     600
cagatcggtc gagcaggagc cggtgcgagg cggctcgagg accgtcgcgg tcgaggaccg     660
gtcacggctg gacgatcgag gagacgcgcc cccgtcgagc gcagcggcca gacgcaagcg     720
agcacctttg aggctgtact ccaaaacccg gagcgccggc tcgggagccg tgtcctcgca     780
ggatcctcgg tcgacagcgc cgagtcggag agggccagcc gacctcgggc cgcccgacgc     840
ccggccgcag ctcctccggt ccgacctgca gctcatccca gcagatcgac tttgagagcg     900
aagcccccag gaagctgcct gagcgacctc gaggcttggg aaggtcgccg agccacggct     960
gggagagcga gctccctcac agtcgagacc ggctccaagt cgaatcgcac actcgtagct    1020
gcaccgcaaa agtgtgtgca gagctggagc gagcgaccgc gcgaggcgcg agggtcgcga    1080
gaaagcgggc gagcggtgcg agtgcgcccg agacgccgag agagggcgcg agggcgagcg    1140
ggcctcgcga gccctctgga gcgtgcagag gcggcgggga ggagcagagt gagggaggga    1200
agaccctcca gagctggcag gagccaacgg agcgcggaaa tcagtgagat cgatgcggtt    1260
ctcgagacga ttcgaccgcc ctcgtcgtca acgtcgcgcc ctcgtccctc tcctcttccc    1320
accacctctc cggtacctct acacgagtgc gttctgtccc gagatctgat ctcgacgccg    1380
cacggcactg actgaccgcc cacctcgtct ccctcgcccg tcccacactc tcccttccga    1440
cctcccacct cctcgctcaa cccctctcgc ctcgccatgg                          1480

<210> SEQ ID NO 71
<211> LENGTH: 1532
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: SpeI cloning site
<220> FEATURE:
<221> NAME/KEY: misc_feature
<222> LOCATION: (1527)..(1532)
<223> OTHER INFORMATION: NcoI cloning site

<400> SEQUENCE: 71
actagtcggg aggattgatg atcgggttgc ggtacaaggc gaggccgagg acgagctgga      60
gggcgccgag gacgagggtc gagatgccga gctgcgaggg gacgaggccg ccaatcgagg     120
tcgtgtcaga cggccgtacc gagtgatctc atagcgggtc cgccgacgca gaaagacgaa     180
gagaaactca cgacgagggg gctcagcttg acaaagttga gctttgtcgt gcagccagac     240
```

```
gagctgcgat aggagcgagg gtcagtgcgc ccgctctcgg atgaatgcgc agtcgaggag      300
ggacaggggc gcaccaggtg acgatgaaca tgtcgaggac gccgtactgc agcatcttgc      360
ggaagaggta gaaatgccac gccgaagcga aggtgacggc aaactgcgag agggacgagg      420
tcagtgcgag ggtccgcaac agggagaggg cactcgtcac ggaccatcat ccagcccagg      480
tcgatctgta gctgatcagg gaagctgtgc cgggtgcgag agaggtcaat gtcgaagctt      540
ggcagctcgt cgaggaagaa gaggacgcg agggacgcac gccatgaact tgatgtgacg       600
ctcgaagacg accgagtagc cgagccacat cattgtgagg acgccggcgc agacgtagtg      660
gaagatgaac ctgagagggc aagaggtcag tctcgaaacg agggaggaag ccggctcgag      720
caggacgagg cgggcgcaac ggacgcacca tttctcggcg gcgacgatat tgcgagccca      780
cacggccccg agcactagac aggtgatgtt ggcgaccgcg ccgccgacgg cgagagcgag      840
aacgctgtag acgaagtgct tgatgcgtcg gtggattggc gctcgtcgga tcctcgcgat      900
ctgggccttg gtgagcggtg gtggcgggcc aagcggtggg ccagcagctg tgctcatcgc      960
agcagcggtg cggcgcaaga gcgactgtgg agctcgaggg agaggagcgc ggcaggggaa      1020
agcgagaccg aggaggagcg agcgcggaca ggcgaggcgg accggacgtt ccggtgcggc      1080
tcgactggcg tgcgagacga gcaggccgtc gccggaagca gccgtgtccg gcggaaagag      1140
ccaggcgcgc gagcggggcg gagcagacag cggcggtccg agcgcgcggg gcaggttcga      1200
cgaaagtcgg gctcgggtca ggctcgcgcg agcgcatgag atgccgtcga gcgagcccat      1260
gtacagagtc gagcgagaga gcgaagtgcg tggaaggaga gtggtccaag agtggagcgc      1320
cgtggagatg agacagatga tggcgaacct cggccacagc ctctcggtcc tgccacagca      1380
gctctgtgag tctccctgac ccgccagccc gcgcttcaga actcacagac cacctacaca      1440
gactcgcgca ccagctcgaa ccgcgccaga ccaccgcctc gccgcctccc cacctcgact      1500
gcttccgaac ctcacaagct cgaccaccat gg                                    1532
```

<210> SEQ ID NO 72
<211> LENGTH: 1222
<212> TYPE: DNA
<213> ORGANISM: Rhodotorula graminis strain WP1
<220> FEATURE:
<221> NAME/KEY: misc_feature
<222> LOCATION: (1271)..(1222)
<223> OTHER INFORMATION: NcoI cloning site

<400> SEQUENCE: 72

```
ggtaccgcga ggggaagggc aggagagtcg ccggaacacc gggcaaggag acaaggacaa       60
agagcgagcg cgcacgcacc gtctggcggt cgggctgggt ggggcgggtc cgagtagcgc      120
tgaccgaaga gcgaggagga ggaaaagcga gcgcggcggg cgtgggaagg agggcaagga      180
gggcggcggc gacgccaaaa aaggccagat tcgcggggca gtgatcgagt gccgtccgcg      240
agctcaacca gcgagcgctc tctcgcgcgc agcggtgcgc ttctttcgcc agccgatgcg      300
caccgttcag aagcacgtcg cccgcaccga gagcgcctcc tcgcgagcct gtgaccacct      360
cgtcgacccg cttcccgcgg cttttctcgc cggcctggac cgccgctatc agatcgtgcc      420
catgagacaa gcgactcgtc gaaaggacga cgatctcgta gtactgggtc cctgcgcaac      480
gctcagccgt ccgtccccgt caaagtgctt cggcggaggg gaccgtgcgc gagacgccca      540
agttggcctc ctcaagtcgg tagatccagc ttaacgctat caagggttgc atggtgtagt      600
tggtcatcac gtcagtttaa cattcagttc actgaaggtc ctcagttcaa acctgggtgc      660
```

-continued

| | |
|---|---|
| gatcaccttt ttggctcggc ggcattgcgc ccttacaccc gcacgggtct acttcccttt | 720 |
| gcaagcgacc aagcgaagca tcctctcgct cgtaaagctg ccggcgagga ggtcagacgg | 780 |
| gttggcgggc cgtcgaaggt cggctcaccc tcaacgctgc cggctgacca cgccaggcga | 840 |
| gctatcattg ctttgaaagc ttcgaaaacg cccaggcatg cacagaaagc cgcccgcgag | 900 |
| aggctcaagt tggcgccgag ctgcggtcga gagacgacga cgacgtggga gctccctcgc | 960 |
| ctctcctcct ttctctccca ccccatcagc ccaagtgagt cgctcgctct tccgcaaggg | 1020 |
| tcagcgcacg cgttgctccg cgacagggca gcgcgtgcgc tcaccaggt ccccgttcg | 1080 |
| cccggcgagt tggcactgac gaggtgcctt gccccctcc gctccctcc ctttggcct | 1140 |
| cctctctcgc acgcacactc tctccctgca ccccttgcac ctcccgaca ctctccccc | 1200 |
| ccttcccacc gtccgaccat gg | 1222 |

<210> SEQ ID NO 73
<211> LENGTH: 1507
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1502)..(1507)
<223> OTHER INFORMATION: NcoI cloning site

<400> SEQUENCE: 73

| | |
|---|---|
| ggtaccacta cctcgtcacg acccagggtg cgttcccctt ctcgccgcgt ccacagccac | 60 |
| gacgttgcga gtccctaacg cgtccgctcc cccgtgcagg tggtcctccg cacggcgcct | 120 |
| acacgcagac atcgtcgacg ccgtcgcacg acgcccactt tgccgtccag accctgtcgc | 180 |
| gcttcggcct cgcgtacctc ctcgcgtcgt ccaacacgct caaggacacg tggctgagcg | 240 |
| tgtgcgcgcc cgccggcgcc aagggccccg aacccgacgt cgacgacctc gagctcgaga | 300 |
| agcgcgagca ccgcgacaag tggctcctcg ggcgcatcat gggccagggc aagcaggact | 360 |
| cggcgctcgg ggacgcagtc gctgtcgtga gtcctctact ctcggccgtt ctcgagactt | 420 |
| ggggtgcgag attgaccttg cgctcccgcc tctcgcttgc agcaattcca caagcacttt | 480 |
| ccgcacctgc gctcggcgca cctcttcccc ggctttgtct ttacgtgcgt ccctctcgtt | 540 |
| ccccctctc tccacgtgcg ccaccagcct gactcgcccc tcgcctgccc cgtcccgcag | 600 |
| caacgccctc gcgtcgacct cgctcgtccc ctcgccgatc ctgtcgctgt caacctcgt | 660 |
| cgggcccctc gcggcgcgca tcctgccctt tggcaacctg cccgagacgt acgccgacgt | 720 |
| gcccgtgtac gtcgcggcca acccggcagc gcgcagccaa gggctcgagt actgcaacga | 780 |
| gcgcatgaag ccgctcggga gcccggcgtg ggccgagggc gcgacgggcg caaaggtgtg | 840 |
| ggacgggctg agggccatga tcgaggagtg agctggtggg cgggcgagcg aggagccgga | 900 |
| gaggaggggc ggaacgtgtt tgagaaggtc gcgctttgct cgtcggtcgc gggcgcagcc | 960 |
| gtggctgtag ccagtctcgc tttgcagtgt cactcttgta catagctgag caaggcctag | 1020 |
| cgtcgcgaga gagctgcgct gtggcgcctg gtcgaggccc gagagcgtcg cgctcagggg | 1080 |
| cgagctgctc gcggctcacc aaggggctcg agcggtgcgc gctcgacagg ggaccgagag | 1140 |
| ctgcaggaga cagaccggag gaaaagctc tggcgagcga ggagcggggc cacactgagt | 1200 |
| ctggggaagc gacggacgag gatgagcgca tccactcttg agtttcgccg aggcgcgagc | 1260 |
| tggcggtcga caaccgagca agctcctcct cttcctccac cacactcgcc cctagcacac | 1320 |

```
gtgagtctcg ctccctcgcc actgtcgacc agcacacgct cgtccaccgc cctgtgcgcc    1380
ctgtgcggct tgcggtcgag cgaggccgcg ggtcgggtct ctgccacccg aggaaccatc    1440
gatgtcgctg acgcttcgct cctcgtcctc ctcctcctcc cacccgccgc agctacctac    1500
accatgg                                                               1507
```

<210> SEQ ID NO 74
<211> LENGTH: 1646
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: AscI cloning site
<220> FEATURE:
<221> NAME/KEY: misc_feature
<222> LOCATION: (1641)..(1646)
<223> OTHER INFORMATION: NcoI cloning site

<400> SEQUENCE: 74

```
ggcgcgcctg aagctgtaca tcgaggtgga cgacagcgcg ggcaaggatg cgccagcaat      60
cgtttgtggg tcgcttcttt cctcgcagca cgcttttgtc ggctccctga tcagcacaca    120
agctaactaa cgctctggtt tcgctggcag tcatgcacgg ccttggctcg tcaacctcgt    180
tctgggaagc gccttctcc cgctcaaacc tgtcctcccg cttccgcctc atccgctacg     240
acttcgacgg ccacggtctc tcgcccgtct cgtccctcga cgcagcagat gacggcgcca    300
tgatcccgct cgacgacctc gtcggggact tggcggctgt gatcgagtgg gctggggtgg    360
agaaggttgc gggagttgtt ggacactcga tgagcgggct ggtggcgagc acatttgcgg    420
ccaagtaccc gcagaagctc gacaagctcg gtgagtcgca ttgaaccttc ctccgccgtc    480
tcttctccgc tgacgattcg tcgacttggc cctgcttctc gcgcagtcct cctcggcgca    540
atgcgctctc tgaaccctac cgtccaaagc aacatgctca agcgagccga tacagtcctc    600
gaatccggcc tctcagcaat cgtcgcacaa gtcgtctccg ccgctttgtc cgacaagtca    660
aagcaggact cgcccctctc ggcagcgatg gtgcgaacgc tcgtgcttgg aacggacccg    720
agagggtacg cggcggcgtg tagggcgctt gcgggtgcga aggaccccgga ttactcgagc    780 atcaaggccg agacgttggg tgcgttcgct tgttctcctt cctctgcttt tctcccagca    840
actgacgcaa gcgtctgcaa cacagtcgtc gcaggcgagt tgactacct ctcgaacaag     900 gagacgaccg acgcgctggt caacgacatc ccgggcgcgg agaaggtcca gatggacagt    960
gtcggccact ggcacgccgt cgaggacccc gttggactcg ccaagatcct cgatgggttc   1020
ttcttgcagg ggaaatgagg ttgggaaggg gggatagact ggggagaacg gcaggtgcgt   1080
acgcagcgga cgtcggtcgg gaggactttt tcggggagga tattcgctga ctgactccga   1140
cgtcgctttc ctccttgcag tatcttcaga agggatggga ggaggcgaac tgcaagggta   1200
atgaacgaga caacgccgag ggaggaagcg ccggaactct cggggcgaa gaaggagtgg   1260 tgtcttcgcc agcgaacagc ttccggggtg ggttggacag cgccagtaga attccagcgt   1320
cgcaacagag ctctagtcga ccgcgatcac ccacaaggac gagagcgggt cgcgccttgt   1380
ccgcttcccc atcctcgtcc tgctcttgct ctcttcccta ccacactctc ccgcttgcgg   1440
gctctctttc tcgcttggcg ctcctgctac cgctactcta gactctccta gtctccctgc   1500
acaaccatcc ctatccctc cgcctctctc gcacaccccc cacagcttcg ttccccaact   1560
tcacttccga tgccgtgcgt cgcctccctt tcgcctggcg ggcccgcgcc tgcttccgag   1620
```

```
<210> SEQ ID NO 75
<211> LENGTH: 1450
<212> TYPE: DNA
<213> ORGANISM: Rhodosporidium toruloides
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1445)..(1450)
<223> OTHER INFORMATION: NcoI cloning site

<400> SEQUENCE: 75
ggtaccggcg cgctagtctg cagaactacg ccctctcaca cccaacttcc gactcgaccg      60
gcggtacgag cacgacctac ttctactgcc tgccatcgac atccgggcgg gtcgctgcct     120
accctgtgcg ttctgcgccc tccctcgtct cgggaggcag tgtctgacag aagctttgcg     180
cgcagtaccc cgtcaagatg caactctacg caacgttcgg cacagaagtc gccaagctcc     240
gcgcatcgcc gcctcaagct ctcgcgctgc ccgacggtgt cgtctattac gaggcggaga     300
agctcgagtt gccggctttg ccagcggcgg tcaaggttga ggtggagacg gagaaggcgg     360
gagtagcggg ggaggacaat gaggcgaagg gtgagatggt gctggtggag actcttacgg     420
tggagcagga ggagattgaa ttgggctcgg gagtcgtgca gattgaggag tcgttgctcg     480
tcaagctgga ggtcagcggc tgatccttcc gttcgttgca aggatcgtct gcatgtttcg     540
cttctctcaa tgacacaacc tggagagcgc tcccgtcagc gagaatcgag acattccgc      600
agctcgtgag caagcggagg tgcgaggctc cctcgaaagc tgcgcctctt cagacggctt     660
gttctctcct gctctggtgg gctggcctga catgtaatgt gctccgccgc aagtccgtcg     720
tcggtctcaa ttcgacgttg aaagggcata gcgcaaggaa gaaccctctg cggacatgca     780
gaattactgg ctcgcctgct ccttcgtcta ctggaataag tcctgtctcg ttaaagcccc     840
aacgtcgttt ttcgacgttt gtaaggcgca agaggtgcta tgggctacgc aggaagctga     900
gaggacatag aagtcggggg aggaacggcg cagagcggca gttgcggaag catgaggaaa     960
gcgagacggt ccagcatctg cagcgccaat ccgcaatctc ctggttgagc ctgcaccgga    1020
agcgtcggaa cagtatgcgc agagtcgaac gcaagtaaga aagacgcacc ctcacactcg    1080
cttacttcga gccatacaac ggatcaaagc tgcgcgtatc tcggcttgta agggccggaa    1140
agcaaccctcg gagatggaca cgtcacatca ccaacttatc gatctcggcc gtcgacgtcg    1200
cagagagggc gagagaagcg gtgaaggagg gaaacaaccc ctcgagagca tgatccgacc    1260
gaatctgcag cgcaggaagc cgttacaagc ccgcctcgag cgcaggtcgg gtccagccgg    1320
gggacgaaac gcgcgaggct gattcgtgag cgaaggaagc cgcatcgaca agttcgctcc    1380
cctttgccct ctttcccatc acccgttctc gccttacccg ctcagaacaa caccagatca    1440
ctcaccatgg                                                           1450

<210> SEQ ID NO 76
<211> LENGTH: 672
<212> TYPE: DNA
<213> ORGANISM: Ustilago maydis
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
```

-continued gacaactact gattgtggga ccatgg      1646

<222> LOCATION: (667)..(672)
<223> OTHER INFORMATION: NcoI cloning site

<400> SEQUENCE: 76

```
ggtaccggcg cgctagtcct taaaactgaa ggcgggaaac gacaatctga tccaagctca        60
agctaagctc tagtgattag atcttgctga taggcaggtt tgcttggaga atgggggaa       120
aagactgacc gaagaaacag cgagatctag aagtgataag cggaaagaat ctgacttgct       180
gtgatcagca gccaattttt ttttcgtttt ttttttttca ctccacatcg tcgtgcgtgc       240
acggtctgca tgtgtaaatt gtattcatcg aaagccacag ttgaatacat cagcccgatg       300
tggatttcga aaaccaatta atcttggaat tcacgcgctc agatcagtcc atagagtcga       360
cttcggctgt ttccaagagc ttcttctctg cgaggtggtt gcccgtgttt ctcgctggga       420
aaaaaggatc gattattatt cgcttctacc tcgctcgcac ccttggcctg ctgaaggaaa       480
cagcgccgag actcggtcac ggttgctggg ctccgtgttg atgctgggac ggcgcaaagt       540
ggggcccgcg cactcttcga gccaaggacc tcactcttca agaacaagcg ctgtcgccat       600
cgtcttcttc tttctgctcc accatcgaat cttctttct cgtttcgaaa ccaaaacact       660
cttccaccat gg                                                          672
```

<210> SEQ ID NO 77
<211> LENGTH: 963
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: AscI cloning site
<220> FEATURE:
<221> NAME/KEY: misc_feature
<222> LOCATION: (958)..(963)
<223> OTHER INFORMATION: NcoI cloning site

<400> SEQUENCE: 77

```
ggcgcgccta cgtctacgtc aagggcaatg ccgacgtgac caaggccatc ggccaggacc        60
tcgccttctt ctcggtccct gtcgagctcg gcgtgcgtcc cgccgctctc tctctctctt       120
tctctcggcc gcgcctcacg tgatccacga cgtcgtactg acccttgcga atgtgcgcgc       180
ccgcagccca acggcgtcga gaaggtgcac ccgctcggcg acctgacggc gttcgagaag       240
gagctcctcg aggcgtgcct cggcgagctg cccgggtcca tctccaaggg cgagtcgttc       300
atccagggct ccaagctctg actcgccggc gcatcgacgg gcgcgagcca caaggcgagg       360
atgtgagagg aggcgtttcc tccaccttgg accccatctg ccgcctccct ttctctctct       420
ttctttccct tcctctctct ctctctctct ctcgttctcc tccttctggg cctctcggac       480
ctcttcctcg ccgtcgactc gtgaaaatgc agtgcgcgtt tctgtacctt gtcctgcgag       540
agagatctgg ttctgcgagg gtgagtcgtt gccttggccg tggcacgcct cgccgcagcg       600
agagagaaga ggccacggtc caggacgacg acgacgagga ggaagcgcaa aaggcgagac       660
accgagtgcc atcgattccc cgctcgaacc tgctcacggc tgtcgaaggc ggtgcgccac       720
ggtgcttgcg ggagcgaaag caagctggcg tcgtcctctt gaactggttc gagtccgtga       780
gggcggcgac gagaactcag gcgaggtgct cgcgtcggaa caagccgggc ttgtggtcga       840
gggagcgaga gcgaggcagc gccgtcgtcg ccgaggcaag agcggcatcg acaagttggc       900
ccgtcgcctc tcgctcctc ttctcctcct cccaccacca cctttctcca gctcgaacca       960
tgg                                                                     963
```

<210> SEQ ID NO 78
<211> LENGTH: 2148
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: AscI cloning site
<220> FEATURE:
<221> NAME/KEY: misc_feature
<222> LOCATION: (2143)..(2148)
<223> OTHER INFORMATION: NcoI cloning site

<400> SEQUENCE: 78

```
ggcgcgccac catctcctcg tcgcttcttc cctctccttc ggcgcccaca ccgcttcgca        60
gggctcacgg actgctcaca tcgtttgtgt gcgtcgctgt gcatgtccac gcaccactcc       120
cagcccccac gagcgcctca aaagacgcgg acgcagacgc ccgccgaacg acggcacgcc       180
cctcttctca ctagcgcgac gaaccagctg cgacgattcg tgcgcttatg ttagccggac       240
ttctggcttg ctttgcgctg ctgcgtccgt cttgtggtgc ggatcggctc gatgggggtt       300
tgctcgtttg ctgggagacg gtcgcctctc cctcctcctc ttcactcctc gttagctttc       360
tacgctcatt ggttctgcga accatctaca tcacgctcgc tcgtcatgct cgtactacga       420
tcaacacccc tgctcgtcgt gctttccctc ctctccgtcc tctcggccgc gtccagcgac       480
ttgcccagcc aacttccccc gcacgccggt gagtctccca cacttccttg cgaccccaac       540
ccagcatctg acatccgcat cacgcagccc tcccgccttc ccactcctcc ctcttcaccg       600
actcctcctc ctcctcccct gattcctcgt ccctcaaagc cccgcagcct cttcccttca       660
aaatcaagcg cccccgctcg ctcgaacaag tgcagcagaa cctcgggaag aggctggcga       720
agcgcggcga ggaggggagt aagacggaga gggtgccgtt tggtcagagg agtgcgacgg       780
cggcgagtgc gggtggacaa ggtggagcgg ggacggggag ggcgacgcag cgcgttacgg       840
gcggaggaag cagaggtgca ggaggaggcg agggagtgt cgcggctgct cagcctgtcc        900
cttcgactac ccagacggtc gagacaggct ctaagatcgt ctcgactggt cttctgaccg       960
tagcgtcgcc gtcgacggca gatggaggag gcgggacggg cacccaggtc gagacggcct      1020
cctcaggggt attgatcacc agcacggcgg gagcggcgag ttcagcggcg gcgtcggacg      1080
tcgctagcgc acaggcagcg gaggcgacgt cgagtacgag catgatcagc ggaggagcgg      1140
cggctggcgg gagtttaagc aggatgctgg cgggaggagt tgcgggtgca gccctgatcc      1200
tcctcgtgcg gtgagcaggc gaagcgagga gctcatgtag atacagcata gacagtatat      1260
atcgccagga tagcttgcaa cagccgccgg tcggtttatt ccattgtcct cgaccccatg      1320
cgaaggcgag ctctgctcgt cagctggcca agctggccag cagacgagcg ttggggtggc      1380
ggaacgccaa cggcatggag taaagcagcc gtgaggatga cggaggagct cgggcgaggt      1440
gatggggatt ctagcaggaa cagcagagcg cgaggaggga gaggaaccgg aagcacagtc      1500
tcgtggccgc ttgttgcaga tcccagtgtc gctagagtgc tcgtcgtcat cagagcgagt      1560
gaacaaagcg atgccctgaa gaacgatgag cgaatgagtc gaagcggcgt ctaccggtga      1620
actcggggtg tggcaaatga gcgagacgag gagtgcccgc cagagttgcc acgtcgaccc      1680
cacgtcggaa tcgacgttga tagagtgaac gaagccattg cagaccccag aaggtggcca      1740
tgttgtggaa gcgagggcag gagcgagggg agaaggcgag gaggaggagg ggctggggaa      1800
gcccgtccgg gaatgcgcga gctgggtgcc ggggatgtgc gcgagtggcg gaggagtcga      1860
gcgtgagagt tctgaacaca ggggcgcgca caagggtcga gggccgtgac gagttcgccg      1920
```

```
ggcggtggtc gggctgaggg cgagcgcgcg ttggggacga cgacgcccga cgccctcgct    1980
cttcgtcctc accgcttccc ggagaacttt gctgtactct gcttctccct tcacactctc    2040
acacccactc acacacccct tccatccacac acaagctatc cgcacacctc tcacacccga    2100
ccccagctcg ccccatcctc ttcgcacccg gctcatcgaa aaccatgg                 2148

<210> SEQ ID NO 79
<211> LENGTH: 1009
<212> TYPE: DNA
<213> ORGANISM: Sporobolomyces roseus
<220> FEATURE:
<221> NAME/KEY: misc_feature
<222> LOCATION: (1)..(6)
<223> OTHER INFORMATION: AscI cloning site
<220> FEATURE:
<221> NAME/KEY: misc_feature
<222> LOCATION: (1004)..(1009)
<223> OTHER INFORMATION: NcoI cloning site

<400> SEQUENCE: 79
ggcgcgccga agttatacct cagaggtctc aaaaacgaaa aagtcatgca agaatctcct      60
ttgacgtgag ggttatttct cttcctctag tagtctacga gaatcgcaaa gatcggaaaa    120
ctgatgcatc tttgtgttca cgggttagcg atttgatctt ttcgattccc aaaatcgtat    180
cgttcctgtc gcagggaact acgctcaaag ccggcactct gatcatcacg ggagtgagtt    240
ttgagctctc cctctatgag agtgcaaggt tcgtcgctga tggtgtaatc cgctcatgcc    300 ttccctctc ccttctcctt tgtccattct ctctactacg gttgtcacat cttccttctc    360
cgacagaccc cgcacggaat tggagcgtac tcgaatcctc cggaattctt caaggacgga    420
gacgtcttca gggtcgagat ctcgggaggc atcgggagtt tggtcaacaa gatcgaatat    480
gaaaagtaga taatccgtta ctcaggtcaa tggtatggct tcgaagatgc tggaatcagc    540
cggaaagcaa agctggagag aaaaatcgag attgcgaaac gtgcgatgtc atttcgtttc    600
gagctcgcaa ccatctcgta tccctctgag ctacatacaa acgtcactac ggcctcggag    660
tgactccctg cgagcggatt gaaggagatc acgtcgaat  cagctagacc ttcgcaacgt    720
tttcgcgctc gcacgttctt atcgatctac tgagattgac tcgaaaaagt cttctctcac    780
ggtcgattga actttgaatg aactctcagg ttgcgcgaga gccaatacga gccgaccaga    840
ggcaattcgg agcttcccgg aacgttccaa ggagagggat tttccgagag attacgattg    900
cgagatagaa aaaaggctag ctttcgattt cgagagagat tactttcaag ttcgctgctt    960
ccaactcttg ctccaacccc ctccactcct tctctacaaa acaccatgg               1009

<210> SEQ ID NO 80
<211> LENGTH: 1858
<212> TYPE: DNA
<213> ORGANISM: Rhodosporidium toruloides

<400> SEQUENCE: 80
atgggccagc aggcgacgct cgaggagctg tacacacgct cagaaatctc caagatcaag      60
caagtcgagc cagctcttct cctcaccacc ccacaacata ccccgcagcc cacgacagct    120
ctcccacagc acccacagcc tgctgaccag ctcgagtgca tccacagatt tgcgcccttt    180
ggcgtcccgc ggtcgcgccg gctgcagacg ttctccgtct ttgcctggac gacggcactg    240
cccatcctac tcggcgtctt cttcctgctc tggtgcgtca ggcttggcgt ggattgggag    300
tagcgggcga ctcagctgac ttgcgcatcc gctccagctc gttcccaccg ctctggccgg    360
```

```
ccgtcatcgc ctacctcacc tgggtctttt tcattgacca ggcgccgact cacggtggac      420
gggcgcagtc ttggctgcgg aagagtcgga tatgggtctg gtttgcagga tattatcccg      480
tcaggtgcgt cgtcccgtct gttgcgcgtc ttgcgacctc gctcacggcc aactcgcccg      540
accggctacc tccgaacttc ccgccaacag cttgatcaag gttcgtccac ctttccttca      600
gcttgagtga tctgtagagg agctgcagga tcaagcccaa cccggggagg acctcggagg      660
acgacgccgc tgacttgctc tcctcctaca gagcgccgac ttgccgcctg accggaagta      720
cgtcttcggc tatcatccgc acggcgtcat aggcatgggc gccatcgcca acttcgcgac      780
cgacgcaacc ggcttctcga cactcttccc cggcttgaac cctcacctcc tcaccctcca      840
aagcaacttc aagctcccgc tctatcgcga gttgctgctc gccctcggca tctgctccgt      900
ctcgatgaag agctgccaga acatcctgcg gcaaggtgcg ccagtcattc cgaacgggcg      960
gtcgagcgtg aactctgggg atgggaagag ctgaccttct gcctcactcc atccatgcag     1020
gtcctggctc ggctctcacc atcgttgtcg gtggcgcagc cgagagcttg agtgcgcatc     1080
ccggaaccgc cgacctcacg ctcaagcgac gaaaaggatt catcaagctc gcgatccggc     1140
aaggcgccga cctcgtgccc gtcttttcgt tcggcgagaa cgacgtgcgt cctctgctcg     1200
acttccgcta gcgaagccct tcgctgacgc tcccggtttc ttcccccaga tcttcggcca     1260
gctgcgaaat gagcgaggga cgcggctgta caagttgcag aagcgtttcc agggcgtatt     1320
cggcttcact ctccgtacgt tgcgccgtgt cgcttcaatc tgtcgagcgt ccagtcgctc     1380
acgcagctac aactcccaca gctctcttct acggtcgggg actcttcaac tgtacgcccg     1440
agtctacgtg actagtctac cgtgggaggc actgaagagc acggctgacg tcccacctct     1500
ccgcgcagat aacgttggct tgatgccgta ccgccatccg atcgtctcgg tcggtgcgtc     1560
cccctcgtc cctcctgacc tgcgggcttc agctaacaat tctcgacgac atctagtcgg     1620
tcgaccaatc tcggtgcagc agaaggacca cccaacgaca gcggatctcg aagaagtcca     1680
ggcgcggtat atcgcagaac tcaagcgtg cgttccagac gtctaccttt gcccgttgtc     1740
tcagactcgg taagacagat cactgacgct tcggtcactg gccgcgcagc atctgggaag     1800
actacaagga cgcctacgcc aaaagtcgca cgcgggagct caatattatc gcctgacc       1858
```

<210> SEQ ID NO 81
<211> LENGTH: 1047
<212> TYPE: DNA
<213> ORGANISM: Rhodosporidium toruloides
<220> FEATURE:
<221> NAME/KEY: CDS
<222> LOCATION: (1)..(1047)

<400> SEQUENCE: 81

```
atg ggc cag cag gcg acg ccc gag gag cta tac aca cgc tca gag atc       48
Met Gly Gln Gln Ala Thr Pro Glu Glu Leu Tyr Thr Arg Ser Glu Ile
1               5                   10                  15 tcc aag atc aaa ttc gca ccc ttt ggc gtc ccg cgg tcg cgc cgg ctg       96
Ser Lys Ile Lys Phe Ala Pro Phe Gly Val Pro Arg Ser Arg Arg Leu
            20                  25                  30 cag acc ttc tcc gtc ttt gcc tgg acg acg gca ctg ccc atc cta ctc      144
Gln Thr Phe Ser Val Phe Ala Trp Thr Thr Ala Leu Pro Ile Leu Leu
        35                  40                  45 ggc gtc ttc ttc ctc ctc tgc tcg ttc cca ccg ctc tgg ccg gct gtc      192
Gly Val Phe Phe Leu Leu Cys Ser Phe Pro Pro Leu Trp Pro Ala Val
    50                  55                  60 att gcc tac ctc acc tgg gtc ttt ttc att gac cag gcg ccg att cac      240
Ile Ala Tyr Leu Thr Trp Val Phe Phe Ile Asp Gln Ala Pro Ile His
```

```
                65                  70                  75                  80
ggt gga cgg gcg cag tct tgg ctg cgg aag agt cgg ata tgg gtc tgg       288
Gly Gly Arg Ala Gln Ser Trp Leu Arg Lys Ser Arg Ile Trp Val Trp
                    85                  90                  95 ttt gca gga tac tat ccc gtc agc ttg atc aag agc gcc gac ttg ccg       336
Phe Ala Gly Tyr Tyr Pro Val Ser Leu Ile Lys Ser Ala Asp Leu Pro
                100                 105                 110 cct gac cgg aag tac gtc ttt ggc tac cac ccg cac ggc gtc ata ggc       384
Pro Asp Arg Lys Tyr Val Phe Gly Tyr His Pro His Gly Val Ile Gly
            115                 120                 125 atg ggc gcc atc gcc aac ttc gcg acc gac gca acc ggc ttc tcg aca       432
Met Gly Ala Ile Ala Asn Phe Ala Thr Asp Ala Thr Gly Phe Ser Thr
    130                 135                 140 ctc ttc ccc ggc ttg aac cct cac ctc ctc acc ctc caa agc aac ttc       480
Leu Phe Pro Gly Leu Asn Pro His Leu Leu Thr Leu Gln Ser Asn Phe
145                 150                 155                 160 aag ctc ccg ctc tac cgc gag ttg ctc ctc gct ctc ggc ata tgc tcc       528
Lys Leu Pro Leu Tyr Arg Glu Leu Leu Leu Ala Leu Gly Ile Cys Ser
                165                 170                 175 gtc tcg atg aag agc tgt cag aac att ctg cga caa ggt cct ggc tcg       576
Val Ser Met Lys Ser Cys Gln Asn Ile Leu Arg Gln Gly Pro Gly Ser
                180                 185                 190 gct ctc act atc gtc gtc ggt ggc gcc gcc gag agc ttg agt gcg cat       624
Ala Leu Thr Ile Val Val Gly Gly Ala Ala Glu Ser Leu Ser Ala His
            195                 200                 205 ccc gga acc gcc gat ctt acg ctc aag cga cga aaa ggc ttc atc aaa       672
Pro Gly Thr Ala Asp Leu Thr Leu Lys Arg Arg Lys Gly Phe Ile Lys
    210                 215                 220 ctc gcg atc cgg caa ggc gcc gac ctt gtg ccc gtc ttt tcg ttc ggc       720
Leu Ala Ile Arg Gln Gly Ala Asp Leu Val Pro Val Phe Ser Phe Gly
225                 230                 235                 240 gag aac gac atc ttt ggc cag ctg cga aac gag cga gga acg cgg ctg       768
Glu Asn Asp Ile Phe Gly Gln Leu Arg Asn Glu Arg Gly Thr Arg Leu
                245                 250                 255 tac aag ttg cag aag cgt ttc caa ggc gtg ttt ggc ttc acc ctc cct       816
Tyr Lys Leu Gln Lys Arg Phe Gln Gly Val Phe Gly Phe Thr Leu Pro
                260                 265                 270 ctc ttc tac ggc cgg gga ctc ttc aac tac aac gtc gga ttg atg ccg       864
Leu Phe Tyr Gly Arg Gly Leu Phe Asn Tyr Asn Val Gly Leu Met Pro
            275                 280                 285 tat cgc cat ccg atc gtc tct gtc gtc ggt cga cca atc tcg gta gag       912
Tyr Arg His Pro Ile Val Ser Val Val Gly Arg Pro Ile Ser Val Glu
    290                 295                 300 cag aag gac cac ccg acc acg gcg gac ctc gaa gaa gtt cag gcg cgg       960
Gln Lys Asp His Pro Thr Thr Ala Asp Leu Glu Glu Val Gln Ala Arg
305                 310                 315                 320 tat atc gca gaa ctc aag cgc atc tgg gaa gaa tac aag gac gcc tac      1008
Tyr Ile Ala Glu Leu Lys Arg Ile Trp Glu Glu Tyr Lys Asp Ala Tyr
                325                 330                 335 gcc aaa agt cgc acg cgg gag ctc aat att atc gcc tga                  1047
Ala Lys Ser Arg Thr Arg Glu Leu Asn Ile Ile Ala
            340                 345

<210> SEQ ID NO 82
<211> LENGTH: 348
<212> TYPE: PRT
<213> ORGANISM: Rhodosporidium toruloides

<400> SEQUENCE: 82

Met Gly Gln Gln Ala Thr Pro Glu Glu Leu Tyr Thr Arg Ser Glu Ile
```

```
              1               5              10              15

Ser Lys Ile Lys Phe Ala Pro Phe Gly Val Pro Arg Ser Arg Arg Leu
                            20              25              30

Gln Thr Phe Ser Val Phe Ala Trp Thr Thr Ala Leu Pro Ile Leu Leu
                            35              40              45

Gly Val Phe Phe Leu Leu Cys Ser Phe Pro Pro Leu Trp Pro Ala Val
                50              55              60

Ile Ala Tyr Leu Thr Trp Val Phe Phe Ile Asp Gln Ala Pro Ile His
            65              70              75              80

Gly Gly Arg Ala Gln Ser Trp Leu Arg Lys Ser Arg Ile Trp Val Trp
                            85              90              95

Phe Ala Gly Tyr Tyr Pro Val Ser Leu Ile Lys Ser Ala Asp Leu Pro
                            100             105             110

Pro Asp Arg Lys Tyr Val Phe Gly Tyr His Pro His Gly Val Ile Gly
                            115             120             125

Met Gly Ala Ile Ala Asn Phe Ala Thr Asp Ala Thr Gly Phe Ser Thr
            130             135             140

Leu Phe Pro Gly Leu Asn Pro His Leu Leu Thr Leu Gln Ser Asn Phe
            145             150             155             160

Lys Leu Pro Leu Tyr Arg Glu Leu Leu Leu Ala Leu Gly Ile Cys Ser
                            165             170             175

Val Ser Met Lys Ser Cys Gln Asn Ile Leu Arg Gln Gly Pro Gly Ser
                            180             185             190

Ala Leu Thr Ile Val Val Gly Gly Ala Ala Glu Ser Leu Ser Ala His
                            195             200             205

Pro Gly Thr Ala Asp Leu Thr Leu Lys Arg Arg Lys Gly Phe Ile Lys
            210             215             220

Leu Ala Ile Arg Gln Gly Ala Asp Leu Val Pro Val Phe Ser Phe Gly
            225             230             235             240

Glu Asn Asp Ile Phe Gly Gln Leu Arg Asn Glu Arg Gly Thr Arg Leu
                            245             250             255

Tyr Lys Leu Gln Lys Arg Phe Gln Gly Val Phe Gly Phe Thr Leu Pro
                            260             265             270

Leu Phe Tyr Gly Arg Gly Leu Phe Asn Tyr Asn Val Gly Leu Met Pro
                            275             280             285

Tyr Arg His Pro Ile Val Ser Val Val Gly Arg Pro Ile Ser Val Glu
                            290             295             300

Gln Lys Asp His Pro Thr Thr Ala Asp Leu Glu Glu Val Gln Ala Arg
            305             310             315             320

Tyr Ile Ala Glu Leu Lys Arg Ile Trp Glu Glu Tyr Lys Asp Ala Tyr
                            325             330             335

Ala Lys Ser Arg Thr Arg Glu Leu Asn Ile Ile Ala
                            340             345

<210> SEQ ID NO 83
<211> LENGTH: 2758
<212> TYPE: DNA
<213> ORGANISM: Rhodotorula glutinis ATCC 204091

<400> SEQUENCE: 83
atgcaccgct cgctcctcgt tgctgctgct gggtccaagc gaccgcgcac tgctgcgtcc      60
agtctcgctg ccgcgcgcag ggcgttccag tctgccgcgc atgtcgagaa caagctgcga     120
ctccaggtca aggaggcgga tgaggagggc gcggcgttgc acgactcgac catctcgaac     180
```

```
aaggagtacc tccagcactc gaagaacgag gtgcgtgcgg ttctagctgg ccgggacggg    240
cgggaggcgt tgttggcgaa gtcggggggcc aggagggagt gaggaggacg agggaggcga    300
cggcagctca gggaggggca gtggcaggcg gtaacggtag caagggctac taacagcagt    360
agacgaccct ctttggcccc caaacgcgcg ctgataccct tccgcccgca tcccggtcct    420
cgctcacttt cctcgacacc ctcttgatcc tcccagcgac ccatctggac cgccctgcga    480
ggtcgtgcgc tcctgaacga gccagcactg aacaaaggcg ccggtttcac gcccgaagag    540
cgggacacgt ttgggttgac gggactcttg ccgtgcgttc ttgctcgctt cgcttgaaga    600
agttgtcgag ctgaccttcc gcgaaacaga catgaggtac actcgcttga ccagcaatgc    660
aagcgcgctt attcgcagct gcaagaacgg ccgagtgctt tggcgaaata cacctgtgcg    720
ttcgcggctc ccttcttgcg tccctctcaa catggcttcg acggcgaaag gtcgtctttt    780
gccttaacga cctcaacaag gttccgcggc ggaaccacat tcgcccatcc gctgacgccg    840
cgcccctctg gcagtcctct cctccctccg cgaccaaaac atcatcctct tctacgccct    900
ctgcctccgc cacctcaacg agctcctccc cgtcatctac actcccaccg tcggcgaagc    960
gatccaaaag tactcgacaa tctggcgcag gccggacggg ttgttcctct cctacgcaca   1020
ccggcacaag atgcgtgaga tgatgatgca ggcgaagagg cctaaggatg tcgacttgat   1080
catcgtcacc gactcggagg gcattctcgg tattggagac caaggtgtgg gagggatctt   1140
gatcgcgcag ggaaaggcga acctctacac cctcggagcc ggtatcgacc cctcgcgcat   1200
cctctcggtc gtcctcgacg tcggaaccga caactctgcg ctcttgaatg atccgctcta   1260
cctcggtttg cgacggaagc gcgtccgtgg tgccgagtac gacaagtttg tcgaccggtt   1320
ttgcgagctc gtgagggagg agtacccgca ggcgttgctg tgagtccgtt cgttcaactg   1380
cgagcggtac tgctgagcct gactttgagc tcgccgtatg cagtcacttt gaggactttg   1440
gcgtctcgaa tgcctcgaag atcctcacga cgtaccggaa caagcagtct gtctgtgcgt   1500
tcttcagcgc tcgatttgtc tccctccaaa agctcactga tccatccgca cagtcaacga   1560
cgacatgcaa ggcaccgcag cagtcgtcct cgccgccctc ctttcggccg tcaaggtcac   1620
gaagagcgag ctcaaggacc aacgcatcgt cgtctttggt ttcggcacgg ctgggtacgg   1680
gatcgcagac gggattcgga acgctttgat gcttgaggcg gggttgtcga gtgaggaggt   1740
tcggaagatc ttctggtgcg tgcgaggacc cgaagcgcga ggcaggcgag actgacgctt   1800
cctgtcgatg tgcaggtgtg tcgaccgacc gggtctgctt acgacggagc actctcccac   1860
cctacgacca ggccaagagc acttcatccg caacgcctcg gaagtctcgt cctgggagcg   1920
cgacgccgaa ggacgaatca gcttgctcga ggtcgtcaag caggccaaac cgacgattct   1980
catcggttgc tcgaccatgt cgggcgcgtt tgatgaggag gtcgtgaggg agatggcgaa   2040
gcatgtcgag cggccgatcg tcttccctct ctcaagtgcg tcgccttccc tttcctgact   2100
ccgagtaacc gctgataaag tcgatgacgt agacccgacg aagctcgccg aggctgaccc   2160
ggccgacatc aacgagtgga cgaacggact ggcgcttatg gcgaccgggt cgccgttccc   2220
gcctgtcaag acgccgcgag gcaaggagca caagatcgcc gaggcgtgag ttggcacata   2280
tccagcattc gtcgacggag cgatggctga catccgcctt ttgcagcaac aacggcctgc   2340
tttaccctgg actcggtctc gggtcagtct agctcttctc agccctcctt gctgtcgcgc   2400
tgacggtgtc tctcgcagtg tcatcgtctc tcgcgcctcg ttcttgacgg agaagatgat   2460
caccgcgggc gttgctgctc tcgccaagat ggtacgtttg cctgctcacc agcgagccat   2520
ccaaacctga ccgtctcgct cacaggctcc cgccctcgac gaccccgacg agtcgctcct   2580
```

```
cctccactc agcgacctcc gtcatgtgtc agtcaaggtc gccacggccg tcgcgaacgc    2640
cgccaaggag gaaggcgtca gccagatcaa gcgcgacgac cccttctccc aggatgaggt    2700
tcgcgcggcg cagtgggacc ctgtctaccg cccgctcgag ctcgtcgacc gtcactag      2758
```

<210> SEQ ID NO 84
<211> LENGTH: 2232
<212> TYPE: DNA
<213> ORGANISM: Rhodotorula glutinis ATCC 204091
<220> FEATURE:
<221> NAME/KEY: CDS
<222> LOCATION: (1)..(2232)

<400> SEQUENCE: 84

```
atg cgc ggg agt gaa ggg ttg ccg tcg tcg tgt gtt cgt tca gcg tgt      48
Met Arg Gly Ser Glu Gly Leu Pro Ser Ser Cys Val Arg Ser Ala Cys
1               5                   10                  15 tcg ttt gcg ggg ttc gct cgt cgt tcc ttc gct tcc tcg tcc tca ctc      96
Ser Phe Ala Gly Phe Ala Arg Arg Ser Phe Ala Ser Ser Ser Ser Leu
                20                  25                  30 gct cgt cgc tgt cct cct cct gct cac cct gct ccc ctc tgc cac gct     144
Ala Arg Arg Cys Pro Pro Pro Ala His Pro Ala Pro Leu Cys His Ala
            35                  40                  45 cac ctt caa ctg aag caa gcg aag aag ccg ggt ctc tcg ctc gac tct     192
His Leu Gln Leu Lys Gln Ala Lys Lys Pro Gly Leu Ser Leu Asp Ser
        50                  55                  60 ggc ctc gtt ccc cac cca gct cac ttc cac tct cac ttg cac tca gta     240
Gly Leu Val Pro His Pro Ala His Phe His Ser His Leu His Ser Val
65                  70                  75                  80 gta ctc gca ccc caa cag cag cac acg gtg agc tcg cat ccc ctc cac     288
Val Leu Ala Pro Gln Gln Gln His Thr Val Ser Ser His Pro Leu His
                85                  90                  95 tcg cgc gac cct ccc atc ccg gcg tgc gac cgc ggc acc cag tcg tgt     336
Ser Arg Asp Pro Pro Ile Pro Ala Cys Asp Arg Gly Thr Gln Ser Cys
                100                 105                 110 gag gct gcc gca ccc tct ccc acc cct ctt tgc aca cag aca cac gat     384
Glu Ala Ala Ala Pro Ser Pro Thr Pro Leu Cys Thr Gln Thr His Asp
            115                 120                 125 ccc gct cgc ccc atc act cgc cgg aac gct ctc ttc ctt cat ccc ccc     432
Pro Ala Arg Pro Ile Thr Arg Arg Asn Ala Leu Phe Leu His Pro Pro
        130                 135                 140 aac tcg ctc tcc ctc tct ctc ttt cct ctc act gag cgc cca aaa gaa     480
Asn Ser Leu Ser Leu Ser Leu Phe Pro Leu Thr Glu Arg Pro Lys Glu
145                 150                 155                 160 ctc ctc atc gag cgc gcc ttg acc cgc ctc cgc tcc atc ccg tcc gac     528
Leu Leu Ile Glu Arg Ala Leu Thr Arg Leu Arg Ser Ile Pro Ser Asp
                165                 170                 175 ctc gag aaa tat acg ttc ctt gcg gga ttg agg tgc agg aac ccg gat     576
Leu Glu Lys Tyr Thr Phe Leu Ala Gly Leu Arg Cys Arg Asn Pro Asp
                180                 185                 190 gtg ttt tat gga ctt gtt ggg ggg aac atg aag gag tgt tgc ggt gtt     624
Val Phe Tyr Gly Leu Val Gly Gly Asn Met Lys Glu Cys Cys Gly Val
            195                 200                 205 ggc gag cgg tac ttg agc gag cgc ggg cgc agg agg aga agg aac ggg     672
Gly Glu Arg Tyr Leu Ser Glu Arg Gly Arg Arg Arg Arg Asn Gly
        210                 215                 220 cga gtt cga gcg gac ttg cgg ttc gcg gcg gct tct tcc ctc aac gct     720
Arg Val Arg Ala Asp Leu Arg Phe Ala Ala Ala Ser Ser Leu Asn Ala
225                 230                 235                 240 tcc ctc gca cga aca act act cac aca ctt cga gac gac gat act gac     768
Ser Leu Ala Arg Thr Thr Thr His Thr Leu Arg Asp Asp Asp Thr Asp
```

```
            Ser Leu Ala Arg Thr Thr His Thr Leu Arg Asp Asp Asp Thr Asp
                            245                 250                 255 gct ttc acc tct ccc gct cgt ctc acg aac cca cag ccg atc atc tac        816
Ala Phe Thr Ser Pro Ala Arg Leu Thr Asn Pro Gln Pro Ile Ile Tyr
                260                 265                 270 acc ccc gtc atc ggt ctc gcg tgc caa aac tgg tct ctc atc cac cct        864
Thr Pro Val Ile Gly Leu Ala Cys Gln Asn Trp Ser Leu Ile His Pro
                275                 280                 285 ccc ccg ccc gaa tcc gac cca aca atc gaa gcc ctc tac ctc tcc tac        912
Pro Pro Pro Glu Ser Asp Pro Thr Ile Glu Ala Leu Tyr Leu Ser Tyr
        290                 295                 300 tcg gac ctc cct aac ctt ccc tcg ctc atc aaa ggc ctc aag acc cgt        960
Ser Asp Leu Pro Asn Leu Pro Ser Leu Ile Lys Gly Leu Lys Thr Arg
305                 310                 315                 320 ctc ccg cac aac cag atg caa atc tcc gtc gtc act gat ggt tcg cgc       1008
Leu Pro His Asn Gln Met Gln Ile Ser Val Val Thr Asp Gly Ser Arg
                325                 330                 335 gtt ctt gga ctt gga gat ctc gga gtt gga ggg atg ggt atc tcc caa       1056
Val Leu Gly Leu Gly Asp Leu Gly Val Gly Gly Met Gly Ile Ser Gln
                340                 345                 350 ggg aaa ctc tcg ctt tac gtc gca gca gga ggg gtc aat cct aaa gcc       1104
Gly Lys Leu Ser Leu Tyr Val Ala Ala Gly Gly Val Asn Pro Lys Ala
                355                 360                 365 acc ctt ccc atc gct atc gac ttc gga acc gat aac gag aag tta ctt       1152
Thr Leu Pro Ile Ala Ile Asp Phe Gly Thr Asp Asn Glu Lys Leu Leu
370                 375                 380 gcg gat ccg ctg tat gtc ggt cag agg atg agg agg ttg agt gag gag       1200
Ala Asp Pro Leu Tyr Val Gly Gln Arg Met Arg Arg Leu Ser Glu Glu
385                 390                 395                 400 aaa tgc ctc gag ttt atg gac gtc ttc atg agg tgt atg cac gag acg       1248
Lys Cys Leu Glu Phe Met Asp Val Phe Met Arg Cys Met His Glu Thr
                405                 410                 415 ttc ccg aat atg gtc atc caa cac gaa gac tgg cag acc ccg ctc gcg       1296
Phe Pro Asn Met Val Ile Gln His Glu Asp Trp Gln Thr Pro Leu Ala
                420                 425                 430 ttc ccg ctc ttg cac aag aac cgc gac ttg tat ccg tgc ttt aat gac       1344
Phe Pro Leu Leu His Lys Asn Arg Asp Leu Tyr Pro Cys Phe Asn Asp
                435                 440                 445 gac atc caa ggc aca ggc gcc gtc gtc cta gcc ggc gcg atc cgc gcc       1392
Asp Ile Gln Gly Thr Gly Ala Val Val Leu Ala Gly Ala Ile Arg Ala
        450                 455                 460 ttc cac ctg aac ggc gtc gcg ctc aag gac caa aag att ctc ttc ttc       1440
Phe His Leu Asn Gly Val Ala Leu Lys Asp Gln Lys Ile Leu Phe Phe
465                 470                 475                 480 ggc gcg ggt tcg tcg ggc gtt gga gtc gcc gag acg att tgc aag tac       1488
Gly Ala Gly Ser Ser Gly Val Gly Val Ala Glu Thr Ile Cys Lys Tyr
                485                 490                 495 ttt gag ctg cag ggg atg agt gag cag gag gcc aag agc aag ttt tgg       1536
Phe Glu Leu Gln Gly Met Ser Glu Gln Glu Ala Lys Ser Lys Phe Trp
                500                 505                 510 ctt gtt gac tcg aag ggc ctc gtc gcg cac aac cga ggc gac acc ctc       1584
Leu Val Asp Ser Lys Gly Leu Val Ala His Asn Arg Gly Asp Thr Leu
                515                 520                 525 ccc tcg cac aag aaa tac ctc gcg cgc tcc gag ccc gac gcg ccg aaa       1632
Pro Ser His Lys Lys Tyr Leu Ala Arg Ser Glu Pro Asp Ala Pro Lys
        530                 535                 540 ctc cgc tcg ctc aag gag gtc gtt gag cat gtg cag ccg act gcg ttg       1680
Leu Arg Ser Leu Lys Glu Val Val Glu His Val Gln Pro Thr Ala Leu
545                 550                 555                 560
```

```
ttg ggg ttg tcg act gtt ggt ggg acg ttt acg aag gag atc ctc gag      1728
Leu Gly Leu Ser Thr Val Gly Gly Thr Phe Thr Lys Glu Ile Leu Glu
                565                 570                 575 tcg atg gca acg tac aac aag cgc cct atc gtc ttc gcc ctc tcg aac      1776
Ser Met Ala Thr Tyr Asn Lys Arg Pro Ile Val Phe Ala Leu Ser Asn
            580                 585                 590 ccc gtc gcc caa gcc gaa tgc acc ttc gaa gaa gcg atc gaa gga aca      1824
Pro Val Ala Gln Ala Glu Cys Thr Phe Glu Glu Ala Ile Glu Gly Thr
        595                 600                 605 gac ggc cgc gtc ttg tat gcc agc ggg agc ccg ttc gat ccg gtc gag      1872
Asp Gly Arg Val Leu Tyr Ala Ser Gly Ser Pro Phe Asp Pro Val Glu
    610                 615                 620 tac aag gag aag agg tat gag cct ggt cag ggg aac aat atg tac atc      1920
Tyr Lys Glu Lys Arg Tyr Glu Pro Gly Gln Gly Asn Asn Met Tyr Ile
625                 630                 635                 640 ttc cct gga ctc ggg atc gga gcg atc ctc gcg cgc gtc tcc aag atc      1968
Phe Pro Gly Leu Gly Ile Gly Ala Ile Leu Ala Arg Val Ser Lys Ile
                645                 650                 655 ccc gaa gaa ctc gtc cac gct tcg gcg cag gga ctc gcc gac tcg ctc      2016
Pro Glu Glu Leu Val His Ala Ser Ala Gln Gly Leu Ala Asp Ser Leu
            660                 665                 670 acg ccg gag gag acg gct cgt cat ctc ctt tac ccg gac atc gag cgc      2064
Thr Pro Glu Glu Thr Ala Arg His Leu Leu Tyr Pro Asp Ile Glu Arg
        675                 680                 685 atc cgc gaa gtc tcg atc aag atc gcc gtg acc gtc atc caa gcc gct      2112
Ile Arg Glu Val Ser Ile Lys Ile Ala Val Thr Val Ile Gln Ala Ala
    690                 695                 700 caa aag ctc ggc gtc gac cgc aac gaa gag ctg cgc ggc aag tcg agt      2160
Gln Lys Leu Gly Val Asp Arg Asn Glu Glu Leu Arg Gly Lys Ser Ser
705                 710                 715                 720 gcc gag att gag gcg tac gtc agg aag ggg atg tac cac ccg ctt ttg      2208
Ala Glu Ile Glu Ala Tyr Val Arg Lys Gly Met Tyr His Pro Leu Leu
                725                 730                 735 gag gcg gag cag cag gcg cag tag                                      2232
Glu Ala Glu Gln Gln Ala Gln
            740

<210> SEQ ID NO 85
<211> LENGTH: 743
<212> TYPE: PRT
<213> ORGANISM: Rhodotorula glutinis ATCC 204091

<400> SEQUENCE: 85

Met Arg Gly Ser Glu Gly Leu Pro Ser Ser Cys Val Arg Ser Ala Cys
1               5                   10                  15

Ser Phe Ala Gly Phe Ala Arg Arg Ser Phe Ala Ser Ser Ser Ser Leu
            20                  25                  30

Ala Arg Arg Cys Pro Pro Pro Ala His Pro Ala Pro Leu Cys His Ala
        35                  40                  45

His Leu Gln Leu Lys Gln Ala Lys Lys Pro Gly Leu Ser Leu Asp Ser
    50                  55                  60

Gly Leu Val Pro His Pro Ala His Phe His Ser His Leu His Ser Val
65                  70                  75                  80

Val Leu Ala Pro Gln Gln Gln His Thr Val Ser Ser His Pro Leu His
                85                  90                  95

Ser Arg Asp Pro Pro Ile Pro Ala Cys Asp Arg Gly Thr Gln Ser Cys
            100                 105                 110

Glu Ala Ala Ala Pro Ser Pro Thr Pro Leu Cys Thr Gln Thr His Asp
        115                 120                 125
```

```
Pro Ala Arg Pro Ile Thr Arg Arg Asn Ala Leu Phe Leu His Pro Pro
    130                 135                 140

Asn Ser Leu Ser Leu Ser Leu Phe Pro Leu Thr Glu Arg Pro Lys Glu
145                 150                 155                 160

Leu Leu Ile Glu Arg Ala Leu Thr Arg Leu Arg Ser Ile Pro Ser Asp
                165                 170                 175

Leu Glu Lys Tyr Thr Phe Leu Ala Gly Leu Arg Cys Arg Asn Pro Asp
                180                 185                 190

Val Phe Tyr Gly Leu Val Gly Gly Asn Met Lys Glu Cys Cys Gly Val
            195                 200                 205

Gly Glu Arg Tyr Leu Ser Glu Arg Gly Arg Arg Arg Arg Arg Asn Gly
    210                 215                 220

Arg Val Arg Ala Asp Leu Arg Phe Ala Ala Ala Ser Ser Leu Asn Ala
225                 230                 235                 240

Ser Leu Ala Arg Thr Thr Thr His Thr Leu Arg Asp Asp Asp Thr Asp
                245                 250                 255

Ala Phe Thr Ser Pro Ala Arg Leu Thr Asn Pro Gln Pro Ile Ile Tyr
                260                 265                 270

Thr Pro Val Ile Gly Leu Ala Cys Gln Asn Trp Ser Leu Ile His Pro
            275                 280                 285

Pro Pro Pro Glu Ser Asp Pro Thr Ile Glu Ala Leu Tyr Leu Ser Tyr
    290                 295                 300

Ser Asp Leu Pro Asn Leu Pro Ser Leu Ile Lys Gly Leu Lys Thr Arg
305                 310                 315                 320

Leu Pro His Asn Gln Met Gln Ile Ser Val Val Thr Asp Gly Ser Arg
                325                 330                 335

Val Leu Gly Leu Gly Asp Leu Gly Val Gly Gly Met Gly Ile Ser Gln
            340                 345                 350

Gly Lys Leu Ser Leu Tyr Val Ala Ala Gly Gly Val Asn Pro Lys Ala
    355                 360                 365

Thr Leu Pro Ile Ala Ile Asp Phe Gly Thr Asp Asn Glu Lys Leu Leu
                370                 375                 380

Ala Asp Pro Leu Tyr Val Gly Gln Arg Met Arg Arg Leu Ser Glu Glu
385                 390                 395                 400

Lys Cys Leu Glu Phe Met Asp Val Phe Met Arg Cys Met His Glu Thr
                405                 410                 415

Phe Pro Asn Met Val Ile Gln His Glu Asp Trp Gln Thr Pro Leu Ala
                420                 425                 430

Phe Pro Leu Leu His Lys Asn Arg Asp Leu Tyr Pro Cys Phe Asn Asp
            435                 440                 445

Asp Ile Gln Gly Thr Gly Ala Val Val Leu Ala Gly Ala Ile Arg Ala
450                 455                 460

Phe His Leu Asn Gly Val Ala Leu Lys Asp Gln Lys Ile Leu Phe Phe
465                 470                 475                 480

Gly Ala Gly Ser Ser Gly Val Gly Val Ala Glu Thr Ile Cys Lys Tyr
                485                 490                 495

Phe Glu Leu Gln Gly Met Ser Glu Gln Glu Ala Lys Ser Lys Phe Trp
                500                 505                 510

Leu Val Asp Ser Lys Gly Leu Val Ala His Asn Arg Gly Asp Thr Leu
            515                 520                 525

Pro Ser His Lys Lys Tyr Leu Ala Arg Ser Glu Pro Asp Ala Pro Lys
530                 535                 540
```

```
Leu Arg Ser Leu Lys Glu Val Val Glu His Val Gln Pro Thr Ala Leu
545                 550                 555                 560

Leu Gly Leu Ser Thr Val Gly Gly Thr Phe Thr Lys Glu Ile Leu Glu
            565                 570                 575

Ser Met Ala Thr Tyr Asn Lys Arg Pro Ile Val Phe Ala Leu Ser Asn
        580                 585                 590

Pro Val Ala Gln Ala Glu Cys Thr Phe Glu Glu Ala Ile Glu Gly Thr
    595                 600                 605

Asp Gly Arg Val Leu Tyr Ala Ser Gly Ser Pro Phe Asp Pro Val Glu
610                 615                 620

Tyr Lys Glu Lys Arg Tyr Glu Pro Gly Gln Gly Asn Asn Met Tyr Ile
625                 630                 635                 640

Phe Pro Gly Leu Gly Ile Gly Ala Ile Leu Ala Arg Val Ser Lys Ile
                645                 650                 655

Pro Glu Glu Leu Val His Ala Ser Ala Gln Gly Leu Ala Asp Ser Leu
            660                 665                 670

Thr Pro Glu Glu Thr Ala Arg His Leu Leu Tyr Pro Asp Ile Glu Arg
        675                 680                 685

Ile Arg Glu Val Ser Ile Lys Ile Ala Val Thr Val Ile Gln Ala Ala
690                 695                 700

Gln Lys Leu Gly Val Asp Arg Asn Glu Glu Leu Arg Gly Lys Ser Ser
705                 710                 715                 720

Ala Glu Ile Glu Ala Tyr Val Arg Lys Gly Met Tyr His Pro Leu Leu
                725                 730                 735

Glu Ala Glu Gln Gln Ala Gln
            740

<210> SEQ ID NO 86
<211> LENGTH: 3875
<212> TYPE: DNA
<213> ORGANISM: Rhodosporidium toruloides

<400> SEQUENCE: 86
gggccgaggg caagcagtgg atcgctgagc gcgcgggcaa gcaggttcag gtgcgtttcc      60
ctcttccgcc tcgcctcctt tttttgcaga aagaacacgc gcactgacac tgcgaacgaa     120
cgcgcacgcg caggtcgaga agacgacagg cacgctcaac aacttcatcg tcgagccgtt     180
ctgcccgcac ccttcggacg ccgagtacta catctgcatc aactcggtcc gcgagggcga     240
cgtgatcctg ttcacgcacg agggcggtgt cgacgtcggc gatgtcgacg ccaaggcgct     300
cacgctcctc gtcccgtcg gcggcgagct cccctcgcgc gacgagatcc gctcccagct     360
cctcaagcac gtcactggcg ccgagcgcca ggaggccctc atcgactaca tcatccgcct     420
ctactcggtc tacgtcgacc tccactttgc ctacctcgag atcaaccctc tcgtcgccgt     480
cgagaacccc tcgactggca agaccgacat cttctacctc gacatggccg ccaagctcga     540
ccagacggcc gagtacgtcg tcggtcccaa gtgggccatc gcgcgcgacc cgtccatcat     600
caaccccgcc gctgcaccca tgtcgaacgg caagatttcg gccgacaagg gcccgcccat     660
gttctggccc cctcccttcg gtcgtgactt gaccaaggag gaggcctaca tcgccaagct     720
cgacggctcg accggcgcat ccctcaagct caccgtcttg aacgccgagg acgcatctg      780 gacgatggtt gccggtggtg gtgcttcggt cgtctactcg gacgccatcg ccgcgcacgg     840
attcgcgcac gagctcgcca actacggcga gtactcgggc gcgcccaccc agacccagac     900
ttacgagtac gccaagacca tccgtgcgtt tccgcccttct ctcttccgct ctcagacagc     960
```

-continued

```
ctcgctgacg ctccgtaacg ctcgcagtcg acctgatgac ccgcggcacg cccaacccgc    1020
agggcaagct cctcttcatc ggcggcggta tcgccaactt caccaacgtc gccgcgacct    1080
tcaagggcat catcacggcg ctcaaggagt accagcaccg tctccaggag cacaaggtcc    1140
gcatctttgt ccgccgcggc ggccccaact accaggaggg cctcaaggcc atgcgcctcc    1200
tcggcgagac gctcggcgtc gagatccagg tctttggccc cgaaacccac atcacctcga    1260
tcgtcccgct cggcctcggc ttgatcaagt cggtcgacga cgccctcaag gttcccggcg    1320
cccgctccgc cgccgacgcg accggcaccc tcaccccgt tccggctcg cccaagtcgc    1380 gcgccgccca gctcccgacc ggcgcgtcga cgccctcgcg cccgcagccc caggacaaca    1440
tcgtcagctt ctcggacaag atccacgcgc ccgactcggg ccgcccgtgg taccgcccct    1500 tgacgagac gacgcgctcg atcgtctacg gtctccagcc ccgcgcgatc cagggcatgc    1560
tcgactttga ctttgcctgc ggccgcgaga cgccctcggt cgccgccatg gtctacccct    1620
tcggcggcca ccacgtccag aagttctact ggggcaccaa ggagaccctc ctccccgtct    1680
tcacctcgat gaaggaggcc gtcgccagt gccccgacgc cgacgtcgtc gtcaactttg    1740
cgtcatcgcg ctcggtctac cagtcgaccc tcgaggcgct cgagttcccc cagatcaagg    1800
ccatcgccct catcgccgag ggtgtccccg agcgccacgc ccgcgagatc ctccacctcg    1860
ccaagaagaa ggaggtcatc atcatcggtc ccgcgacggt cggcggcatc aagcccggct    1920
gcttccgtat cggcaacacg ggcggcatga acgagaacat cctctcgtcc aagctttacc    1980
gcgccggttc cgtcggctac gtctccaagt ccggaggcat gtcgaacgag ctcaacaaca    2040
tcctttcgct cacgaccgac ggcgcgtacg agggcatcgc catcggcggt gaccgctacc    2100
cgggcaccac cttcatcgac caccttctcc gctacgaggc cgacccgaac tgcaagatgc    2160
tcgtcctcct cggagaggtc ggcggtgtcg aggagtaccg cgtcatcgag gccgtcaagt    2220
cgggccagat caagaagccc atcgtcgcgt gggccatcgg cacctgcgcc aagatgtttg    2280
cgaccgacgt ccagttcggc cacgccggtt ccatggccaa ctcggacctc gagaccgccg    2340
aggccaagaa caacgccatg cgcgccgccg gcttcatcgt ccccccgacc ttcgaggagc    2400
tcccgcaggt cctcgccgag acctaccaga agctcgtcgg cgacggcacg atccagccca    2460
agcccgaggt tcctccccct cagatcccga tggactacaa ctgggctcag acgctcggca    2520
tggtccgcaa gcccgccgcc ttcatctcga ccatctcgga cgagcgcggc caggagctcc    2580
tctacgccgg catgcccatc tccaaggtct tcgaggagga catcggcatc ggcggcgtcg    2640
tctcgctcct ctggttcaag cgccgcctcc ccgcctacgc gaccaagttc ctcgagatgg    2700
tcctcatgct cacggccgac cacggtcccg ccgtctcggg cgccatgacc accgtcatca    2760
ccacccgtgc cggcaaggac ctcgtctcgt cgctcgtcgc cggtctcctc accatcggcg    2820
accgcttcgg tggcgcgctc gacggcgccg cgcaggagtt cacgcgcgct ttcgaggccg    2880
gcctcacgcc ccgcgagttt gtcgactcga tgcgcaaggc caacaagctc atccccggta    2940
tcggccacaa ggtcaagtcc aaggccaacc cggacaagcg cgtcgagctc gtcaagaact    3000
acgtcttcaa gcacttcccg tcgacaaagc tcctcgagta cgctctcgct gtcgaggacg    3060
tcacgagcgc gaagaaggac accctcatcc tcaacgtcga cggaggtgag ccttcgcttg    3120
ctcctcctcg acttatcctt gtactgacgc ttcctcctcg tccagcaatc gccgtggcct    3180
tctgcgattt gctcaaaaag tagcgctctt tcactgcgtc aaaaacagga cgaaggagaa    3240
ctgacccgcc ccgcttcctt cccgcagctc gggcgcgttc accaccgagg aggctgccga    3300
gtacatgaag gtgtgtcctt gctcttctat agcgttcgtg cgaccgaacg aaggagcgtg    3360
```

```
gaacgttcag aggcgcggga aggaagagga ggggagacgg ggcgaacgga attgctgacc    3420
tcgcgccttc gcagatcgga accttgaacg gtctcttcgt tcttggtcgc tcgatcggct    3480
tcattgccca ccacctcgac cagaagcgcc tcaagcagcc gctctaccgt cacccggccg    3540
agtgcgctcc atctcctcct tgccatctcg acctttccgc tgacctgctc ctcctccgca    3600
gcgacatctt catccagccc ttcaacaccg accgcatcct cgtccagcag cgccagtaaa    3660
tggcgcacgc tcgatgcgtc accgccgtgg ccgcctagac ttcgctcgca tccgcctctc    3720
tcgttctcgc tcgttcgac  attagagttc ccttcttgtt ttcgcgtcgt tccgtctttc    3780
ttgctttctt gttctttctc tttttctcgc tctctttccg gcagtacctc ctctcatggg    3840
ctctcagtcg tcgtgcatca aagtttcgtt tctcc                              3875

<210> SEQ ID NO 87
<211> LENGTH: 3489
<212> TYPE: DNA
<213> ORGANISM: Rhodosporidium toruloides

<400> SEQUENCE: 87
gggccgaggg caagcagtgg atcgctgagc gcgcgggcaa gcaggttcag gtgcgtttcc      60
ctcttccgcc tcgcctcctt tttttgcaga aagaacacgc gcactgacac tgcgaacgaa     120
cgcgcacgcg caggtcgaga agacgacagg cacgctcaac aacttcatcg tcgagccgtt     180
ctgcccgcac ccttcggacg ccgagtacta catctgcatc aactcggtcc gcgagggcga     240
cgtgatcctg ttcacgcacg agggcggtgt cgacgtcggc gatgtcgacg ccaaggcgct     300
cacgctcctc gtccccgtcg gcggcgagct ccctcgcgc  gacgagatcc gctcccagct     360
cctcaagcac gtcactggcg ccgagcgcca ggaggcctc  atcgactaca tcatccgcct     420
ctactcggtc tacgtcgacc tccactttgc ctacctcgag atcaaccctc tcgtcgccgt     480
cgagaacccc tcgactggca agaccgacat cttctacctc gacatggccg ccaagctcga     540
ccagacggcc gagtacgtcg tcggtcccaa gtgggccatc gcgcgcgacc cgtccatcat     600
caaccccgcc gctgcaccca tgtcgaacgg caagatttcg gccgacaagg gcccgcccat     660
gttctggccc cctcccttcg gtcgtgactt gaccaaggag gaggcctaca tcgccaagct     720
cgacggctcg accggcgcat ccctcaagct caccgtcttg aacgccgagg acgcatctg      780 gacgatggtt gccggtggtg gtgcttcggt cgtctactcg gacgccatcg ccgcgcacgg     840
attcgcgcac gagctcgcca actacggcga gtactcgggc gcgcccaccc agacccagac     900
ttacgagtac gccaagacca tcctcgacct gatgacccgc ggcacgccca acccgcaggg     960
caagctcctc ttcatcggcg gcggtatcgc caacttcacc aacgtcgccg cgaccttcaa    1020
gggcatcatc acgcgcctca aggagtacca gcaccgtctc caggagcaca aggtccgcat    1080
ctttgtccgc cgcggcggcc ccaactacca ggagggcctc aaggccatgc gcctcctcgg    1140
cgagacgctc ggcgtcgaga tccaggtctt tggccccgaa acccacatca cctcgatcgt    1200
cccgctcggc ctcggcttga tcaagtcggt cgacgacgcc ctcaaggttc ccggcgcccg    1260
ctccgccgcc gacgcgaccg gcaccctcac cccgttcc   ggctcgccca agtcgcgcgc    1320
cgcccagctc ccgaccggcg cgtcgacgcc ctcgcgcccg cagccccagg acaacatcgt    1380
cagcttctcg gacaagatcc acgcgcccga ctcgggccgc ccgtggtacc gcccctttga    1440
cgagacgacg cgctcgatcg tctacggtct ccagcccgc  gcgatccagg gcatgctcga    1500
ctttgacttt gcctgcggcc gcgagacgcc ctcggtcgcc gccatggtct acccccttcgg   1560
```

-continued

```
cggccaccac gtccagaagt tctactgggg caccaaggag accctcctcc ccgtcttcac    1620
ctcgatgaag gaggccgtcg ccaagtgccc cgacgccgac gtcgtcgtca actttgcgtc    1680
atcgcgctcg gtctaccagt cgaccctcga ggcgctcgag ttcccccaga tcaaggccat    1740
cgccctcatc gccgagggtg tccccgagcc cacgcccgc gagatcctcc acctcgccaa    1800
gaagaaggag gtcatcatca tcggtcccgc gacggtcggc ggcatcaagc ccggctgctt    1860
ccgtatcggc aacacgggcg gcatgaacga gaacatcctc tcgtccaagc tttaccgcgc    1920
cggttccgtc ggctacgtct ccaagtccgg aggcatgtcg aacgagctca caacatcct    1980
ttcgctcacg accgacggcg cgtacgaggg catcgccatc ggcggtgacc gctacccggg    2040
caccaccttc atcgaccacc ttctccgcta cgaggccgac ccgaactgca agatgctcgt    2100
cctcctcgga gaggtcggcg gtgtcgagga gtaccgcgtc atcgaggccg tcaagtcggg    2160
ccagatcaag aagcccatcg tcgcgtgggc catcggcacc tgcgccaaga tgtttgcgac    2220
cgacgtccag ttcggccacg ccggttccat ggccaactcg gacctcgaga ccgccgaggc    2280
caagaacaac gccatgcgcg ccgccggctt catcgtcccc ccgaccttcg aggagctccc    2340
gcaggtcctc gccgagacct accagaagct cgtcggcgac ggcacgatcc agcccaagcc    2400
cgaggttcct ccccctcaga tcccgatgga ctacaactgg gctcagacgc tcggcatggt    2460
ccgcaagccc gccgccttca tctcgaccat ctcggacgag cgcggccagg agctcctcta    2520
cgccggcatg cccatctcca aggtcttcga ggaggacatc ggcatcggcg cgtcgtctc    2580
gctcctctgg ttcaagcgcc gcctccccgc ctacgcgacc aagttcctcg agatggtcct    2640
catgctcacg gccgaccacg gtcccgccgt ctcgggcgcc atgaccaccg tcatcaccac    2700
ccgtgccggc aaggacctcg tctcgtcgct cgtcgccggt ctcctcacca tcggcgaccg    2760
cttcggtggc gcgctcgacg gcgccgcgca ggagttcacg cgcgctttcg aggccggcct    2820
cacgccccgc gagtttgtcg actcgatgcg caaggccaac aagctcatcc ccgtatcgg    2880
ccacaaggtc aagtccaagg ccaacccgga caagcgcgtc gagctcgtca gaactacgt    2940
cttcaagcac ttcccgtcga caaagctcct cgagtacgct ctcgctgtcg aggacgtcac    3000
gagcgcgaag aaggacaccc tcatcctcaa ccaatcgccg tggccttctg cgatttgctc    3060
aaaaactcgg gcgcgttcac caccgaggag gctgccgagt acatgaagat cggaaccttg    3120
aacggtctct tcgttcttgg tgctcgatc ggcttcattg cccaccacct cgaccagaag    3180
cgcctcaagc agccgctcta ccgtcacccg gccgacgaca tcttcatcca gcccttcaac    3240
accgaccgca tcctcgtcca gcagcgccag taaatggcgc acgctcgatg cgtcaccgcc    3300
gtggccgcct agacttcgct cgcatccgcc tctctcgttc tcgcctcgtt cgacattaga    3360
gttcccttct tgttttcgcg tcgttccgtc tttcttgctt tcttgttctt tctctttttc    3420
tcgctctctt tccggcagta cctcctctca tgggctctca gtcgtcgtgc atcaaagttt    3480
cgtttctcc                                                            3489
```

<210> SEQ ID NO 88
<211> LENGTH: 1148
<212> TYPE: PRT
<213> ORGANISM: Rhodosporidium toruloides

<400> SEQUENCE: 88

Met Ser Ala Lys Pro Ile Arg Glu Tyr Asp Ala Lys Leu Leu Leu Ala
1               5                   10                  15

Tyr His Leu Ala Arg Ala Pro Thr Ala Gly Ser Lys Ala Val Ala Arg
            20                  25                  30

-continued

Asp Gly Phe Gln Ser Pro Glu Val Lys Val Ala Gln Val Ser Trp Asp
    35                  40                  45
Pro Glu Thr Asn Gln Val Thr Pro Asp Ala Ala Leu Pro His Trp Val
 50                  55                  60
Phe Thr Glu Lys Leu Val Val Lys Pro Asp Gln Leu Ile Lys Arg Arg
 65                  70                  75                  80
Gly Lys Ala Gly Leu Leu Ala Leu Asn Lys Thr Trp Ala Glu Gly Lys
                 85                  90                  95
Gln Trp Ile Ala Glu Arg Ala Gly Lys Gln Val Gln Val Glu Lys Thr
                100                 105                 110
Thr Gly Thr Leu Asn Asn Phe Ile Val Glu Pro Phe Cys Pro His Pro
            115                 120                 125
Ser Asp Ala Glu Tyr Tyr Ile Cys Ile Asn Ser Val Arg Glu Gly Asp
        130                 135                 140
Val Ile Leu Phe Thr His Glu Gly Gly Val Asp Val Gly Asp Val Asp
145                 150                 155                 160
Ala Lys Ala Leu Thr Leu Leu Val Pro Val Gly Gly Glu Leu Pro Ser
                165                 170                 175
Arg Asp Glu Ile Arg Ser Gln Leu Leu Lys His Val Thr Gly Ala Glu
            180                 185                 190
Arg Gln Glu Ala Leu Ile Asp Tyr Ile Ile Arg Leu Tyr Ser Val Tyr
        195                 200                 205
Val Asp Leu His Phe Ala Tyr Leu Glu Ile Asn Pro Leu Val Ala Val
210                 215                 220
Glu Asn Pro Ser Thr Gly Lys Thr Asp Ile Phe Tyr Leu Asp Met Ala
225                 230                 235                 240
Ala Lys Leu Asp Gln Thr Ala Glu Tyr Val Val Gly Pro Lys Trp Ala
                245                 250                 255
Ile Ala Arg Asp Pro Ser Ile Ile Asn Pro Ala Ala Pro Met Ser
            260                 265                 270
Asn Gly Lys Ile Ser Ala Asp Lys Gly Pro Pro Met Phe Trp Pro Pro
        275                 280                 285
Pro Phe Gly Arg Asp Leu Thr Lys Glu Glu Ala Tyr Ile Ala Lys Leu
    290                 295                 300
Asp Gly Ser Thr Gly Ala Ser Leu Lys Leu Thr Val Leu Asn Ala Glu
305                 310                 315                 320
Gly Arg Ile Trp Thr Met Val Ala Gly Gly Ala Ser Val Tyr
                325                 330                 335
Ser Asp Ala Ile Ala Ala His Gly Phe Ala His Glu Leu Ala Asn Tyr
            340                 345                 350
Gly Glu Tyr Ser Gly Ala Pro Thr Gln Thr Gln Thr Tyr Glu Tyr Ala
        355                 360                 365
Lys Thr Ile Leu Asp Leu Met Thr Arg Gly Thr Pro Asn Pro Gln Gly
    370                 375                 380
Lys Leu Leu Phe Ile Gly Gly Ile Ala Asn Phe Thr Asn Val Ala
385                 390                 395                 400
Ala Thr Phe Lys Gly Ile Ile Thr Ala Leu Lys Glu Tyr Gln His Arg
                405                 410                 415
Leu Gln Glu His Lys Val Arg Ile Phe Val Arg Arg Gly Gly Pro Asn
            420                 425                 430
Tyr Gln Glu Gly Leu Lys Ala Met Arg Leu Leu Gly Glu Thr Leu Gly
        435                 440                 445

```
Val Glu Ile Gln Val Phe Gly Pro Glu Thr His Ile Thr Ser Ile Val
450                 455                 460

Pro Leu Gly Leu Gly Leu Ile Lys Ser Val Asp Asp Ala Leu Lys Val
465             470                 475                 480

Pro Gly Ala Arg Ala Ala Asp Ala Thr Gly Thr Leu Thr Pro Val
            485                 490                 495

Pro Gly Ser Pro Lys Ser Arg Ala Ala Gln Leu Pro Thr Gly Ala Ser
            500                 505                 510

Thr Pro Ser Arg Gln Gln Pro Gln Asp Asn Ile Val Ser Phe Ser Asp
            515                 520                 525

Lys Val His Ala Pro Asp Ser Gly Arg Pro Trp Tyr Arg Pro Phe Asp
530             535                 540

Glu Thr Thr Arg Ser Ile Val Tyr Gly Leu Gln Pro Arg Ala Ile Gln
545             550                 555                 560

Gly Met Leu Asp Phe Asp Phe Ala Cys Gly Arg Glu Thr Pro Ser Val
                565             570                 575

Ala Ala Met Val Tyr Pro Phe Gly Gly His His Val Gln Lys Phe Tyr
            580             585                 590

Trp Gly Thr Lys Glu Thr Leu Leu Pro Val Phe Thr Ser Met Lys Glu
        595                 600                 605

Ala Val Ala Lys Cys Pro Asp Ala Asp Val Val Asn Phe Ala Ser
        610             615                 620

Ser Arg Ser Val Tyr Gln Ser Thr Leu Glu Ala Leu Glu Phe Pro Gln
625             630                 635                 640

Ile Lys Ala Ile Ala Leu Ile Ala Glu Gly Val Pro Glu Arg His Ala
                645                 650                 655

Arg Glu Ile Leu His Leu Ala Lys Lys Lys Glu Val Ile Ile Ile Gly
                660                 665                 670

Pro Ala Thr Val Gly Gly Ile Lys Pro Gly Cys Phe Arg Ile Gly Asn
            675                 680                 685

Thr Gly Gly Met Asn Glu Asn Ile Leu Ser Ser Lys Leu Tyr Arg Ala
            690                 695                 700

Gly Ser Val Gly Tyr Val Ser Lys Ser Gly Gly Met Ser Asn Glu Leu
705             710                 715                 720

Asn Asn Ile Leu Ser Leu Thr Thr Asp Gly Ala Tyr Glu Gly Ile Ala
                725                 730                 735

Ile Gly Gly Asp Arg Tyr Pro Gly Thr Thr Phe Ile Asp His Leu Leu
            740                 745                 750

Arg Tyr Glu Ala Asp Pro Asn Cys Lys Met Leu Val Leu Leu Gly Glu
        755                 760                 765

Val Gly Gly Val Glu Glu Tyr Arg Val Ile Glu Ala Val Lys Ser Gly
        770                 775                 780

Gln Ile Lys Lys Pro Ile Val Ala Trp Ala Ile Gly Thr Cys Ala Lys
785             790                 795                 800

Met Phe Ala Thr Asp Val Gln Phe Gly His Ala Gly Ser Met Ala Asn
            805                 810                 815

Ser Asp Leu Glu Thr Ala Glu Ala Lys Asn Asn Ala Met Arg Ala Ala
            820                 825                 830

Gly Phe Ile Val Pro Pro Thr Phe Glu Glu Leu Pro Gln Val Leu Ala
            835                 840                 845

Glu Thr Tyr Gln Lys Leu Val Gly Asp Gly Thr Ile Gln Pro Lys Pro
850                 855                 860

Glu Val Pro Pro Pro Gln Ile Pro Met Asp Tyr Asn Trp Ala Gln Thr
```

```
    865                 870                 875                 880
Leu Gly Met Val Arg Lys Pro Ala Ala Phe Ile Ser Thr Ile Ser Asp
                885                 890                 895
Glu Arg Gly Gln Glu Leu Leu Tyr Ala Gly Met Pro Ile Ser Lys Val
                900                 905                 910
Phe Glu Glu Asp Ile Gly Ile Gly Gly Val Val Ser Leu Leu Trp Phe
                915                 920                 925
Lys Arg Arg Leu Pro Ala Tyr Ala Thr Lys Phe Leu Glu Met Val Leu
                930                 935                 940
Met Leu Thr Ala Asp His Gly Pro Ala Val Ser Gly Ala Met Thr Thr
945                 950                 955                 960
Val Ile Thr Thr Arg Ala Gly Lys Asp Leu Val Ser Ser Leu Val Ala
                965                 970                 975
Gly Leu Leu Thr Ile Gly Asp Arg Phe Gly Gly Ala Leu Asp Gly Ala
                980                 985                 990
Ala Gln Glu Phe Thr Arg Ala Phe Glu Ala Gly Leu Thr Pro Arg Glu
                995                1000                1005
Phe Val Asp Ser Met Arg Lys Ala Asn Lys Leu Ile Pro Gly Ile
        1010                1015                1020
Gly His Lys Val Lys Ser Lys Ala Asn Pro Asp Lys Arg Val Glu
        1025                1030                1035
Leu Val Lys Asn Tyr Val Phe Lys His Phe Pro Ser Ala Lys Leu
        1040                1045                1050
Leu Glu Tyr Ala Leu Ala Val Glu Asp Val Thr Ser Ala Lys Lys
        1055                1060                1065
Asp Thr Leu Ile Leu Asn Gln Ser Arg Phe Leu Ser Ser Gly Ala
        1070                1075                1080
Phe Thr Ala Glu Glu Ala Ala Glu Tyr Met Lys Ile Gly Thr Leu
        1085                1090                1095
Asn Gly Leu Phe Val Leu Gly Arg Ser Ile Gly Phe Ile Ala His
        1100                1105                1110
His Leu Asp Gln Lys Arg Leu Lys Gln Pro Leu Tyr Arg His Pro
        1115                1120                1125
Ala Asp Asp Ile Phe Ile Gln Pro Phe Asn Thr Asp Arg Ile Leu
        1130                1135                1140
Val Gln Gln Arg Gln
        1145

<210> SEQ ID NO 89
<211> LENGTH: 7222
<212> TYPE: DNA
<213> ORGANISM: Rhodosporidium toruloides

<400> SEQUENCE: 89
accacactct cccgcttgcg ggctctcttt ctcgcttggc gctcctgcta ccgctactct      60
agactctcct agtctccctg cacaaccatc cctatcccct ccgcctctct cgcacacccc     120
ccacagcttc gttccccaac ttcacttccg atgccgtgcg tcgcctccct ttcgcctggc     180
gggcccgcgc ctgcttccga ggacaactac tgattgtggg atcatgcgac gacaggttct     240
ctggcgaggc gaaggcggtc aacggatcgc actcggtcga cgaggcgccg aagaacccca     300
agtacgacca tgggcgggtc gtaaagtacc tcggtgcgtt tcatgggtc ctttgagcac      360 tctggagact ttctggaccg gcggacgggc agttgggctg accttgcatt tcctctcctc     420
ctcgacttcg ctcacctcga caggcggcaa ctcgctcgag tctgcgcccc cttccaaggt     480
```

```
cgctgactgg gtcagggagc gtggtggaca caccgtcatc acaaaggtgc gctcactcgg    540 accccctcttg caccgcccct cccgaccgtc cccaactcgc tcgtcctgac ccaactcgcg    600
ctccgcacag atcctgatcg ccaacaatgg tatcgctgca gtcaaggaga tccgctcggt    660
gcgcaagtgg gcgtacgaga cgttcggaag cgagcgcgcg atcgagttta ccgtcatggc    720
gaccccggag gacctcaagg tcaatgcaga ctacatccgc atggccgacc agtacgtcga    780
ggtacccggt ggaaccaaca acaacaacta cgcgaacgtc gatgtcatcg ttgatgttgc    840
cgagcgcgct ggcgtccacg ccgtctgggc aggatggttc gtcccgtttc cttcccgctc    900
ccttcagcgg aagtgcccgt gctaacttgc cttcgacgga cacaggggcc acgcttccga    960 gaaccccgc cttcccgagt cgctcgccgc ctcgaagcac aagatcgtct tcatcggtcc    1020
tcccggctcc gccatgcgct cgctcggcga caagatctcg tcgaccatcg ttgcgcagca    1080
cgcccaggtt ccgtgcatgg actggtccgg acagggcgtc gaccaggtca cccagtcgcc    1140
cgagggctac gttaccgtcg ccgacgacgt ctaccagcag gcctgtgtgc acgacgccga    1200
cgagggtctc gcccgcgcgt cgaggatcgg ataccccgtc atgatcaagg cgtccgaggg    1260
aggaggagga aagggtattc gcaaggtcga aaggagcag gacttcaagc aggctttcca    1320
ggccgtcctc accgaggttc ccggtgcgtc gattcgcttt cagtttgaag catccttagc    1380
tgactcgccg cttccatagg ctcgcccgtc ttcatcatga agctcgctgg cgctgctcgc    1440
cacctcgagg ttcaggttct cgccgaccag tacggcaacg ccatctcgct cttcggccgt    1500
gactgctcgg tccagcgtcg ccaccagaag atcatcgaag aggcgcccgt caccatcgcc    1560
aagcccgaca cgttcgagca gatggaaaag tcggccgtcc gccttgccaa gctcgtcggt    1620
tacgtctcgg cgggaaccgt cgagttcctc tactcggctg ccgacgacaa gttcgccttc    1680
ctcgagctca acccgcgtct ccaggttgag cacccgacga ccgagatggt ctcgggcgtc    1740
aaccttcccg ccgctcagct ccaggtcgcc atgggtgtcc ctctccaccg catccgcgac    1800
atccgcaccc tctacggcaa ggcacccaac ggcagcagcg agatcgactt cgacttcgag    1860
aatcccgaat cggccaagac gcagcgcaag ccctcgccga agggtcacgt cgtcgccgtc    1920
cgtatcacgg ctgagaaccc tgatgccggc ttcaagccgt cgatgggtac cctccaggag    1980
ctcaacttcc gttcgagcac gaacgtctgg ggttacttct ccgtcggcag cgccggtggt    2040
ctccacgagt ttgccgactc gcagtttggc cacatctttg cgtacggctc ggaccgttcc    2100
gagtcgcgca agaacatggt cgtcgcgctc aaggagctct cgattcgcgg tgacttccgc    2160
acgaccgtcg agtacctcat caagcttctc gagaccgatg cgttcgagca gaacacgatt    2220
acgaccgcct ggctcgacag cctcatctcg gctcgcctga ccgccgagag gcccgacacg    2280
actctcgcca tcatctgcgg cgccgtcacg aaggctcacc tcgcttccga ggccaacatc    2340
gccgagtaca agcgcatcct cgagaagggt cagagccccg ccaaggagct cctggccacc    2400
gtcgtccctc tcgagttcgt cctcgaggac gtcaagtacc gcgcgaccgc ctcgcgctcg    2460
tcgccttcga gctggtccat ctacgtcaac ggctcgaacg tctcggtcgg catccgccct    2520
ctcgccgatg gcggtctcct catcctcctc gacggccgct catacacctg ctacgccaag    2580
gaggaggtcg gcgcgcttcg cctctcaatc gactcgagga ctgtcctcat cgctcaggag    2640
aacgacccca cccagcttcg ctcgccatcg cccggcaagc tcgtccgcta cttcatcgag    2700
tcgggcgagc acatctcaaa gggcgaggcg tacgccgaga tcgaggtcat gaaggtcgct    2760
cgccccggca ttccctgctc gtgttcgtct cgctgacgct cgatgcctcg cagatgatca    2820
```

```
tgcccctcat cgctgctgag gacggtatcg cgcagttcat caagcagccg ggagcgacgc    2880
tcgaggctgg cgacatcctg ggtatcttgt cgctcgacga cccgagccgc gtccaccacg    2940
ccaagccgtt cgacggccag cttccggccc ttggcttgcc ttccatcatc ggcaacaagc    3000
cgcaccagcg cttcgcctac ctcaaggacg tcctctcgaa catcctcatg ggctacgaca    3060
accaggctgt gatgcagtcg agcatcaagg agctcatctc ggtccttcgc aaccccgagc    3120
tcccgtacgg cgaggccaac gccgtcctct caacgctttc gggccgtatc cccgccaagc    3180
tcgagcagac cctccgccag tacattgacc aagctcacga gtctggcgcc gagttcccgt    3240
ccgccaagtg ccgcaaggcg atcgacacga ccctcgagca gctccgccct gccgaggcgc    3300
agaccgtccg caacttcctc gtcgcgttcg acgacatcgt ctaccgctac cgctcgggcc    3360
tcaagcacca cgagtggtcg acgtcgccg gcatctttgc cgcgtacgcc gagacggaga    3420
agccgttcag cggcaaggac ggcgacgtcg tcctcgagct ccgcgacgcc caccgcgact    3480
cgctcgactc ggtcgtcaag atcgtcctct cgcactacaa ggccgcctcg aagaactcgc    3540
tcgtcctcgc cctcctcgac attgtcaagg actcggactc ggtcccgctc atcgagcagg    3600
tcgtcagccc cgcgctcaag gaccttgccg acctcgattc gaaggccacg accaaggtcg    3660
ccctcaaggc tcgcgaggtg ctcatccaca tccagctccc ctcgctcgac gagcgcctcg    3720
gccagcttga gcagatcctc aaggcctcgg tcacgcccac cgtctacggc gagcctggcc    3780
acgatcgcac tcctcgcggg gaggtcctca aggatgtcat cgactcgcgc ttcaccgtct    3840
tcgacgttct cccgagcttc ttccagcacc aggaccactg ggtctcgctt ccgcgctcg    3900 acacctacgt ccgccgcgct taccgctcgt acaatctcct caacatcgag cacattgagg    3960
ccgatgctgc cgaggacgag cccgcgaccg tcgcctggtc gttccgcatg cgtaaggctg    4020
cgtccgaatc cgagccgcct acgcccacga ccggcctcac ctcgcagcgc accgcctcgt    4080
actcggactt gaccttcctc ctcaacaacg cccagtccga gccgatccgc tacggcgcga    4140
tgttctcggt ccgctcgctc gaccgcttcc gccaggagct cggcaccgtc ctccgccact    4200
tccccgactc gaacaagggc aagctccagc agcagcctgc cgcttcgtcg agccaggagc    4260
agtggaacgt catcaatgtt gcgctcacgg tccccgccag cgcgcaggtc gacgaggacg    4320
ctctccgtgc cgacttcgcc gctcacgtca acgcgatgag cgccgagatc gacgctcgcg    4380
gcatgcgccg cctcacccta ctcatctgcc gcgagggcca gtaccgtcc tactacaccg    4440 tccgcaagca ggacggcacc tggaaggagc tcgagacgat ccgcgacatc gagcctgccc    4500
tcgccttcca gctcgagctc ggccgcctct ccaacttcca cctcgagccg tgcccagtcg    4560
agaaccgcca ggttcacgtc tactacgcga ccgccaaggg caactcgtcc gactgccgct    4620
tcttcgtccg tgcgctcgtc cgccctggcc gcctccgcgg caacatgaag acggccgact    4680
accttgtgtc cgaggccgac cgcctcgtca ccgacgtcct cgactcgctc gaggtcgcca    4740
gctcgcagcg ccgcgccgcc gacggcaacc acatctcggt gcgtactcgc agccttgccc    4800
tccctcgttc tcgcgctgac tcgctctcgt ttcgcagctc aacttcctgt actcgctccg    4860
tctcgacttt gacgaggttc aggctgccct cgccggcttc atcgaccgcc acggcaagcg    4920
cttctggcgt ctccgcgtca ccggcgccga gatccgcatc gtcctcgagg acgcgcaggg    4980
caacatccag cccatccgcg ccatcattga gaacgtctcg ggcttcgtcg tcaagtacga    5040
ggcgtaccgc gaggtcacga ctgacaaggg ccaggtcatc ctcaagtcga tcggtccgca    5100
gggcgccctg caccttcagc cggtcaactt cccctacccg accaaggagt ggcttcagcc    5160
gaagcgctac aaggcccacg tcgtcggcac gacgtacgtc tacgacttcc ccgacctttt    5220
```

```
ccgccaggct atccgcaagc agtggaaggc cgccggcaag accgcgcccg ccgagctcct    5280
cgtcgccaag gagctcgtcc tcgacgaatt cggcaagccc caggaggtcg cccgcccgcc    5340
tggcactaac aacatcggca tggtcggctg gatctacaca atcttcacgc ccgagtaccc    5400
gaccggccgc cgcgtcgtcg tcatcgccaa cgacatcacc ttcaagattg gttcgttcgg    5460
ccccgaggag gaccgctact tcttcgccgt cacgcagctc gcgcgccagc ttggcttgcc    5520
gcgcgtctac ctctcggcca actcgggcgc tcgcctcggt attgccgagg agctcgtcga    5580
cttgttcagc gtcgcgtggg tcgacagctc gcggccggag aagggcttca agtacctcta    5640
cctcaccgcc gagaagctcg gcgagctcaa gaacaagggc gagaagagcg tcattacgaa    5700
gcgcatcgag gacgagggcg agacgcgcta ccagatcacc gacatcatcg gcttgcagga    5760
gggtctcggt gtcgagtcgc tcaagggctc tggcctcatc gccggtgaga cctcgcgcgc    5820
gtacgacgac atcttcacga tcacgctcgt caccgcccgc tcggtcggta tcggtgcgta    5880
cctcgtccgc ctcggccagc gtgccgtcca ggtcgagggc cagccgatca tcctcaccgg    5940
tgccggcgcg ctcaacaagg tcctcggtcg cgaggtctac tcgtccaact gcagctcgg    6000 cggcacgcaa atcatgtaca agaacggtgt ctcgcacttg acggccgcca acgacctcga    6060
gggtgtcctc agcatcgtcc agtggctcgc ctttgtcccc gagcaccgcg gcgcgcctct    6120
cccgatcatg ccttcgcccg tcgacccgtg ggaccgctcg atcgactaca cgcccatcaa    6180
gggcgcgtac gacccgcgct ggttcctcgc cggcaagacg gacgaggccg acggccgctg    6240
gctctctggc ttcttcgaca agggctcgtt ccaggagacg ctctcgggct gggcgcagac    6300
cgtcgtcgtc ggccgcgctc gcctcggcgg catccccatg ggcgctatcg cagtcgaaac    6360
ccgcaccatc gagcgcatcg ttcccgccga ccccgccaac cctctctcga acgagcagaa    6420
gatcatggag gccggtcagg tgcgcaacaa cctccacttt gtccgaaacc tccactcgtg    6480
tccaaactcc tcgtcgccaa cttctcctcg acctttctcg tcctcctcga cagctgctga    6540
cctgcttcca ccttgtacca tgcgcaggtc tggtacccga acagctcgtt caagacggga    6600
caggcgatct tcgacttcaa ccgcgagggt ctcccgctca tcatcttcgc caactggcgc    6660
ggcttctcgg gcgccagca ggacatgttt gacgaggtcc tcaagcgcgg ctcgctcatc    6720
gtcgacggtc tctcggcgta caagcagccc gtcttcgtct acatcgtccc gaacggcgaa    6780
cttcgcggcg gtgcttgggt cgtcctcgac ccgtcgatca acgccgaggg catgatggag    6840
atgtacgtcg atgagactgc tcgcgccggt gtcctcgagc ccgagggcat cgtcgagatc    6900
aagctccgca aggacaagct cctcgccctc atggaccgcc tcgacccgac ctaccacgcc    6960
ctccgcgtca gtcgaccga cgtctcgctc tcgcccgccg acgctgcgca ggccaagacc    7020
gagctcgccg cgcgcgagaa gcagctcatg ccgatctacc agcaggtcgc gctccagttc    7080
gccgactcgc acgacaaggc cggccgcatc ctcagcaagg gctgcgcgcg cgaggcgctc    7140
gagtggtcga acgctcgtcg ctacttctac gcccgcctcc gccgccgtgt cgccgaggag    7200
gccgccgtca agcgcctggg cg                                             7222
```

<210> SEQ ID NO 90
<211> LENGTH: 6702
<212> TYPE: DNA
<213> ORGANISM: Rhodosporidium toruloides
<220> FEATURE:
<221> NAME/KEY: CDS
<222> LOCATION: (1)..(6702)

<400> SEQUENCE: 90

```
atg cca ttc tct ggc gag gcg aag gcg gtc aac gga tcg cac tcg gtc    48
Met Pro Phe Ser Gly Glu Ala Lys Ala Val Asn Gly Ser His Ser Val
1               5                  10                  15 gac gag gcg ccg aag aac ccc aag tac gac cat ggg cgg gtc gta aag    96
Asp Glu Ala Pro Lys Asn Pro Lys Tyr Asp His Gly Arg Val Val Lys
            20                  25                  30 tac ctc ggc ggc aac tcg ctc gaa tct gcg ccc cct tcc aag gtc gcc   144
Tyr Leu Gly Gly Asn Ser Leu Glu Ser Ala Pro Pro Ser Lys Val Ala
        35                  40                  45 gac tgg gtc agg gag cgt ggt gga cac acc gtc atc aca aag atc ctc   192
Asp Trp Val Arg Glu Arg Gly Gly His Thr Val Ile Thr Lys Ile Leu
    50                  55                  60 atc gcc aac aat ggt atc gcc gca gtc aag gag atc cgc tcg gtg cgc   240
Ile Ala Asn Asn Gly Ile Ala Ala Val Lys Glu Ile Arg Ser Val Arg
65                  70                  75                  80 aag tgg gcg tac gag acg ttc gga agc gag cgc gcg atc gag ttt acc   288
Lys Trp Ala Tyr Glu Thr Phe Gly Ser Glu Arg Ala Ile Glu Phe Thr
                85                  90                  95 gtc atg gcg acc ccg gag gac ctc aag gtc aac gca gac tac atc cgc   336
Val Met Ala Thr Pro Glu Asp Leu Lys Val Asn Ala Asp Tyr Ile Arg
            100                 105                 110 atg gcc gat cag tac gtc gag gtt ccc ggt gga acc aac aac aac aac   384
Met Ala Asp Gln Tyr Val Glu Val Pro Gly Gly Thr Asn Asn Asn Asn
        115                 120                 125 tac gcc aac gtc gat gtc atc gtc gat gtt gcc gag cgc gca ggc gtc   432
Tyr Ala Asn Val Asp Val Ile Val Asp Val Ala Glu Arg Ala Gly Val
    130                 135                 140 cac gcc gtc tgg gca gga tgg ggc cac gcc tcc gag aac ccc cgc ctt   480
His Ala Val Trp Ala Gly Trp Gly His Ala Ser Glu Asn Pro Arg Leu
145                 150                 155                 160 ccc gag tcg ctc gcc gcc tcg aag cac aag atc gtc ttc atc ggt cct   528
Pro Glu Ser Leu Ala Ala Ser Lys His Lys Ile Val Phe Ile Gly Pro
                165                 170                 175 ccc ggc tcc gcc atg cgc tcg ctc gga gac aag atc tcg tcg acc atc   576
Pro Gly Ser Ala Met Arg Ser Leu Gly Asp Lys Ile Ser Ser Thr Ile
            180                 185                 190 gtc gcg cag cac gcc cag gtt ccg tgc atg gac tgg tcc ggc cag ggc   624
Val Ala Gln His Ala Gln Val Pro Cys Met Asp Trp Ser Gly Gln Gly
        195                 200                 205 gtc gac caa gtc acc cag tcg ccc gag ggc tac gtt act gtc gcc gac   672
Val Asp Gln Val Thr Gln Ser Pro Glu Gly Tyr Val Thr Val Ala Asp
    210                 215                 220 gac gtc tac cag cag gcc tgt gtg cac gac gcc gac gag ggt ctc gcc   720
Asp Val Tyr Gln Gln Ala Cys Val His Asp Ala Asp Glu Gly Leu Ala
225                 230                 235                 240 cgc gcg tcg agg atc gga tac ccc gtc atg atc aag gcg tcc gag gga   768
Arg Ala Ser Arg Ile Gly Tyr Pro Val Met Ile Lys Ala Ser Glu Gly
                245                 250                 255 gga gga gga aag ggt att cgc aag gtc gag aag gag cag gac ttt aag   816
Gly Gly Gly Lys Gly Ile Arg Lys Val Glu Lys Glu Gln Asp Phe Lys
            260                 265                 270 cag gcc ttc cag gct gtc ctc acc gag gtt ccc ggc tcg ccc gtc ttt   864
Gln Ala Phe Gln Ala Val Leu Thr Glu Val Pro Gly Ser Pro Val Phe
        275                 280                 285 atc atg aag ctc gcc ggc gca gct cgc cac ctc gag gtc cag gtt ctc   912
Ile Met Lys Leu Ala Gly Ala Ala Arg His Leu Glu Val Gln Val Leu
    290                 295                 300 gcc gac cag tac ggc aac gcc atc tcg ctc ttc ggc cgt gac tgc tcg   960
Ala Asp Gln Tyr Gly Asn Ala Ile Ser Leu Phe Gly Arg Asp Cys Ser
```

```
                305                 310                 315                 320
gtt cag cgt cgc cac cag aag atc atc gaa gag gcg ccc gtc acc atc       1008
Val Gln Arg Arg His Gln Lys Ile Ile Glu Glu Ala Pro Val Thr Ile
                    325                 330                 335 gcc aag ccc gac acg ttc gag cag atg gaa aag tcg gcc gtc cgc ctt       1056
Ala Lys Pro Asp Thr Phe Glu Gln Met Glu Lys Ser Ala Val Arg Leu
                340                 345                 350 gcc aag ctc gtc ggc tac gtc tcg gcg ggt acc gtc gag ttc ctc tac       1104
Ala Lys Leu Val Gly Tyr Val Ser Ala Gly Thr Val Glu Phe Leu Tyr
            355                 360                 365 tcg gct gcc gac gac aag ttt gcc ttc ctc gag ctc aac ccg cgt ctc       1152
Ser Ala Ala Asp Asp Lys Phe Ala Phe Leu Glu Leu Asn Pro Arg Leu
370                 375                 380 cag gtc gag cac ccg acc acc gag atg gtt tcg ggc gtc aac ctt ccc       1200
Gln Val Glu His Pro Thr Thr Glu Met Val Ser Gly Val Asn Leu Pro
385                 390                 395                 400 gcc gcc cag ctc cag gtc gct atg ggt gtt ccc ctc cat cgc atc cgc       1248
Ala Ala Gln Leu Gln Val Ala Met Gly Val Pro Leu His Arg Ile Arg
                    405                 410                 415 gac atc cgc acg ctc tac ggc aag gca ccc aac ggc agc agc gag atc       1296
Asp Ile Arg Thr Leu Tyr Gly Lys Ala Pro Asn Gly Ser Ser Glu Ile
                420                 425                 430 gat ttc gac ttc gag aac ccc gag tcg gcc aag acg cag cgc aag ccc       1344
Asp Phe Asp Phe Glu Asn Pro Glu Ser Ala Lys Thr Gln Arg Lys Pro
            435                 440                 445 tcg ccg aag ggt cac gtc gtt gcc gta cgt atc acg gct gag aac cct       1392
Ser Pro Lys Gly His Val Val Ala Val Arg Ile Thr Ala Glu Asn Pro
450                 455                 460 gac gcc ggc ttc aag ccg tcc atg ggt act ctc caa gag ctc aac ttc       1440
Asp Ala Gly Phe Lys Pro Ser Met Gly Thr Leu Gln Glu Leu Asn Phe
465                 470                 475                 480 cgc tcg agc acg aac gtc tgg ggt tac ttc tcc gtc ggc agc gcc ggt       1488
Arg Ser Ser Thr Asn Val Trp Gly Tyr Phe Ser Val Gly Ser Ala Gly
                    485                 490                 495 gga ctg cac gag ttt gcc gac tcg cag ttc ggc cac atc ttt gcg tac       1536
Gly Leu His Glu Phe Ala Asp Ser Gln Phe Gly His Ile Phe Ala Tyr
                500                 505                 510 ggc tcg gac cgt tcc gag tcg cgc aag aac atg gtc gtc gcg ctc aag       1584
Gly Ser Asp Arg Ser Glu Ser Arg Lys Asn Met Val Val Ala Leu Lys
            515                 520                 525 gag ctc tcg att cgc ggt gac ttc cgc acg acc gtc gag tac ctc atc       1632
Glu Leu Ser Ile Arg Gly Asp Phe Arg Thr Thr Val Glu Tyr Leu Ile
530                 535                 540 aag ctt ctc gag acg gac gcg ttc gag cag aac acg atc acg acc gcg       1680
Lys Leu Leu Glu Thr Asp Ala Phe Glu Gln Asn Thr Ile Thr Thr Ala
545                 550                 555                 560 tgg ctc gac agc ctc atc tcg gct cgc ctg acc gcc gag agg ccc gac       1728
Trp Leu Asp Ser Leu Ile Ser Ala Arg Leu Thr Ala Glu Arg Pro Asp
                    565                 570                 575 acg act ctc gcc atc atc tgc ggc gcc gtt acc aag gcc cac ctc gct       1776
Thr Thr Leu Ala Ile Ile Cys Gly Ala Val Thr Lys Ala His Leu Ala
                580                 585                 590 tcc gag gcc aac atc gcc gag tac aag cgc atc ctc gag aag ggt cag       1824
Ser Glu Ala Asn Ile Ala Glu Tyr Lys Arg Ile Leu Glu Lys Gly Gln
            595                 600                 605 agc ccc gcc aag gag ctc ctc gcc acc gtc gtc ccg ctc gag ttc gtc       1872
Ser Pro Ala Lys Glu Leu Leu Ala Thr Val Val Pro Leu Glu Phe Val
610                 615                 620 ctc gag gac gtc aag tac cgc gcg acc gcc tcg cgc tcg tcg cct tcg       1920
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Leu | Glu | Asp | Val | Lys | Tyr | Arg | Ala | Thr | Ala | Ser | Arg | Ser | Ser | Pro | Ser |      |
| 625 |     |     |     |     | 630 |     |     |     |     | 635 |     |     |     |     | 640 |      |

```
agc tgg tcc atc tac gtc aac ggc tcg aac gtc tcc gtc ggc atc cgc       1968
Ser Trp Ser Ile Tyr Val Asn Gly Ser Asn Val Ser Val Gly Ile Arg
                645                 650                 655 cct ctc gcc gac ggc ggt ctc ctc atc ctc ctt gac ggc cgc tcg tac       2016
Pro Leu Ala Asp Gly Gly Leu Leu Ile Leu Leu Asp Gly Arg Ser Tyr
                660                 665                 670 acc tgc tac gcc aag gag gag gtc ggc gcg ctc cgc ctc tcg atc gac       2064
Thr Cys Tyr Ala Lys Glu Glu Val Gly Ala Leu Arg Leu Ser Ile Asp
                675                 680                 685 tcg agg acc gtc ctc att gct cag gag aac gac ccc acc cag ctt cgc       2112
Ser Arg Thr Val Leu Ile Ala Gln Glu Asn Asp Pro Thr Gln Leu Arg
                690                 695                 700 tcg cct tca ccc ggc aag ctc gtc cgc tac ttc atc gag tcc ggc gag       2160
Ser Pro Ser Pro Gly Lys Leu Val Arg Tyr Phe Ile Glu Ser Gly Glu
705                 710                 715                 720 cac atc tcg aag ggc gag gcg tac gct gag atc gag gtc atg aag atg       2208
His Ile Ser Lys Gly Glu Ala Tyr Ala Glu Ile Glu Val Met Lys Met
                725                 730                 735 atc atg ccc ctc atc gct gcc gag gac ggt atc gcg caa ttc atc aag       2256
Ile Met Pro Leu Ile Ala Ala Glu Asp Gly Ile Ala Gln Phe Ile Lys
                740                 745                 750 cag ccg gga gcg acg ctc gag gcc ggc gac atc ctc ggt atc ttg tcg       2304
Gln Pro Gly Ala Thr Leu Glu Ala Gly Asp Ile Leu Gly Ile Leu Ser
                755                 760                 765 ctc gac gac ccg agc cgc gtc cac cac gcc aag ccg ttc gat ggc cag       2352
Leu Asp Asp Pro Ser Arg Val His His Ala Lys Pro Phe Asp Gly Gln
770                 775                 780 ctt ccc gcc ctt ggc ttg ccc tcc atc gtc ggc aac aag ccg cac cag       2400
Leu Pro Ala Leu Gly Leu Pro Ser Ile Val Gly Asn Lys Pro His Gln
785                 790                 795                 800 cgc ttc gcc tac ctc aaa gac gtg ctc tca aac atc ctc atg ggc tac       2448
Arg Phe Ala Tyr Leu Lys Asp Val Leu Ser Asn Ile Leu Met Gly Tyr
                805                 810                 815 gac aac cag gcc gtc atg cag tcg agc atc aag gag ctc atc tcg gtt       2496
Asp Asn Gln Ala Val Met Gln Ser Ser Ile Lys Glu Leu Ile Ser Val
                820                 825                 830 ctt cgc aac ccc gag ctc ccc tac ggc gag gcc aac gct gtc ctc tcg       2544
Leu Arg Asn Pro Glu Leu Pro Tyr Gly Glu Ala Asn Ala Val Leu Ser
                835                 840                 845 acg ctt tcg ggt cgc atc ccc gcc aag ctc gag cag acc ctc cgc cag       2592
Thr Leu Ser Gly Arg Ile Pro Ala Lys Leu Glu Gln Thr Leu Arg Gln
850                 855                 860 tac atc gac cag gct cac gag tct ggc gcc gag ttc ccg tcc gcc aag       2640
Tyr Ile Asp Gln Ala His Glu Ser Gly Ala Glu Phe Pro Ser Ala Lys
865                 870                 875                 880 tgc cgc aag gcg atc gac acg acc ctt gag cag ctc cgc ccc gcc gag       2688
Cys Arg Lys Ala Ile Asp Thr Thr Leu Glu Gln Leu Arg Pro Ala Glu
                885                 890                 895 gcg cag act gtc cgc aac ttc ctc gtc gcg ttc gac gac atc gtc tac       2736
Ala Gln Thr Val Arg Asn Phe Leu Val Ala Phe Asp Asp Ile Val Tyr
                900                 905                 910 cgc tac cgc tcg ggc ctc aag cac cac gag tgg tca acg ctc gcc ggc       2784
Arg Tyr Arg Ser Gly Leu Lys His His Glu Trp Ser Thr Leu Ala Gly
                915                 920                 925 atc ttt gcc gcg tac gcc gag acg gag aag ccg ttc agc ggc aag gac       2832
Ile Phe Ala Ala Tyr Ala Glu Thr Glu Lys Pro Phe Ser Gly Lys Asp
930                 935                 940
```

```
ggc gac gtc gtc ctc gag ctc cgc gac gcc cac cgc gac tcg ctc gac    2880
Gly Asp Val Val Leu Glu Leu Arg Asp Ala His Arg Asp Ser Leu Asp
945                 950                 955                 960 tcg gtc gtc aag atc gtt ctc tcg cac tac aag gct gcc tcg aag aac    2928
Ser Val Val Lys Ile Val Leu Ser His Tyr Lys Ala Ala Ser Lys Asn
                965                 970                 975 tcg ctt gtc ctt gcg ctc ctc gac atc gtc aag gac tcg gac gcg gtt    2976
Ser Leu Val Leu Ala Leu Leu Asp Ile Val Lys Asp Ser Asp Ala Val
            980                 985                 990 ccg ctc atc gag cag gtc gtc agc cct gcg ctc aag gac ctc gcc gac    3024
Pro Leu Ile Glu Gln Val Val Ser Pro Ala Leu Lys Asp Leu Ala Asp
        995                 1000                1005 ctc gac tcg aag gcc acg act aag gtc gcc ctg aag gcc cgc gag        3069
Leu Asp Ser Lys Ala Thr Thr Lys Val Ala Leu Lys Ala Arg Glu
    1010            1015                1020 gtg ctc atc cac atc cag ctc ccc tcg ctc gac gag cgc ctc gga        3114
Val Leu Ile His Ile Gln Leu Pro Ser Leu Asp Glu Arg Leu Gly
    1025            1030                1035 cag ctc gag cag att ctc aag gcc tcg gtg acg ccc acc gtt tac        3159
Gln Leu Glu Gln Ile Leu Lys Ala Ser Val Thr Pro Thr Val Tyr
    1040            1045                1050 ggc gag ccc ggc cac gac cgc act cct cgc ggt gaa gtc ctt aag        3204
Gly Glu Pro Gly His Asp Arg Thr Pro Arg Gly Glu Val Leu Lys
    1055            1060                1065 gac gtc atc gac tcg cgc ttc acc gtc ttt gac gtt ctc ccg agc        3249
Asp Val Ile Asp Ser Arg Phe Thr Val Phe Asp Val Leu Pro Ser
    1070            1075                1080 ttc ttc cag cac cag gac cac tgg gtc tcg ctc gcc gcg ctc gac        3294
Phe Phe Gln His Gln Asp His Trp Val Ser Leu Ala Ala Leu Asp
    1085            1090                1095 acc tac gtc cgc cgc gcc tac cgc tcg tac aac ctc ctc aac atc        3339
Thr Tyr Val Arg Arg Ala Tyr Arg Ser Tyr Asn Leu Leu Asn Ile
    1100            1105                1110 gag cac atc gag gcc gat gcc gcc gag gac gag ccc gcg acg gtt        3384
Glu His Ile Glu Ala Asp Ala Ala Glu Asp Glu Pro Ala Thr Val
    1115            1120                1125 gcc tgg tcg ttc cgc atg cgc aag gct gcg tcc gag tct gag ccg        3429
Ala Trp Ser Phe Arg Met Arg Lys Ala Ala Ser Glu Ser Glu Pro
    1130            1135                1140 ccc acg ccc acg acc ggc ctc acg tcg cag cgc acc gcc tcg tac        3474
Pro Thr Pro Thr Thr Gly Leu Thr Ser Gln Arg Thr Ala Ser Tyr
    1145            1150                1155 tcg gac ttg acg ttc ctc ctc aac aac gcc cag tcc gag ccg atc        3519
Ser Asp Leu Thr Phe Leu Leu Asn Asn Ala Gln Ser Glu Pro Ile
    1160            1165                1170 cgc tac ggc gcg atg ttc tcg gtc cgc tcg ctc gac cgc ttc cgc        3564
Arg Tyr Gly Ala Met Phe Ser Val Arg Ser Leu Asp Arg Phe Arg
    1175            1180                1185 cag gag ctc ggt acc gtc ctc cga cac ttc ccc gac tcg aac aag        3609
Gln Glu Leu Gly Thr Val Leu Arg His Phe Pro Asp Ser Asn Lys
    1190            1195                1200 ggc aag ctc cag cag cag cct gcc gcg tcg tcg agc cag gag cag        3654
Gly Lys Leu Gln Gln Gln Pro Ala Ala Ser Ser Ser Gln Glu Gln
    1205            1210                1215 tgg aac gtc atc aac gtc gcg ctc acg gtc ccc gcc agc gcg cag        3699
Trp Asn Val Ile Asn Val Ala Leu Thr Val Pro Ala Ser Ala Gln
    1220            1225                1230 gtc gac gag gac gct ctc cgc gcc gac ttt gcc gct cac gtg aac        3744
Val Asp Glu Asp Ala Leu Arg Ala Asp Phe Ala Ala His Val Asn
    1235            1240                1245
```

| | | | | | | | | | | | |
|---|---|---|---|---|---|---|---|---|---|---|---|
| gcg | atg | agc | gcc | gag | atc | gac | gct | cgc | ggc | atg | cgc | cgc | ctc | acc | 3789 |
| Ala | Met | Ser | Ala | Glu | Ile | Asp | Ala | Arg | Gly | Met | Arg | Arg | Leu | Thr | |
| | 1250 | | | | 1255 | | | | 1260 | | | | | | |

```
gcg atg agc gcc gag atc gac gct cgc ggc atg cgc cgc ctc acc        3789
Ala Met Ser Ala Glu Ile Asp Ala Arg Gly Met Arg Arg Leu Thr
    1250            1255            1260 ctc ctc atc tgc cgc gag ggc cag tac ccg tcc tac tac acc gtc        3834
Leu Leu Ile Cys Arg Glu Gly Gln Tyr Pro Ser Tyr Tyr Thr Val
1265            1270            1275 cgc aag cag gac ggc acc tgg aag gag ctc gag acg atc cgc gac        3879
Arg Lys Gln Asp Gly Thr Trp Lys Glu Leu Glu Thr Ile Arg Asp
        1280            1285            1290 atc gag ccc gcc ctc gcc ttc cag ctc gag ttg ggc cgc ctc tcc        3924
Ile Glu Pro Ala Leu Ala Phe Gln Leu Glu Leu Gly Arg Leu Ser
    1295            1300            1305 aac ttc cac ctc gag ccg tgc ccc gtt gag aac cgc cag gtc cac        3969
Asn Phe His Leu Glu Pro Cys Pro Val Glu Asn Arg Gln Val His
1310            1315            1320 gtc tac tac gcg acc gcc aag ggc aac tcg tcc gac tgc cgc ttc        4014
Val Tyr Tyr Ala Thr Ala Lys Gly Asn Ser Ser Asp Cys Arg Phe
        1325            1330            1335 ttc gtc cgc gca ctc gtc cgc cct ggc cgt ctc cgc ggt aac atg        4059
Phe Val Arg Ala Leu Val Arg Pro Gly Arg Leu Arg Gly Asn Met
    1340            1345            1350 aag acg gcc gac tac ctc gtc tcc gag gct gac cgc ctc gtc acc        4104
Lys Thr Ala Asp Tyr Leu Val Ser Glu Ala Asp Arg Leu Val Thr
1355            1360            1365 gat gtc ctc gac tcg ctc gag gtc gcc agc tcg cag cgc cgc gct        4149
Asp Val Leu Asp Ser Leu Glu Val Ala Ser Ser Gln Arg Arg Ala
        1370            1375            1380 gcc gac ggc aac cac atc tcg ctc aac ttc ctg tac tct ctc cgt        4194
Ala Asp Gly Asn His Ile Ser Leu Asn Phe Leu Tyr Ser Leu Arg
    1385            1390            1395 ctc gac ttt gac gag gtc cag gct gcc ctc gcc ggc ttc atc gac        4239
Leu Asp Phe Asp Glu Val Gln Ala Ala Leu Ala Gly Phe Ile Asp
1400            1405            1410 cgc cac ggc aag cgc ttc tgg cgt ctc cgc gtc acc ggc gcc gag        4284
Arg His Gly Lys Arg Phe Trp Arg Leu Arg Val Thr Gly Ala Glu
        1415            1420            1425 atc cgc atc gtc ctc gag gac gcg cag ggc aac att cag ccc atc        4329
Ile Arg Ile Val Leu Glu Asp Ala Gln Gly Asn Ile Gln Pro Ile
    1430            1435            1440 cgc gcc atc atc gag aac gtc tcg ggt ttc gtc gtc aag tac gag        4374
Arg Ala Ile Ile Glu Asn Val Ser Gly Phe Val Val Lys Tyr Glu
1445            1450            1455 gcg tac cgc gag gtc acg acc gac aag ggc cag gtc atc ctc aag        4419
Ala Tyr Arg Glu Val Thr Thr Asp Lys Gly Gln Val Ile Leu Lys
        1460            1465            1470 tcg atc ggt ccg cag ggc gcg ttg cac ctt cag ccg gtc aac ttc        4464
Ser Ile Gly Pro Gln Gly Ala Leu His Leu Gln Pro Val Asn Phe
    1475            1480            1485 ccc tac ccg acc aag gag tgg ctt cag ccg aag cgc tac aag gcc        4509
Pro Tyr Pro Thr Lys Glu Trp Leu Gln Pro Lys Arg Tyr Lys Ala
1490            1495            1500 cac gtc gtc ggc acg acg tac gtc tac gac ttc ccc gac ctt ttc        4554
His Val Val Gly Thr Thr Tyr Val Tyr Asp Phe Pro Asp Leu Phe
        1505            1510            1515 cgc cag gca atc cgc aag cag tgg aag gcg gcc ggc aag act gcg        4599
Arg Gln Ala Ile Arg Lys Gln Trp Lys Ala Ala Gly Lys Thr Ala
    1520            1525            1530 ccc gcc gag ctc ctc gtc gcc aag gag ctc gtc ctc gac gag ttc        4644
Pro Ala Glu Leu Leu Val Ala Lys Glu Leu Val Leu Asp Glu Phe
```

|            |            |            | 1535       |            |            |            | 1540       |            |            |            | 1545       |            |            |      |
|------------|------------|------------|------------|------------|------------|------------|------------|------------|------------|------------|------------|------------|------------|------|
| ggc<br>Gly | aag<br>Lys<br>1550 | cct<br>Pro | cag<br>Gln | gag<br>Glu | gtc<br>Val | gcc<br>Ala<br>1555 | cgc<br>Arg | ccg<br>Pro | cct<br>Pro | ggc<br>Gly | acc<br>Thr<br>1560 | aac<br>Asn | aat<br>Asn | atc<br>Ile | 4689 |
| ggc<br>Gly | atg<br>Met<br>1565 | gtc<br>Val | ggc<br>Gly | tgg<br>Trp | atc<br>Ile | tac<br>Tyr<br>1570 | acg<br>Thr | atc<br>Ile | ttc<br>Phe | acg<br>Thr | ccc<br>Pro<br>1575 | gaa<br>Glu | tac<br>Tyr | ccc<br>Pro | 4734 |
| tct<br>Ser | ggc<br>Gly<br>1580 | cgc<br>Arg | cgc<br>Arg | gtc<br>Val | gtc<br>Val | gtc<br>Val<br>1585 | atc<br>Ile | gcg<br>Ala | aac<br>Asn | gac<br>Asp | atc<br>Ile<br>1590 | acg<br>Thr | ttc<br>Phe | aag<br>Lys | 4779 |
| att<br>Ile | ggt<br>Gly<br>1595 | tcg<br>Ser | ttc<br>Phe | ggc<br>Gly | ccg<br>Pro | gag<br>Glu<br>1600 | gag<br>Glu | gac<br>Asp | cgc<br>Arg | tac<br>Tyr | ttc<br>Phe<br>1605 | ttc<br>Phe | gcc<br>Ala | gtc<br>Val | 4824 |
| acg<br>Thr | cag<br>Gln<br>1610 | ctc<br>Leu | gcg<br>Ala | cgc<br>Arg | caa<br>Gln | ctt<br>Leu<br>1615 | ggc<br>Gly | ttg<br>Leu | ccg<br>Pro | cgc<br>Arg | gtc<br>Val<br>1620 | tac<br>Tyr | ctc<br>Leu | tcg<br>Ser | 4869 |
| gcc<br>Ala | aac<br>Asn<br>1625 | tcg<br>Ser | ggt<br>Gly | gct<br>Ala | cgt<br>Arg | ctc<br>Leu<br>1630 | ggc<br>Gly | att<br>Ile | gcc<br>Ala | gag<br>Glu | gag<br>Glu<br>1635 | ctc<br>Leu | gtc<br>Val | gac<br>Asp | 4914 |
| ttg<br>Leu | ttc<br>Phe<br>1640 | agc<br>Ser | gtc<br>Val | gcg<br>Ala | tgg<br>Trp | gtc<br>Val<br>1645 | gac<br>Asp | agc<br>Ser | tcg<br>Ser | cgg<br>Arg | ccg<br>Pro<br>1650 | gag<br>Glu | aag<br>Lys | ggc<br>Gly | 4959 |
| ttc<br>Phe | aag<br>Lys<br>1655 | tac<br>Tyr | ctc<br>Leu | tac<br>Tyr | cta<br>Leu | acc<br>Thr<br>1660 | gcc<br>Ala | gag<br>Glu | aag<br>Lys | ctc<br>Leu | ggc<br>Gly<br>1665 | gag<br>Glu | ctc<br>Leu | aag<br>Lys | 5004 |
| aac<br>Asn | aag<br>Lys<br>1670 | ggc<br>Gly | gag<br>Glu | aag<br>Lys | agc<br>Ser | gtc<br>Val<br>1675 | atc<br>Ile | acg<br>Thr | aag<br>Lys | cgc<br>Arg | atc<br>Ile<br>1680 | gag<br>Glu | gac<br>Asp | gag<br>Glu | 5049 |
| ggc<br>Gly | gag<br>Glu<br>1685 | acg<br>Thr | cgc<br>Arg | tac<br>Tyr | cag<br>Gln | atc<br>Ile<br>1690 | acc<br>Thr | gac<br>Asp | atc<br>Ile | atc<br>Ile | ggc<br>Gly<br>1695 | ttg<br>Leu | cag<br>Gln | gag<br>Glu | 5094 |
| ggt<br>Gly | ctc<br>Leu<br>1700 | ggt<br>Gly | gtc<br>Val | gag<br>Glu | tcg<br>Ser | ctc<br>Leu<br>1705 | aag<br>Lys | ggc<br>Gly | tct<br>Ser | ggc<br>Gly | ctc<br>Leu<br>1710 | atc<br>Ile | gcc<br>Ala | ggt<br>Gly | 5139 |
| gag<br>Glu | acg<br>Thr<br>1715 | tcg<br>Ser | cgc<br>Arg | gcg<br>Ala | tac<br>Tyr | gac<br>Asp<br>1720 | gac<br>Asp | atc<br>Ile | ttc<br>Phe | acg<br>Thr | atc<br>Ile<br>1725 | acg<br>Thr | ctc<br>Leu | gtc<br>Val | 5184 |
| acc<br>Thr | gcc<br>Ala<br>1730 | cgc<br>Arg | tcg<br>Ser | gtc<br>Val | ggt<br>Gly | atc<br>Ile<br>1735 | ggt<br>Gly | gcg<br>Ala | tac<br>Tyr | ctc<br>Leu | gtc<br>Val<br>1740 | cgc<br>Arg | ctc<br>Leu | ggc<br>Gly | 5229 |
| cag<br>Gln | cgt<br>Arg<br>1745 | gcc<br>Ala | gtc<br>Val | cag<br>Gln | gtc<br>Val | gag<br>Glu<br>1750 | ggc<br>Gly | cag<br>Gln | ccg<br>Pro | atc<br>Ile | atc<br>Ile<br>1755 | ctc<br>Leu | acc<br>Thr | ggt<br>Gly | 5274 |
| gcc<br>Ala | ggc<br>Gly<br>1760 | gcg<br>Ala | ctc<br>Leu | aac<br>Asn | aag<br>Lys | gtc<br>Val<br>1765 | ctc<br>Leu | ggt<br>Gly | cgc<br>Arg | gag<br>Glu | gtg<br>Val<br>1770 | tac<br>Tyr | tcg<br>Ser | tcc<br>Ser | 5319 |
| aac<br>Asn | ttg<br>Leu<br>1775 | cag<br>Gln | ctc<br>Leu | ggc<br>Gly | ggc<br>Gly | acg<br>Thr<br>1780 | cag<br>Gln | atc<br>Ile | atg<br>Met | tac<br>Tyr | aag<br>Lys<br>1785 | aac<br>Asn | ggt<br>Gly | gtc<br>Val | 5364 |
| tcg<br>Ser | cac<br>His<br>1790 | ttg<br>Leu | acg<br>Thr | gcc<br>Ala | gcc<br>Ala | aac<br>Asn<br>1795 | gac<br>Asp | ctc<br>Leu | gag<br>Glu | ggt<br>Gly | gtc<br>Val<br>1800 | ctc<br>Leu | agc<br>Ser | atc<br>Ile | 5409 |
| gtc<br>Val | cag<br>Gln<br>1805 | tgg<br>Trp | ctc<br>Leu | gcc<br>Ala | ttc<br>Phe | gtc<br>Val<br>1810 | ccc<br>Pro | gag<br>Glu | cac<br>His | cgc<br>Arg | ggc<br>Gly<br>1815 | gcg<br>Ala | cct<br>Pro | ctc<br>Leu | 5454 |
| ccg<br>Pro | atc<br>Ile<br>1820 | atg<br>Met | cct<br>Pro | tcg<br>Ser | ccc<br>Pro | gtc<br>Val<br>1825 | gac<br>Asp | ccg<br>Pro | tgg<br>Trp | gac<br>Asp | cgc<br>Arg<br>1830 | tcg<br>Ser | atc<br>Ile | gac<br>Asp | 5499 |
| tac<br>Tyr | acg<br>Thr | ccc<br>Pro | atc<br>Ile | aag<br>Lys | ggc<br>Gly | gcg<br>Ala | tac<br>Tyr | gac<br>Asp | ccg<br>Pro | cgc<br>Arg | tgg<br>Trp | ttc<br>Phe | ctc<br>Leu | gcc<br>Ala | 5544 |

-continued

| | | | | | | | | | | | | | | |
|---|---|---|---|---|---|---|---|---|---|---|---|---|---|---|
| Tyr | Thr 1835 | Pro | Ile | Lys | Gly 1840 | Ala | Tyr | Asp | Pro | Arg 1845 | Trp | Phe | Leu | Ala |

```
ggc aag acg gac gag gcc gac ggt cgc tgg ctc tct ggc ttc ttc    5589
Gly Lys Thr Asp Glu Ala Asp Gly Arg Trp Leu Ser Gly Phe Phe
    1850                1855                1860 gac aag ggc tcg ttc cag gag acg ctc tcg ggc tgg gcg cag acc    5634
Asp Lys Gly Ser Phe Gln Glu Thr Leu Ser Gly Trp Ala Gln Thr
    1865                1870                1875 gtc gtc gtc ggt cgc gct cgc ctc ggc ggc atc ccc atg ggc gcc    5679
Val Val Val Gly Arg Ala Arg Leu Gly Gly Ile Pro Met Gly Ala
    1880                1885                1890 atc gcg gtc gag acc cgc acc atc gag cgc gtc gtg ccc gcc gac    5724
Ile Ala Val Glu Thr Arg Thr Ile Glu Arg Val Val Pro Ala Asp
    1895                1900                1905 cct gcc aac cct ctc tcg aac gag cag aag atc atg gag gcc ggt    5769
Pro Ala Asn Pro Leu Ser Asn Glu Gln Lys Ile Met Glu Ala Gly
    1910                1915                1920 cag gtc tgg tat ccc aac agc tcg ttc aag acg gga cag gcg atc    5814
Gln Val Trp Tyr Pro Asn Ser Ser Phe Lys Thr Gly Gln Ala Ile
    1925                1930                1935 ttc gac ttc aac cgc gag ggt ctc ccg ctc atc atc ttc gcc aac    5859
Phe Asp Phe Asn Arg Glu Gly Leu Pro Leu Ile Ile Phe Ala Asn
    1940                1945                1950 tgg cgc ggc ttc tcg ggc ggc cag cag gac atg ttc gac gag gtc    5904
Trp Arg Gly Phe Ser Gly Gly Gln Gln Asp Met Phe Asp Glu Val
    1955                1960                1965 ctc aag cgc ggt tcg ctc att gtc gac ggt ctc tcg gcg tac aag    5949
Leu Lys Arg Gly Ser Leu Ile Val Asp Gly Leu Ser Ala Tyr Lys
    1970                1975                1980 cag ccc gtc ttc gtc tac atc gtc ccg aac ggc gaa ctt cgc ggc    5994
Gln Pro Val Phe Val Tyr Ile Val Pro Asn Gly Glu Leu Arg Gly
    1985                1990                1995 ggt gct tgg gtc gtc ctc gac ccg tcg atc aac gcc gag ggc atg    6039
Gly Ala Trp Val Val Leu Asp Pro Ser Ile Asn Ala Glu Gly Met
    2000                2005                2010 atg gag atg tac gtc gac gag act gct cgc gcc ggt gtc ctc gag    6084
Met Glu Met Tyr Val Asp Glu Thr Ala Arg Ala Gly Val Leu Glu
    2015                2020                2025 ccc gag ggc atc gtc gag atc aag ctc cgc aag gac aag ctc ctc    6129
Pro Glu Gly Ile Val Glu Ile Lys Leu Arg Lys Asp Lys Leu Leu
    2030                2035                2040 gcc ctc atg gac cgc ctc gac ccg acc tac cac gcc ctc cgc gtc    6174
Ala Leu Met Asp Arg Leu Asp Pro Thr Tyr His Ala Leu Arg Val
    2045                2050                2055 aag tcg acc gac gct tcg ctc tcg ccc gcc gac gcc gcg cag gcc    6219
Lys Ser Thr Asp Ala Ser Leu Ser Pro Ala Asp Ala Ala Gln Ala
    2060                2065                2070 aag acc gag ctc gcc gcg cgc gag aag cag ctc atg ccg atc tac    6264
Lys Thr Glu Leu Ala Ala Arg Glu Lys Gln Leu Met Pro Ile Tyr
    2075                2080                2085 cag cag gtc gcg ctc cag ttc gcc gac tcg cac gac aag gcc ggc    6309
Gln Gln Val Ala Leu Gln Phe Ala Asp Ser His Asp Lys Ala Gly
    2090                2095                2100 cgc atc ctc agc aag ggc tgc gcg cgc gag gcc ctc gag tgg tcg    6354
Arg Ile Leu Ser Lys Gly Cys Ala Arg Glu Ala Leu Glu Trp Ser
    2105                2110                2115 aac gct cgt cgc tac ttc tac gcc cgc ctc cgc cgc cgt ctc gcc    6399
Asn Ala Arg Arg Tyr Phe Tyr Ala Arg Leu Arg Arg Arg Leu Ala
    2120                2125                2130
```

| | | | | | | | | | | | | | | |
|---|---|---|---|---|---|---|---|---|---|---|---|---|---|---|
| gag | gag | gcc | gcc | gtc | aag | cgt | ctc | ggc | gac | gcc | gac | ccg | acc | ctc | 6444 |
| Glu | Glu | Ala | Ala | Val | Lys | Arg | Leu | Gly | Asp | Ala | Asp | Pro | Thr | Leu | |
| 2135 | | | | 2140 | | | | | 2145 | | | | | | |

| tcg | cgc | gac | gag | cgc | ctc | gcc | atc | gtc | cac | gac | gcc | gtc | ggc | cag | 6489 |
| Ser | Arg | Asp | Glu | Arg | Leu | Ala | Ile | Val | His | Asp | Ala | Val | Gly | Gln | |
| 2150 | | | | 2155 | | | | | 2160 | | | | | | |

| ggt | gtc | gac | ctc | aac | aac | gac | ctc | gct | gct | gcc | gcc | gcg | ttc | gag | 6534 |
| Gly | Val | Asp | Leu | Asn | Asn | Asp | Leu | Ala | Ala | Ala | Ala | Ala | Phe | Glu | |
| 2165 | | | | 2170 | | | | | 2175 | | | | | | |

| cag | ggc | gcc | gcc | gcc | atc | acc | gag | cgc | gtc | aag | ctc | gcg | cgc | gcg | 6579 |
| Gln | Gly | Ala | Ala | Ala | Ile | Thr | Glu | Arg | Val | Lys | Leu | Ala | Arg | Ala | |
| 2180 | | | | 2185 | | | | | 2190 | | | | | | |

| acg | acc | gtc | gcc | tcg | act | ctc | gcg | cag | ctc | gcg | cag | gac | gac | aag | 6624 |
| Thr | Thr | Val | Ala | Ser | Thr | Leu | Ala | Gln | Leu | Ala | Gln | Asp | Asp | Lys | |
| 2195 | | | | 2200 | | | | | 2205 | | | | | | |

| gag | gct | ttc | gcc | gcc | tcg | ctc | cag | cag | gtc | ctc | ggc | gac | aag | ctc | 6669 |
| Glu | Ala | Phe | Ala | Ala | Ser | Leu | Gln | Gln | Val | Leu | Gly | Asp | Lys | Leu | |
| 2210 | | | | 2215 | | | | | 2220 | | | | | | |

| acc | gcc | gcc | gac | ctc | gcc | cgc | atc | ctc | gcc | tag | | | | | 6702 |
| Thr | Ala | Ala | Asp | Leu | Ala | Arg | Ile | Leu | Ala | | | | | | |
| 2225 | | | | 2230 | | | | | | | | | | | |

```
<210> SEQ ID NO 91
<211> LENGTH: 2233
<212> TYPE: PRT
<213> ORGANISM: Rhodosporidium toruloides

<400> SEQUENCE: 91
```

| Met | Pro | Phe | Ser | Gly | Glu | Ala | Lys | Ala | Val | Asn | Gly | Ser | His | Ser | Val |
|---|---|---|---|---|---|---|---|---|---|---|---|---|---|---|---|
| 1 | | | | 5 | | | | | 10 | | | | | 15 | |

| Asp | Glu | Ala | Pro | Lys | Asn | Pro | Lys | Tyr | Asp | His | Gly | Arg | Val | Val | Lys |
| | | | 20 | | | | | 25 | | | | | 30 | | |

| Tyr | Leu | Gly | Gly | Asn | Ser | Leu | Glu | Ser | Ala | Pro | Pro | Ser | Lys | Val | Ala |
| | | | 35 | | | | | 40 | | | | | 45 | | |

| Asp | Trp | Val | Arg | Glu | Arg | Gly | Gly | His | Thr | Val | Ile | Thr | Lys | Ile | Leu |
| | 50 | | | | | 55 | | | | | 60 | | | | |

| Ile | Ala | Asn | Asn | Gly | Ile | Ala | Ala | Val | Lys | Glu | Ile | Arg | Ser | Val | Arg |
| 65 | | | | | 70 | | | | | 75 | | | | | 80 |

| Lys | Trp | Ala | Tyr | Glu | Thr | Phe | Gly | Ser | Glu | Arg | Ala | Ile | Glu | Phe | Thr |
| | | | | 85 | | | | | 90 | | | | | 95 | |

| Val | Met | Ala | Thr | Pro | Glu | Asp | Leu | Lys | Val | Asn | Ala | Asp | Tyr | Ile | Arg |
| | | | 100 | | | | | 105 | | | | | 110 | | |

| Met | Ala | Asp | Gln | Tyr | Val | Glu | Val | Pro | Gly | Gly | Thr | Asn | Asn | Asn | Asn |
| | | | 115 | | | | | 120 | | | | | 125 | | |

| Tyr | Ala | Asn | Val | Asp | Val | Ile | Val | Asp | Val | Ala | Glu | Arg | Ala | Gly | Val |
| | | 130 | | | | | 135 | | | | | 140 | | | |

| His | Ala | Val | Trp | Ala | Gly | Trp | Gly | His | Ala | Ser | Glu | Asn | Pro | Arg | Leu |
| 145 | | | | | 150 | | | | | 155 | | | | | 160 |

| Pro | Glu | Ser | Leu | Ala | Ala | Ser | Lys | His | Lys | Ile | Val | Phe | Ile | Gly | Pro |
| | | | | 165 | | | | | 170 | | | | | 175 | |

| Pro | Gly | Ser | Ala | Met | Arg | Ser | Leu | Gly | Asp | Lys | Ile | Ser | Ser | Thr | Ile |
| | | | 180 | | | | | 185 | | | | | 190 | | |

| Val | Ala | Gln | His | Ala | Gln | Val | Pro | Cys | Met | Asp | Trp | Ser | Gln | Gly | Gly |
| | | | 195 | | | | | 200 | | | | | 205 | | |

| Val | Asp | Gln | Val | Thr | Gln | Ser | Pro | Glu | Gly | Tyr | Val | Thr | Val | Ala | Asp |
| | | 210 | | | | | 215 | | | | | 220 | | | |

| Asp | Val | Tyr | Gln | Gln | Ala | Cys | Val | His | Asp | Ala | Asp | Glu | Gly | Leu | Ala |

-continued

```
                225                 230                 235                 240
Arg Ala Ser Arg Ile Gly Tyr Pro Val Met Ile Lys Ala Ser Glu Gly
                    245                 250                 255
Gly Gly Gly Lys Gly Ile Arg Lys Val Glu Lys Glu Gln Asp Phe Lys
                    260                 265                 270
Gln Ala Phe Gln Ala Val Leu Thr Glu Val Pro Gly Ser Pro Val Phe
                    275                 280                 285
Ile Met Lys Leu Ala Gly Ala Ala Arg His Leu Glu Val Gln Val Leu
                    290                 295                 300
Ala Asp Gln Tyr Gly Asn Ala Ile Ser Leu Phe Gly Arg Asp Cys Ser
305                 310                 315                 320
Val Gln Arg Arg His Gln Lys Ile Ile Glu Glu Ala Pro Val Thr Ile
                    325                 330                 335
Ala Lys Pro Asp Thr Phe Glu Gln Met Glu Lys Ser Ala Val Arg Leu
                    340                 345                 350
Ala Lys Leu Val Gly Tyr Val Ser Ala Gly Thr Val Glu Phe Leu Tyr
                    355                 360                 365
Ser Ala Ala Asp Asp Lys Phe Ala Phe Leu Glu Leu Asn Pro Arg Leu
                    370                 375                 380
Gln Val Glu His Pro Thr Thr Glu Met Val Ser Gly Val Asn Leu Pro
385                 390                 395                 400
Ala Ala Gln Leu Gln Val Ala Met Gly Val Pro Leu His Arg Ile Arg
                    405                 410                 415
Asp Ile Arg Thr Leu Tyr Gly Lys Ala Pro Asn Gly Ser Ser Glu Ile
                    420                 425                 430
Asp Phe Asp Phe Glu Asn Pro Glu Ser Ala Lys Thr Gln Arg Lys Pro
                    435                 440                 445
Ser Pro Lys Gly His Val Val Ala Val Arg Ile Thr Ala Glu Asn Pro
                    450                 455                 460
Asp Ala Gly Phe Lys Pro Ser Met Gly Thr Leu Gln Glu Leu Asn Phe
465                 470                 475                 480
Arg Ser Ser Thr Asn Val Trp Gly Tyr Phe Ser Val Gly Ser Ala Gly
                    485                 490                 495
Gly Leu His Glu Phe Ala Asp Ser Gln Phe Gly His Ile Phe Ala Tyr
                    500                 505                 510
Gly Ser Asp Arg Ser Glu Ser Arg Lys Asn Met Val Val Ala Leu Lys
                    515                 520                 525
Glu Leu Ser Ile Arg Gly Asp Phe Arg Thr Thr Val Glu Tyr Leu Ile
                    530                 535                 540
Lys Leu Leu Glu Thr Asp Ala Phe Glu Gln Asn Thr Ile Thr Thr Ala
545                 550                 555                 560
Trp Leu Asp Ser Leu Ile Ser Ala Arg Leu Thr Ala Glu Arg Pro Asp
                    565                 570                 575
Thr Thr Leu Ala Ile Ile Cys Gly Ala Val Thr Lys Ala His Leu Ala
                    580                 585                 590
Ser Glu Ala Asn Ile Ala Glu Tyr Lys Arg Ile Leu Glu Lys Gly Gln
                    595                 600                 605
Ser Pro Ala Lys Glu Leu Leu Ala Thr Val Val Pro Leu Glu Phe Val
                    610                 615                 620
Leu Glu Asp Val Lys Tyr Arg Ala Thr Ala Ser Arg Ser Ser Pro Ser
625                 630                 635                 640
Ser Trp Ser Ile Tyr Val Asn Gly Ser Asn Val Ser Val Gly Ile Arg
                    645                 650                 655
```

```
Pro Leu Ala Asp Gly Gly Leu Ile Leu Leu Asp Gly Arg Ser Tyr
            660                 665                 670

Thr Cys Tyr Ala Lys Glu Val Gly Ala Leu Arg Leu Ser Ile Asp
        675                 680                 685

Ser Arg Thr Val Leu Ile Ala Gln Glu Asn Asp Pro Thr Gln Leu Arg
690                 695                 700

Ser Pro Ser Pro Gly Lys Leu Val Arg Tyr Phe Ile Glu Ser Gly Glu
705                 710                 715                 720

His Ile Ser Lys Gly Glu Ala Tyr Ala Glu Ile Glu Val Met Lys Met
                725                 730                 735

Ile Met Pro Leu Ile Ala Ala Glu Asp Gly Ile Ala Gln Phe Ile Lys
            740                 745                 750

Gln Pro Gly Ala Thr Leu Glu Ala Gly Asp Ile Leu Gly Ile Leu Ser
        755                 760                 765

Leu Asp Asp Pro Ser Arg Val His His Ala Lys Pro Phe Asp Gly Gln
770                 775                 780

Leu Pro Ala Leu Gly Leu Pro Ser Ile Val Gly Asn Lys Pro His Gln
785                 790                 795                 800

Arg Phe Ala Tyr Leu Lys Asp Val Leu Ser Asn Ile Leu Met Gly Tyr
                805                 810                 815

Asp Asn Gln Ala Val Met Gln Ser Ser Ile Lys Glu Leu Ile Ser Val
            820                 825                 830

Leu Arg Asn Pro Glu Leu Pro Tyr Gly Glu Ala Asn Ala Val Leu Ser
        835                 840                 845

Thr Leu Ser Gly Arg Ile Pro Ala Lys Leu Glu Gln Thr Leu Arg Gln
850                 855                 860

Tyr Ile Asp Gln Ala His Glu Ser Gly Ala Glu Phe Pro Ser Ala Lys
865                 870                 875                 880

Cys Arg Lys Ala Ile Asp Thr Thr Leu Glu Gln Leu Arg Pro Ala Glu
                885                 890                 895

Ala Gln Thr Val Arg Asn Phe Leu Val Ala Phe Asp Asp Ile Val Tyr
            900                 905                 910

Arg Tyr Arg Ser Gly Leu Lys His His Glu Trp Ser Thr Leu Ala Gly
        915                 920                 925

Ile Phe Ala Ala Tyr Ala Glu Thr Glu Lys Pro Phe Ser Gly Lys Asp
930                 935                 940

Gly Asp Val Val Leu Glu Leu Arg Asp Ala His Arg Asp Ser Leu Asp
945                 950                 955                 960

Ser Val Val Lys Ile Val Leu Ser His Tyr Lys Ala Ser Lys Asn
                965                 970                 975

Ser Leu Val Leu Ala Leu Leu Asp Ile Val Lys Asp Ser Asp Ala Val
            980                 985                 990

Pro Leu Ile Glu Gln Val Val Ser  Pro Ala Leu Lys Asp  Leu Ala Asp
        995                 1000                1005

Leu Asp  Ser Lys Ala Thr Thr  Lys Val Ala Leu Lys  Ala Arg Glu
    1010                1015                1020

Val Leu  Ile His Ile Gln Leu  Pro Ser Leu Asp Glu  Arg Leu Gly
    1025                1030                1035

Gln Leu  Glu Gln Ile Leu Lys  Ala Ser Val Thr Pro  Thr Val Tyr
    1040                1045                1050

Gly Glu  Pro Gly His Asp Arg  Thr Pro Arg Gly Glu  Val Leu Lys
    1055                1060                1065
```

```
Asp Val Ile Asp Ser Arg Phe Thr Val Phe Asp Val Leu Pro Ser
    1070            1075            1080

Phe Phe Gln His Gln Asp His Trp Val Ser Leu Ala Ala Leu Asp
    1085            1090            1095

Thr Tyr Val Arg Arg Ala Tyr Arg Ser Tyr Asn Leu Leu Asn Ile
    1100            1105            1110

Glu His Ile Glu Ala Asp Ala Ala Glu Asp Glu Pro Ala Thr Val
    1115            1120            1125

Ala Trp Ser Phe Arg Met Arg Lys Ala Ala Ser Glu Ser Glu Pro
    1130            1135            1140

Pro Thr Pro Thr Thr Gly Leu Thr Ser Gln Arg Thr Ala Ser Tyr
    1145            1150            1155

Ser Asp Leu Thr Phe Leu Leu Asn Asn Ala Gln Ser Glu Pro Ile
    1160            1165            1170

Arg Tyr Gly Ala Met Phe Ser Val Arg Ser Leu Asp Arg Phe Arg
    1175            1180            1185

Gln Glu Leu Gly Thr Val Leu Arg His Phe Pro Asp Ser Asn Lys
    1190            1195            1200

Gly Lys Leu Gln Gln Gln Pro Ala Ala Ser Ser Gln Glu Gln
    1205            1210            1215

Trp Asn Val Ile Asn Val Ala Leu Thr Val Pro Ala Ser Ala Gln
    1220            1225            1230

Val Asp Glu Asp Ala Leu Arg Ala Asp Phe Ala Ala His Val Asn
    1235            1240            1245

Ala Met Ser Ala Glu Ile Asp Ala Arg Gly Met Arg Arg Leu Thr
    1250            1255            1260

Leu Leu Ile Cys Arg Glu Gly Gln Tyr Pro Ser Tyr Tyr Thr Val
    1265            1270            1275

Arg Lys Gln Asp Gly Thr Trp Lys Glu Leu Glu Thr Ile Arg Asp
    1280            1285            1290

Ile Glu Pro Ala Leu Ala Phe Gln Leu Glu Leu Gly Arg Leu Ser
    1295            1300            1305

Asn Phe His Leu Glu Pro Cys Pro Val Glu Asn Arg Gln Val His
    1310            1315            1320

Val Tyr Tyr Ala Thr Ala Lys Gly Asn Ser Ser Asp Cys Arg Phe
    1325            1330            1335

Phe Val Arg Ala Leu Val Arg Pro Gly Arg Leu Arg Gly Asn Met
    1340            1345            1350

Lys Thr Ala Asp Tyr Leu Val Ser Glu Ala Asp Arg Leu Val Thr
    1355            1360            1365

Asp Val Leu Asp Ser Leu Glu Val Ala Ser Ser Gln Arg Arg Ala
    1370            1375            1380

Ala Asp Gly Asn His Ile Ser Leu Asn Phe Leu Tyr Ser Leu Arg
    1385            1390            1395

Leu Asp Phe Asp Glu Val Gln Ala Ala Leu Ala Gly Phe Ile Asp
    1400            1405            1410

Arg His Gly Lys Arg Phe Trp Arg Leu Arg Val Thr Gly Ala Glu
    1415            1420            1425

Ile Arg Ile Val Leu Glu Asp Ala Gln Gly Asn Ile Gln Pro Ile
    1430            1435            1440

Arg Ala Ile Ile Glu Asn Val Ser Gly Phe Val Val Lys Tyr Glu
    1445            1450            1455

Ala Tyr Arg Glu Val Thr Thr Asp Lys Gly Gln Val Ile Leu Lys
```

-continued

```
            1460                1465                1470
Ser Ile Gly Pro Gln Gly Ala Leu His Leu Gln Pro Val Asn Phe
    1475                1480                1485
Pro Tyr Pro Thr Lys Glu Trp Leu Gln Pro Lys Arg Tyr Lys Ala
    1490                1495                1500
His Val Val Gly Thr Thr Tyr Val Tyr Asp Phe Pro Asp Leu Phe
    1505                1510                1515
Arg Gln Ala Ile Arg Lys Gln Trp Lys Ala Ala Gly Lys Thr Ala
    1520                1525                1530
Pro Ala Glu Leu Leu Val Ala Lys Glu Leu Val Leu Asp Glu Phe
    1535                1540                1545
Gly Lys Pro Gln Glu Val Ala Arg Pro Pro Gly Thr Asn Asn Ile
    1550                1555                1560
Gly Met Val Gly Trp Ile Tyr Thr Ile Phe Thr Pro Glu Tyr Pro
    1565                1570                1575
Ser Gly Arg Arg Val Val Ile Ala Asn Asp Ile Thr Phe Lys
    1580                1585                1590
Ile Gly Ser Phe Gly Pro Glu Glu Asp Arg Tyr Phe Phe Ala Val
    1595                1600                1605
Thr Gln Leu Ala Arg Gln Leu Gly Leu Pro Arg Val Tyr Leu Ser
    1610                1615                1620
Ala Asn Ser Gly Ala Arg Leu Gly Ile Ala Glu Glu Leu Val Asp
    1625                1630                1635
Leu Phe Ser Val Ala Trp Val Asp Ser Ser Arg Pro Glu Lys Gly
    1640                1645                1650
Phe Lys Tyr Leu Tyr Leu Thr Ala Glu Lys Leu Gly Glu Leu Lys
    1655                1660                1665
Asn Lys Gly Glu Lys Ser Val Ile Thr Lys Arg Ile Glu Asp Glu
    1670                1675                1680
Gly Glu Thr Arg Tyr Gln Ile Thr Asp Ile Ile Gly Leu Gln Glu
    1685                1690                1695
Gly Leu Gly Val Glu Ser Leu Lys Gly Ser Gly Leu Ile Ala Gly
    1700                1705                1710
Glu Thr Ser Arg Ala Tyr Asp Asp Ile Phe Thr Ile Thr Leu Val
    1715                1720                1725
Thr Ala Arg Ser Val Gly Ile Gly Ala Tyr Leu Val Arg Leu Gly
    1730                1735                1740
Gln Arg Ala Val Gln Val Glu Gly Gln Pro Ile Ile Leu Thr Gly
    1745                1750                1755
Ala Gly Ala Leu Asn Lys Val Leu Gly Arg Glu Val Tyr Ser Ser
    1760                1765                1770
Asn Leu Gln Leu Gly Gly Thr Gln Ile Met Tyr Lys Asn Gly Val
    1775                1780                1785
Ser His Leu Thr Ala Ala Asn Asp Leu Glu Gly Val Leu Ser Ile
    1790                1795                1800
Val Gln Trp Leu Ala Phe Val Pro Glu His Arg Gly Ala Pro Leu
    1805                1810                1815
Pro Ile Met Pro Ser Pro Val Asp Pro Trp Asp Arg Ser Ile Asp
    1820                1825                1830
Tyr Thr Pro Ile Lys Gly Ala Tyr Asp Pro Arg Trp Phe Leu Ala
    1835                1840                1845
Gly Lys Thr Asp Glu Ala Asp Gly Arg Trp Leu Ser Gly Phe Phe
    1850                1855                1860
```

Asp Lys Gly Ser Phe Gln Glu Thr Leu Ser Gly Trp Ala Gln Thr
1865                1870                1875

Val Val Val Gly Arg Ala Arg Leu Gly Gly Ile Pro Met Gly Ala
1880                1885                1890

Ile Ala Val Glu Thr Arg Thr Ile Glu Arg Val Val Pro Ala Asp
1895                1900                1905

Pro Ala Asn Pro Leu Ser Asn Glu Gln Lys Ile Met Glu Ala Gly
1910                1915                1920

Gln Val Trp Tyr Pro Asn Ser Ser Phe Lys Thr Gly Gln Ala Ile
1925                1930                1935

Phe Asp Phe Asn Arg Glu Gly Leu Pro Leu Ile Ile Phe Ala Asn
1940                1945                1950

Trp Arg Gly Phe Ser Gly Gly Gln Gln Asp Met Phe Asp Glu Val
1955                1960                1965

Leu Lys Arg Gly Ser Leu Ile Val Asp Gly Leu Ser Ala Tyr Lys
1970                1975                1980

Gln Pro Val Phe Val Tyr Ile Val Pro Asn Gly Glu Leu Arg Gly
1985                1990                1995

Gly Ala Trp Val Val Leu Asp Pro Ser Ile Asn Ala Glu Gly Met
2000                2005                2010

Met Glu Met Tyr Val Asp Glu Thr Ala Arg Ala Gly Val Leu Glu
2015                2020                2025

Pro Glu Gly Ile Val Glu Ile Lys Leu Arg Lys Asp Lys Leu Leu
2030                2035                2040

Ala Leu Met Asp Arg Leu Asp Pro Thr Tyr His Ala Leu Arg Val
2045                2050                2055

Lys Ser Thr Asp Ala Ser Leu Ser Pro Ala Asp Ala Ala Gln Ala
2060                2065                2070

Lys Thr Glu Leu Ala Ala Arg Glu Lys Gln Leu Met Pro Ile Tyr
2075                2080                2085

Gln Gln Val Ala Leu Gln Phe Ala Asp Ser His Asp Lys Ala Gly
2090                2095                2100

Arg Ile Leu Ser Lys Gly Cys Ala Arg Glu Ala Leu Glu Trp Ser
2105                2110                2115

Asn Ala Arg Arg Tyr Phe Tyr Ala Arg Leu Arg Arg Arg Leu Ala
2120                2125                2130

Glu Glu Ala Ala Val Lys Arg Leu Gly Asp Ala Asp Pro Thr Leu
2135                2140                2145

Ser Arg Asp Glu Arg Leu Ala Ile Val His Asp Ala Val Gly Gln
2150                2155                2160

Gly Val Asp Leu Asn Asn Asp Leu Ala Ala Ala Ala Phe Glu
2165                2170                2175

Gln Gly Ala Ala Ala Ile Thr Glu Arg Val Lys Leu Ala Arg Ala
2180                2185                2190

Thr Thr Val Ala Ser Thr Leu Ala Gln Leu Ala Gln Asp Asp Lys
2195                2200                2205

Glu Ala Phe Ala Ala Ser Leu Gln Gln Val Leu Gly Asp Lys Leu
2210                2215                2220

Thr Ala Ala Asp Leu Ala Arg Ile Leu Ala
2225                2230

<210> SEQ ID NO 92
<211> LENGTH: 1925

<212> TYPE: DNA
<213> ORGANISM: Rhodosporidium toruloides

<400> SEQUENCE: 92

```
accgcgtcca aggagaagga gcacgatgtc ctcgcctctt ccgactccga ggacgagcac      60
aaccaggacc cgctcaaggc cctcgagaac gagtacccgc cgttcgtcgt gcccaactac     120
tccatcaagg agttgctcgg cgccatcccc gcccactgct tcgagcgcag cgccctccgc     180
tcgtcgctgt acgtcctcgg cgactttgcc atgctcgcgg gtctcgggta cgccgcgtcg     240
cacatcgacc cggccttttc gttcgacggc ggcaaggtgc tcagcggctg ggccggattc     300
gcagccaagt gggccctctg gtccgcctac tgggtcctcg ccggctgggt cggaacgggc     360
gtctggatcc tcggacacga gtgcggccac caggcgttct cgacgtccaa gacgatcaac     420
aacacgatgg gcctcttcct ccactcattc gttctcgtcc cgtaccactc gtggcgcatc     480
tcgcacgcca agcaccacgc cgccacggga cacatgactc gcgacgaggt ctttgtcccg     540
cgcaccgcgt cgttccgcaa ccccaagccc accggcaaga aactccgcgt ctcgcacaac     600
atcgagctcg acgagctcct cgaggatgcg cccctgtacc gcctcggctg gcttctcgtc     660
cagcagctct cggctggcc cgcgtacctc ttctcgaacg catcgggaca gctctggtac     720
cccaagtgga ccaaccactt cgacccgtcg tcgctcgtct ttgacgcccg ccaccgcggt     780
caggtcctcg tctcggacgc cttcctcgca ggcatggtcg gcctcctcgt cgcctttggc     840
caggtcgtcg gactcgcagg cgtcgtcaag tactacttca ttccttacct ctttgtgtga     900
gtcccgactt ccgatcctcc gaacttgctt cctcctcct tgatctttcg ccagttcccc     960
gctgactctc ccggacctcc ctgcgcgatc acagcaacca ctggctcgtc atgatcacct    1020
acctccagca cacggacccc tcgctccctc actacaacgc cggcatgtgg aacttccagc    1080
gcggcgcgct ctgcaccatg accgcaaca tgctcggccc cgtcggtcct tacctgatgc    1140
acggcatctg cgagacccac ggtgcgttgc agtctcgcgc gaatctcgtt tagttgggcg    1200
gcagtggctg actttgcttc tcctccctct cttcgtccct tctcactccc ttcctccctt    1260
cccacgcttc ctacgacccc tctccacatt ccacacatcg atgtgcacca cccgcagtcg    1320
cgcaccacct ctcgtccaag atcccgcact accacgcgtg ggaggcgaca gaggcgctca    1380
agaacttcct tggcgagcac tacaactaca ccgatgaggg gatgttcagg tcgctctgga    1440
aggcgtatag gcagtgccgg ttcgtcgcag cttctctggg ccttgtttga acctttctag    1500
acgtcgacga tcatattctg acctcccgct cgccttcct cgcttcacgc agctacgtcg    1560
acgatgaggg cgacgtcctc ttctaccgcg acgcctacgg ccgcgcacgc cgcgtcgccg    1620
tccccgccga ggtcccctcc gactcgggcg tcgaggact ctagacgatg ccctagagcg    1680
agactctttc cttcaccttc cccgcttctc gtagatccct ctctttggtt caagacgcga    1740
ctcctctcgt cgtcgtcggt agatttctcc ttccctctcc ctcctcctca ccactctcct    1800
ctcgagtcgc tcgagtcgtc gttctgttcg gtctgtgccg tgtgccctcc cttcttcgag    1860
tgaagggagg acgcaaaggt ctttgtgtga agcaattatc cactctctac gctccttta     1920
cacct                                                                 1925
```

<210> SEQ ID NO 93
<211> LENGTH: 1107
<212> TYPE: DNA
<213> ORGANISM: Rhodosporidium toruloides
<220> FEATURE:
<221> NAME/KEY: CDS
<222> LOCATION: (1)..(1107)

<400> SEQUENCE: 93

| | | |
|---|---|---|
| atg ctc gcg ggt ctc ggg tac gcc gcg tcg cac atc gac ccg gcc ttt<br>Met Leu Ala Gly Leu Gly Tyr Ala Ala Ser His Ile Asp Pro Ala Phe<br>1                          5                      10                     15 | 48 |
| tcg ttc gac ggc ggc aag gtg ctc agc ggc tgg gcc gga ttc gca gcc<br>Ser Phe Asp Gly Gly Lys Val Leu Ser Gly Trp Ala Gly Phe Ala Ala<br>                  20                      25                     30 | 96 |
| aag tgg gcc ctc tgg tcc gcc tac tgg gtc ctc gcc ggc tgg gtc gga<br>Lys Trp Ala Leu Trp Ser Ala Tyr Trp Val Leu Ala Gly Trp Val Gly<br>        35                      40                     45 | 144 |
| acg ggc gtc tgg atc ctc gga cac gag tgc ggc cac cag gcg ttc tcg<br>Thr Gly Val Trp Ile Leu Gly His Glu Cys Gly His Gln Ala Phe Ser<br>  50                      55                     60 | 192 |
| acg tcc aag acg atc aac aac acg atg ggc ctc ttc ctc cac tca ttc<br>Thr Ser Lys Thr Ile Asn Asn Thr Met Gly Leu Phe Leu His Ser Phe<br>65                       70                      75                   80 | 240 |
| gtt ctc gtc ccg tac cac tcg tgg cgc atc tcg cac gcc aag cac cac<br>Val Leu Val Pro Tyr His Ser Trp Arg Ile Ser His Ala Lys His His<br>                         85                      90                     95 | 288 |
| gcc gcc acg gga cac atg act cgc gac gag gtc ttt gtc ccg cgc acc<br>Ala Ala Thr Gly His Met Thr Arg Asp Glu Val Phe Val Pro Arg Thr<br>                100                   105                 110 | 336 |
| gcg tcg ttc cgc aac ccc aag ccc acc ggc aag aaa ctc cgc gtc tcg<br>Ala Ser Phe Arg Asn Pro Lys Pro Thr Gly Lys Lys Leu Arg Val Ser<br>        115                   120                 125 | 384 |
| cac aac atc gag ctc gac gag ctc ctc gag gat gcg ccc ctg tac cgc<br>His Asn Ile Glu Leu Asp Glu Leu Leu Glu Asp Ala Pro Leu Tyr Arg<br>130                      135                   140 | 432 |
| ctc ggc tgg ctt ctc gtc cag cag ctc ttc ggc tgg ccc gcg tac ctc<br>Leu Gly Trp Leu Leu Val Gln Gln Leu Phe Gly Trp Pro Ala Tyr Leu<br>145                      150                   155                 160 | 480 |
| ttc tcg aac gca tcg gga cag ctc tgg tac ccc aag tgg acc aac cac<br>Phe Ser Asn Ala Ser Gly Gln Leu Trp Tyr Pro Lys Trp Thr Asn His<br>                  165                   170                 175 | 528 |
| ttc gac ccg tcg tcg ctc gtc ttt gac gcc cgc cac cgc ggt cag gtc<br>Phe Asp Pro Ser Ser Leu Val Phe Asp Ala Arg His Arg Gly Gln Val<br>                180                   185                 190 | 576 |
| ctc gtc tcg gac gcc ttc ctc gca ggc atg gtc ggc ctc ctc gtc gcc<br>Leu Val Ser Asp Ala Phe Leu Ala Gly Met Val Gly Leu Leu Val Ala<br>        195                   200                 205 | 624 |
| ttt ggc cag gtc gtc gga ctc gca ggc gtc gtc aag tac tac ttc att<br>Phe Gly Gln Val Val Gly Leu Ala Gly Val Val Lys Tyr Tyr Phe Ile<br>210                      215                   220 | 672 |
| cct tac ctc ttt gtc aac cac tgg ctc gtc atg atc acc tac ctc cag<br>Pro Tyr Leu Phe Val Asn His Trp Leu Val Met Ile Thr Tyr Leu Gln<br>225                      230                   235                 240 | 720 |
| cac acg gac ccc tcg ctc cct cac tac aac gcc ggc atg tgg aac ttc<br>His Thr Asp Pro Ser Leu Pro His Tyr Asn Ala Gly Met Trp Asn Phe<br>                245                   250                 255 | 768 |
| cag cgc ggc gcg ctc tgc acc atg gac cgc aac atg ctc ggc ccc gtc<br>Gln Arg Gly Ala Leu Cys Thr Met Asp Arg Asn Met Leu Gly Pro Val<br>        260                   265                 270 | 816 |
| ggt cct tac ctg atg cac ggc atc tgc gag acc cac gtc gcg cac cac<br>Gly Pro Tyr Leu Met His Gly Ile Cys Glu Thr His Val Ala His His<br>275                      280                   285 | 864 |
| ctc tcg tcc aag atc ccg cac tac cac gcg tgg gag gcg aca gag gcg<br>Leu Ser Ser Lys Ile Pro His Tyr His Ala Trp Glu Ala Thr Glu Ala<br>290                      295                   300 | 912 |

| | | |
|---|---|---|
| ctc aag aac ttc ctt ggc gag cac tac aac tac acc gat gag ggg atg<br>Leu Lys Asn Phe Leu Gly Glu His Tyr Asn Tyr Thr Asp Glu Gly Met<br>305                       310                      315                     320 | | 960 |
| ttc agg tcg ctc tgg aag gcg tat agg cag tgc cgc tac gtc gac gat<br>Phe Arg Ser Leu Trp Lys Ala Tyr Arg Gln Cys Arg Tyr Val Asp Asp<br>                      325                      330                     335 | | 1008 |
| gag ggc gac gtc ctc ttc tac cgc gac gcc tac ggc cgc gca cgc cgc<br>Glu Gly Asp Val Leu Phe Tyr Arg Asp Ala Tyr Gly Arg Ala Arg Arg<br>            340                     345                     350 | | 1056 |
| gtc gcc gtc ccc gcc gag gtc ccc tcc gac tcg ggc gtc gag gga ctc<br>Val Ala Val Pro Ala Glu Val Pro Ser Asp Ser Gly Val Glu Gly Leu<br>        355                     360                     365 | | 1104 |
| tag | | 1107 |

<210> SEQ ID NO 94
<211> LENGTH: 368
<212> TYPE: PRT
<213> ORGANISM: Rhodosporidium toruloides

<400> SEQUENCE: 94

Met Leu Ala Gly Leu Gly Tyr Ala Ala Ser His Ile Asp Pro Ala Phe
1                5                    10                 15

Ser Phe Asp Gly Gly Lys Val Leu Ser Gly Trp Ala Gly Phe Ala Ala
             20                    25                    30

Lys Trp Ala Leu Trp Ser Ala Tyr Trp Val Leu Ala Gly Trp Val Gly
        35                    40                    45

Thr Gly Val Trp Ile Leu Gly His Glu Cys Gly His Gln Ala Phe Ser
     50                    55                    60

Thr Ser Lys Thr Ile Asn Asn Thr Met Gly Leu Phe Leu His Ser Phe
65               70                   75                 80

Val Leu Val Pro Tyr His Ser Trp Arg Ile Ser His Ala Lys His His
               85                    90                 95

Ala Ala Thr Gly His Met Thr Arg Asp Glu Val Phe Val Pro Arg Thr
            100                 105                 110

Ala Ser Phe Arg Asn Pro Lys Pro Thr Gly Lys Lys Leu Arg Val Ser
       115                  120                 125

His Asn Ile Glu Leu Asp Glu Leu Leu Glu Asp Ala Pro Leu Tyr Arg
   130                  135                 140

Leu Gly Trp Leu Leu Val Gln Gln Leu Phe Gly Trp Pro Ala Tyr Leu
145             150                   155                 160

Phe Ser Asn Ala Ser Gly Gln Leu Trp Tyr Pro Lys Trp Thr Asn His
               165                  170                175

Phe Asp Pro Ser Ser Leu Val Phe Asp Ala Arg His Arg Gly Gln Val
            180                 185                 190

Leu Val Ser Asp Ala Phe Leu Ala Gly Met Val Gly Leu Leu Val Ala
       195                  200                 205

Phe Gly Gln Val Val Gly Leu Ala Gly Val Val Lys Tyr Tyr Phe Ile
   210                  215                 220

Pro Tyr Leu Phe Val Asn His Trp Leu Val Met Ile Thr Tyr Leu Gln
225             230                   235                 240

His Thr Asp Pro Ser Leu Pro His Tyr Asn Ala Gly Met Trp Asn Phe
               245                  250                255

Gln Arg Gly Ala Leu Cys Thr Met Asp Arg Asn Met Leu Gly Pro Val
            260                 265                 270

Gly Pro Tyr Leu Met His Gly Ile Cys Glu Thr His Val Ala His His
       275                  280                 285

```
Leu Ser Ser Lys Ile Pro His Tyr His Ala Trp Glu Ala Thr Glu Ala
        290                 295                 300

Leu Lys Asn Phe Leu Gly Glu His Tyr Asn Tyr Thr Asp Glu Gly Met
305                 310                 315                 320

Phe Arg Ser Leu Trp Lys Ala Tyr Arg Gln Cys Arg Tyr Val Asp Asp
                325                 330                 335

Glu Gly Asp Val Leu Phe Tyr Arg Asp Ala Tyr Gly Arg Ala Arg Arg
                340                 345                 350

Val Ala Val Pro Ala Glu Val Pro Ser Asp Ser Gly Val Glu Gly Leu
                355                 360                 365

<210> SEQ ID NO 95
<211> LENGTH: 1371
<212> TYPE: DNA
<213> ORGANISM: Phytophthora infestans
<220> FEATURE:
<221> NAME/KEY: CDS
<222> LOCATION: (1)..(1371)

<400> SEQUENCE: 95 atg gtg gac ggc ccc aag acc aag cgc aag att tcg tgg cag gag gtc      48
Met Val Asp Gly Pro Lys Thr Lys Arg Lys Ile Ser Trp Gln Glu Val
1               5                   10                  15 aag cag cac gcc tcg tac gac aac gcg tgg atc gtc atc cac cac aag      96
Lys Gln His Ala Ser Tyr Asp Asn Ala Trp Ile Val Ile His His Lys
                20                  25                  30 gtc tac gac atc tcc aag tgg gac gcg cac ccc ggc ggc atg gtc atg     144
Val Tyr Asp Ile Ser Lys Trp Asp Ala His Pro Gly Gly Met Val Met
            35                  40                  45 ctc tcg cag gcg ggc gag gac gcg acc gac atc ttc acc gtc tgc cac     192
Leu Ser Gln Ala Gly Glu Asp Ala Thr Asp Ile Phe Thr Val Cys His
        50                  55                  60 ccc acc tcg tcg tgg aag cag ctt gag cag ttc tac atc ggc gac gtg     240
Pro Thr Ser Ser Trp Lys Gln Leu Glu Gln Phe Tyr Ile Gly Asp Val
65                  70                  75                  80 gac gag tcc acc gcg acc gtc aac gag gac ctc tcg gag gag gag aag     288
Asp Glu Ser Thr Ala Thr Val Asn Glu Asp Leu Ser Glu Glu Glu Lys
                85                  90                  95 gcc aag aag gcg aag acc gac gag ttc atc tcg gcg tac cgc cgc ctc     336
Ala Lys Lys Ala Lys Thr Asp Glu Phe Ile Ser Ala Tyr Arg Arg Leu
                100                 105                 110 cgc atc aag atc aag ggc atg ggc ctt tac gac gcg tcg atg gtc ttc     384
Arg Ile Lys Ile Lys Gly Met Gly Leu Tyr Asp Ala Ser Met Val Phe
            115                 120                 125 tac gcg tgg aag atc ctc tcg acc ttc ggc ctc tgg atg gcg tcg gcg     432
Tyr Ala Trp Lys Ile Leu Ser Thr Phe Gly Leu Trp Met Ala Ser Ala
        130                 135                 140 gcg atc tgc tgg cac ttc gac tcg tgg ccc atg tac atg ctt gcg gcg     480
Ala Ile Cys Trp His Phe Asp Ser Trp Pro Met Tyr Met Leu Ala Ala
145                 150                 155                 160 tgc gtc atg gga ctt ttc tgg cag cag tcg ggc tgg ctc gcg cac gac     528
Cys Val Met Gly Leu Phe Trp Gln Gln Ser Gly Trp Leu Ala His Asp
                165                 170                 175 gtg ctc cac cac cag gtc tgg gac aac cac atg atc ggc aac gtc atg     576
Val Leu His His Gln Val Trp Asp Asn His Met Ile Gly Asn Val Met
                180                 185                 190 ggc gtc atc atc gga gac gtc tgg atg ggc ttc tcc gtc cag tgg tgg     624
Gly Val Ile Ile Gly Asp Val Trp Met Gly Phe Ser Val Gln Trp Trp
            195                 200                 205
```

-continued

| | | |
|---|---|---|
| aag aac aag cac aac ttc cac cac gcg gtc ccc aac ctc atc ggt gac<br>Lys Asn Lys His Asn Phe His His Ala Val Pro Asn Leu Ile Gly Asp<br>210                       215                     220 | 672 |
| gag aag acg aag tac ctc ggc gac ccc gac atc gac acc atg ccc ctc<br>Glu Lys Thr Lys Tyr Leu Gly Asp Pro Asp Ile Asp Thr Met Pro Leu<br>225                         230                 235                240 | 720 |
| ctc gcg tgg tcg aag cac atg gcg tcg aag gcg tac gag tcg tcg tgg<br>Leu Ala Trp Ser Lys His Met Ala Ser Lys Ala Tyr Glu Ser Ser Trp<br>                     245                     250                255 | 768 |
| ggc ccc ttc ttc gtc ggc cac cag gcg gtc atc tac ttc ccc ctc ctc<br>Gly Pro Phe Phe Val Gly His Gln Ala Val Ile Tyr Phe Pro Leu Leu<br>   260                     265                     270 | 816 |
| ctc ttc gcg cgc ttc tcg tgg ctc ctc cag tcg tac tac tac gtc ttc<br>Leu Phe Ala Arg Phe Ser Trp Leu Leu Gln Ser Tyr Tyr Tyr Val Phe<br>275                       280                     285 | 864 |
| aag ggc ttc gcg ttc ggc aag tac gac ccc gtg gac ctc ccc aac ggc<br>Lys Gly Phe Ala Phe Gly Lys Tyr Asp Pro Val Asp Leu Pro Asn Gly<br>   290                     295                     300 | 912 |
| gag aag gtc ggc ctc atg ctc cac tac atc tgg aac gtc atg ctc ccc<br>Glu Lys Val Gly Leu Met Leu His Tyr Ile Trp Asn Val Met Leu Pro<br>305                       310                 315                320 | 960 |
| gtc gtc acc gga atg tcc gtc gcg cag ggc ctc gcg ttc ttc atg ctt<br>Val Val Thr Gly Met Ser Val Ala Gln Gly Leu Ala Phe Phe Met Leu<br>                     325                     330                335 | 1008 |
| gcg cag atg tcg tgc ggc ggc ttc ctc gcg gcg gtc ttc tcg gtc ggc<br>Ala Gln Met Ser Cys Gly Gly Phe Leu Ala Ala Val Phe Ser Val Gly<br>         340                     345                     350 | 1056 |
| cac aac ggc atg tcg gtc tac gag cgc gag gac aag ccc gac ttc tgg<br>His Asn Gly Met Ser Val Tyr Glu Arg Glu Asp Lys Pro Asp Phe Trp<br>355                       360                     365 | 1104 |
| cag ctc cag gtc acc acc acc cgc aac atc acc ccc ggc ttc ttc atg<br>Gln Leu Gln Val Thr Thr Thr Arg Asn Ile Thr Pro Gly Phe Phe Met<br>   370                     375                     380 | 1152 |
| gac tgg ttc tgc ggc ggc ctc aac tac cag atc gag cac cac ctc ttc<br>Asp Trp Phe Cys Gly Gly Leu Asn Tyr Gln Ile Glu His His Leu Phe<br>385                       390                 395                400 | 1200 |
| ccc atg atg ccc cgc cac aac ctc cag aag gtc aac ccc ctc gtc aag<br>Pro Met Met Pro Arg His Asn Leu Gln Lys Val Asn Pro Leu Val Lys<br>         405                     410                     415 | 1248 |
| tcg ctc tgc aag cag tac gac gtg cgc ttc cac gag acg ggc ttc tac<br>Ser Leu Cys Lys Gln Tyr Asp Val Arg Phe His Glu Thr Gly Phe Tyr<br>420                       425                     430 | 1296 |
| cgg ggc ctc gtc gag gtc gtg gac gag ctt gcg gac atc tcg aag gag<br>Arg Gly Leu Val Glu Val Val Asp Glu Leu Ala Asp Ile Ser Lys Glu<br>   435                     440                     445 | 1344 |
| ttc ctc ctt gag ttc ccc gcg atg tag<br>Phe Leu Leu Glu Phe Pro Ala Met<br>   450                     455 | 1371 |

<210> SEQ ID NO 96
<211> LENGTH: 456
<212> TYPE: PRT
<213> ORGANISM: Phytophthora infestans

<400> SEQUENCE: 96

Met Val Asp Gly Pro Lys Thr Lys Arg Lys Ile Ser Trp Gln Glu Val
1               5                   10                  15

Lys Gln His Ala Ser Tyr Asp Asn Ala Trp Ile Val Ile His Lys
                   20                   25                 30

Val Tyr Asp Ile Ser Lys Trp Asp Ala His Pro Gly Gly Met Val Met

```
                35                  40                  45
Leu Ser Gln Ala Gly Glu Asp Ala Thr Asp Ile Phe Thr Val Cys His
         50                  55                  60
Pro Thr Ser Ser Trp Lys Gln Leu Glu Gln Phe Tyr Ile Gly Asp Val
 65                  70                  75                  80
Asp Glu Ser Thr Ala Thr Val Asn Glu Asp Leu Ser Glu Glu Glu Lys
                 85                  90                  95
Ala Lys Lys Ala Lys Thr Asp Glu Phe Ile Ser Ala Tyr Arg Arg Leu
             100                 105                 110
Arg Ile Lys Ile Lys Gly Met Gly Leu Tyr Asp Ala Ser Met Val Phe
         115                 120                 125
Tyr Ala Trp Lys Ile Leu Ser Thr Phe Gly Leu Trp Met Ala Ser Ala
         130                 135                 140
Ala Ile Cys Trp His Phe Asp Ser Trp Pro Met Tyr Met Leu Ala Ala
 145                 150                 155                 160
Cys Val Met Gly Leu Phe Trp Gln Gln Ser Gly Trp Leu Ala His Asp
                 165                 170                 175
Val Leu His His Gln Val Trp Asp Asn His Met Ile Gly Asn Val Met
             180                 185                 190
Gly Val Ile Ile Gly Asp Val Trp Met Gly Phe Ser Val Gln Trp Trp
         195                 200                 205
Lys Asn Lys His Asn Phe His His Ala Val Pro Asn Leu Ile Gly Asp
         210                 215                 220
Glu Lys Thr Lys Tyr Leu Gly Asp Pro Asp Ile Asp Thr Met Pro Leu
225                 230                 235                 240
Leu Ala Trp Ser Lys His Met Ala Ser Lys Ala Tyr Glu Ser Ser Trp
                 245                 250                 255
Gly Pro Phe Phe Val Gly His Gln Ala Val Ile Tyr Phe Pro Leu Leu
             260                 265                 270
Leu Phe Ala Arg Phe Ser Trp Leu Leu Gln Ser Tyr Tyr Tyr Val Phe
         275                 280                 285
Lys Gly Phe Ala Phe Gly Lys Tyr Asp Pro Val Asp Leu Pro Asn Gly
         290                 295                 300
Glu Lys Val Gly Leu Met Leu His Tyr Ile Trp Asn Val Met Leu Pro
305                 310                 315                 320
Val Val Thr Gly Met Ser Val Ala Gln Gly Leu Ala Phe Phe Met Leu
                 325                 330                 335
Ala Gln Met Ser Cys Gly Gly Phe Leu Ala Ala Val Phe Ser Val Gly
             340                 345                 350
His Asn Gly Met Ser Val Tyr Glu Arg Glu Asp Lys Pro Asp Phe Trp
         355                 360                 365
Gln Leu Gln Val Thr Thr Thr Arg Asn Ile Thr Pro Gly Phe Phe Met
         370                 375                 380
Asp Trp Phe Cys Gly Gly Leu Asn Tyr Gln Ile Glu His His Leu Phe
385                 390                 395                 400
Pro Met Met Pro Arg His Asn Leu Gln Lys Val Asn Pro Leu Val Lys
                 405                 410                 415
Ser Leu Cys Lys Gln Tyr Asp Val Arg Phe His Glu Thr Gly Phe Tyr
             420                 425                 430
Arg Gly Leu Val Glu Val Val Asp Glu Leu Ala Asp Ile Ser Lys Glu
         435                 440                 445
Phe Leu Leu Glu Phe Pro Ala Met
         450                 455
```

<210> SEQ ID NO 97
<211> LENGTH: 1374
<212> TYPE: DNA
<213> ORGANISM: Mortierella alpina
<220> FEATURE:
<221> NAME/KEY: CDS
<222> LOCATION: (1)..(1374)

<400> SEQUENCE: 97

```
atg gcg gcg gcg ccc tcg gtc cgc acc ttc acc cgc gcg gag atc ctc      48
Met Ala Ala Ala Pro Ser Val Arg Thr Phe Thr Arg Ala Glu Ile Leu
1               5                   10                  15 aac gcc gag gcc ctc aac gag ggc aag aag gac gcg gag gcg ccg ttc      96
Asn Ala Glu Ala Leu Asn Glu Gly Lys Lys Asp Ala Glu Ala Pro Phe
            20                  25                  30 ctt atg atc atc gac aac aag gtc tac gac gtg cgc gag ttc gtc ccc     144
Leu Met Ile Ile Asp Asn Lys Val Tyr Asp Val Arg Glu Phe Val Pro
        35                  40                  45 gac cac ccc ggc ggc tcg gtc atc ctc acc cac gtc ggc aag gac ggc     192
Asp His Pro Gly Gly Ser Val Ile Leu Thr His Val Gly Lys Asp Gly
    50                  55                  60 acc gac gtg ttc gac acc ttc cac ccc gag gcg gcg tgg gag acg ctc     240
Thr Asp Val Phe Asp Thr Phe His Pro Glu Ala Ala Trp Glu Thr Leu
65                  70                  75                  80 gcg aac ttc tac gtc ggc gac att gac gag tcc gac cgc gcg atc aag     288
Ala Asn Phe Tyr Val Gly Asp Ile Asp Glu Ser Asp Arg Ala Ile Lys
                85                  90                  95 aac gac gac ttc gcg gcg gag gtc cgc aag ctc cgc acc ctc ttc cag     336
Asn Asp Asp Phe Ala Ala Glu Val Arg Lys Leu Arg Thr Leu Phe Gln
            100                 105                 110 tcg ctc ggc tac tac gac tcg tcg aag gcg tac tac gcg ttc aag gtg     384
Ser Leu Gly Tyr Tyr Asp Ser Ser Lys Ala Tyr Tyr Ala Phe Lys Val
        115                 120                 125 tcg ttc aac ctc tgc atc tgg ggc ctc tcg acc ttc atc gtc gcg aag     432
Ser Phe Asn Leu Cys Ile Trp Gly Leu Ser Thr Phe Ile Val Ala Lys
    130                 135                 140 tgg ggc cag acc tcg acc ctc gcg aac gtc ctc tcg gcc gcg ctc ctc     480
Trp Gly Gln Thr Ser Thr Leu Ala Asn Val Leu Ser Ala Ala Leu Leu
145                 150                 155                 160 ggc ctt ttc tgg cag cag tgc ggc tgg ctc gcc cac gac ttc ctc cac     528
Gly Leu Phe Trp Gln Gln Cys Gly Trp Leu Ala His Asp Phe Leu His
                165                 170                 175 cac cag gtc ttc cag gac cgc ttc tgg ggc gac ctc ttc ggc gcg ttc     576
His Gln Val Phe Gln Asp Arg Phe Trp Gly Asp Leu Phe Gly Ala Phe
            180                 185                 190 ctc ggc ggc gtc tgc cag ggc ttc tcg tcg tcg tgg tgg aag gac aag     624
Leu Gly Gly Val Cys Gln Gly Phe Ser Ser Ser Trp Trp Lys Asp Lys
        195                 200                 205 cac aac acc cac cac gcg gcg ccc aac gtc cac ggc gag gac ccc gac     672
His Asn Thr His His Ala Ala Pro Asn Val His Gly Glu Asp Pro Asp
    210                 215                 220 atc gac acc cac ccc ctc ctc acc tgg tcg gag cac gcg ctt gag atg     720
Ile Asp Thr His Pro Leu Leu Thr Trp Ser Glu His Ala Leu Glu Met
225                 230                 235                 240 ttc tcg gac gtg ccc gac gag gag ctt acc cgc atg tgg tcg cgc ttc     768
Phe Ser Asp Val Pro Asp Glu Glu Leu Thr Arg Met Trp Ser Arg Phe
                245                 250                 255 atg gtc ctc aac cag acc tgg ttc tac ttc ccc atc ctc tcg ttc gcg     816
Met Val Leu Asn Gln Thr Trp Phe Tyr Phe Pro Ile Leu Ser Phe Ala
            260                 265                 270
```

| | | |
|---|---|---|
| cgc ctc tcg tgg tgc ctc cag tcc atc atg ttc gtc ctc ccc aac ggc<br>Arg Leu Ser Trp Cys Leu Gln Ser Ile Met Phe Val Leu Pro Asn Gly<br>            275                  280                  285 | 864 |
| cag gcg cac aag ccc tcg ggc gcg cgc gtc ccc atc tcg ctc gtc gag<br>Gln Ala His Lys Pro Ser Gly Ala Arg Val Pro Ile Ser Leu Val Glu<br>290                  295                  300 | 912 |
| cag ctc tcg ctc gcg atg cac tgg acc tgg tac ttg gcg acc atg ttc<br>Gln Leu Ser Leu Ala Met His Trp Thr Trp Tyr Leu Ala Thr Met Phe<br>305                 310                315              320 | 960 |
| ctc ttc atc aag gac ccc gtc aac atg atc gtc tac ttc ctc gtc tcg<br>Leu Phe Ile Lys Asp Pro Val Asn Met Ile Val Tyr Phe Leu Val Ser<br>                 325                  330              335 | 1008 |
| cag gcg gtc tgc ggc aac ctc ctc gcg atc gtc ttc tcc ctc aac cac<br>Gln Ala Val Cys Gly Asn Leu Leu Ala Ile Val Phe Ser Leu Asn His<br>            340                  345              350 | 1056 |
| aac gga atg ccc gtc atc tcg aag gag gag gcg gtg gac atg gac ttc<br>Asn Gly Met Pro Val Ile Ser Lys Glu Glu Ala Val Asp Met Asp Phe<br>                 355                  360              365 | 1104 |
| ttc acc aag cag atc atc acc ggc cgc gac gtg cac ccc ggc ctc ttc<br>Phe Thr Lys Gln Ile Ile Thr Gly Arg Asp Val His Pro Gly Leu Phe<br>370                 375                  380 | 1152 |
| gcg gac tgg ttc acc ggc ggc ctc aac tac cag atc gag cac cac ctc<br>Ala Asp Trp Phe Thr Gly Gly Leu Asn Tyr Gln Ile Glu His His Leu<br>385                 390                395              400 | 1200 |
| ttc ccc tcg atg ccc cgc cac aac ttc tcg aag atc cag ccc gcc gtc<br>Phe Pro Ser Met Pro Arg His Asn Phe Ser Lys Ile Gln Pro Ala Val<br>                 405                  410              415 | 1248 |
| gag acg ctc tgc aag aag tac ggc gtc cgc tac cac acc acc ggc atg<br>Glu Thr Leu Cys Lys Lys Tyr Gly Val Arg Tyr His Thr Thr Gly Met<br>            420                  425              430 | 1296 |
| atc gag ggc acc gcc gag gtc ttc tcg cgc ctt aac gag gtg tcc aag<br>Ile Glu Gly Thr Ala Glu Val Phe Ser Arg Leu Asn Glu Val Ser Lys<br>                 435                  440              445 | 1344 |
| gcg gcg tcg aag atg ggc aag gcg cag tag<br>Ala Ala Ser Lys Met Gly Lys Ala Gln<br>            450                  455 | 1374 |

<210> SEQ ID NO 98
<211> LENGTH: 457
<212> TYPE: PRT
<213> ORGANISM: Mortierella alpina

<400> SEQUENCE: 98

Met Ala Ala Ala Pro Ser Val Arg Thr Phe Thr Arg Ala Glu Ile Leu
1                  5                    10                15

Asn Ala Glu Ala Leu Asn Glu Gly Lys Lys Asp Ala Glu Ala Pro Phe
                 20                  25                30

Leu Met Ile Ile Asp Asn Lys Val Tyr Asp Val Arg Glu Phe Val Pro
            35                  40                45

Asp His Pro Gly Gly Ser Val Ile Leu Thr His Val Gly Lys Asp Gly
        50                  55                60

Thr Asp Val Phe Asp Thr Phe His Pro Glu Ala Ala Trp Glu Thr Leu
65                 70                75              80

Ala Asn Phe Tyr Val Gly Asp Ile Asp Glu Ser Asp Arg Ala Ile Lys
                 85                  90              95

Asn Asp Asp Phe Ala Ala Glu Val Arg Lys Leu Arg Thr Leu Phe Gln
                 100              105              110

Ser Leu Gly Tyr Tyr Asp Ser Ser Lys Ala Tyr Tyr Ala Phe Lys Val 115                 120                 125
        Ser Phe Asn Leu Cys Ile Trp Gly Leu Ser Thr Phe Ile Val Ala Lys
            130                 135                 140

Trp Gly Gln Thr Ser Thr Leu Ala Asn Val Leu Ser Ala Ala Leu Leu
        145                 150                 155                 160

Gly Leu Phe Trp Gln Gln Cys Gly Trp Leu Ala His Asp Phe Leu His
                        165                 170                 175

His Gln Val Phe Gln Asp Arg Phe Trp Gly Asp Leu Phe Gly Ala Phe
                    180                 185                 190

Leu Gly Gly Val Cys Gln Gly Phe Ser Ser Trp Trp Lys Asp Lys
                195                 200                 205

His Asn Thr His His Ala Ala Pro Asn Val His Gly Glu Asp Pro Asp
            210                 215                 220

Ile Asp Thr His Pro Leu Leu Thr Trp Ser Glu His Ala Leu Glu Met
        225                 230                 235                 240

Phe Ser Asp Val Pro Asp Glu Glu Leu Thr Arg Met Trp Ser Arg Phe
                        245                 250                 255

Met Val Leu Asn Gln Thr Trp Phe Tyr Phe Pro Ile Leu Ser Phe Ala
                    260                 265                 270

Arg Leu Ser Trp Cys Leu Gln Ser Ile Met Phe Val Leu Pro Asn Gly
                275                 280                 285

Gln Ala His Lys Pro Ser Gly Ala Arg Val Pro Ile Ser Leu Val Glu
            290                 295                 300

Gln Leu Ser Leu Ala Met His Trp Thr Trp Tyr Leu Ala Thr Met Phe
        305                 310                 315                 320

Leu Phe Ile Lys Asp Pro Val Asn Met Ile Val Tyr Phe Leu Val Ser
                        325                 330                 335

Gln Ala Val Cys Gly Asn Leu Leu Ala Ile Val Phe Ser Leu Asn His
                    340                 345                 350

Asn Gly Met Pro Val Ile Ser Lys Glu Glu Ala Val Asp Met Asp Phe
                355                 360                 365

Phe Thr Lys Gln Ile Ile Thr Gly Arg Asp Val His Pro Gly Leu Phe
            370                 375                 380

Ala Asp Trp Phe Thr Gly Gly Leu Asn Tyr Gln Ile Glu His His Leu
        385                 390                 395                 400

Phe Pro Ser Met Pro Arg His Asn Phe Ser Lys Ile Gln Pro Ala Val
                        405                 410                 415

Glu Thr Leu Cys Lys Lys Tyr Gly Val Arg Tyr His Thr Thr Gly Met
                    420                 425                 430

Ile Glu Gly Thr Ala Glu Val Phe Ser Arg Leu Asn Glu Val Ser Lys
                435                 440                 445

Ala Ala Ser Lys Met Gly Lys Ala Gln
            450                 455

<210> SEQ ID NO 99
<211> LENGTH: 1408
<212> TYPE: DNA
<213> ORGANISM: Rhodosporidium toruloides

<400> SEQUENCE: 99
atgacctcgt acgccgccca tcctcgcgcg tcgtccttcc tcgcctcgtt cgcagacggt    60
cccaagccac caacaccgac aggcatcccc gcgcccctcg cttcgacgta cgacttgttc   120
ttgaaccccg tcacgcccct cgctttcgga ctcgtctact tcgcgacggc caaaaccctc   180

-continued

```
tcccacttcc agaacggcaa gaaccgcatc aagggcaagg gctgggacgt cgctgtcctc    240
gtgcacaata tcctccttgc ggtctactcg gcgtggacgt tcctcggaac cgcgccgcag    300
atcttcggcg ctttcgttcg cggctacatg gcggacgggt tcgccggatt gacccacgcg    360
tgagttccgc gcgcttttac attcgagcgt catctctttg caggaggggc gtcgaattct    420
gaaagacgag cggcgctaac tcgctcgcca actccgacag cttctgcgac tcgtcgttcg    480
cgatctggca gcagacgacg ttccccaagt tcgcctacct cttctacgtc agcaagttct    540
acgtgcgtct ctcctcgctc catctcatag cagtcactca ctcggctcgc tcgcgcagga    600
aatcgtcgac acggccatct tgctgttgaa gggcaagaag gtcggcatgc tccagtcgta    660
ccaccacatg ggcgcgatct ggactatgta cgccgcgtac gctacgcaag ccatgcctgt    720
cgtgcgtccc gcttcctccc tcgctcgaaa acggagaact ctcgctgacg ctcgactccc    780
gcgcgtgcag tggctcttcg tcgtcttcaa ctcgttcatc cactcaatca tgtacaccta    840
ctacgccttc tcgaccgtct cgctccccct tcccgcgctt ctcaagaaat ccctcacgcg    900
actccaaatc acccagttcc tcgtcggcgg ttcgctcgcc gcctcgtacc tcttcattaa    960
gcttcccgaa ctcccttcgg cggaggagat gtccgctgcg gcgacttcga gcttcgaggc   1020
gggcgtcggc gcgctcaagc gcgagggtcc gacgtgcctc gtcaatgcgg cgcagaggca   1080
tgcgacgttg ctcaattgcg cgtacctcgt gccgttgacg tacctctttg tcgcattctt   1140
cttcaagacg taccagaaga actcggcggc taacgccgcg gcaaaggcca aggccaacgc   1200
gaagaaggcc aactagcgcg gtcccttcct ccctctcttt cgctcctttc gcatccgttt   1260
caactgtcgt gatttcgcac cctcttcgct tgcatacctc tccttagccc tcgtcgtttc   1320
gtcgcagcta gatctcctct cctctctttc tcgtgtccgt attcaccagc tctcttctct   1380
tgggtctctc gtcgtaatcc atagcctc                                       1408
```

<210> SEQ ID NO 100
<211> LENGTH: 990
<212> TYPE: DNA
<213> ORGANISM: Rhodosporidium toruloides
<220> FEATURE:
<221> NAME/KEY: CDS
<222> LOCATION: (1)..(990)

<400> SEQUENCE: 100

```
atg acc tcg tac gcc gcc cat cct cgc gcg tcg tcc ttc ctc gcc tcg       48
Met Thr Ser Tyr Ala Ala His Pro Arg Ala Ser Ser Phe Leu Ala Ser
1               5                   10                  15 ttc gca gac ggt ccc aag cca cca aca ccg aca ggc atc ccc gcg ccc       96
Phe Ala Asp Gly Pro Lys Pro Pro Thr Pro Thr Gly Ile Pro Ala Pro
            20                  25                  30 ctc gct tcg acg tac gac ttg ttc ttg aac ccc gtc acg ccc ctc gct      144
Leu Ala Ser Thr Tyr Asp Leu Phe Leu Asn Pro Val Thr Pro Leu Ala
        35                  40                  45 ttc gga ctc gtc tac ttc gcg acg gcc aaa acc ctc tcc cac ttc cag      192
Phe Gly Leu Val Tyr Phe Ala Thr Ala Lys Thr Leu Ser His Phe Gln
    50                  55                  60 aac ggc aag aac cgc atc aag ggc aag ggc tgg gac gtc gct gtc ctc      240
Asn Gly Lys Asn Arg Ile Lys Gly Lys Gly Trp Asp Val Ala Val Leu
65                  70                  75                  80 gtg cac aat atc ctc ctt gcg gtc tac tcg gcg tgg acg ttc ctc gga      288
Val His Asn Ile Leu Leu Ala Val Tyr Ser Ala Trp Thr Phe Leu Gly
                85                  90                  95 acc gcg ccg cag atc ttc ggc gct ttc gtt cgc ggc tac atg gcg gac      336
Thr Ala Pro Gln Ile Phe Gly Ala Phe Val Arg Gly Tyr Met Ala Asp
```

```
          100                 105                 110
ggg ttc gcc gga ttg acc cac gcc ttc tgc gac tcg tcg ttc gcg atc     384
Gly Phe Ala Gly Leu Thr His Ala Phe Cys Asp Ser Ser Phe Ala Ile
            115                 120                 125 tgg cag cag acg acg ttc ccc aag ttc gcc tac ctc ttc tac gtc agc     432
Trp Gln Gln Thr Thr Phe Pro Lys Phe Ala Tyr Leu Phe Tyr Val Ser
130                 135                 140 aag ttc tac gaa atc gtc gac acg gcc atc ttg ctg ttg aag ggc aag     480
Lys Phe Tyr Glu Ile Val Asp Thr Ala Ile Leu Leu Leu Lys Gly Lys
145                 150                 155                 160 aag gtc ggc atg ctc cag tcg tac cac cac atg ggc gcg atc tgg act     528
Lys Val Gly Met Leu Gln Ser Tyr His His Met Gly Ala Ile Trp Thr
                165                 170                 175 atg tac gcc gcg tac gct acg caa gcc atg cct gtc tgg ctc ttc gtc     576
Met Tyr Ala Ala Tyr Ala Thr Gln Ala Met Pro Val Trp Leu Phe Val
            180                 185                 190 gtc ttc aac tcg ttc atc cac tca atc atg tac acc tac tac gcc ttc     624
Val Phe Asn Ser Phe Ile His Ser Ile Met Tyr Thr Tyr Tyr Ala Phe
        195                 200                 205 tcg acc gtc tcg ctc ccc ttc ccg cgc ttc ctc aag aaa tcc ctc acg     672
Ser Thr Val Ser Leu Pro Phe Pro Arg Phe Leu Lys Lys Ser Leu Thr
    210                 215                 220 cga ctc caa atc acc cag ttc ctc gtc ggc ggt tcg ctc gcc gcc tcg     720
Arg Leu Gln Ile Thr Gln Phe Leu Val Gly Gly Ser Leu Ala Ala Ser
225                 230                 235                 240 tac ctc ttc att aag ctt ccc gaa ctc cct tcg gcg gag gag atg tcc     768
Tyr Leu Phe Ile Lys Leu Pro Glu Leu Pro Ser Ala Glu Glu Met Ser
                245                 250                 255 gct gcg gcg act tcg agc ttc gag gcg ggc gtc ggc gcg ctc aag cgc     816
Ala Ala Ala Thr Ser Ser Phe Glu Ala Gly Val Gly Ala Leu Lys Arg
            260                 265                 270 gag ggt ccg acg tgc ctc gtc aat gcg gcg cag agg cat gcg acg ttg     864
Glu Gly Pro Thr Cys Leu Val Asn Ala Ala Gln Arg His Ala Thr Leu
        275                 280                 285 ctc aat tgc gcg tac ctc gtg ccg ttg acg tac ctc ttt gtc gca ttc     912
Leu Asn Cys Ala Tyr Leu Val Pro Leu Thr Tyr Leu Phe Val Ala Phe
    290                 295                 300 ttc ttc aag acg tac cag aag aac tcg gcg gct aac gcc gcg gca aag     960
Phe Phe Lys Thr Tyr Gln Lys Asn Ser Ala Ala Asn Ala Ala Ala Lys
305                 310                 315                 320 gcc aag gcc aac gcg aag aag gcc aac tag                             990
Ala Lys Ala Asn Ala Lys Lys Ala Asn
                325

<210> SEQ ID NO 101
<211> LENGTH: 329
<212> TYPE: PRT
<213> ORGANISM: Rhodosporidium toruloides

<400> SEQUENCE: 101

Met Thr Ser Tyr Ala Ala His Pro Arg Ala Ser Ser Phe Leu Ala Ser
1               5                   10                  15

Phe Ala Asp Gly Pro Lys Pro Pro Thr Pro Thr Gly Ile Pro Ala Pro
            20                  25                  30

Leu Ala Ser Thr Tyr Asp Leu Phe Leu Asn Pro Val Thr Pro Leu Ala
        35                  40                  45

Phe Gly Leu Val Tyr Phe Ala Thr Ala Lys Thr Leu Ser His Phe Gln
    50                  55                  60

Asn Gly Lys Asn Arg Ile Lys Gly Lys Gly Trp Asp Val Ala Val Leu
```

```
            65                  70                  75                  80
Val His Asn Ile Leu Leu Ala Val Tyr Ser Ala Trp Thr Phe Leu Gly
                    85                  90                  95

Thr Ala Pro Gln Ile Phe Gly Ala Phe Val Arg Gly Tyr Met Ala Asp
                100                 105                 110

Gly Phe Ala Gly Leu Thr His Ala Phe Cys Asp Ser Ser Phe Ala Ile
                115                 120                 125

Trp Gln Gln Thr Thr Phe Pro Lys Phe Ala Tyr Leu Phe Tyr Val Ser
        130                 135                 140

Lys Phe Tyr Glu Ile Val Asp Thr Ala Ile Leu Leu Lys Gly Lys
145                 150                 155                 160

Lys Val Gly Met Leu Gln Ser Tyr His His Met Gly Ala Ile Trp Thr
                165                 170                 175

Met Tyr Ala Ala Tyr Ala Thr Gln Ala Met Pro Val Trp Leu Phe Val
                180                 185                 190

Val Phe Asn Ser Phe Ile His Ser Ile Met Tyr Thr Tyr Tyr Ala Phe
                195                 200                 205

Ser Thr Val Ser Leu Pro Phe Pro Arg Phe Leu Lys Lys Ser Leu Thr
        210                 215                 220

Arg Leu Gln Ile Thr Gln Phe Leu Val Gly Gly Ser Leu Ala Ala Ser
225                 230                 235                 240

Tyr Leu Phe Ile Lys Leu Pro Glu Leu Pro Ser Ala Glu Glu Met Ser
                245                 250                 255

Ala Ala Ala Thr Ser Ser Phe Glu Ala Gly Val Gly Ala Leu Lys Arg
                260                 265                 270

Glu Gly Pro Thr Cys Leu Val Asn Ala Ala Gln Arg His Ala Thr Leu
        275                 280                 285

Leu Asn Cys Ala Tyr Leu Val Pro Leu Thr Tyr Leu Phe Val Ala Phe
        290                 295                 300

Phe Phe Lys Thr Tyr Gln Lys Asn Ser Ala Ala Asn Ala Ala Lys
305                 310                 315                 320

Ala Lys Ala Asn Ala Lys Lys Ala Asn
                325

<210> SEQ ID NO 102
<211> LENGTH: 1620
<212> TYPE: DNA
<213> ORGANISM: Rhodosporidium toruloides

<400> SEQUENCE: 102
ttagttggtc ttcttggcga cggtcgcggc ggcgcccttt gcggcgtcga ccttgttctg     60
gccggccttc ttgtacgtgc gttggtaaaa tgcgataaag aggaagaggt aactggctgt    120
tttcgccagc ccctcgggcg tcagccttgc tcgtagaaaa aaccgagagg aaagggaaa     180 atggacgacg aggaggaggg gggaaggact cactgaggag tgcgcagccg aagatcgcag    240
ctccctccgt cccagcgcac gacccgaggg tcggagcgac cccgcgggcg tacgtccagg    300
cgaagtagct gtagctggcg aagtagaccg tgaagaggtc gatcacgaac tgggtgattt    360
ggagcgtcgt gaggtaccta taccacgggg gctcgtcagg tctagcacaa agggagagga    420
ggggagagac ggacttcttc accagatct tgtagccggc ggccgtcata agtagtagt      480 agtactttac gacggcccac aagcggcgtc agcttccgcg tcgactccag gatgacagga    540
ctcgccgcaa cgcaccatga ggacatgcac aaagaggttg agggtgatga cgacccacga    600
gacggaggtg cgtccattga gctgcgtgta gcagaggacg gcggtcgcgg tgtggtggaa    660
```

-continued

```
gacgtggagg aactgaaggg gcttcttctt gacgacgagg aagaccgtgt cgaacaactc      720
ccagtctgcg cgcgaggttg cgttaggttg cgcaagcagg ggggcgtgag aaggtcggag      780
agggcgtaca cttgaactgc gcggcgttac aacgtcagtt tcggcatctt cgagggacag      840
agggacaaca cacgtagtag ttgaagatgt agtaggtctc gaggcggggc gtccaggcct      900
cgttggcgca gatggcgtgg aagaggccgt gcttccagat gatgggacg atctgggcgc      960
gggagagcgt aagcgacgtc ctccaaagaa tcagatcgtc gaacgcacct cctcaagcat     1020
cagggcgaga agaaggccgg agccggtcga gaggaggaag ttgtgcagca tgaaaagggg     1080
cttgaagcct gtgcgtcgca ggacgaggtc caagtcagtt tctgtagact ctgcaagctc     1140
aagactttgc tggtgaagct tctgtgcgac aggcgagccc atccgctcga cggtgtcatg     1200
acctcgagcg gttgaagcgt gatcggaacg cgttctcctc gtctatccgg ccttttgctg     1260
ccggtccgag gctcttcagc ctgccagcgt cccattgacg cgtctgcatc tctgatccga     1320
cgccgccgac gcgttgtccc tgcacgagcc caacttctt gtcgaagcaa accccaaact     1380
cacggtacgg cttgatccg cgcatgagcg cctgacctcc gaagatgacc gcgaggtaga     1440
ccgcaacggc aatgacgacc tcgggcgtgg tcgagagggg tgtttggccc gggatccagt     1500
gctcgatggt gcgcgggagg gaggggatgg ggagcgcgtg caggagcgag tagacggggc     1560
cggggggacgg tgcgaccata gtgaatggac ctgagcgggt cgagagcgta gcctgggtgc     1620
```

```
<210> SEQ ID NO 103
<211> LENGTH: 879
<212> TYPE: DNA
<213> ORGANISM: Rhodosporidium toruloides
<220> FEATURE:
<221> NAME/KEY: CDS
<222> LOCATION: (1)..(879)

<400> SEQUENCE: 103 atg gtc gca ccg tcc ccc ggc ccc gtc tac tcg ctc ctg cac gcg ctc      48
Met Val Ala Pro Ser Pro Gly Pro Val Tyr Ser Leu Leu His Ala Leu
1               5                  10                  15 ccc atc ccc tcc ctc ccg cgc acc atc gag cac tgg atc ccg ggc caa      96
Pro Ile Pro Ser Leu Pro Arg Thr Ile Glu His Trp Ile Pro Gly Gln
            20                  25                  30 aca ccc ctc tcg acc acg ccc gag gtc gtc att gcc gtt gcg gtc tac     144
Thr Pro Leu Ser Thr Thr Pro Glu Val Val Ile Ala Val Ala Val Tyr
        35                  40                  45 ctc gcg gtc atc ttc gga ggt cag gcg ctc atg cgc gga tca aag ccg     192
Leu Ala Val Ile Phe Gly Gly Gln Ala Leu Met Arg Gly Ser Lys Pro
    50                  55                  60 tac cgc ttc aag ccc ctt ttc atg ctg cac aac ttc ctc ctc tcg acc     240
Tyr Arg Phe Lys Pro Leu Phe Met Leu His Asn Phe Leu Leu Ser Thr
65                  70                  75                  80 ggc tcc ggc ctt ctt ctc gcc ctg atg ctt gag gag atc gtc ccc atc     288
Gly Ser Gly Leu Leu Leu Ala Leu Met Leu Glu Glu Ile Val Pro Ile
                85                  90                  95 atc tgg aag cac ggc ctc ttc cac gcc atc tgc gcc aac gag gcc tgg     336
Ile Trp Lys His Gly Leu Phe His Ala Ile Cys Ala Asn Glu Ala Trp
            100                 105                 110 acg ccc cgc ctc gag acc tac tac atc ttc aac tac tac ttc aag tac     384
Thr Pro Arg Leu Glu Thr Tyr Tyr Ile Phe Asn Tyr Tyr Phe Lys Tyr
        115                 120                 125 tgg gag ttg ttc gac acg gtc ttc ctc gtc gtc aag aag aag ccc ctt     432
Trp Glu Leu Phe Asp Thr Val Phe Leu Val Val Lys Lys Lys Pro Leu
    130                 135                 140
```

-continued

```
cag ttc ctc cac gtc ttc cac cac acc gcg acc gcg gtc ctc tgc tac    480
Gln Phe Leu His Val Phe His His Thr Ala Thr Ala Val Leu Cys Tyr
145                 150                 155                 160 acg cag ctc aat gga cgc acc tcc gtc tcg tgg gtc gtc atc acc ctc    528
Thr Gln Leu Asn Gly Arg Thr Ser Val Ser Trp Val Val Ile Thr Leu
                165                 170                 175 aac ctc ttt gtg cat gtc ctc atg tac tac tac ttt atg acg gcc        576
Asn Leu Phe Val His Val Leu Met Tyr Tyr Tyr Phe Met Thr Ala
            180                 185                 190 gcc ggc tac aag atc tgg tgg aag aag tac ctc acg acg ctc caa atc    624
Ala Gly Tyr Lys Ile Trp Trp Lys Lys Tyr Leu Thr Thr Leu Gln Ile
        195                 200                 205 acc cag ttc gtg atc gac ctc ttc acg gtc tac ttc gcc agc tac agc    672
Thr Gln Phe Val Ile Asp Leu Phe Thr Val Tyr Phe Ala Ser Tyr Ser
    210                 215                 220 tac ttc gcc tgg acg tac gcc cgc ggg tcg ctc ccg acc ctc ggg tcg    720
Tyr Phe Ala Trp Thr Tyr Ala Arg Gly Ser Leu Pro Thr Leu Gly Ser
225                 230                 235                 240 tgc gct ggg acg gag gga gct gcg atc ttc ggc tgc gca ctc ctc acc    768
Cys Ala Gly Thr Glu Gly Ala Ala Ile Phe Gly Cys Ala Leu Leu Thr
                245                 250                 255 agt tac ctc ttc ctc ttt atc gca ttt tac caa cgc acg tac aag aag    816
Ser Tyr Leu Phe Leu Phe Ile Ala Phe Tyr Gln Arg Thr Tyr Lys Lys
            260                 265                 270 gcc ggc cag aac aag gtc gac gcc gca aag ggc gcc gcc gcg acc gtc    864
Ala Gly Gln Asn Lys Val Asp Ala Ala Lys Gly Ala Ala Ala Thr Val
        275                 280                 285 gcc aag aag acc aac                                                 879
Ala Lys Lys Thr Asn
    290
```

<210> SEQ ID NO 104
<211> LENGTH: 293
<212> TYPE: PRT
<213> ORGANISM: Rhodosporidium toruloides

<400> SEQUENCE: 104

```
Met Val Ala Pro Ser Pro Gly Pro Val Tyr Ser Leu Leu His Ala Leu
1               5                   10                  15

Pro Ile Pro Ser Leu Pro Arg Thr Ile Glu His Trp Ile Pro Gly Gln
            20                  25                  30

Thr Pro Leu Ser Thr Thr Pro Glu Val Val Ile Ala Val Ala Val Tyr
        35                  40                  45

Leu Ala Val Ile Phe Gly Gly Gln Ala Leu Met Arg Gly Ser Lys Pro
    50                  55                  60

Tyr Arg Phe Lys Pro Leu Phe Met Leu His Asn Phe Leu Leu Ser Thr
65                  70                  75                  80

Gly Ser Gly Leu Leu Leu Ala Leu Met Leu Glu Glu Ile Val Pro Ile
                85                  90                  95

Ile Trp Lys His Gly Leu Phe His Ala Ile Cys Ala Asn Glu Ala Trp
            100                 105                 110

Thr Pro Arg Leu Glu Thr Tyr Tyr Ile Phe Asn Tyr Tyr Phe Lys Tyr
        115                 120                 125

Trp Glu Leu Phe Asp Thr Val Phe Leu Val Val Lys Lys Lys Pro Leu
    130                 135                 140

Gln Phe Leu His Val Phe His His Thr Ala Thr Ala Val Leu Cys Tyr
145                 150                 155                 160
```

Thr Gln Leu Asn Gly Arg Thr Ser Val Ser Trp Val Ile Thr Leu
                165                 170                 175

Asn Leu Phe Val His Val Leu Met Tyr Tyr Tyr Phe Met Thr Ala
            180                 185                 190

Ala Gly Tyr Lys Ile Trp Trp Lys Lys Tyr Leu Thr Thr Leu Gln Ile
        195                 200                 205

Thr Gln Phe Val Ile Asp Leu Phe Thr Val Tyr Phe Ala Ser Tyr Ser
    210                 215                 220

Tyr Phe Ala Trp Thr Tyr Ala Arg Gly Ser Leu Pro Thr Leu Gly Ser
225                 230                 235                 240

Cys Ala Gly Thr Glu Gly Ala Ala Ile Phe Gly Cys Ala Leu Leu Thr
                245                 250                 255

Ser Tyr Leu Phe Leu Phe Ile Ala Phe Tyr Gln Arg Thr Tyr Lys Lys
            260                 265                 270

Ala Gly Gln Asn Lys Val Asp Ala Ala Lys Gly Ala Ala Ala Thr Val
        275                 280                 285

Ala Lys Lys Thr Asn
    290

<210> SEQ ID NO 105
<211> LENGTH: 527
<212> TYPE: PRT
<213> ORGANISM: Agaricus bisporus

<400> SEQUENCE: 105

Met Val Asp Leu Lys Tyr Thr Pro Val Glu Glu Ile Glu Lys Ile Gln
1               5                   10                  15

Ala Thr Leu Arg Asn Gly Phe Arg Ser Gly Arg Thr Lys Asn Ile Glu
            20                  25                  30

Tyr Arg Lys Tyr Gln Leu Leu Gln Leu Ala Tyr Met Leu Gln Asp Asn
        35                  40                  45

Val Lys Arg Leu Glu Glu Ala Leu Ala Ala Asp Leu Gly Arg Pro Pro
    50                  55                  60

Leu Glu Ser Gln Phe Leu Glu Ile Gly Pro Ser Met Met Asp Ala Arg
65                  70                  75                  80

Asn Ala Trp Ala Gly Val Asp Lys Trp Ala Lys Thr Glu Arg Ala Pro
                85                  90                  95

Phe Ser Ile Asn Gly Phe Ala Met Arg Pro Val Ile Tyr Lys Glu Pro
            100                 105                 110

Lys Gly Val Val Leu Ile Ile Ser Pro Phe Asn Tyr Pro Val Trp Leu
        115                 120                 125

Cys Met Ser Pro Leu Ala Gly Ala Ile Ala Ala Gly Asn Ala Val Leu
    130                 135                 140

Leu Lys Pro Ser Glu Ser Thr Pro His Val Ser Ser Leu Phe Ala Glu
145                 150                 155                 160

Leu Ile Pro Lys Tyr Leu Asp Pro Glu Leu Val Ala Val Val Asn Gly
                165                 170                 175

Gly Val Pro Glu Thr Thr Lys Leu Leu Asp Leu Pro Trp Asp His Ile
            180                 185                 190

Leu Tyr Thr Gly Ser Gly Gln Val Gly Arg Ile Val Ser Ala Ala Ala
        195                 200                 205

Ala Lys His Leu Thr Pro Val Ser Leu Glu Leu Gly Gly Lys Ser Pro
    210                 215                 220

Val Phe Ile Asp Pro Asn Cys Asp Ile Glu Leu Ala Ala Lys Arg Ile
225                 230                 235                 240

Leu Trp Gly Lys Cys Val Asn Ala Gly Gln Thr Cys Thr Ala Pro Asp
                245                 250                 255

Tyr Val Leu Val Pro Arg Glu Val Gln Asp Lys Phe Val Asn Ala Leu
            260                 265                 270

Lys Asn Ser Met Asp Asn Phe Tyr Pro Glu Ser Val Ala Thr Pro Gly
        275                 280                 285

Val Phe Ser Arg Leu Val Thr Pro Gln Ala Phe Asn Arg Ile Lys Gly
    290                 295                 300

Leu Leu Asp Asn Thr Lys Gly Thr Ile Val Ile Gly Gly Glu Met Asp
305                 310                 315                 320

Glu Ala Thr Lys Phe Ile Ala Pro Thr Ile Val Lys Asp Val Pro Thr
                325                 330                 335

Asn Asp Ser Leu Met Asn Glu Glu Ile Phe Gly Pro Val Leu Pro Ile
            340                 345                 350

Val Pro Val Lys Asp Val Glu Glu Ala Ile Ala Tyr Val Asn Ser Asn
        355                 360                 365

Asp His Pro Leu Ala Val Tyr Val Phe Ser Gln Asp Ala Ala Tyr Lys
    370                 375                 380

Gln Lys Val Phe Ser Arg Thr Gln Ser Gly Ser Ala Val Ala Asn Glu
385                 390                 395                 400

Val Val Ile Gln Pro Gly Ile Glu Gly Leu Pro Phe Gly Gly Ile Gly
                405                 410                 415

Pro Ser Gly Ser Gly Tyr His Thr Gly Lys Tyr Thr Phe Asp Met Phe
            420                 425                 430

Thr His Leu Arg Ala Ser Leu Asp Ser Pro Gly Trp Leu Asp Lys Ile
        435                 440                 445

Leu Gly Phe Arg Phe Pro Pro Tyr Thr Asp Lys Ser Ile Lys Ala Ser
    450                 455                 460

Gln Arg Ile Leu Lys Ser Leu Pro Arg Pro Thr Gly Pro Pro Arg
465                 470                 475                 480

Thr Asn Asn Ala Met Ala Asn Gly Ser Ala Thr Lys Trp Trp Gly Lys
                485                 490                 495

Tyr Phe Phe Leu Ala Phe Val Leu Ala Thr Ile Gly Gly Leu Thr Lys
            500                 505                 510

Pro Val Lys Ile Leu Gly Arg Lys Phe Val Pro Lys Ile Leu Gly
        515                 520                 525

<210> SEQ ID NO 106
<211> LENGTH: 487
<212> TYPE: PRT
<213> ORGANISM: Phanerochaete carnosa

<400> SEQUENCE: 106

Met Thr Arg Leu Glu Tyr Thr Asn Ile Asp Asn Val Pro Lys Ile His
1               5                   10                  15

Ala Glu Leu Lys Glu Thr Phe Arg Ser Gly Lys Thr Arg Pro Val Pro
            20                  25                  30

Phe Arg Lys Glu Gln Leu Ala Gln Leu Ala Trp Leu Leu Lys Asp Asn
        35                  40                  45

Thr Asp Arg Ile Ala Asp Ile His Thr Asp Leu Gly Arg Pro Ala
    50                  55                  60

Ile Glu Ser Asp Leu Leu Asp Ile Asn Pro Ser Ile Gly Glu Ala Lys
65                  70                  75                  80

Asp Ala Tyr Asp Asn Val Ala Lys Trp Ala Lys Thr Glu Lys Ala Arg

```
                        85                  90                  95
Trp Thr Phe Asn Phe Ala Met Arg Pro Lys Ile Arg Lys Glu Pro
                       100                 105                 110

Lys Gly Val Val Leu Ile Ile Ser Pro Phe Asn Phe Pro Val Leu Leu
                       115                 120                 125

Leu Leu Gly His Leu Ala Ser Ala Leu Ala Ala Gly Asn Thr Val Val
                       130                 135                 140

Leu Lys Pro Ser Glu Leu Val Pro Ala Thr Ser Gln Leu Ile Ser Asp
145                    150                 155                 160

Leu Ile Ser Gln Tyr Met Asp Pro Gly Val Arg Val Val Asn Gly
                       165                 170                 175

Asp Val Ser Val Thr Lys Leu Leu Glu Leu Pro Trp Asp His Ile
                       180                 185                 190

Leu Tyr Thr Gly Ser Ser Arg Val Ala Lys Ile Ile Cys Thr Ala Ala
                       195                 200                 205

Ala Lys His Leu Thr Pro Val Thr Thr Glu Leu Gly Gly Lys Ser Pro
                       210                 215                 220

Val Ile Ile Asp Pro Lys Cys Asp Met Lys Leu Ala Ala Arg Arg Ile
225                    230                 235                 240

Leu Trp Gly Lys Ile Ala Asn Ala Gly Gln Thr Cys Val Ala Pro Asp
                       245                 250                 255

Tyr Val Leu Val Pro Arg Glu Ala Gln Asp Ala Leu Val Asn Glu Leu
                       260                 265                 270

Met Glu Val Tyr Gln Thr Phe Tyr Pro Glu Gly Asp Pro Ala Thr Ser
                       275                 280                 285

Ala Ser Phe Ser Arg Ile Val Ser Gln Ala His Thr Thr Arg Ile Lys
                       290                 295                 300

Arg Leu Ile Asp Gly Thr Lys Gly Thr Val Val Val Gly Gly Thr Val
305                    310                 315                 320

Asp Val Glu Lys Arg Tyr Ile Ala Pro Thr Ile Ile Arg Asp Val Pro
                       325                 330                 335

Val Asp Asp Ser Thr Met Asp Glu Glu Ile Phe Gly Pro Val Leu Pro
                       340                 345                 350

Ile Val Pro Val Arg Asp Val Glu Glu Ala Ile Gln Ile Val Asn Ser
                       355                 360                 365

Arg Asp His Pro Leu Ser Leu Tyr Val Phe Thr Gln Asp Ala Ala Phe
                       370                 375                 380

Lys Glu Asn Val Phe Ser Arg Thr Gln Ser Gly Ala Ala Leu Ala Asn
385                    390                 395                 400

Glu Val Leu Val His Val Gly Ala Thr Gly Leu Pro Phe Gly Gly Ile
                       405                 410                 415

Gly Pro Ser Gly Ser Gly Ser Leu Thr Gly Lys His Gly Phe Asp Ala
                       420                 425                 430

Phe Thr His Leu Arg Ser Thr Leu Asp Asn Pro Lys Trp Val Asp Ala
                       435                 440                 445

Ile Met Lys Gly Arg Tyr Pro Pro Tyr Thr Pro Glu Lys Leu Ala Arg
                       450                 455                 460

Leu Arg Thr Ala Leu Lys Val Arg Met Pro Pro Arg Pro Gly Gly Ala
465                    470                 475                 480

Arg Pro Ala Gln Lys Ser Ala
                       485

<210> SEQ ID NO 107
```

```
<211> LENGTH: 514
<212> TYPE: PRT
<213> ORGANISM: malassezia globosa

<400> SEQUENCE: 107
```

| | | | | | | | | | | | | | | |
|---|---|---|---|---|---|---|---|---|---|---|---|---|---|---|
| Met | Lys | Thr | Thr | Pro | Ala | Asp | Thr | Ile | Pro | Ala | Leu | Val | Gly | Arg | Leu |
| 1 | | | | 5 | | | | | 10 | | | | | 15 |

Arg Ala Thr Phe Leu Thr Gly Lys Thr Arg Cys Val Glu Tyr Arg Lys
            20                  25                  30

Asn Gln Leu Lys Gln Leu Tyr Phe Leu Val Lys Asp Asn Glu Glu Ala
        35                  40                  45

Phe Val Asp Ala Ile Gly Gln Asp Leu Gly Arg Pro Gly Met Glu Thr
50                  55                  60

Thr Phe Ala Glu Val Ile Gly Ile Glu Asn Asp Leu Ala Thr Ser Ile
65                  70                  75                  80

Ser Gln Leu Ser Lys Trp Ser Lys Asp Glu Cys Val Gly Ala Gly Pro
                85                  90                  95

Pro Phe Met Leu His Gly Thr Lys Ile Arg Lys Asp Pro Lys Gly Thr
            100                 105                 110

Val Leu Val Leu Gly Ala Trp Asn Tyr Pro Ile Thr Val Gln Leu Gly
        115                 120                 125

Pro Met Val Gly Ala Ile Ala Ala Gly Asn Thr Val Ile Leu Lys Pro
130                 135                 140

Ser Glu Leu Ser Pro His Thr Ala Gln Leu Ile Ala Asp Leu Trp Ser
145                 150                 155                 160

Lys Tyr Met Asp Thr Glu Thr Thr Ala Val Val Asn Gly Gly Ile Pro
                165                 170                 175

Glu Ala Thr Ala Leu Leu Asp Gln Arg Phe Glu His Ile Phe Tyr Thr
            180                 185                 190

Gly Asn Gly Arg Val Gly Arg Ile Val Ala Glu Lys Ala Ala Arg Trp
        195                 200                 205

Leu Cys Pro Val Ser Leu Glu Leu Gly Gly Lys Ser Pro Val Ile Val
210                 215                 220

Asp Ala Ser Ala Asp Leu Lys Ile Ala Ala His Arg Thr Leu Trp Ala
225                 230                 235                 240

Lys Ala Phe Asn Ala Gly Gln Thr Cys Val Ala Pro Asp Tyr Cys Leu
                245                 250                 255

Val Asp Arg Arg Val Gln Asp Lys Phe Ala His Glu Leu Leu Gln Ala
            260                 265                 270

Gln Arg Glu Phe Trp Pro Ser Arg Asp His Gln Glu Arg Asp Phe Gly
        275                 280                 285

Arg Ile Val Ser Asp Asn His Trp Lys Arg Ile His Ser Leu Val Ser
290                 295                 300

Ser Ser Lys Ala Glu Leu Val Val Gly Gly Thr Ala Gly Ala Asp Gln
305                 310                 315                 320

Ala Lys Arg Phe Ile Pro Leu Thr Ile Leu Lys Asn Val Asp Ala Ser
                325                 330                 335

Asp Ser Val Met Thr Asp Glu Ile Phe Gly Pro Val Leu Pro Ile Val
            340                 345                 350

Pro Phe Asp Thr Ile Arg Asp Ala Val Asp Phe Val Asn Glu Arg Asp
        355                 360                 365

Gln Pro Leu Ala Leu Tyr Val Phe Thr Ser Cys Asn Glu Thr Arg Asp
370                 375                 380

Tyr Ile Leu Ala Tyr Thr Arg Ser Gly Gly Val Val Arg Gly Asp Cys

```
385                 390                 395                 400
Leu Leu His Tyr Ala Ile Asp Ser Leu Pro Phe Gly Thr Gly Pro
                405                 410                 415

Ser Gly Tyr Gly Ser Tyr His Gly Lys Ala Gly Phe Asp Cys Phe Thr
                420                 425                 430

His Glu Arg Ala Val Val Asp Ala Pro Ser Tyr Gly Met Leu Gly Lys
                435                 440                 445

Leu Val Glu Val Val Met Ala Arg Arg Tyr Pro Pro Tyr Ser Lys Ser
    450                 455                 460

Lys Leu Asp Phe Phe Arg Phe Val Leu Pro Lys Leu Val Trp Phe Gly
465                 470                 475                 480

Arg Pro Pro Gln Pro Thr Arg Ser Ser Lys Ser Ile Asp His Pro Pro
                485                 490                 495

Ser Lys Val Arg Thr Thr Ala Pro Arg His Gly His Pro Leu Ser
                500                 505                 510

Leu Val

<210> SEQ ID NO 108
<211> LENGTH: 538
<212> TYPE: PRT
<213> ORGANISM: Sporisorium reilianum

<400> SEQUENCE: 108

Met Ala Ala Ala Thr Ala Ala Glu Ala Gly Leu Gln Tyr Thr
1               5                   10                  15

Pro Ile Asp Asp Ile Pro Lys Ile Val Ser Asp Leu Arg Ala Ala Phe
                20                  25                  30

Leu Thr Gly Lys Thr Arg Ser Ile Glu Tyr Arg Lys Asn Gln Leu Lys
                35                  40                  45

Gln Leu Ala Tyr Met Leu Lys Asp His Gln Asp Asp Phe Ile Gln Ser
    50                  55                  60

Leu Gln Lys Asp Leu Gly Arg Ser Arg Phe Glu Ser Ile Phe Ala Glu
65                  70                  75                  80

Leu Met Gly Thr Thr Asn Glu Ile Val Glu Ala Val His Asn Leu Asp
                85                  90                  95

Lys Trp Ala Lys Pro Ser Lys Pro Trp Ala Gly Ala Ala Trp Ala Met
                100                 105                 110

His Gly Ala Ser Ile Arg Ser Glu Pro Lys Gly Thr Val Leu Val Leu
                115                 120                 125

Gly Ala Trp Asn Tyr Pro Ile Thr Val Gln Ile Gly Pro Val Val Gly
                130                 135                 140

Ala Ile Ala Ala Gly Asn Thr Val Val Leu Lys Pro Ser Glu Val Ala
145                 150                 155                 160

Ser His Thr Ala Lys Leu Ile Ala Glu Leu Trp Asn Lys Tyr Leu Asp
                165                 170                 175

Pro Glu Cys Tyr Arg Ile Ile Asn Gly Ala Ile Pro Glu Thr Thr Ala
                180                 185                 190

Ala Leu Asp Gln Arg Tyr Glu His Ile Phe Tyr Thr Gly Asn Gly Thr
                195                 200                 205

Val Gly Arg Ile Ile Ala Glu Lys Ala Lys Trp Leu Cys Pro Thr
                210                 215                 220

Thr Leu Glu Leu Gly Gly Lys Ser Pro Val Tyr Val Asp Lys Ser Ala
225                 230                 235                 240

Asp Leu Lys Ile Ala Ala His Arg Ile Leu Trp Gly Lys Ser Phe Asn
```

```
                    245                 250                 255
        Cys Gly Gln Thr Cys Ile Ala Pro Asp Tyr Val Leu Ile Pro His Glu
                    260                 265                 270

Leu Gln His Lys Phe Val His Glu Leu His Lys Ala Tyr Glu Arg Phe
                    275                 280                 285

Tyr Pro Glu Ile Lys Gly Gly Val Ser Gln Ser Glu Ser Tyr Ala Arg
                    290                 295                 300

Ile Ile Asn Pro Gly His Trp Lys Arg Leu Thr Ala Met Leu Ser Gly
        305                 310                 315                 320

Thr Lys Gly Lys Ile Val Leu Gly Gly Glu Gly Asp Glu Ala Thr Lys
                        325                 330                 335

Phe Leu Pro Pro Thr Val Ile Ala Asn Val Lys Thr Asp Asp Pro Val
                        340                 345                 350

Met Ala Gly Glu Ile Phe Gly Pro Leu Leu Pro Ile Val Pro Val Lys
                        355                 360                 365

Asp Val Lys Ala Ala Val Asp Phe Ile Asn Ser Arg Asp Gln Pro Leu
        370                 375                 380

Ala Leu Tyr Leu Phe Ala Gly Asp Ser Lys Val Lys Glu Tyr Phe Phe
        385                 390                 395                 400

Asp Asn Thr Arg Ser Gly Ala Cys Val Gln Gly Asp Thr Leu Leu His
                        405                 410                 415

Phe Ala Val Asp Ala Leu Pro Phe Gly Gly Thr Gly Pro Ser Gly Tyr
                        420                 425                 430

Gly Asn Tyr His Gly Lys Ala Ser Phe Asp Gln Phe Ser His Gln Arg
                        435                 440                 445

Ala Ser Leu Asp Ala Pro Ser Thr Gly Leu Leu Gly Lys Ile Ile Glu
                        450                 455                 460

Ile Val Met Ser Ser Arg Tyr Pro Pro Tyr Thr Asn Ala Asn Leu Asn
        465                 470                 475                 480

Lys Met Arg Met Leu Ala Glu Tyr Ser Val Ser Phe Lys Arg Pro Ser
                        485                 490                 495

Asn Pro His Lys Ser Thr Thr Ser Ser Ser Gly Gln Gly Ala Val
                        500                 505                 510

Ala Lys Arg Leu Ala Val Val Leu Leu Ile Ser Leu Val Leu Gly
                    515                 520                 525

Ala Arg Asn Arg Gly Leu Ile Gly Trp Ile
                    530                 535

<210> SEQ ID NO 109
<211> LENGTH: 640
<212> TYPE: PRT
<213> ORGANISM: Ustilago maydis

<400> SEQUENCE: 109

Met Arg Glu Trp Leu Gly Gly Asn Leu Arg Phe Ala Ala Ile Phe Ile
1               5                   10                  15

Arg Ile Gln Ser Arg Pro Asp His Ser Leu Arg Phe Thr Val Leu Asp
                20                  25                  30

Pro Leu Pro Val His Tyr Arg Leu Ser Pro Pro Ser Ser Thr Leu Ala
            35                  40                  45

Arg Leu His Gln Pro Arg Leu Ala Leu Thr Ser Phe Ala His Leu Ala
        50                  55                  60

Leu Leu Pro Ser Ser Ile Ser Pro Ser Pro Thr Thr Leu Arg Leu Val
65                  70                  75                  80
```

```
Val Cys Leu Val Thr Asn Ser His His Ser Val Ser Ser Ser Leu Lys
                85                  90                  95
Arg Gln Ser Pro Ile Met Ala Ala Ala Ala Thr Ala Ala Thr Glu
            100                 105                 110
Ala Gly Leu Gln Tyr Thr Pro Ile Asp Asp Ile Pro Ser Ile Val Ser
            115                 120                 125
Asp Leu Arg Ala Ala Phe Leu Thr Gly Lys Thr Arg Ser Val Glu Tyr
        130                 135                 140
Arg Lys Asn Gln Leu Lys Gln Leu Ala Tyr Met Ile Lys Asp Asn Gln
145                 150                 155                 160
Glu Ala Phe Val Glu Ser Leu Arg Lys Asp Leu Gly Arg Ser Arg Phe
                165                 170                 175
Glu Ser Ile Phe Ala Glu Leu Met Gly Thr Thr Asn Glu Ile Val Glu
                180                 185                 190
Ala Val Thr Lys Ile Asp Lys Trp Ala Lys Pro Ala Lys Pro Trp Ala
                195                 200                 205
Gly Ala Ala Trp Ala Met His Gly Ala Thr Ile Arg Ser Glu Pro Lys
            210                 215                 220
Gly Thr Val Leu Val Leu Gly Ala Trp Asn Tyr Pro Ile Thr Val Gln
225                 230                 235                 240
Ile Gly Pro Val Ile Gly Ala Ile Ala Ala Gly Asn Thr Val Ile Leu
                245                 250                 255
Lys Pro Ser Glu Val Ala Ser His Thr Ala Lys Leu Ile Ala Glu Leu
                260                 265                 270
Trp Asn Lys Tyr Leu Asp Pro Glu Cys Phe Arg Val Val Asn Gly Gly
            275                 280                 285
Ile Pro Glu Thr Thr Ala Leu Leu Asp Gln Arg Phe Glu His Ile Phe
    290                 295                 300
Tyr Thr Gly Asn Gly Thr Val Gly Arg Ile Ile Ala Glu Lys Ala Ala
305                 310                 315                 320
Lys Trp Leu Cys Pro Thr Thr Leu Glu Leu Gly Gly Lys Ser Pro Val
                325                 330                 335
Tyr Val Asp Lys Ser Ala Asp Leu Ser Ile Ala Ala His Arg Ile Leu
            340                 345                 350
Trp Gly Lys Ser Phe Asn Cys Gly Gln Thr Cys Ile Ala Pro Asp Tyr
        355                 360                 365
Val Leu Ile Gln Pro Asp Leu Gln Asp Lys Phe Val Gln Glu Leu Lys
        370                 375                 380
Lys Ala Tyr Gln Arg Phe Tyr Pro Glu Leu Gln Gly Gly Val Asn Asn
385                 390                 395                 400
Ser Glu Ser Tyr Ala Arg Ile Ile Asn Pro Gly His Trp Lys Arg Leu
                405                 410                 415
Asn Ala Met Leu Ser Gly Thr Lys Gly Lys Val Val Leu Gly Gly Glu
                420                 425                 430
Gly Glu Glu Ala Thr Lys Phe Leu Pro Pro Thr Val Ile Ala Asp Val
            435                 440                 445
Lys Pro Asp Asp Ala Ile Met Ser Gly Glu Ile Phe Gly Pro Leu Leu
    450                 455                 460
Pro Ile Val Pro Val Arg Asp Val Glu Ala Ala Val Asp Leu Ile Asn
465                 470                 475                 480
Ser Arg Asp Gln Pro Leu Ala Leu Tyr Leu Phe Ala Gly Asp Asn Arg
                485                 490                 495
Val Lys Asn Phe Phe Phe Asp Asn Thr Arg Ser Gly Ala Cys Val Gln
```

```
                    500                 505                 510
Gly Asp Thr Leu Leu His Phe Ala Val Asp Val Leu Pro Phe Gly Gly
                515                 520                 525

Thr Gly Pro Ser Gly Tyr Gly Asn Tyr His Gly Lys Ala Ser Phe Asp
            530                 535                 540

Gln Phe Ser His Gln Arg Ala Ser Leu Asp Ala Pro Ser Thr Gly Leu
545                 550                 555                 560

Leu Gly Lys Leu Val Glu Leu Ile Met Ser Ser Arg Tyr Pro Pro Tyr
                565                 570                 575

Thr Glu Ala Asn Leu Lys Lys Leu Arg Ala Leu Ala Ala Tyr Ser Val
            580                 585                 590

Ser Phe Lys Arg Pro Ser Asn Pro His Lys Ser Ile Ala Ser Ser Ser
        595                 600                 605

Val Ser Leu Cys Leu Ser His Ser Arg Pro Ser Pro Phe Leu Ser Met
    610                 615                 620

Ser Gln Ser Leu Phe Pro Met Val His Tyr Asn Met Leu Pro Thr Gln
625                 630                 635                 640

<210> SEQ ID NO 110
<211> LENGTH: 578
<212> TYPE: PRT
<213> ORGANISM: Melampsora larici-populina

<400> SEQUENCE: 110

Met Ser Leu Ser Ser Lys Ala Gln Asp Gln Leu Asn Ser Gln Phe Thr
1               5                   10                  15

Ser Ile Asp Glu Ile Pro Lys Ile His Gln Glu Leu Arg Lys Ala Phe
            20                  25                  30

Ser Asn Arg Ile Thr Lys Thr Leu Glu Trp Arg Thr His Gln Leu Lys
        35                  40                  45

Gln Leu Gly Phe Leu Leu Gln Asp Asn Glu Gln Leu Ile Glu Glu Ala
    50                  55                  60

Leu Ala Ile Asp Leu Gly Lys Pro Lys Thr Glu Ser His Ile Gly Glu
65                  70                  75                  80

Leu Val Gly Thr Arg His Glu Val Leu Tyr Ala Leu Asn Asn Val Lys
                85                  90                  95

Ser Trp Met Glu Pro Gln Ser Val Lys Thr Asp Leu Ala Trp Leu Val
            100                 105                 110

Thr Lys Pro Lys Thr Phe His Glu Pro Lys Gly Val Val Leu Ile Phe
        115                 120                 125

Gly Thr Trp Asn Tyr Pro Ile Ser Leu Ser Ile Ile Pro Leu Val Gly
    130                 135                 140

Ala Ile Ala Gly Gly Asn Ala Val Val Leu Lys Leu Ser Glu Gln Ala
145                 150                 155                 160

Pro Ala Ile Ala Asn Leu Leu Thr Lys Leu Ile Pro Gln Tyr Leu Asp
                165                 170                 175

Asn Asn His Ile Arg Val Val Asn Gly Ala Ala Asp His Cys Asn Ala
            180                 185                 190

Leu Leu Asp Leu Lys Phe Asp His Ile Phe Phe Thr Gly Ser Thr Gln
        195                 200                 205

Val Gly Arg Thr Val Ala Lys Arg Ala Ala Glu His Met Thr Pro Val
    210                 215                 220

Thr Leu Glu Leu Gly Gly Lys Ser Pro Ala Ile Val Phe Asp Asp Ala
225                 230                 235                 240
```

```
Asp Phe Pro Val Ile Ala Arg Arg Leu Ile Trp Gly Lys Gly Met Asn
                245                 250                 255

Ala Gly Gln Thr Cys Val Ala Pro Asp Tyr Ile Leu Val Ser Lys Lys
            260                 265                 270

Ser Glu Ala Lys Leu Ile Thr Ser Leu Lys Lys Ala Met Gln Glu Leu
        275                 280                 285

Tyr Pro Leu Asp Ser Ala Ser Gly Leu Ser Ala Lys Lys Ile Ile Asn
    290                 295                 300

Ala Ser Gly Lys Ser Asp Gly Pro Asp Leu Gln Tyr Ser Lys
305                 310                 315                 320

Ile Val Asn Gln Asn Gln Phe Asn Arg Leu Asn Asn Val Leu Gln Glu
                325                 330                 335

Thr Lys Gly Glu Phe Ile Pro Thr Asp Asp Thr Phe Gln Ala Gly Thr
            340                 345                 350

Lys Asp Ser Ser Asp Ala Gln Glu Leu Lys Met Pro Leu Thr Leu Val
        355                 360                 365

Arg Asn Leu Thr Met Glu Asp Pro Val Met Gln Asn Glu Ile Phe Gly
    370                 375                 380

Pro Ile Phe Pro Ile Leu Thr Tyr Asp Leu Gln Ser Glu Ser Met Ala
385                 390                 395                 400

Glu Ile Leu Arg Pro Ile Ala Asp Ala Glu Pro Leu Ala Leu Tyr Val
                405                 410                 415

Phe Thr Gln Ser Ser Gln Asn Phe Glu Leu Val Arg Gln His Thr Lys
            420                 425                 430

Ser Gly Gln Ile Met Cys Asn Asp Leu Leu Ile Gln Phe Ala Ile Pro
        435                 440                 445

Gly Leu Pro Phe Gly Gly Ile Gly Gln Ser Gly Ser Gly Asn Tyr His
    450                 455                 460

Gly Tyr Tyr Ser Phe Leu Thr Phe Thr Tyr Glu Arg Ser Ser Ala Asn
465                 470                 475                 480

Leu Pro Thr Trp Ala Asp Phe Leu Phe Asn Ala Arg Tyr Pro Pro Tyr
                485                 490                 495

Thr Pro Phe Lys Leu Lys Leu Phe Ser Ala Ile Met Gly Pro Ala Arg
            500                 505                 510

Ile Lys Gly Lys Ser Asn Pro Gly Leu Val Pro Lys Ser Ala Glu Val
        515                 520                 525

Gly Lys Arg Ser Trp Leu Pro Thr Leu Thr Pro Leu Ser Phe Ser Thr
    530                 535                 540

Leu Leu Leu Ala Gly Tyr Tyr Ala Leu Ser Arg Arg Tyr Gly Ser Asp
545                 550                 555                 560

Tyr Leu Lys Ile Trp Met Thr Arg Phe Ile Gly Ala Ile Lys Gln Ser
                565                 570                 575

Asn Arg

<210> SEQ ID NO 111
<211> LENGTH: 576
<212> TYPE: PRT
<213> ORGANISM: Puccinia graminis f. sp. tritici

<400> SEQUENCE: 111

Met Ser Ser Thr Ser Pro Leu Glu Phe Thr Pro Thr Glu Gln Ile Lys
1               5                   10                  15

Glu Ile Tyr Ala Thr Val Ser Gln Gly His Ser Ser Gly Ile Thr Lys
            20                  25                  30
```

```
Ser Tyr Glu Trp Arg Glu His Gln Leu Lys Gln Leu Gly Tyr Leu Leu
         35                  40                  45

Gln Glu Asn Glu Ser Leu Leu Glu Glu Ala Leu Thr Ile Asp Leu Gly
 50                  55                  60

Arg Pro Asn Leu Glu Asn His Val Gly Glu Leu Val Gly Thr Arg Asn
 65                  70                  75                  80

Glu Val Leu Ser Ala Leu Lys Asn Leu Lys Lys Trp Ile Lys Pro Gln
                 85                  90                  95

Ser Val Lys Thr Glu Leu Thr Trp Leu Ile Ala Lys Pro Arg Val Ser
             100                 105                 110

His Glu Pro Lys Gly Ile Val Ala Ile Phe Gly Ala Trp Asn Tyr Pro
         115                 120                 125

Val Ala Val Leu Phe Gly Pro Leu Val Gly Ala Ile Ala Gly Gly Asn
 130                 135                 140

Ser Ile Ile Leu Lys Pro Ser Glu Asn Cys Pro Ala Thr Ser Asn Leu
145                 150                 155                 160

Met Thr Thr Leu Val Arg Lys Tyr Leu Asp Pro Arg Asn Ile Cys Val
                 165                 170                 175

Val Asn Gly Gly Gln Glu Gln Ser Thr Ala Leu Leu Asp Cys Arg Phe
             180                 185                 190

Asp His Ile Phe Phe Thr Gly Gly Thr Ser Ile Gly Lys Ile Ile Ala
         195                 200                 205

Leu Lys Ala Ala Glu Thr Leu Thr Thr Thr Thr Leu Glu Leu Gly Gly
 210                 215                 220

Lys Ser Pro Val Val Val Leu Asp Asp Ala Asp Phe Leu Val Ala Ala
225                 230                 235                 240

Arg Arg Ile Leu Trp Ala Lys Gly Leu Asn Ala Gly Gln Thr Cys Ile
                 245                 250                 255

Ala Pro Asp Tyr Val Leu Val Ser Glu Gln Ser Glu Ser Lys Leu Ile
             260                 265                 270

Ala Ala Met Lys Gln Val Leu Lys Glu Phe Phe Pro Pro Asp Ala Gln
         275                 280                 285

Gly Asp Lys Ala Ser Thr Asn Arg Asp Thr Thr Asp Pro Ser Asp Ser
 290                 295                 300

Lys Phe Cys Lys Ile Ile Asn Gln Arg His Phe Asp Arg Leu Asn Ser
305                 310                 315                 320

Tyr Leu Ser Gln Thr Lys Gly Glu Ile Val Lys Leu Asp Leu Asn Ser
                 325                 330                 335

Ser Ala Gln Pro Glu Ser Ala Asp Pro Ala Ser Leu Lys Ile Pro Leu
             340                 345                 350

Thr Leu Ile Arg Asn Val Gln His Asp Asp Ile Leu Met Glu Asn Glu
         355                 360                 365

Leu Phe Gly Pro Leu Leu Pro Ile Leu Thr Tyr Asn Asn Asp His Glu
 370                 375                 380

Asp Ile Val Gln Cys Leu His Arg Ile Ser Gln Ser Ala Pro Leu Ala
385                 390                 395                 400

Leu Tyr Ala Phe Gly Gln Ser Glu Glu Lys Leu Glu Phe Ile Arg Arg
                 405                 410                 415

Gln Thr Lys Ser Gly Gln Phe Val Cys Asn Asp Leu Leu Ile Gln Phe
             420                 425                 430

Asn Ile Pro Gly Leu Pro Phe Gly Gly Val Gly Ala Ser Gly Leu Gly
         435                 440                 445

Asn Tyr His Gly Tyr Tyr Ser Phe Leu Ala Phe Thr Tyr Glu Arg Pro
```

450 455 460

Met Val Asn Phe Pro Phe Trp Ala Asp Val Leu Leu Lys Ser Arg Tyr
465 470 475 480

Pro Pro Tyr Thr Ser Phe Lys Phe Lys Phe Met Gln Ala Val Leu Gly
485 490 495

Pro Ser Lys Leu Lys Gly Lys Ser Asn Pro Asn Pro Pro Ala Leu Thr
500 505 510

Asp Pro Leu Asp Phe Lys Arg Leu Leu Asp Pro Ser Ser Thr Gly Trp
515 520 525

Leu Ala Lys Ile Pro Val Lys Leu Ser Leu Met Ala Leu Leu Phe Ala
530 535 540

Phe Tyr Cys Ser Arg Arg Gln Asp Ser Leu Gly Gln Lys Gly Leu Phe
545 550 555 560

Asn Ser Phe Lys Lys Val Gln Asp Gln Val Lys Gln Phe Ile Ser Ser
565 570 575

<210> SEQ ID NO 112
<211> LENGTH: 28
<212> TYPE: PRT
<213> ORGANISM: Puccinia triticina

<400> SEQUENCE: 112

Met Ser Ser Thr Ser Pro Leu Glu Phe Thr Pro Thr Asp His Asp Lys
1 5 10 15

Glu Ile Tyr Ala Thr Val Ser Cys Gly His Ser Ser
20 25

<210> SEQ ID NO 113
<211> LENGTH: 18
<212> TYPE: PRT
<213> ORGANISM: Puccinia striiformis

<400> SEQUENCE: 113

Met Ala Ser Leu Glu Thr Pro Thr Asp Glu Ile Lys Gln Ile Tyr Ala
1 5 10 15

Thr Val

<210> SEQ ID NO 114
<211> LENGTH: 505
<212> TYPE: PRT
<213> ORGANISM: Microbotryum violaceum

<400> SEQUENCE: 114

Ser Ser Asp Tyr Thr Pro Val Asp Gln Ile Glu Pro Ala Tyr Asp Glu
1 5 10 15

Ile Val Lys Thr Phe Leu Thr Gly Lys Thr Arg Ser Ile Lys Trp Arg
20 25 30

Lys Gln Gln Leu Lys Gln Leu Gly Phe Leu Ile Gln Asp Asn Glu Ala
35 40 45

Ala Phe Ile Lys Ala Leu Arg Ser Asp Leu Ser Arg Pro Glu Phe Glu
50 55 60

Thr Thr Ile Ala Glu Leu Asn Pro Leu Lys Thr Asp Val Asn Glu Ala
65 70 75 80

Tyr Asp His Leu Asp Lys Trp Ala Lys Pro Val Lys Ala Lys Thr Thr
85 90 95

Ala Val Trp Ala Leu Ala Asn Ala Tyr Ile Tyr Asn Glu Pro Lys Gly
100 105 110

-continued

```
Ala Val Phe Ile Ile Gly Thr Trp Asn Tyr Pro Leu Val Leu Leu
            115                 120                 125

Ser Pro Leu Val Gly Ala Ile Ala Gly Cys Thr Ala Leu Leu Lys
130                 135                 140

Pro Ala Glu Gln Ala Pro Ala Val Ala Lys Leu Val Gln Glu Leu Leu
145                 150                 155                 160

Pro Lys Tyr Leu Asp Thr Ser Ala Tyr Lys Ile Ile Leu Gly Ala Val
                165                 170                 175

Asp Gln Val Thr Arg Ala Leu Glu Leu Lys Phe Asp His Ile Phe Tyr
            180                 185                 190

Thr Gly Ser Gly Gly Ile Gly Lys Ile Ile Ala Arg Ala Ala Ala Glu
        195                 200                 205

His Leu Thr Pro Phe Thr Leu Glu Leu Gly Gly Lys Ser Pro Ala Val
    210                 215                 220

Val Phe Asp Asp Ala Asn Ile Asp Ile Thr Ala Arg Arg Ile Met Trp
225                 230                 235                 240

Gly Lys Phe Val Asn Ser Gly Gln Thr Cys Ile Ser Pro Asp Tyr Val
                245                 250                 255

Leu Cys Thr Ala Asp Val Gln Asp Lys Leu Val Ala Ala Met Gln Lys
            260                 265                 270

Val Tyr Lys Glu Phe Thr Thr Asp Ala Lys Gly Gln Glu Lys Ser Met
        275                 280                 285

Val Asn Gly Glu Gly Tyr Ala Arg Ile Val Asn Met Asn His Phe Gly
    290                 295                 300

Arg Ile Ser Thr Met Leu Asp Glu Thr Lys Gly Arg Val Val Val Gly
305                 310                 315                 320

Gly Gly Arg Asn Lys Glu Thr Gly Lys Ile Glu Thr Thr Ile Ile Ala
                325                 330                 335

Asp Val Gly Ala Asp Asp Pro Leu Met Lys Gly Glu Ile Phe Gly Pro
            340                 345                 350

Val Met Pro Ile Val Val Lys Gln Thr Lys Glu Glu Met Val Glu Phe
        355                 360                 365

Ile Gln Glu Arg Asp Asn Pro Leu Ala Leu Tyr Val Phe Thr Gln Ser
    370                 375                 380

Thr Lys Asn Arg Asp Tyr Ile Phe Glu Arg Thr Arg Ser Gly Gly Phe
385                 390                 395                 400

Val Gln Asn Asp Thr Ile Leu His Phe Thr Ile Pro Gly Leu Pro Phe
                405                 410                 415

Gly Gly Ala Gly Ala Ser Gly Ile Gly Ala Tyr His Gly Lys Trp Ser
            420                 425                 430

Phe Asp Thr Phe Ser His Gln Arg Ala Ser Ala His Ile Pro Thr Trp
        435                 440                 445

Met Asp Val Ala Leu Asn Ser Arg Tyr Pro Pro Tyr Thr Pro Lys Lys
450                 455                 460

Leu Lys Met Met Leu Leu Ala Thr Lys Ala Val Ile Lys Arg Glu Ser
465                 470                 475                 480

Lys Trp Ser Leu Lys Ser Leu Phe Gly Val Leu Ala Val Val Ala Ala
                485                 490                 495

Ile Val Arg Tyr Arg Gln Ser Lys Leu
            500                 505

<210> SEQ ID NO 115
<211> LENGTH: 15
<212> TYPE: PRT
```

<213> ORGANISM: Rhodotorula glutinis ATCC 204091

<400> SEQUENCE: 115

Met Gln Asp Thr Pro Ile Asp Ser Ile Pro Cys Ala Thr Tyr Val
1               5                   10                  15

<210> SEQ ID NO 116
<211> LENGTH: 504
<212> TYPE: PRT
<213> ORGANISM: Rhodosporidium toruloides NP11

<400> SEQUENCE: 116

Met Ala Ala Met Gln Asp Thr Pro Ile Asp Ser Ile Pro Gln Ala Tyr
1               5                   10                  15

Asp Thr Val Thr Lys Ala Phe Leu Ser Gly Lys Thr Arg Pro Ile Ala
                20                  25                  30

Trp Arg Lys Ala Gln Ile Lys Lys Leu Gly Phe Leu Val Gln Asp Asn
            35                  40                  45

Glu Asp Ala Phe Val Arg Ala Leu Glu Gln Asp Phe Gly Arg Pro Ala
        50                  55                  60

Phe Glu Thr Ile Thr Ala Glu Ile Asn Pro Val Lys Ala Glu Ile Asn
65                  70                  75                  80

Glu Val Tyr Asp His Leu Glu Lys Trp Ala Lys Pro Arg Arg Val Lys
                85                  90                  95

Thr Ser Ala Thr Trp Tyr Ala Thr Lys Pro Thr Val Tyr Ser Glu Pro
            100                 105                 110

Lys Gly Val Thr Leu Val Ile Gly Thr Trp Asn Tyr Pro Ile Thr Leu
        115                 120                 125

Leu Leu Val Pro Leu Leu Gly Ala Ile Ser Ala Gly Cys Thr Ala Leu
    130                 135                 140

Val Lys Pro Ala Glu Gln Ala Pro His Val Ala Ala Leu Val Ala Asp
145                 150                 155                 160

Leu Leu Pro Lys Tyr Leu Asp Pro Thr Ala Phe Ile Cys Ile Asn Gly
                165                 170                 175

Ala Ile Pro Gln Ala Thr Ala Leu Leu Lys Leu Lys Phe Asp His Ile
            180                 185                 190

Phe Tyr Thr Gly Ser Gly Thr Val Gly Lys Ile Val Ala Arg Ala Ala
        195                 200                 205

Ala Glu His Leu Cys Pro Val Thr Leu Glu Leu Gly Lys Ser Pro
    210                 215                 220

Ala Val Val Leu Asp Asp Ala Asp Ile Glu Val Val Ala Arg Arg Ile
225                 230                 235                 240

Val Trp Ala Lys Phe Thr Asn Ala Gly Gln Ile Cys Ile Ser Thr Asp
                245                 250                 255

Tyr Val Leu Thr Thr Pro Gln Thr Glu Pro Lys Leu Leu Glu Ala Leu
            260                 265                 270

Lys Arg Ala Leu Ala Ala Phe Ser Ala Asn Pro Ala Ala Ser Ser Ser
        275                 280                 285

Ser Glu Lys Ser Ser Thr Ser Leu Val His Asn Pro Asn Tyr Ser Arg
    290                 295                 300

Ile Ile Asn Gln Asn His Tyr Asn Arg Val Ser Lys Leu Leu Asp Ala
305                 310                 315                 320

Thr Lys Gly Glu Val Val Val Gly Gly Gly Arg Asp Glu Lys Glu Arg
                325                 330                 335

Lys Ile Glu Val Thr Ile Val Arg Gly Val Lys Pro Asp Asp Ser Leu

```
                340             345             350
Met Ser Glu Glu Ile Phe Gly Pro Val Leu Pro Ile Met Thr Leu Pro
            355                 360             365

Thr Leu Asp Asp Met Val Lys Phe Ile Gln Ser Arg Asp Thr Pro Leu
            370                 375                 380

Ala Leu Tyr Val Phe Thr Gln Ser Lys Lys Asn Arg Asp Phe Ile Phe
385                 390                 395                 400

Glu Arg Thr Arg Ser Gly Gly Phe Val Gln Asn Asp Val Leu Val Gln
                405                 410                 415

Phe Met Ile Pro Gly Leu Pro Phe Gly Gly Thr Gly Ala Ala Gly Tyr
                420                 425                 430

Gly Asn Tyr His Gly Arg Arg Thr Phe Asp Thr Phe Ser His Glu Arg
            435                 440                 445

Ala Ser Ala Asn Val Pro Thr Trp Met Asp Met Ile Met Ala Ser Arg
            450                 455                 460

Tyr Pro Pro Tyr Thr Gln Lys Lys Leu Lys Met Leu Leu Phe Ala Thr
465                 470                 475                 480

Lys Ala Val Ile Lys Lys Pro Ser Lys Phe Gly Ser Ile Ser Arg Leu
                485                 490                 495

Leu Lys Lys Leu Thr Gly Gln Ala
            500

<210> SEQ ID NO 117
<211> LENGTH: 16
<212> TYPE: PRT
<213> ORGANISM: Rhodosporidium toruloides ATCC 10657

<400> SEQUENCE: 117

Met Gln Asp Ile Pro Ile Asp Ser Asp Pro Gln Ala Tyr Asp Thr Val
1               5                   10                  15

<210> SEQ ID NO 118
<211> LENGTH: 21
<212> TYPE: DNA
<213> ORGANISM: Rhodosporidium toruloides

<400> SEQUENCE: 118
gcgagggatg gcagtaagac g                                           21

<210> SEQ ID NO 119
<211> LENGTH: 28
<212> TYPE: DNA
<213> ORGANISM: Rhodosporidium toruloides

<400> SEQUENCE: 119
aaaggatcca acttgctcgc ccagtacc                                    28

<210> SEQ ID NO 120
<211> LENGTH: 30
<212> TYPE: DNA
<213> ORGANISM: Rhodosporidium toruloides

<400> SEQUENCE: 120
tttaagcttc acgtacagcc tgtggtagcc                                  30

<210> SEQ ID NO 121
<211> LENGTH: 30
<212> TYPE: DNA
<213> ORGANISM: Rhodosporidium toruloides
```

<400> SEQUENCE: 121
tttaggcctg gaggagtcga gcgtgagagt                                     30

<210> SEQ ID NO 122
<211> LENGTH: 29
<212> TYPE: DNA
<213> ORGANISM: Rhodosporidium toruloides

<400> SEQUENCE: 122
tttccatggc tgcctcgtcg gcactcgag                                      29

<210> SEQ ID NO 123
<211> LENGTH: 29
<212> TYPE: DNA
<213> ORGANISM: Rhodosporidium toruloides

<400> SEQUENCE: 123
tttgatatcc attacgcctt gaccgtcag                                      29

<210> SEQ ID NO 124
<211> LENGTH: 30
<212> TYPE: DNA
<213> ORGANISM: Rhodosporidium toruloides

<400> SEQUENCE: 124
aaagagctcg gtgactgcat gctccgttac                                     30

<210> SEQ ID NO 125
<211> LENGTH: 30
<212> TYPE: DNA
<213> ORGANISM: Rhodosporidium toruloides

<400> SEQUENCE: 125
aaaggatcct gatggagtag ttgggcacga                                     30

<210> SEQ ID NO 126
<211> LENGTH: 31
<212> TYPE: DNA
<213> ORGANISM: Rhodosporidium toruloides

<400> SEQUENCE: 126
tttaagcttc ctcctccttg atctttcgcc g                                   31

<210> SEQ ID NO 127
<211> LENGTH: 30
<212> TYPE: DNA
<213> ORGANISM: Rhodosporidium toruloides

<400> SEQUENCE: 127
tttaggcctg acctttgcgt cctcccttca                                     30

<210> SEQ ID NO 128
<211> LENGTH: 44
<212> TYPE: DNA
<213> ORGANISM: Rhodosporidium toruloides

<400> SEQUENCE: 128
tcagaacaac accagatcac tcacaatggc cgctaccctc cgcc                     44

<210> SEQ ID NO 129
<211> LENGTH: 26
<212> TYPE: DNA
<213> ORGANISM: Rhodosporidium toruloides

<400> SEQUENCE: 129
tttcatatgg ccgctaccct ccgcca                                        26

<210> SEQ ID NO 130
<211> LENGTH: 30
<212> TYPE: DNA
<213> ORGANISM: Rhodosporidium toruloides

<400> SEQUENCE: 130
tttgatatct ctagggcatc gtctagagtc                                    30

<210> SEQ ID NO 131
<211> LENGTH: 33
<212> TYPE: DNA
<213> ORGANISM: Rhodosporidium toruloides

<400> SEQUENCE: 131
aaagagctct attgttcgac tagactgcgc cac                                33

<210> SEQ ID NO 132
<211> LENGTH: 32
<212> TYPE: DNA
<213> ORGANISM: Rhodosporidium toruloides

<400> SEQUENCE: 132
aaaggatcca aggaggatat tgtgcacgag ga                                 32

<210> SEQ ID NO 133
<211> LENGTH: 24
<212> TYPE: DNA
<213> ORGANISM: Rhodosporidium toruloides

<400> SEQUENCE: 133
cgactccaaa tcacccagtt cctc                                          24

<210> SEQ ID NO 134
<211> LENGTH: 28
<212> TYPE: DNA
<213> ORGANISM: Rhodosporidium toruloides

<400> SEQUENCE: 134
tttaggcctg accgactttg acgacgac                                      28

<210> SEQ ID NO 135
<211> LENGTH: 30
<212> TYPE: DNA
<213> ORGANISM: Rhodosporidium toruloides

<400> SEQUENCE: 135
aaagagctcg cggcactgta cttcactacg                                    30

<210> SEQ ID NO 136
<211> LENGTH: 28
<212> TYPE: DNA
<213> ORGANISM: Rhodosporidium toruloides

<400> SEQUENCE: 136
aaaggatcca cgagacctat ccaaacgc                                      28

<210> SEQ ID NO 137
<211> LENGTH: 30
<212> TYPE: DNA

<213> ORGANISM: Rhodosporidium toruloides

<400> SEQUENCE: 137
tttaagctta aggtcaagtc caaggccaac                                              30

<210> SEQ ID NO 138
<211> LENGTH: 30
<212> TYPE: DNA
<213> ORGANISM: Rhodosporidium toruloides

<400> SEQUENCE: 138
tttaggcctg gctgctggag aaacgaaact                                              30

<210> SEQ ID NO 139
<211> LENGTH: 30
<212> TYPE: DNA
<213> ORGANISM: Rhodosporidium toruloides

<400> SEQUENCE: 139
aaaaggcctc attccctcga ctcgacgcat                                              30

<210> SEQ ID NO 140
<211> LENGTH: 21
<212> TYPE: DNA
<213> ORGANISM: Rhodosporidium toruloides

<400> SEQUENCE: 140
agaggaggaa gttgtgcagc a                                                       21

<210> SEQ ID NO 141
<211> LENGTH: 30
<212> TYPE: DNA
<213> ORGANISM: Rhodosporidium toruloides

<400> SEQUENCE: 141
tttggatccg ttgcggcgag tcctgtcatc                                              30

<210> SEQ ID NO 142
<211> LENGTH: 28
<212> TYPE: DNA
<213> ORGANISM: Rhodosporidium toruloides

<400> SEQUENCE: 142
tttgagctcc ggagcgagta agacgagg                                                28

<210> SEQ ID NO 143
<211> LENGTH: 28
<212> TYPE: DNA
<213> ORGANISM: Rhodosporidium toruloides

<400> SEQUENCE: 143
tttccatggc ctcgtacgcc gcccatcc                                                28

<210> SEQ ID NO 144
<211> LENGTH: 29
<212> TYPE: DNA
<213> ORGANISM: Rhodosporidium toruloides

<400> SEQUENCE: 144
tttgatatcg gaagggaccg cgctagttg                                               29

<210> SEQ ID NO 145
<211> LENGTH: 24

```
<212> TYPE: DNA
<213> ORGANISM: Rhodosporidium toruloides

<400> SEQUENCE: 145
tttccatggt cgcaccgtcc cccg                                          24

<210> SEQ ID NO 146
<211> LENGTH: 24
<212> TYPE: DNA
<213> ORGANISM: Rhodosporidium toruloides

<400> SEQUENCE: 146
tttccatggt cgcaccgtcc cccg                                          24
```